US009034343B2

(12) United States Patent
Skiadopoulos et al.

(10) Patent No.: US 9,034,343 B2
(45) Date of Patent: May 19, 2015

(54) ATTENUATED HUMAN PARAINFLUENZA VIRUS, METHODS AND USES THEREOF

(75) Inventors: Mario H. Skiadopoulos, Potomac, MD (US); Brian R. Murphy, Bethesda, MD (US); Peter L. Collins, Silver Spring, MD (US); Sheila Nolan, Pleasantville, NY (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 2154 days.

(21) Appl. No.: 13/501,447

(22) PCT Filed: Jan. 10, 2006

(86) PCT No.: PCT/US2006/000666
§ 371 (c)(1),
(2), (4) Date: Jul. 20, 2012

(87) PCT Pub. No.: WO2007/120120
PCT Pub. Date: Oct. 25, 2007

(65) Prior Publication Data
US 2013/0052718 A1 Feb. 28, 2013

Related U.S. Application Data

(60) Provisional application No. 60/643,310, filed on Jan. 12, 2005.

(51) Int. Cl.
| A61K 39/155 | (2006.01) |
| C12N 15/86 | (2006.01) |
| C12N 7/04 | (2006.01) |
| C12N 7/01 | (2006.01) |
| C07K 14/005 | (2006.01) |
| C12N 7/00 | (2006.01) |
| A61K 39/00 | (2006.01) |

(52) U.S. Cl.
CPC ....... *C07K 14/005* (2013.01); *A61K 2039/5254* (2013.01); *A61K 2039/5256* (2013.01); *C12N 7/00* (2013.01); *C12N 15/86* (2013.01); *C12N 2760/18722* (2013.01); *C12N 2760/18743* (2013.01); *C12N 2760/18761* (2013.01)

(58) Field of Classification Search
CPC ............. C12N 7/00; A61K 2039/5254; A61K 2039/525; C07K 14/005; C07K 16/1027
See application file for complete search history.

(56) References Cited

U.S. PATENT DOCUMENTS

2003/0082209 A1* 5/2003 Skiadopoulos et al. ... 424/210.1
2003/0095987 A1* 5/2003 Haller et al. ............... 424/206.1

FOREIGN PATENT DOCUMENTS

WO WO 2004/027037 A1 4/2004

OTHER PUBLICATIONS

Southern et. al. NCBI GenBank Seq. Dep. AAA46808.1, Dep. Aug. 2, 1993.*
Bowie JU, Reidhaar-Olson JF, Lim WA, Sauer RT. Deciphering the message in protein sequences: tolerance to amino acid substitutions. Science. Mar. 16, 1990;247(4948):1306-10.*
Andrejeva et al., "The p127 subunit (DDB1) of the UV-DNA damage repair binding protein is essential for the targeted degradation of STAT1 by the V protein of the paramyxovirus simian virus 5", J. Virol., Nov. 2002, 76(22),11379-11386.
Andrejeva et al., "Degradation of STAT1 and STAT2 by the V proteins of simian virus 5 and human parainfluenza virus type 2, respectively: consequences for virus replication in the presence of alpha/beta and gamma interferons", J. Virol., Mar. 2002, 76(5), 2159-2167.
Bukreyev et al., "Recovery of Infectious Respiratory Syncytial Virus Expressing an Additional, Foreign Gene", J. Virol., Oct. 1996, 70(10), 6634-6641.
Calain et al., "The rule of six, a basic feature for efficient replication of Sendai virus defective interfering RNA", J. Virol., Aug. 1993, 67(8), 4822-4830.
Chanock et al., "Parainfluenza Viruses", Fields Virology, Knipe et al., eds., 4$^{th}$ Ed., 2001 (no month), vol. 1,1341-1379, Lippincott, Phila., PA.
Delenda et al., "Normal cellular replication of Sendai virus without the trans-frame, nonstructural V protein", Virology, Feb. 3, 1997, 228(1), 55-62.
Devaux et al., "Measles virus phosphoprotein gene products: conformational flexibility of the P/V protein amino-terminal domain and C protein infectivity factor function", J. Virology, Nov. 2004, 11633-11635.
Dillon et al., "Role for the phosphoprotein P subunit of the paramyxovirus polymerase in limiting induction of host cell antiviral responses", J. Virol., Oct. 2007, 81(20), 11116-11127. Epub. Aug. 8, 2007.
Dunnet, "Pairwise multiple comparisons in the homogeneous variance, unequal sample size case", Journal of the American Statistical Association, Dec. 1980, 75(372), 789-795.

(Continued)

*Primary Examiner* — Benjamin P Blumel
*Assistant Examiner* — Rachel Gill

(57) ABSTRACT

The invention provides self replicating infectious recombinant paramyxoviruses. The recombinant paramyxovirus preferably have one or more attenuating mutations. In some embodiments, the recombinant paramyxovirus has a separate variant polynucleotide encoding a P protein and a separate monocistronic polynucleotide encoding a V protein. In some embodiments, recombinant paramyxovirus have at least one temperature sensitive mutation and one non-temperature sensitive mutation. Also provided are compositions and methods for using the recombinant paramyxoviruses as described herein.

14 Claims, 15 Drawing Sheets

(56) References Cited

OTHER PUBLICATIONS

Durbin et al., "Minimum Protein Requirements for Transcription and RNA Replication of a Minigenome of Human Parainfluenza Virus Type 3 and Evaluation of the Rule of Six", Virology, Jul. 1997, 234(1), 74-83.
Durbin et al., "Recovery of Infectious Human Parainfluenza Virus Type 3 From cDNA", Virology, Jun. 1997, 235, 323-332.
Durbin et al., "African green monkeys provide a useful nonhuman primate model for the study of human parainfluenza virus types-1, -2, and -3 infection [In Process Citation]", Vaccine, May 2000, 18(22), 2462-2469.
Durbin et al., "Mutations in the C, D, and V open reading frames of human parainfluenza virus type 3 attenuate replication in rodents and primates", Virology, Sep. 1, 1999, 261(2), 319-330.
Elroy-Stein et al., "Cap-Independent Translation of mRNA Conferred by Encephalomyocarditis Virus 5' Sequence Improves the Performance of the Vaccinia Virus/Bacteriophage T7 Hybrid Expression Systems", Proc. Natl. Acad. Sci. USA., Aug. 1989, 86(16), 6126-6130.
Fukuhara et al., "Mutational analysis of the Sendai virus V protein: importance of the conserved residues for Zn binding, virus pathogenesis, and efficient RNA editing", Virology, Aug. 2002, 299(2),172-181.
Hall et al., "Cold-Passaged Human Parainfluenza Type 3 Viruses Contain ts and non-ts Mutations Leading to Attenuation in Rhesus Monkeys", Virus Res., Mar. 1992, 22(3), 173-184.
Hasan et al., "Creation of an Infectious Recombinant Sendai Virus Expressing the Firefly Luciferase Gene From the 3' Proximal First Locus", Journal of General Virology, Nov. 1997, 78(11), 2813-2820.
He et al., "Recovery of Paramyxovirus Simian Virus 5 with a V Protein Lacking the Conserved Cysteine-rich Domain: The Multifunctional V Protein Blocks both Interferon-beta Induction and Interferon Signaling", Virology, Nov. 10, 2002, 303(1), 15-32.
Heikkinen et al., "Prevalence of Various Respiratory Viruses in the Middle Ear During Acute Otitis Media", N. Engl. J. Med., Jan. 28, 1999, 340(4), 260-264.
Huang et al., "Involvement of the zinc-binding capacity of Sendai virus V protein in viral pathogenesis", J. Virol., Sep. 2000, 74(17), 7834-7841.
Jacques et al., "Pseudo-templated transcription in prokaryotic and eukaryotic organisms", Genes Dev., May 1991, 5(5), 707-713.
Jin et al., "Recombinant Human Respiratory Syncytial Virus (RSV) From cDNA and Construction of Subgroup A and B Chimeric RSV", Virology, Nov. 10, 1998, 251(1), 206-214.
Juhasz et al., "The major attenuating mutations of the respiratory syncytial virus vaccine candidate cpts530/1009 specify temperature-sensitive defects in transcription and replication and a non-temperature-sensitive alteration in mRNA termination", J. Virol., Jun. 1999, 73(6), 5176-5180.
Juhasz et al., "The two amino acid substitutions in the L protein of cpts530/1009, a live-attenuated respiratory syncytial virus candidate vaccine, are independent temperature-sensitive and attenuation mutations", Vaccine, May 1999, 17(11-12), 1416-1424.
Karron et al., "A Live Attenuated Bovine Parainfluenza Virus Type 3 Vaccine is Safe, Infectious, Immunogenic, and Phenotypically Stable in Infants and Children", J. Infect. Dis., May 1995, 171(5), 1107-1114.
Karron et al., "Evaluation of a Live Attenuated Bovine Parainfluenza Type 3 Vaccine in Two-to-Six-Month-Old Infants", Pediatric Infectious Dis. J., Aug. 1996, 15(8), 650-654.
Karron et al., "A Live Human Parainfluenza Type 3 Vaccine is Attenuated and Immunogenic in Healthy Infants and Children", J. Infect. Dis., Dec. 1995, 172(6), 1445-1450.
Kato et al., "The paramyxovirus, Sendai virus, V protein encodes a luxury function required for viral pathogenesis", Embo. J., Feb. 3, 1997, 16(3), 578-587.

Kawano et al., "Recovery of infectious human parainfluenza type 2 virus from cDNA clones and properties of the defective virus without V-specific cysteine-rich domain", Virology, May 25, 2001, 284(1), 99-112.
Kawano et al., "Sequence determination of the P gene of simian virus 41: presence of irregular deletions near the RNA-editing sites of paramyxoviruses", J. Gen. Virol., May 1993, 74(Pt 5), 911-916.
Kolakofsky et al., "Paramyxovirus RNA synthesis and the requirement for hexamer genome length: the rule of six revisited", J. Virol., Feb. 1998, 72(2), 891-899.
Kozuka et al., "Identification of amino acids essential for the human parainfluenza type 2 virus V protein to lower the intracellular levels of the STAT2", Virology, Dec. 2003, 317(2), 208-219.
Lin et al., "The RNA binding region of the paramyxovirus SV5 V and P proteins", Virology, Nov. 24, 1997, 238(2), 460-469.
Lin et al., "The V protein of the paramyxovirus SV5 interacts with damage-specific DNA binding protein", Virology, Sep. 15, 1998, 249(1), 189-200.
Liston et al., "Measles virus V protein binds zinc", Virology, Jan. 1994, 198(1), 399-404.
McAuliffe et al., "Codon substitution mutations at two positions in the L polymerase protein of human parainfluenza virus type 1 yield viruses with a spectrum of attenuation in vivo and increased phenotypic stability in vitro", J. Virol., Feb. 2004, 78(4), 2029-2036.
Moeller et al., "Recombinant measles viruses expressing altered hemagglutinin (H) genes: functional separation of mutations determining H antibody escape from neurovirulence", J. Virol., Aug. 2001, 75(16), 7612-7620.
Murphy et al., "Current Approaches to the Development of Vaccines Effective Against Parainfluenza and Respiratory Syncytial Viruses", Virus Res., Aug. 1988, 11(1), 1-15.
Newman et al., "Generation of recombinant human parainfluenza virus type 1 vaccine candidates by importation of temperature-sensitive and attenuating mutations from heterologous paramyxoviruses", J. Virol., Feb. 2004, 78(4), 2017-2028.
Newman et al., "Sequence analysis of the Washington/1964 strain of human parainfluenza virus type 1 (HPIV1) and recovery and characterization of wild-type recombinant HPIV1 produced by reverse genetics", Virus Genes, (no month) 2002, 24(1), 77-92.
Nolan et al., "Recombinant human parainfluenza virus type 2 vaccine candidates containing a 3' genomic promoter mutation and L polymerase mutations are attenuated and protective in non-human primates", Vaccine, Aug. 21, 2007, 25(34), 6409-6422.
Ohgimoto et al., "Sequence analysis of P gene of human parainfluenza type 2 virus: P and cysteine-rich proteins are translated by two mRNAs that differ by two nontemplated G residues", Virology, Jul. 1990, 177(1), 116-123.
Parisien et al., "STAT2 acts as a host range determinant for species-specific paramyxovirus interferon antagonism and simian virus 5 replication", J. Virol., Jul. 2002, 76(13), 6435-6441.
Parisien et al., "The V protein of human parainfluenza virus 2 antagonizes type I interferon responses by destabilizing signal transducer and activator of transcription 2", Virology, May 10, 2001, 283(2), 230-239.
Park et al., "Newcastle disease virus V protein is a determinant of host range restriction", J. Virol., Sep. 2003, 77(17), 9522-9532.
Paterson et al., "The paramyxovirus SV5 V protein binds two atoms of zinc and is a structural component of virions", Virology, Apr. 1, 1995, 208(1),121-131.
Precious et al., "Inducible expression of the P, V, and NP genes of the paramyxovirus simian virus 5 in cell lines and an examination of NP-P and NP-V interactions", J. Virol., Dec. 1995, 69(12), 8001-8010.
Randall et al., "NP:P and NP:V interactions of the paramyxovirus simian virus 5 examined using a novel protein:protein capture assay", Virology, Oct. 1, 1996, 224(1), 121-129.
Rodriguez et al., "Identification of the nuclear export signal and STAT-binding domains of the Nipah virus V protein reveals mechanisms underlying interferon evasion", J. Virol., May 2004, 78(10), 5358-5367.
Schmidt et al., "Bovine Parainfluenza Virus Type 3 (BPIV3) Fusion and Hemagglutinin-Neuraminidase Glycoproteins Make an Impor-

(56) References Cited

OTHER PUBLICATIONS tant Contribution to the Restricted Replication of BPIV3 in Primates", J. Virol., Oct. 2000, 74(19), 8922-8929.
Schmidt et al., "Recombinant bovine/human parainfluenza virus type 3 (B/HPIV3) expressing the respiratory syncytial virus (RSV) G and F proteins can be used to achieve simultaneous mucosal immunization against RSV and HPIV3", J. Virol., May 2001, 75(10), 4594-4603.
Skiadopoulos et al., "Three amino acid substitutions in the L protein of the human parainfluenza virus type 3 cp45 live attenuated vaccine candidate contribute to its temperature-sensitive and attenuation phenotypes", J. Virol., Mar. 1998, 72(3), 1762-1768.
Skiadopoulos et al., "Determinants of the host range restriction of replication of bovine parainfluenza virus type 3 in rhesus monkeys are polygenic", J. Virol., Jan. 2003, 77(2), 1141-1148.
Skiadopoulos et al., "Long nucleotide insertions between the HN and L protein coding regions of human parainfluenza virus type 3 yield viruses with temperature-sensitive and attenuation phenotypes", Virology, Jun. 20, 2000, 272(1), 225-234.
Skiadopoulos et al., "Evaluation of the replication and immunogenicity of recombinant human parainfluenza virus type 3 vectors expressing up to three foreign glycoproteins", Virology, May 25, 2002, 297(1), 136-152.
Skiadopoulos et al., "Attenuation of the recombinant human parainfluenza virus type 3 cp45 candidate vaccine virus is augmented by importation of the respiratory syncytial virus cpts530 L polymerase mutation", Virology, Jul. 20, 1999, 260(1), 125-135.
Skiadopoulos et al., "Identification of mutations contributing to the temperature-sensitive, cold-adapted, and attenuation phenotypes of the live-attenuated cold-passage 45 (cp45) human parainfluenza virus 3 candidate vaccine", J. Virol., Feb. 1999, 73(2), 1374-1381.
Skiadopoulos et al., "Generation of a parainfluenza virus type 1 vaccine candidate by replacing the HN and F glycoproteins of the live-attenuated PIV3 cp45 vaccine virus with their PIV1 counterparts", Vaccine, Oct. 14, 1999, 18(5-6), 503-510.
Skiadopoulos et al., "The genome length of human parainfluenza virus type 2 follows the rule of six, and recombinant viruses recovered from non-polyhexameric-length antigenomic cDNAs contain a biased distribution of correcting mutations", J. Virol., Jan. 2003, 77(1), 270-279.
Sun et al., "Conserved cysteine-rich domain of paramyxovirus simian virus 5 V protein plays an important role in blocking apoptosis", J. Virol., May 2004, 78(10), 5068-5078.

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1", J. Virol., Apr. 1998, 72(4), 2955-2961.
Tao et al., "A Live Attenuated Chimeric Recombinant Parainfluenza Virus (PIV) Encoding the Internal Proteins of PIV Type 3 and the Surface Glycoproteins of PIV Type 1 Induces Complete Resistance to PIV1 Challenge and Partial Resistance to PIV3 Challenge", Vaccine, Mar. 5, 1999, 17(9-10), 1100-1108.
Tao et al., "A live attenuated recombinant chimeric parainfluenza virus (PIV) candidate vaccine containing the hemagglutinin-neuraminidase and fusion glycoproteins of PIV1 and the remaining proteins from PIV3 induces resistance to PIV1 even in animals immune to PIV3", Vaccine, Jan. 31, 2000, 18(14), 1359-1366.
Tao et al., "Replacement of the ectodomains of the hemagglutinin-neuraminidase and fusion glycoproteins of recombinant parainfluenza virus type 3 (PIV3) with their counterparts from PIV2 yields attenuated PIV2 vaccine candidates", J. Virol., Jul. 2000, 74(14), 6448-6458.
Ulane et al., "Paramyxoviruses SV5 and HPIV2 assemble STAT protein ubiquitin ligase complexes from cellular components", Virology, Dec. 20, 2002, 304(2), 160-166.
Vulliemoz et al., "Rule of six": how does the Sendai virus RNA polymerase keep count?, J. Virol., May 2001, 75(10), 4506-4518.
Watanabe et al., "Identification of the sequences responsible for nuclear targeting of the V protein of human parainfluenza virus type 2", J. Gen. Virol., Feb. 1996, 77 ( Pt 2 ), 327-338.
Watanabe et al., "Binding of the V proteins to the nucleocapsid proteins of human parainfluenza type 2 virus", Med. Microbiol. Immunol. (Berl), Sep. 1996, 185(2), 89-94.
Wells et al., "Cassette Mutagenesis: An Efficient Method for Generation of Multiple Mutations at Defined Sites", Gene, 1985 (no month), 34(2-3), 315-323.
Wells et al., "Importance of Hydrogen-Bond Formation in Stabilizing the Transition State of Subtilisin", Philos. Trans. R. Soc. London SerA, 1986 (no month), 317(1540), 415-423.
Whitehead et al., "Addition of a missense mutation present in the L gene of respiratory syncytial virus (RSV) cpts530/1030 to RSV vaccine candidate cpts248/404 increases its attenuation and temperature sensitivity", J. Virol., Feb. 1999, 73(2), 871-877.
Zoller et al., "Oligonucleotide-Directed Mutagenesis Using M13-Derived Vectors: An Efficient and General Procedure for the Production of Point Mutations in any Fragment of DNA", Nucl. Acids Res., Oct. 25, 1987, 10(20), 6487-6500.

* cited by examiner

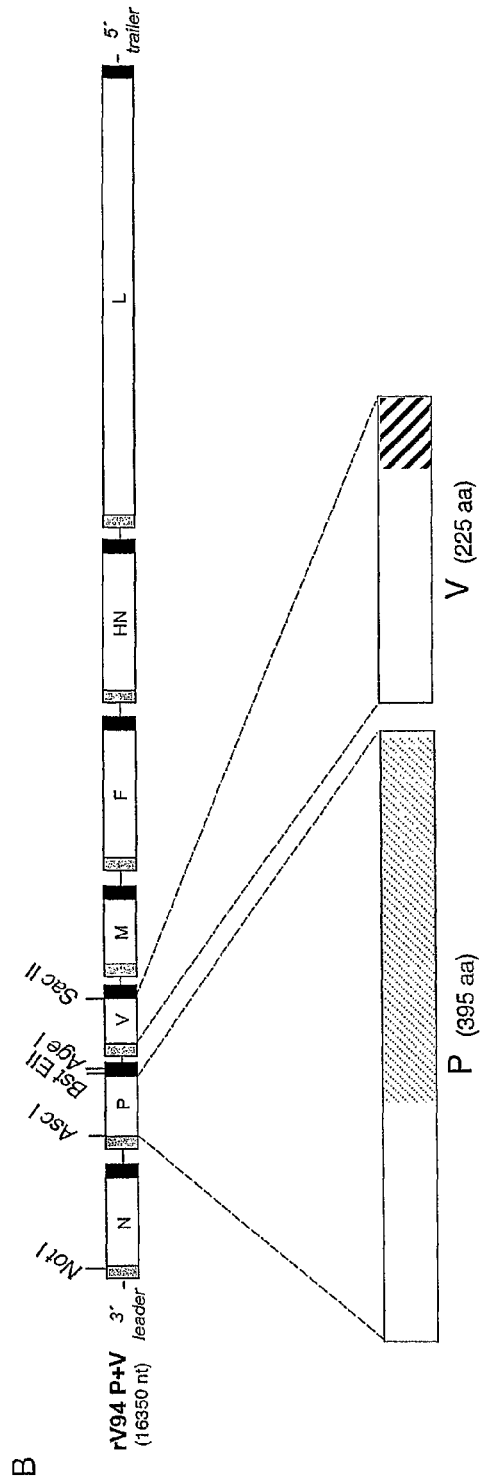
FIGURE 5 A, B

A

```
1                                                              60
MAEEPTYTTEQVDELIHAGL GTVDFFLSRPIDAQSSLGKG SIPPGVTAVLTNAAEAKSKP
                 I                                      II
         20                  80                       100                    120
VAAGPVKPRRKKVISNTTPY TIADNIPPEKLPINTPIPNP LLPLARPHGKMTDIDIVTGN
     III                IV                                      V
ITEGSYKGVELAKLGKQTLL TRFTSNEPVSSAGSAQDPNF KRGANRERARGNHRREWSI
                            140                   160                   180
                                                       VI
AWVGDQVKVFEWCNPRCAPV TASARKFTCTCGSCPSICGE CEGDH
                     200                  220    225
```

B

| | | | |
|---|---|---|---|
| HPIV2/V94 | 174 | HRREWSIAWGDQVKVFEWCNPRQAPVTASARKFTCTCGSCPSICGECEGD | 224 AF533010 |
| SV41 | 174 | HRREWSIAWGDEVKVYEWCNFTCAPVTATDRKFSCTCGTCPRCGECEGD | 224 P363153 |
| SV5 | 171 | HRREYSIGWGDEVKVTEWCNFSCSPITAAARRFECTCHQCFVICSECERD | 221 P11207 |
| Mumps virus | 170 | HRREWSLSWVQGEVRVFEWCNFICSPITAAARFHSCKCGNCPAKCDQCERD | 220 AAL83741 |
| PIV4A | 178 | HRREYSIWVNGRTTISEWCNFCCAPVKSTASVEKCTCGRCPKICEICIRD | 228 P21739 |
| PIV4B | 178 | HRREHSISWVNGRTTISEWCNFCCAPVKSIASVEKCTCGRCPKICEICIRD | 228 P21740 |
| NDV | 176 | HRREHSISWTMGGVTTISWCNFSCSPIRAEPRQYSCTCGSCPATCRICASD | 226 JQ2393 |
| Tioman virus | 164 | HRREIAISWATGTPRVTEWCNFICHPISQFTYRGTCRCGCCFDVCSLCERD | 214 NP_665866 |
| Menangle virus | 166 | HRREIAIDWIGGRPRVTEWCNFICHPISQSTFRGSCRCGNCPGICSLCERD | 216 AAK62279 |
| Porcine rubulavirus | 181 | HRREYSIGWVCGTVRVLEWCNFACSPISMEPRYYQCTCGTCPAKCPQCAGD | 231 AAL09693 |
| CDV | 232 | HRREVSLITWNGDSCWIDKWCNFICTQVNWGIIRAKCVCGECPPICSECKDD | 282 AAQ96302 |
| PDV | 232 | HRREVSLTWNDDRCWLDKWCNFICTQVNWGVIRAKCICGECPPVCDDCKDD | 282 P35941 |
| Rinderpest virus | 232 | HRREIDLIWNDGRVFIDRWCNFTCSKVTVGTVRAKCICGECPRVCEQCITD | 282 Q03340 |
| Measles virus | 232 | HRREISLIWNGDRVFIDRWCNPMCSKVTLGTIRARCICGECPRVCEQCRTD | 282 Q9IC37 |
| Salem virus | 252 | HRREYSIIWDSEGIQIESWCNPVCSKVRSTPRREKCRCGKCPARCSECGDD | 302 AAF63742 |
| Fer-de-lance virus | 170 | HRREISTSTIDGIFEVWEFCNPMWEFCNPMCSKIRPIPRQESCVCGECPKQCRYCIKD | 220 NP_899657 |
| BPIV3Ka | 348 | HRREHSIYRKGDYILTESWCNFICSKIRPIPRQESCVCGECPKQCRYCIKD | 398 NC_002161 |
| Sendai virus | 318 | HRREHIIYERDGYIVNESWCNPMCSRIRVISRRELCVCKACPKICKLCRDD | 368 BAB20021 |
| Mossman virus | 244 | HRREYNFVWTDSGFRVEAWCNPICSRIRNLPRREKCRCGWCPKECPECALG | 294 NP_958050 |
| Tupaia paramyxovirus | 230 | HRREYSMVWSNDGVFIESWCNPMCARIRPLPIREICVSRITPQPRKQECYCGECPTEQSQCCHE | 280 NP_054692 |
| Hendra virus | 406 | HRREVSICWDGRRAWVEEWCNPVEEWCNPVCSRITPQPRKQECYCGECPTEQSQCCHE | 456 NP_047108 |
| Nipah virus | 408 | HRREISICWDGKRAWVEEWCNPACSRITPLPRRQECQQGECPTECFHCG | 456 AAM13407 |

```
   1 ATGGCCGAGG AACCAACATA CACCACTGAG CAAGTTGATG AATTAATCCA TGCTGGACTA GGAACAGTAG ATTTCTTCCT ATCTAGACCC ATAGATGCTC  100
 101 AGTCTTCTTT AGGTAAAGGC AGCATCCCAC CAGGTGTCAC GGCTGTTCTA ACCAAACCA CAGAGGCAAA ATCCAAACCA GTTGCTGCTG GTCCAGTAAA  200
 201 ACCCAGACGG AAGAAAGTGA TCAGCAATAC CACTCCATAC ACTATTGCAG ACAACATCCC ACCTGAGAAG CTACCGATCA ACACTCCAAT ACCAATCCA  300
 301 TTACTTCCAC TGGCACGCCC TCACGGAAAG ATGACAGACA TTGACATTGT CACTGGGAAC GATCATACAA AGGTGTGGAG CTTGCCAAAT  400
 401 TAGGAAGCA ACACTACTC ACAAGGTTCA CCTCGAATGA GCCAGTCTCC CCGCCCAAGA CCCCAACTTT AAGAGAGGAG GTGAGCTAAT  500
 501 AGAGAAAGAG CAAGAGGCAA CCATAGGAGA GAATGGAGTA TTGCATGGGT TCAGTCATCAG GTCAAAGTCT TCGAGTGGTG TAATCCCAGG TGTGCCCCAG  600
 601 TCACGGCTTC AGCTCGCAAG TTCACCTGCA CATGTGGATC CTGCCCCAGC ATCTGCGGAG AATGTGAAGG AGATCATTGA GCTCTTAAAA GGGCTTGATC  700
 701 TTCGCCTTCA GACTGTAGAA GGGAAAGTAG ATAAAATTCT TGCAACCTCT GCAACTATAA AATGAAAATG ACTAGTCTTA AGGCGAGCGT  800
 801 TGCAACTGTG GAAGGTATGA TAACAACAAT TAAAATCATG GATCCCAGTA CACCAACCAA TGTCCCTGTA GAGGAGATCA GAAAGAGTTT ACACAATGTT  900
 901 CCAGTAGTAA TTGCTGGTCC GACTAGTGGA GGCTTCACAG CCGAAGGCAG TGACATGATT TCAATGGATG AACTAGCTAG GCCTACACTC TCATCAACAA 1000
1001 AAAAGATCAC ACGAAAGCCT GAATCCAAGA AAGATTTAAC AGGCATAAAA CTAACCCTGA TGCAGCTTGC AAATGACTGC ATCTCGCGTC CAGATACCAA 1100
1101 GACTGAGTTT GTGACTAAGA TTCAAGCAGC AACCACAGAA TCACAGCTCA ACGAAATCAA ACGGTCAATA ATACGCTCTG CAATATAA              1188
```

FIGURE 11

```
  1 ATGGCCGAGG AACCAACATA CACCACTGAG CAAGTTGATG AATTAATCCA TGCTGGACTA GGAACAGTAG ATTTCTTCCT ATCTAGACCC ATAGATGCTC 100
101 AGTCTTCTTT AGTAAAGGC AGCATCCCAC CAGTGTCAC GGCTGTTCTA ACCAATGCAG CAGAGGCAAA ATCCAAACCA GTTGCTGCTG GTCCAGTAAA 200
201 ACCCAGACGG AAGAAAGTGA TCAGCAATAC CACTCCATAC ACTATTGCAG ACAACATCCC ACCTGAGAAG CTACCGATCA ACACTCCAAT ACCCAATCCA 300
301 TTACTTCCAC TGGCACGCCC TCACGGAAAG ATGACAGACA TTGACATTGT GCCAGTCTCC CACTGGGAAC ATTACAGAAG GATCATACAA AGGTGTGGAG CTTGCCAAAT 400
401 TAGGAAGCA AACACTACTC ACAAGTTCA CCTCGAATGA GCCAGTCTCC TCAGCTGGAT CCGCCCAAGA CCCAACTTT AAGAGAGGCG GAGCTAATAG 500
501 AGAAAGAGCA AGAGGCAACC ATAGGAGAGA ATGGAGTATT GCATGGGTCG GAGATCAGGT CAAAGTCTTC GAGTGGTGTA ATCCCAGGTG TGCCCCAGTC 600
601 ACGGCTTCAG CTCGCAAGTT CACCTGCACA TGTGGATCCT GCCCCAGCAT CTGCGGAGAA TGTGAAGGAG ATCATTGA                      678
```

ATTENUATED HUMAN PARAINFLUENZA VIRUS, METHODS AND USES THEREOF

This application is the National Stage under 35 USC §371 of International Application Number PCT/US2006/000666 filed on Jan. 10, 2006, which claims priority under 35 USC §119(e) of Application No. 60/643,310 filed in the United States on Jan. 12, 2005.

STATEMENT OF RIGHTS TO INVENTIONS MADE UNDER FEDERALLY SPONSORED RESEARCH AND DEVELOPMENT

Part of the work performed during the development of this invention utilized United States government funds under National Institute of Allergy and Infectious Diseases, Department of Health and Human Services.

SEQUENCE LISTING

The instant application contains a sequence listing which has been submitted electronically in ASCII format and is hereby incorporated by reference in its entirety. Said ASCII copy, created on Feb. 12, 2014, is named NIHB-2560 SL.txt and is 171,926 bytes in size.

BACKGROUND OF THE INVENTION

Human parainfluenza viruses (HPIVs) are members of the Paramyxovirinae subfamily of the Paramyxoviridae family of viruses. Paramyxoviruses are enveloped viruses that replicate in the cytoplasm and bud at the plasma membrane and have a single-stranded negative-sense non-segmented RNA genome of approximately 13-19 kb. HPIVs are important pathogens in human populations, causing severe lower respiratory tract infections in infants and young children. Human parainfluenza virus type 1 (HPIV1) and type 2 (HPIV2) are the principal etiologic agents of laryngotracheobronchitis (croup) and also cause pneumonia and bronchitis (Chanock et al., 2001, Parainfluenza Viruses 4th Ed., Knipe et al. eds., Lippincott (Philadelphia, Pa.) 1341-1379). Human parainfluenza virus type 3 (HPIV3) is a leading cause of hospitalization for viral lower respiratory tract disease in infants and young children (Chanock et al., 2001, supra). HPIVs are also important causes of respiratory tract disease in adults. Collectively, HPIV1, HPIV2, and HPIV3 have been identified as the etiologic agents responsible for approximately 18% of hospitalizations for pediatric respiratory disease (Murphy et al., 1988, Virus Res., 11:1-15). HPIVs have also been implicated in a significant proportion of cases of virally induced middle ear effusions in children with otitis media (Heikkinen et al., 1999, N. Engl. J. Med., 340:260-264).

Despite considerable efforts, there are currently no parainfluenza virus vaccines available. Attenuated paramyxoviruses suitable for use in vaccines are currently under development. Two live attenuated HPIV3 vaccine candidates, a temperature sensitive (ts) derivative of the wild type HPIV3 JS strain and a bovine PIV3 strain, are currently being tested. (Karron et al, Pediatric Infectious Dis. J., 15:650, 1996; Karron et al, J. Infect. Dis., 171:1107, 1995; Karyon et al., J. Infect. Dis., 172:1445, 1995). A chimeric PIV1 vaccine candidate has been generated by replacing the PIV3 HN and F open reading frames with those of PIV1 in a PIV3 full length cDNA (Tao et al., 2000a). A chimeric HPIV3 bearing the glycoproteins of HPIV2 was also generated previously (Tao et al., 2000b). Attenuated HPIV2 strains have previously been made by introducing mutations into the L protein (WO 04/027037). Recombinant viruses include HPIV3 recombinant viruses having three identified mutations in the L gene. (Skiadopoulos et al, J. Virol. 72:1762, 1998; Tao et al, J. Virol. 72:2955, 1998; Tao et al, Vaccine, 17:1100, 1999). These live attenuated vaccine candidates can induce protection against HPIV infection in some experimental animal models. (Karyon et al, J. Infect. Dis., 172:1445, 1995b; Skiadopoulos et al, Vaccine 18:503, 1999; Skiadopoulos, Virology, 297: 136, 2002). However immunity to previous HPIV3 infection could limit the use of chimeric HPIV3 vaccines bearing heterologous HPIV1 or HPIV2 glycoproteins. Strategies to develop live viral vaccines are important in the design of safe and stable viral vaccine candidates.

In addition to providing possible vaccine candidates for protection against parainfluenza virus infection and disease, candidate vaccines may also be useful in expressing heterologous antigens. Studies demonstrate that foreign genes may be inserted into a paramyxovirus genome and are well expressed. (Bukereyev et al, J. Virol., 70:6634, 1996; Hassan et al, Virology, 237:249, 1997; Jin et al, Virology 251:206, 1998; Schmidt et al., 2001; Skiadopoulos et al., 2002). However, in order to develop vectors for vaccine use, more than a high level of protein expression is required. Factors in the design of a vector for delivery of heterologous antigens include viral host range, immunogenicity, and pathogenicity. Some negative strand viruses are undesirable as vectors because of their pathogenicity, such as measles and rabies virus.

Thus, there remains a need to develop effective immunogenic compositions to alleviate health problems associated with HPIV viruses and other pathogens, and to immunize against multiple HPIV serotypes. There is also a need to develop immunogenic compositions to deliver heterologous antigens.

SUMMARY OF THE INVENTION

The invention provides self-replicating, infectious, recombinant paramyxoviruses (PIV), methods of making the paramyxoviruses of the invention, and uses thereof. The PIV of the invention can have one or more amino acid or nucleic acid mutations that confer an attenuated phenotype. In some embodiments, the number of nucleotides inserted or deleted is such that the total number of nucleotides in the variant viral genome is divisible by six (known as the "rule of six"). The mutation can be stabilized by at least two changes in the codon specifying the mutation. The PIV of the invention can be human parainfluenza virus (HPIV), such as for example HPIV2. In an embodiment, the PIV of the invention comprise a nucleotide sequence having at least 80% sequence identity with SEQ ID NO:1.

The PIV of the invention can include a P protein, V protein, major nucleocapsid (N) protein, and/or large polymerase (L) protein. The proteins may be variant or naturally occurring. In an embodiment, P protein has an amino acid sequence having at least 80% sequence identity with SEQ ID NO:15. In an embodiment, V protein has an amino acid sequence having at least 80% sequence identity with SEQ ID NO:45. In an embodiment, N protein has an amino acid sequence having at least 80% sequence identity with SEQ ID NO:16. In an embodiment, L protein has an amino acid sequence having at least 80% sequence identity with SEQ ID NO:17.

In some embodiments, the PIV of the invention comprise a partial or complete polyhexameric genome or antigenome comprising a variant polynucleotide encoding a P protein and a monocistronic polynucleotide encoding a V protein. Preferably, PIV comprising a monocistronic polynucleotide encoding a V protein have an attenuated phenotype. The variant polynucleotide encoding a P protein and the monocistronic polynucleotide encoding a V protein can be separated by a non-coding polynucleotide spacer sequence and optionally, can be on separate vectors. In some embodiments, the non-coding spacer comprises a gene end transcription signal, intergenic transcription signal, and gene start transcription signal. The non-coding spacer can be upstream of the V ORF.

The polynucleotide encoding the V protein can encode a variant V protein containing a mutation that inhibits the ability of the V protein to interrupt production of interferon in an infected host or signaling though its receptor. The mutation can be amino acid or nucleic acid substitution(s) or deletion(s). Preferably, the number of nucleotides inserted or deleted is such that the total number of nucleotides in the variant viral genome is divisible by six. The mutation can be stabilized by at least two changes in the codon specifying the mutation. In some embodiments, the V protein comprises one or more amino acid substitutions at or between amino acid residues corresponding to a position 67, 68, 69, 70, 71, 72, 105, 106, 107, 108, 121, 122, 123, 124, 125, 126, 127, 130, 131, 132, 133, 134, 135, 136, 137, 138, 139, 140, 167, 168, 169, 170, 171, 172, or mixtures thereof, or any one of the amino acids of 174-225 of SEQ ID NO:45. The polynucleotide encoding the V protein can include a mRNA editing site having a heptaguanosine run. The heptaguanosine run can be substituted such that editing of V gene mRNA is inhibited.

The variant polynucleotide encoding the P protein can comprise a P ORF having one or more nucleotide substitutions wherein the substitution(s) introduces one or more stop codons in an overlapping V ORF reading frame but does not alter the amino acid sequence of P protein encoded by the variant polynucleotide encoding the P protein. The polynucleotide encoding the protein can include a mRNA editing site having a heptaguanosine run. One or more nucleotides can be inserted into the mRNA editing site such that the nucleotide sequence encoding a carboxy-terminal of P protein is in frame. The heptaguanosine run can be substituted such that editing of P gene mRNA is inhibited.

The invention also includes polynucleotides and methods of using polynucleotides. In some embodiments, an isolated nucleic acid comprises a polynucleotide having at least 80% sequence identity to a polynucleotide of SEQ ID NO: 1. In other embodiments, an isolated nucleic acid comprises a polynucleotide having a sequence of SEQ ID NO:2. In further embodiments, an isolated nucleic acid comprises a polynucleotide having a sequence of SEQ ID NO:3. The invention also includes an isolated nucleic acid comprising a polynucleotide encoding a polypeptide having at least 80% sequence identity to a V polypeptide of SEQ ID NO:45. Other embodiments include an isolated nucleic acid comprising a polynucleotide encoding a polypeptide having at least 80% sequence identity to a polypeptide of SEQ ID NO:17. The invention also includes vectors including any of the polynucleotides as well as a partial or complete genome or antigenome. Also provided are methods of producing a paramyxovirus polypeptide by culturing a host cell comprising any of the polynucleotides described herein.

Another aspect of the invention includes paramyxovirus polypeptides. In some embodiments, an isolated V polypeptide comprises at least one mutation at an amino acid residue corresponding to a position 67, 68, 69, 70, 71, 72, 105, 106, 107, 108, 121, 122, 123, 124, 125, 126, 127, 130, 131, 133, 134, 135, 136, 137, 138, 139, 140, 167, 168, 169, 170, 171, 172, or mixtures thereof of SEQ ID NO:45. In other embodiments, an isolated L polypeptide comprises at least one mutation at one amino acid residue corresponding to a position 460, 948, 1566, 1724 or mixtures thereof of an L protein having an amino acid sequence of SEQ ID NO:17. In some embodiments, the L protein comprises one or more of the following substitutions: position 460 is substituted with A or P, position 948 is substituted with A, L or G or position 1724 is substituted with I.

In some embodiments, the PIV of the invention comprise one or more attenuating mutations. The attenuating mutations(s) can be temperature sensitive. Replication of PIV of the invention comprising one or more temperature sensitive mutations is attenuated in vitro at about 37° C. or greater, as compared to wild type PIV. Temperature sensitive mutations can comprise amino acid substitution or deletion of one or more amino acid residues corresponding to position 460, 948, 1566, 1724, or 1725 of an L protein having an amino acid sequence of SEQ ID NO:17. In an embodiment, the substitution comprises F460L, F460A, or F460P. In an embodiment, the substitution comprises Y948A, Y948L, or Y948G. In an embodiment, the substitution comprises L1566I. In an embodiment, the substitution comprises S1724I. In an embodiment, amino acid residues at positions 1724 and 1725 are deleted.

The attenuating mutation(s) can be non-temperature sensitive. Non-temperature sensitive mutations can comprise a nucleic acid substitution at a position corresponding to position 15 of a 3' leader sequence having an nucleic acid sequence of SEQ ID NO:18. In an embodiment, the substitution comprises T15C. In preferred embodiments, the recombinant paramyxovirus comprises a polynucleotide having a C at position 15 and has little or no detectable virus with a T at that position. Non-temperature sensitive mutations can be host range restricted. In an embodiment, the PIV of the invention replicates in hamsters but not African green monkeys.

The PIV of the invention can comprise at least one temperature sensitive mutation and at least one non-temperature sensitive mutation. In an embodiment, at least one of the temperature sensitive mutations comprises an amino acid substitution or deletion of one or more amino acid residues corresponding to position 460, 948, 1566, 1724, or 1725 or mixtures thereof of an L protein having an amino acid sequence of SEQ ID NO:17 and at least one of the non-temperature sensitive mutations comprises a nucleic acid substitution at a position corresponding to position 15 of a 3' leader sequence having an nucleic acid sequence of SEQ ID NO:18. In preferred embodiments, the recombinant paramyxovirus comprises a polynucleotide having a C at position 15 and has no detectable virus with a T at that position.

In some embodiments, the PIV of the invention comprise one or more supernumerary heterologous polynucleotides or genome segments encoding one or more antigenic determinants of a heterologous pathogen. The heterologous pathogen can comprise HPIV1, HPIV3, measles virus, subgroup A or subgroup B respiratory syncytial virus, mumps virus, human papilloma virus, type 1 or type 2 human immunodeficiency virus, herpes simplex virus, cytomegalovirus, rabies virus, Epstein Barr virus, filovirus, bunyavirus, flavivirus, alphavirus, human metapneumovirus, or influenza virus. In an embodiment, the antigenic determinant comprises measles HA, HPIV1 HN, or HPIV1 F. Preferably, PIV of the invention containing one or more determinants of a heterologous pathogen have an attenuated phenotype.

Another aspect of the invention includes methods of making the PIV and polynucleotides of the invention. In some embodiments, the methods of the invention comprise removing a bicistronic polynucleotide encoding P and V proteins from viral genome or antigenome of a PIV and inserting a variant polynucleotide encoding a P protein and a monocistronic polynucleotide encoding a V protein into a full length or partial genome or antigenome of a PIV. The polynucleotide encoding a variant P protein and the monocistronic polynucleotide encoding a V protein can be on the same vector or separate vectors. The variant polynucleotide encoding a P protein can comprise a mutated mRNA editing site such that editing of mRNA encoding P protein is inhibited. The monocistronic polynucleotide encoding a V protein can comprise a mutated mRNA editing unit such that editing of mRNA encoding V protein is inhibited. In some embodiments, the variant polynucleotide encoding a P protein and a monocistronic polynucleotide encoding a V protein are separated by a non-coding polynucleotide spacer sequence comprising a gene end transcription signal, intergenic transcription signal, and gene start transcription signal.

In an embodiment, the removing step comprises introducing unique restriction enzyme recognition sequences into the genome or antigenome such that the recognition sequences flank the bicistronic polynucleotide, and digesting the genome with one or more restriction enzymes that cut the genome at the restriction sites flanking the bicistronic polynucleotide. In an embodiment, the inserting step comprises inserting the variant polynucleotide encoding a P protein and a monocistronic polynucleotide encoding a V protein at the cleaved restriction sites, and religating the genome or antigenome.

In some embodiments, the methods of the invention comprise coexpressing in a cell an expression vector comprising a partial or complete polyhexameric genome or antigenome encoding a PIV of the invention and one or more polynucleotides encoding N protein, P protein, and L protein and incubating the cell under conditions that allow for viral replication. The cells can be, for example, Hep-2 cells, Vero cells, or LLC-MK2 cells.

Another aspect of the invention is a composition comprising PIV of the invention. The PIV of the invention are useful, for example, in immunogenic compositions for eliciting an immune response in an animal, including live virus vaccines and vectors for expressing heterologous antigens. PIV of the invention can be combined with viruses of other PIV serotypes, strains, or genera in a composition to elicit an immune response against multiple genera, serotypes, and strains.

The compositions of the invention comprise an immunogenic effective amount of a PIV of the invention and a physiologically acceptable carrier. The compositions of the invention can also comprise an adjuvant. In an embodiment, the composition of the invention comprises PIV from two or more serotypes. Preferably, at least one or more of the serotypes is HPIV1, HPIV2, HPIV3, or HPIV4. The HPIV2 can be strain V94, V98, or Greer. In an embodiment, the composition of the invention comprises PIV from two or more genera. Preferably, at least one genus is *Rubulavirus* genus.

Another aspect of the invention is methods of eliciting an immune response in an animal. The methods generally comprise administering an immunogenic effective amount of a composition of the invention to the animal. Preferably the immune response produces anti-PIV antibodies that are protective. In an embodiment, the antibodies are IgA. In an embodiment, the immune response produces antibodies that bind one or more antigenic determinants of a heterologous pathogen encoded by a supernumerary gene or genome segment of the PIV of the invention. The heterologous pathogen can be HPIV1, HPIV3, measles virus, subgroup A or subgroup B respiratory syncytial virus, mumps virus, human papilloma virus, type 1 or type 2 human immunodeficiency virus, herpes simplex virus, cytomegalovirus, rabies virus, Epstein Barr virus, filovirus, bunyavirus, flavivirus, alphavirus, human metapneumovirus, or influenza virus. In an embodiment, the antigenic determinant is measles HA, HPIV1 HN, or HPIV1 F.

BRIEF DESCRIPTION OF THE DRAWINGS

FIGS. 1A-B show the level of replication of the biologically derived HPIV2 V94 strain and recombinant derivatives (r) thereof in the upper (nasal turbinates; 1A) and lower (lungs; 1B) respiratory tract of hamsters. The mean level of replication for each group is shown±standard error (error bars). Values that are significantly different (P<0.05; Tukey-Kramer test (Winer, 1971; Dunnet, 1980)) than the parent rV94Not virus are indicated with an asterisk (*). The lower limit of detection of virus replication, which is indicated by the dashed line, is 1.5 $\log_{10}$ TCID$_{50}$/g. Greer, V94 and V98 are wild-type HPIV2 strains.

In FIG. 4A, individual genes are shown as boxes separated by gene-start (GS) and gene-end (GE) signals for each gene, which are shaded in gray and black, respectively. The 3' extragenic leader and 5' extragenic trailer regions are indicated. The exploded view in FIG. 4A shows the nucleotide sequence in the region of the editing site in unedited mRNA encoding V protein (top sequence; SEQ ID NO:46) and the nucleotide sequence in the edited mRNA that includes two inserted G residues and encodes the P protein (bold, bottom sequence; SEQ ID NO:47). The sequence is in antigenomic sense and is arranged by codon triplets. Codons 164 and 165 are numbered. Codon 164 encodes the last common amino acid in the N-terminal half of the P and V polypeptides. Codon 165 and all subsequent codons encode amino acids of the distinct C-terminal portions of the P and V proteins. FIG. 4B shows a diagrammatic representation of the P and V polypeptides including the common amino-terminal domains (white box) and distinct carboxy-terminal domains (hatched boxes), numbered according to the amino acid sequence.

FIG. 5A shows the introduction of unique restriction enzyme recognition sequences at four positions in the recombinant V94 (SEQ ID NO:12) genome for use in both alteration of the PN gene and introduction of a supernumerary gene encoding the V protein.

FIG. 5B shows a diagram of the genome of the HPIV2 rV94 P+V virus, which includes a polynucleotide engineered to express the P protein separate from a polynucleotide engineered to express only the V protein. Gene-start and gene-end signals for each polynucleotide are shaded in gray and black, respectively. The exploded view of the P and V proteins shows their common amino acid domains (white box) and distinct carboxy-terminal domains (hatched boxes).

FIG. 9A shows the primary amino acid sequence of the HPIV2 strain V94 V polypeptide (SEQ ID NO:45). Regions that are potential targets for point or deletion mutagenesis are highlighted: I, similar to a sequence identified in SV5 that is required for RNA binding. II, similar to a sequence identified in SV5 that is required for STAT binding. III, similar to a sequence identified in SV5 that is required for STAT degradation. IV, putative leucine (bold font) rich nuclear export signal sequence. V, this highly conserved sequence may also form part of a zinc finger binding domain. VI, this region includes 5 of 7 conserved cysteine residues in the cysteine rich domain (CRD). *, indicates Ala-165 (bolded and underlined) the first amino acid unique to the carboxy-terminal half of the V protein.

FIG. 9B shows a sequence comparison of amino acid residues 174 to 224 of the V94 V polypeptide (SEQ ID NO:45) with the highly conserved carboxy-terminal cysteine-rich domain of other members of the Paramyxovirus family (SEQ ID NOs: 23 to 44, respectively). Boxed and bolded sequences are highly conserved. Residues indicated with * may directly interact with one or more zinc ions and can be targets of amino acid deletion or substitution mutagenesis.

FIG. 10A-C shows the complete rV94 P+V antigenomic cDNA sequence from nucleotides 1 through 16350 (SEQ ID NO:1).

FIG. 11 shows the antigenomic cDNA P ORF sequence (1188 nucleotides) from nucleotides 1997 through 3184 of the rV94 P+V antigenomic cDNA sequence (SEQ ID NO:2).

FIG. 12 shows the antigenomic cDNA V ORF sequence (678 nucleotides) from nucleotides 3239 through 3916 of the rV94 P+V antigenomic cDNA sequence (SEQ ID NO:3).

DETAILED DESCRIPTION OF INVENTION

I. Definitions

Figure 2:
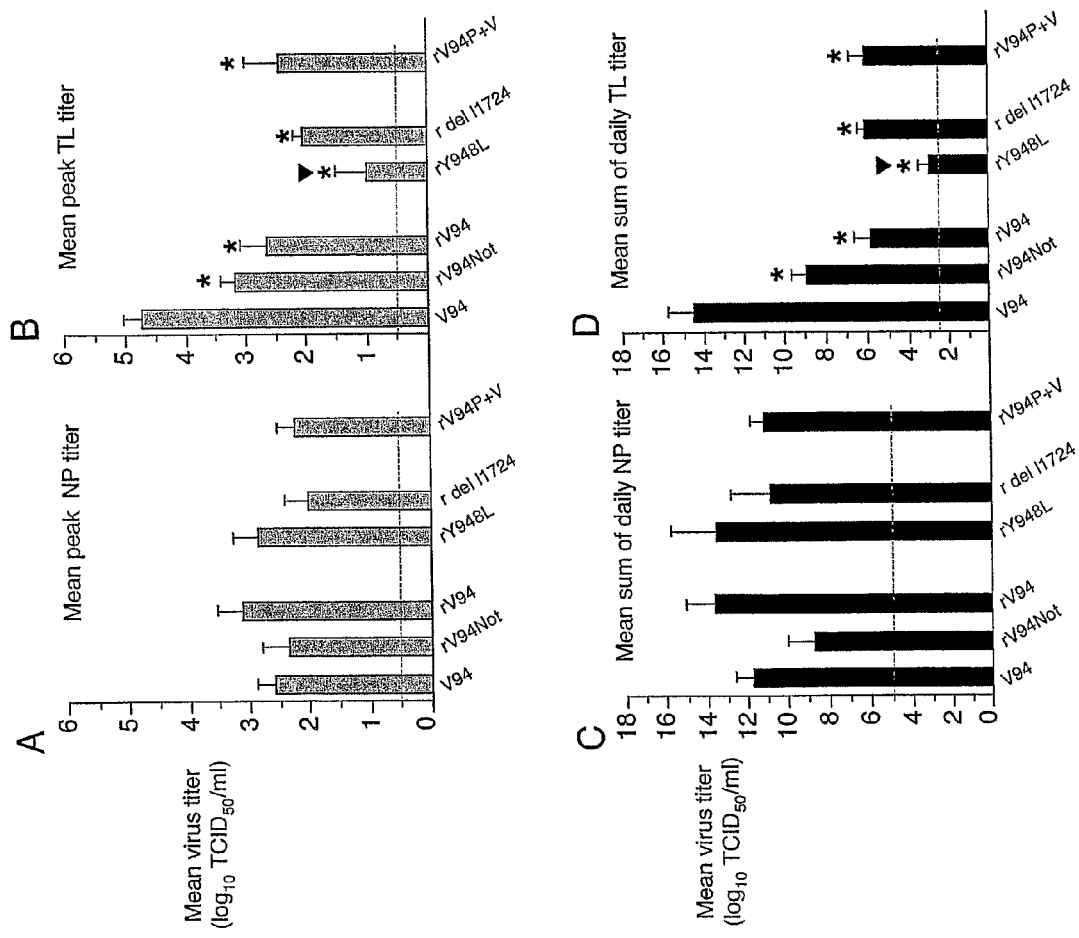
FIGS. 2A-D show the level of replication of recombinant and biologically derived V94 and recombinant derivatives thereof in the upper (nasal turbinates) and lower (lung) respiratory tract of African green monkeys. Nasopharyngeal (NP) swab samples are shown in FIGS. 2A and 2C. Tracheal lavage (TL) samples are shown in FIGS. 2B and 2D. The mean of the peak virus titer for each animal irrespective of sampling day is shown in FIGS. 2A and 2B±standard error (error bars). The lower limit of detection (dashed line) of virus titer in FIGS. 2A and 2B was 0.5 $\log_{10}$ TCID$_{50}$/ml. The mean sum of the viral titers obtained for each animal on all sampling days is shown in FIGS. 2C and 2D±standard error (error bars). The lower limit of detection (dashed line) is 5.0 $\log_{10}$ TCID$_{50}$/ml for NP swab (FIG. 2C) and 2.5 $\log_{10}$ TCID$_{50}$/ml for TL samples (FIG. 2D). Mean titers and mean of sum titers with an asterisk are statistically different (P<0.05; Tukey-Kramer test) than the parent V94 virus. ▼, indicates values where the difference as compared to rV94Not (P<0.05; Tukey-Kramer test) are statistically significant. The number of animals in each group is indicated in Table 5.

Paramyxovirus as used herein refers to a paramyxovirus of the Paramyxovirinae subfamily of the Paramyxoviridae family. Paramyxoviruses are enveloped viruses that have a single strand of negative sense RNA of approximately 13 to 19 kb as a genome. Examples of paramyxoviruses include, but are not limited to, human parainfluenza virus (HPIV) including types 1, 2, 3, 4A, and 4B (HPIV1, HPIV2, HPIV3, HPIV4A, and HPIV4B, respectively), mouse parainfluenza type 1 (Sendai virus, MPIV1), bovine parainfluenza virus type 3 (BPIV3), simian virus 5 (SV5), simian virus 41 (SV41), and mumps virus. HPIV1, HPIV3, MPIV1, and BPIV3 are classified in the genus *Respirovirus*. HPIV2, HPIV4, SV5, SV41, and mumps virus are classified in the genus *Rubulavirus*. MPIV1, SV5, and BPIV3 are animal counterparts of HPIV1, HPIV2, and HPIV3, respectively (Chancock et al., Parainfluenza Viruses, Knipe et al. (Eds.), pp. 1341-1379, Lippincott Williams & Wilkins, Philadelphia, 2001). HPIV1, HPIV2, and HPIV3 represent distinct serotypes and do not elicit significant cross immunity. HPIVs are etiological agents of respiratory infections such as croup, pneumonia, or bronchitis.

The term "human parainfluenza virus type 2" or "HPIV2" refers to an isolate, clone, recombinant, or variant of human parainfluenza virus type 2 of the Paramyxovirinae subfamily. A "naturally occurring" isolate or "wild type" HPIV2 is a virus isolated from a natural source or has the sequence of a HPIV2 isolated from a natural source. Naturally occurring isolates may differ from one another in sequence. In some embodiments, a naturally occurring isolate of HPIV2 of the invention has at least 90% nucleic acid sequence identity to HPIV2 strain V94 (SEQ ID NO:4; Table 6; Genbank Accession No. AF533010). "Recombinant HPIV2" refers to virus derived from a polynucleotide that has been constructed to encode a HPIV genome or antigenome, and may include a sequence of a wild type or variant HPIV2. In some embodiments, the recombinant HPIV2 comprises an expression vector.

The HPIV2 genome encodes at least seven polypeptides. The ribonucleocapsid-associated polypeptides include the nucleocapsid protein (N) (Table 9; SEQ ID NO:16), the phosphoprotein (P) (Table 10; SEQ ID NO:15), and the large polymerase (L) protein (Table 11; SEQ ID NO:17) that carry out transcription and replication. Similar to other Rubulaviruses, the P/V gene of HPIV2 includes an alternative open reading frame (ORF) that is accessed by a shift in reading frame mediated by cotranscriptional editing to generate the mRNA encoding P protein. The unedited mRNA encodes the V protein. The internal matrix protein (M) and the major protective antigens, fusion glycoprotein (F) and hemagglutinin-neuraminidase glycoprotein (HN), are envelope-associated proteins. The gene order is 3'-N-P/V-M-F-HN-L-5'. A HPIV2 encoding polynucleotide can be isolated from infected humans or cells or can be prepared as described herein.

"Variants" of HPIV refer to a virus that has a genomic sequence that differs from the sequence of a reference virus. In some embodiments, a variant may be prepared by altering or modifying the nucleic acid sequence of the viral genome by addition, substitution, and deletion of nucleotides. As discussed previously, it is preferred that variants that have a modification due to addition or deletion of nucleotides conform to the rule of six. In some embodiments, variants may be obtained by passage of a viral particle or genome in vitro in a host cell or in vivo in a non-human host. In some embodiments, the number of nucleotides inserted or deleted is such that the total number of nucleotides in the variant viral genome is divisible by six (known as the "rule of six").

In some embodiments, the variants have at least one altered phenotype. The altered phenotypes can include, without limitation, a change in growth characteristics, attenuation, temperature sensitive growth, cold adaptation, plaque size, host range restriction or a change in immunogenicity. In some embodiments, variant HPIV2 can be immunogenic and elicit protective antibodies in a mammal. Preferably, the HPIV2 variants are attenuated.

In some embodiments, the variant HPIV2 genome or antigenome has at least 80% sequence identity, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to a paramyxovirus reference genomic or antigenomic sequence. The reference sequence may be HPIV2 strain V94 (SEQ ID NO:4; Table 6; Genbank Accession No. AF533010), HPIV2 strain V98 (SEQ ID NO:5; Table 7; Genbank Accession No. AF533011), or HPIV2 strain Greer (SEQ ID NO:6; Table 8; Genbank Accession No. AF533012). Preferably, the reference sequence is strain V94 having a sequence of SEQ ID NO:4.

In some embodiments, the variant HPIV2 genome is composed of a polynucleotide encoding a V protein having at least 80% sequence identity, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to a V gene reference genomic sequence from HPIV2 strain V94 (SEQ ID NO:4; Table 6), HPIV2 strain V98 (SEQ ID NO:5; Table 7), HPIV2 strain Greer (SEQ ID NO:6; Table 8), or a V polypeptide comprising an amino acid sequence of SEQ ID NO:45. In some embodiments, the reference sequence may be encoded by the antigenomic polynucleotide sequence of SEQ ID NO:3. Preferably, the V protein encoded by the variant HPIV2 has reduced activity as compared to V protein encoded by HPIV2 strain V94, HPIV2 strain V98, or HPIV2 strain Greer.

In some embodiments, the variant HPIV2 genome is composed of a polynucleotide encoding an L protein having at least 80% sequence identity, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to a reference polynucleotide sequence encoding an L protein from HPIV2 strain V94 (SEQ ID NO:4; Table 6), HPIV2 strain V98 (SEQ ID NO:5; Table 7), HPIV2 strain Greer (SEQ ID NO:6; Table 8) or a L polypeptide comprising a sequence of SEQ ID NO:17. Preferably, the L protein encoded by the variant HPIV2 has reduced activity as compared to L protein encoded by HPIV2 strain V94, HPIV strain V98, or HPIV2 strain Greer.

The term "antigenome" means a viral RNA molecule or DNA molecule complementary to the negative sense single stranded viral RNA genome.

A paramyxovirus that is "attenuated" or has an "att phenotype" refers to a paramyxovirus that has decreased replication in a mammal as compared to replication of a reference wild-type paramyxovirus under similar conditions of infection. In some embodiments, a paramyxovirus that is attenuated exhibits at least about 10-fold or greater decrease, more preferably at least about 100-fold or greater decrease, more preferably at least about 1000-fold or greater decrease in virus titer in the upper or lower respiratory tract of a mammal compared to non attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceroptihecus aethiops*. An attenuated paramyxovirus may display different phenotypes including without limitation altered growth, temperature sensitive growth, host range restricted growth or plaque size alteration.

"Carriers" as used herein include pharmaceutically acceptable carriers, excipients, or stabilizers, which are nontoxic to the cell or mammal being exposed thereto at the dosages and concentrations, employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

An "infectious clone" of a paramyxovirus as used herein refers to a full-length genome or portion of a genome of a paramyxovirus isolate cloned into a replicable vector that provides for amplification of the viral genome in a cell and in some embodiments, results in viral particles. In some embodiments, a portion of the paramyxovirus genome comprises a polyhexameric nucleic acid sequence encoding at least N protein, P protein, and L protein in a single replicable vector. In other embodiments, the viral genome is a full-length genome. The replicable vector provides for introduction and amplification of the viral genome in a wide variety of prokaryotic and eukaryotic cells.

The term "immunogenic effective amount" of a paramyxovirus, component thereof, or other antigenic determinant refers to an amount of a paramyxovirus, component thereof, or other antigenic determinant that induces an immune response in an animal. The immune response may be determined by measuring a T or B cell response, or by challenging an immunized animal with a virus capable of replicating in the host species. Typically, the induction of an immune response is determined by the detection of antibodies specific for paramyxovirus, a component thereof, or other antigenic determinants.

An "isolated" nucleic acid molecule refers to a nucleic acid molecule that is identified and separated from at least one contaminant nucleic acid molecule with which it is ordinarily associated in the natural source. Preferably, the isolated nucleic is free of association with all components with which it is naturally associated. An isolated nucleic acid molecule is other than in the form or setting in which it is found in nature.

A "monocistronic" polynucleotide refers to a polynucleotide that encodes only one protein. For example, a monocistronic polynucleotide encoding V protein only encodes V protein, it does not encode for both V protein and P protein.

"Percent (%) nucleic acid sequence identity" with respect to the nucleic acid sequences identified herein is defined as the percentage of nucleotides in a candidate sequence that are identical with the nucleotides in a reference paramyxovirus nucleic acid sequence, after aligning the sequences and introducing gaps, if necessary, to achieve the maximum percent sequence identity. In some embodiments, the reference paramyxovirus nucleic acid sequence is HPIV2 Strain V94 (SEQ ID NO:4). Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

$$100 \text{ times the fraction } W/Z$$

where W is the number of nucleotides scored as identical matches by the sequence alignment program in that program's alignment of A and B, and where Z is the total number of nucleotides in B. It will be appreciated that where the length of nucleic acid sequence A is not equal to the length of nucleic acid sequence B, the % nucleic acid sequence identity of A to B will not equal the % nucleic acid sequence identity of B to A.

"Percent (%) amino acid sequence identity" with respect to the amino acid sequences identified herein is defined as the percentage of amino acid residues in a candidate sequence that are identical with the amino acid residues polypeptide reference sequence, such as for example the amino acid sequence of N protein, P protein, V protein, M protein, F protein, HN, or L protein, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, ALIGN-2, clustal V (DNASTAR) or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, "stable" paramyxovirus refers to a paramyxovirus that has a low risk of reversion to a reference virus sequence or phenotype after passaging, infection, or selective pressure. In some embodiments, the reference sequence is the sequence from which an altered or variant paramyxovirus is derived. In other embodiments, the reference sequence or phenotype may be that of a wild type strain such as V94, V98 or Greer. Non-wild type phenotypes include without limitation, a change in growth characteristics, attenuation, temperature sensitive growth, cold adaptation, plaque size, host range restriction or a change in immunogenicity, or mixtures thereof. In some embodiments, the mutation is stable if it does not revert to the reference sequence or phenotype after at least 8 in vitro cell culture passages. In some embodiments, the mutation is stable if it does not revert to a reference sequence or phenotype when grown at 38-40° C. In some embodiments, the mutation is stable if it does not revert to a reference sequence or phenotype at least 10 days post-infection of a mammal. Generally, genetic stability increases as the number of nucleotide substitutions increases. For example, a codon substitution that would require 3 nucleotides changes to revert to the wild type or wild type-like codon is more stable than a codon substitution that would require only 1 nucleotide change to revert to the wild type or wild type-like codon. Deletion mutations generally confer a greater level of genetic stability than codon substitutions. For example, deletion of a codon would require insertion of 3 nucleotides to revert to wild type.

"Recombinant" in reference to a polynucleotide refers to a polynucleotide that has been isolated and/or altered by the hand of man and includes recombinant molecules and recombinant viruses. "Recombinant" in reference to a paramyxovirus refers to a virus that is encoded or has been produced from such a polynucleotide. "Recombinant HPIV2 genome or antigenome" or "rHPIV2" refers to a polynucleotide that has been constructed to encode a HPIV strain or variant, and may include a sequence of a wild type or variant HPIV2. In some embodiments, the recombinant HPIV2 genome or antigenome is in the form of a cDNA. In some embodiments, a polynucleotide sequence encoding all or a portion of a paramyxovirus viral genome or antigenome may be isolated and combined with other control sequences in a vector. The other control sequences may be those that are found in the naturally occurring gene or from other sources. The vector provides for amplification of the recombinant molecule(s) in prokaryotic or eukaryotic cells. It also can provide for introduction into host cells and expression of the polynucleotide. The vectors described herein for recombinant paramyxovirus sequences are introduced into eukaryotic cells and propagated under suitable conditions as known to those of skill in the art, and are introduced into animal cells and expressed under suitable conditions as known to those of skill in the art.

The term "replicable vector," as used herein, refers to a nucleic acid molecule capable of transporting another nucleic acid to which it has been linked into a cell and providing for amplification of the nucleic acid. One type of vector is a "plasmid", which refers to a circular double stranded DNA loop into which additional DNA segments may be ligated. Another type of vector is a phage vector. Another type of vector is a viral vector, wherein additional nucleic acid segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. In the present specification, "plasmid" and "vector" may be used interchangeably as the plasmid is the most commonly used form of vector. In some embodiments, the vector is a vector that can replicate to high copy number in a cell.

The term "shut-off temperature" refers to a temperature at which the reduction of virus titer compared to its titer at a reference temperature is 100-fold greater than the reduction of wild type virus at the same temperature. In some embodiments, the reference temperature is about 32° C., and the shutoff temperature is about 39° C., more preferably 38° C. or 37° C. A determination of the shut off temperature allows a comparison of the temperature sensitivity of different virus strains or isolates and is often indicative of the level of attenuation. The lower the shutoff temperature the higher the level of attenuation of the paramyxovirus isolate or strain.

The term "transfection" as used herein refers to introducing DNA into a eukaryotic cell so that the DNA is replicable and/or expressed, either as an extrachromosomal element or by chromosomal integrant. Depending on the host cell used, transfection is done using standard techniques appropriate to such cells. Methods for transfecting eukaryotic cells include polyethyleneglycol/DMSO, liposomes, electroporation, and electrical nuclear transport.

Polypeptide sequences defined herein are represented by one-letter or three letter symbols for amino acid residues as follows:

| A | ala, alanine | L | leu, leucine |
|---|---|---|---|
| R | arg, arginine | K | lys, lysine |
| N | asn, asparagine | M | met, methionine |
| D | asp, aspartic acid | F | phe, phenylalanine |
| C | cys, cysteine | P | pro, proline |
| Q | gln, glutamine | S | ser, serine |
| E | glu, glutamic acid | T | thr, threonine |
| G | gly, glycine | W | try, tryptophan |
| H | his, histidine | Y | tyr, tyrosine |
| I | ile, isoleucine | V | val, valine |

II. Aspects of the Invention

Strategies to generate attenuated viruses are important in the design of safe and stable viral constructs useful in an immunogenic composition. The phenotype of a viral isolate or strain may be modified to achieve a balance between attenuation of viral replication and immunogenicity of the modified variant. In some embodiments, viral replication may be decreased about 100 to 1000 fold and yet still retain immunogenicity. In some embodiments, it is desirable to generate an attenuated virus that has at least one temperature sensitive attenuating mutation and one non-is attenuating mutation. Attenuated viruses that have more than one mutation and/or more than one phenotype can have enhanced stability.

The V protein of paramyxoviruses is an attractive target for introduction of one or more mutations. V protein inhibits production of a α/β interferons and decreases signaling of a α/β interferons through their receptors. A paramyxovirus with a modified V protein should have decreased pathogenicity since it may be defective in counteracting host cell interferon response. Replication of paramyxoviruses expressing V protein with a carboxy terminal deletion has been found to be defective in vivo and in vitro, including in Vero cells which do not express antiviral interferons α and β (Kato et al., 1997, *Embo J.*, 16(3):578-587; Delenda et al., 1997, *Virology*, 228 (1):55-62; Durbin et al., 1999, *Virology*, 261(2):319-330; Kawano et al., 2001, *Virology*, 284(1):99-112; He et al., 2002, *Virology*, 303(1):15-32; Park et al., 2003, *J. Virol.*, 77(17): 9522-9532). The V protein might also have other functions during viral infection, and mutations might also achieve an attenuating effect by interfering with additional functions.

V protein is encoded by a bicistronic polynucleotide encoding both the P and V proteins. The bicistronic polynucleotide encodes a nucleocapsid-associated P phosphoprotein from an overlapping reading frame (Ohgimoto et al., 1990). P protein is a structural protein that plays a major role in transcription and replication of the viral genome. The alternative reading frames are accessed by an unusual cotranscriptional editing of the P/V encoding mRNA, a feature unique to most members of the Paramyxovirinae subfamily. The polynucleotide encoding the P and V protein includes an alternative open reading frame (ORF) that is accessed by a shift in reading frame mediated by cotranscriptional editing to generate the mRNA encoding a P protein. A V protein is generated from an unedited mRNA encoding P and V. Therefore, the P and V genes have a common amino-terminal sequence and unique carboxy-termini. The overlapping nature of the P and V ORFs, however, greatly restricts the number and types of mutations that can be introduced into the V protein without also affecting the P protein, and vice versa.

One aspect of the invention includes polynucleotides, vectors and a viral construct comprising a polynucleotide encoding a variant P protein and a monocistronic polynucleotide encoding a V protein. Separation of the coding sequence of the V and P protein allows changes to the V protein without affecting the function of the P protein. Insertion of a polynucleotide encoding a V protein into the viral genome provides an attenuating phenotype. Preferably, the polynucleotide encoding the V protein is modified with at least one mutation that decreases the ability of the V protein to inhibit interferon production and/or signaling. The polynucleotide encoding a variant P protein and the monocistronic polynucleotide encoding the V protein can be on the same vector or separate vectors.

Another aspect of the invention involves a novel attenuating mutation of the L polymerase. In some embodiments, residue positions are selected for substitution based on a comparison to other related viruses and an indication that when an amino acid at the position is substituted in other related viruses an attenuating phenotype is observed. The amino acids selected for substitution at those positions are chosen from those amino acids that are encoded by a codon that differs in at least two nucleotide positions from the wild type amino acid found at that position. In some embodiments, at least two nucleotide changes are made in a codon specifying the changed amino acid. In some embodiments, mutations of the L polymerase have a temperature sensitive phenotype.

In yet another aspect, an attenuating mutation may be made in a noncoding region of the genome including the 3' leader and/or 5' trailer of the viral genome. In some embodiments, a recombinant and infectious parainfluenza virus comprises an attenuating mutation at a position corresponding to nucleotide position 15 of the 3' leader of viral genome or antigenome. In some embodiments, a recombinant parainfluenza virus with a mutation at a position corresponding to position 15 has a host range restriction phenotype.

The attenuating mutations and methods of the invention provide recombinant, infectious, self-replicating paramyxoviruses comprising a partial or complete polyhexameric genome or antigenome having a polynucleotide encoding a variant P protein and a monocistronic polynucleotide encoding a V protein, as well as novel attenuating mutations in the L polymerase and 3' leader sequence. In some embodiments, an attenuated paramyxovirus has a temperature sensitive and at least one other attenuating mutation that provides a phenotype including host range restriction, reduced plaque size, or change in immunogenicity. The attenuated infectious virus can be utilized in live virus vaccines and/or in immunogenic compositions to protect against HPIV infection and/or to deliver heterologous antigens. The attenuating mutations can be utilized as part of a menu of attenuating mutations to develop attenuated paramyxovirus strains that may be utilized in vaccines.

A. Mutations

1. L polymerase

One aspect of the invention provides a recombinant and infectious variant of HPIV2 having one or more attenuating mutations in the L polymerase (L protein). In some embodiments, residue positions are selected for substitution based on a comparison to other related viruses and an indication that when an amino acid at a position is substituted in other related viruses an attenuating phenotype is observed. The amino acids selected for substitution at those positions are chosen from those amino acids that are encoded by a codon that differs in at least two nucleotide positions from the wild type amino acid found at that position. In some embodiments, at least two nucleotide changes are made in a codon specifying the changed amino acid.

In some embodiments, an attenuating mutation comprises a substitution at one or more amino acid residues corresponding to positions 460, 948, or 1724 of SEQ ID NO:17. Preferred amino acid substitutions include F460A, F460P, Y948A, Y948L, Y948G, S1724I, or mixtures thereof.

The attenuating mutations are preferably stable. Amino acid substitutions that require two or three nucleotide substitutions are preferred. For example, F460A requires three nucleotide substitution mutations (wild type TTT, variant GCA). The nucleotide substitutions encoding the preferred amino acid substitutions described above are shown in Table 2.

The attenuating mutation(s) can be temperature sensitive. In an embodiment, the L protein mutations are not attenuating for replication at permissive temperature, such as for example 30-32° C., but are attenuating for replication at restrictive temperatures, such as for example 37° C.-40° C. In an embodiment, replication of the HPIV2 variants is reduced at about 39° C. In some embodiments, the shut-off temperature of the HPIV2 variants is preferably about 39° C., more preferably about 38° C., or about 37° C. Preferably, the paramyxovirus strains with mutations in L polymerase have a lower shutoff temperature than control paramyxovirus. In some embodiments, the control is a wild type virus. In other embodiments, the control is another attenuated paramyxovirus.

Preferably, the HPIV2 variants are attenuated in vivo. In an embodiment, the HPIV2 variants exhibit reduced replication in the upper and/or lower respiratory tract of a mammal as compared to wild-type HPIV2 or other attenuated paramyxoviruses. In an embodiment, the replication is reduced at least about 10 fold, 100 fold, more preferably about 500 fold, more preferably about 1000 fold, more preferably about 1500 fold, more preferably about 2000 fold, more preferably about 3000 fold, more preferably about 4000 fold, more preferably about 5000 fold, more preferably about 6000 fold as compared to wild-type HPIV2 or other attenuated paramyxoviruses. In an embodiment, the mammal is a golden Syrian hamster (*Mesocricetus auratus*). In another embodiment, the mammal is an African green monkey (*Cercopithecus aethiops*).

The HPIV2 variants preferably comprise a partial or complete polyhexameric genome or antigenome encoding a major nucleocapsid (N) protein, a nucleocapsid phosphoprotein (P) and a L polymerase (L) protein. HPIV2 variants may further comprise a genome or antigenome encoding a fusion (F) protein and a hemaglutinin-neuraminidase (HN) protein. HPIV2 variants that further comprise F and HN proteins are useful in immunogenic compositions.

Another aspect of the invention includes an isolated nucleic acid or vector comprising a polynucleotide encoding a polypeptide with at least 80% sequence identity to a L protein having a sequence of SEQ ID NO:17. An isolated polypeptide comprising at least 80% sequence identity to a L polypeptide of SEQ ID NO: 17 and preferably, comprising at least one mutation of amino acid residues corresponding to positions 460, 948, or 1724 of SEQ ID NO:17 is also provided.

An attenuating mutation in the L protein can be generated by PCR mutagenesis and standard molecular cloning techniques. Examples of PCR primers useful for generating the attenuating mutations of the invention are described in Example 1 and Table 2.

2. 3' Leader Sequence

One aspect of the invention provides recombinant and infectious variants of HPIV2 having an attenuating mutation in the 3' leader of a viral genome. In some embodiments, an attenuating mutation comprises a nucleic acid substitution at a position corresponding to T15 of SEQ ID NO:4. In an embodiment, the nucleotide substitution comprises T15C. In some embodiments, the recombinant and infectious variants predominantly have a C at position 15 and more preferably, have little or no detectable virus with a T at position 15.

In some embodiments, the attenuating mutation may also have a phenotype selected from a change in growth characteristics, attenuation, temperature sensitivity, cold adaption, plaque size, host range restriction or changes in immunogenicity. Preferably, the attenuating mutation has a phenotype of host range restriction. In an embodiment, HPIV2 including a nucleotide substitution at a position corresponding to T15 of SEQ ID NO:5 is attenuated in the respiratory tract of African green monkeys, but not in the respiratory tract of golden Syrian hamsters. In some embodiments, the attenuating mutation does not confer a temperature sensitive phenotype.

An attenuating mutation in the 3' leader of HPIV2 can be generated by PCR mutagenesis and standard molecular cloning techniques. Examples of PCR primers useful for generating the attenuating mutation of the invention are described in Example 2.

3. Separation of Bicistronic Polynucleotides Encoding P and V Proteins into a Polynucleotide Encoding a P or a V Protein.

One aspect of the invention provides recombinant, infectious, self-replicating paramyxovirus comprising a partial or complete polyhexameric genome or antigenome having a variant polynucleotide encoding a P protein and a monocistronic polynucleotide encoding a V protein. The polynucleotide encoding a P protein has been altered to no longer encode the V protein. The paramyxovirus of the invention preferably includes a major nucleocapsid protein (N protein), a nucleocapsid phosphoprotein (P protein), and a large polymerase protein (L protein). The N protein, P protein, or L protein can be from a heterologous *Rubulavirus*, such as HPIV2, HPIV4HPIV2, HPIV4, mumps, SV41 and SV5. Paramyxovirus variants may further comprise a genome or antigenome encoding a fusion (F) protein and a hemaglutinin-neuraminidase (HN) protein. Paramyxovirus variants that further comprise F and HN proteins are useful in immunogenic compositions. In some embodiments, the polynucleotide encoding a variant P protein and the monocistronic polynucleotide encoding the V protein are on separate vectors.

The paramyxovirus can be a parainfluenza virus (PIV). A number of paramyxovirus have a polynucleotide encoding both a P and V protein including HPIV2, murine P1V1 (Sendai virus) HPIV4A, HPIV5, SV41, SV5, mumps virus, and NDV. In an embodiment, the PIV is human PIV (HPIV). Preferably, the HPIV is HPIV type 2 (HPIV2). In an embodiment, the HPIV2 is strain V94, V98, or Greer. In an embodiment, the genome or antigenome sequence is derived from a variant HPIV2 comprising at least 80% or greater nucleotide sequence identity with a HPIV2 reference sequence. In an embodiment, the reference sequence is the genomic sequence of HPIV2 of strain V94 (SEQ ID NO:4), V98 (SEQ ID NO:5), or Greer (SEQ ID NO:6). In an embodiment, the genomic sequence comprises a nucleotide sequence of SEQ ID NO:4.

The polynucleotide encoding the monocistronic V protein can be inserted anywhere into the genome, antigenome, or vector. In some embodiments, the polynucleotide encoding the monocistronic V protein may be inserted at the 3' end. In some embodiments, the gene order, for example, may be 3' V-N-P-M-F-HN-L-5'. In other embodiments, the gene order, for example, may be 3' N-V-P-M-F-NH-L-5'. In some embodiments, the monocistronic polynucleotide encoding a protein is inserted into a restriction site in the genome. Restriction sites may include Asc I, Bst EII, AgeI or Sac II as shown in FIG. 5. In an embodiment, a recombinant virus encoding a separate P and V protein has an antigenomic cDNA sequence of SEQ ID NO:1.

The variant polynucleotide encoding the P protein can be inserted anywhere into the genome or antigenome. In addition, the variant polynucleotide encoding the P protein and the monocistronic polynucleotide encoding the V protein can be located on separate vectors. In some embodiments, the variant polynucleotide encoding a P protein is inserted into a restriction site in the genome or antigenome. Restriction sites may include Asc I, Bst EII, AgeI or Sac II as shown in FIG. 5.

The variant polynucleotide encoding a P protein and a monocistronic polynucleotide encoding a V protein, optionally, are separated by a non-coding polynucleotide spacer sequence. In an embodiment, the spacer sequence is upstream of a V coding sequence or open reading frame (ORF) in the polynucleotide encoding the V protein. In an embodiment, the spacer sequence comprises a gene end transcription signal, intergenic transcription signal, and/or gene start transcription signal. In an embodiment, the gene start transcription signal is cis-acting. In an embodiment, the gene start transcription signal includes a first adenosine at position 6n+1. In an embodiment, the spacer sequence comprises a nucleotide sequence of SEQ ID NO:7.

When a polynucleotide encoding a monocistronic V protein is inserted into the viral genome, the inserted polynucleotide is a heterologous sequence. Viral recombinant virus comprising a polynucleotide encoding a V protein may have an altered phenotype. In some embodiments, the phenotype may be attenuating. In some embodiments, the phenotype is temperature sensitive. Additional nucleotide changes may be introduced into a recombinant virus encoding separate P and V genes to introduce other phenotypic changes selected from a change in growth characteristics, attenuation, temperature sensitivity, cold adaptation, plaque size, host range restriction, or a change in immunogenicity.

An attenuating phenotype can be temperature sensitive. In an embodiment, a recombinant virus encoding separate P and V proteins is not attenuated for replication at permissive temperature (for example, about 30-32° C.) but is attenuated for replication at restrictive temperatures, such as for example 37° C.-40° C. In an embodiment, replication of the paramyxovirus variants is reduced at about 38° C. In some embodiments, the shut-off temperature of the variants is preferably about 38° C., more preferably about 37° C. Preferably, a recombinant virus encoding separate P and V proteins have a lower shutoff temperature than control paramyxovirus. In some embodiments, the control is a wild type virus. In other embodiments, the control is other attenuated paramyxoviruses.

Preferably, a recombinant paramyxovirus encoding separate P and V proteins is attenuated in vivo. In an embodiment, the recombinant virus encoding separate P and V proteins exhibit reduced replication in the upper and/or lower respiratory tract of a mammal as compared to wild-type HPIV2 or other attenuated paramyxoviruses. In an embodiment, the replication is reduced at least about 10 fold, 100 fold, more preferably about 500 fold, more preferably about 1000 fold, more preferably about 1500 fold, more preferably about 2000 fold, more preferably about 3000 fold, more preferably about 4000 fold, more preferably about 5000 fold, more preferably about 6000 fold as compared to wild-type HPIV2 or other attenuated paramyxoviruses. In an embodiment, the mammal is a golden Syrian hamster (*Mesocricetus auratus*). In another embodiment, the mammal is an African green monkey (*Cercopithecus aethiops*). In some embodiments, the attenuated paramyxovirus is immunogenic and elicits sufficient antibodies to protect against infection.

The monocistronic polynucleotide encoding a V protein can encode a V protein having a sequence of a naturally occurring or variant V protein. The V protein can be from a heterologous paramyxovirus, including but not limited to HPIV4A, HPIV4B, SV5, SV41, mumps, NDV, or Sendai virus. In an embodiment, the nucleotide sequence encoding the V protein comprises at least 80% sequence identity, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to a nucleotide sequence encoding V protein in a reference sequence. In an embodiment, the reference sequence is HPIV2 strain V94 (SEQ ID NO:4; Table 6), HPIV strain V98 (SEQ ID NO:5 Table 7), HPIV2 strain Greer (SEQ ID NO:6; Table 8) or a polynucleotide encoding a V protein comprising an amino acid sequence of SEQ ID NO:45. In an embodiment, the antigenomic cDNA sequence encoding the V ORF is that of SEQ ID NO:3, shown in FIG. 12. In some embodiments, an isolated monocistronic nucleic acid comprising a polynucleotide encoding a polypeptide having at least 80% sequence identity to a V protein having a sequence of SEQ ID NO:45 is provided.

In an embodiment, the nucleotide sequence encoding V protein comprises a mutation that inhibits the ability of V protein to interrupt production or signaling of interferon in an infected host or host cell. Preferably, the mutation does not substantially impact virus replication in cell culture. In an embodiment, the V protein has reduced activity as compared to V protein encoded by HPIV2 strain V94, HPIV2 strain V98, or HPIV2 strain Greer. Preferably the mutation does not affect P protein expression or activity in cell culture.

One of several approaches can be taken to identify mutations in the V protein that render rHPIV2 P+V attenuated for replication in vivo. The first is random mutagenesis of the V ORF to generate viruses that are restricted for replication in the respiratory tract of experimental animals. For example, alanine mutations can be introduced at each position and those positions important in the function of the protein can be identified. In other embodiments, deletions of at least 2 amino acids can be generated. Recombinant viruses bearing these mutations can be characterized in vitro and in vivo.

Alternatively, sequence alignment with heterologous paramyxovirus V proteins can be used as a guide for targeted mutagenesis. For example, there are two ways to use the sequence alignment as a guide. First, conserved sequences, which are likely required for specific V protein activities, can be directly targeted with conservative amino acid substitutions or small (2 amino acid) deletions. A less conservative approach can be taken and unrelated amino acids can be used for amino acid substitutions, or large portions of the conserved regions (6 or more amino acids) can be deleted. Unrelated amino acids may be selected that require at least two nucleotide changes in the codon as compared to the codon encoding the wild type amino acid at that position. The selection of sites for mutagenesis is not limited to conserved sequences.

Substantial modifications in the biological properties of V protein are accomplished by selecting substitutions that differ significantly in their effect on maintaining (a) the structure of the polypeptide backbone in the area of the substitution, for example, as a sheet conformation, helical conformation, or loop structure, (b) the charge or hydrophobicity of the molecule at the target site, or (c) the bulk of the side chain. Naturally occurring residues are divided into groups based on common side-chain properties:

(1) hydrophobic: leucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class. Such substituted residues also can be introduced into the conservative substitution sites or, more preferably, into the remaining (non-conserved) sites.

Examples of candidate sites for point or deletion mutagenesis in V protein are summarized and highlighted in FIG. 9A: (I) similarity to a sequence identified in SV5 that is required for RNA binding; (II) similarity to a sequence identified in SV5 that is required for STAT binding; (III) similarity to a sequence identified in SV5 that is required for STAT degradation; (IV) putative leucine (bold font) rich nuclear export signal sequence; (V) highly conserved sequence that may form part of a zinc finger binding domain; (VI) region includes 5 of 7 conserved cysteine residues in the cysteine rich domain (CRD). FIG. 9B shows an amino acid sequence comparison of a highly conserved carboxy-terminal cysteine-rich domain, a critical V protein domain known to bind zinc ions, of 22 members of the Paramyxovirus family. Boxed and bolded sequences are highly conserved. Residues indicated with * may directly interact with one or more zinc ions and are targets for amino acid deletion or substitution mutagenesis. In some embodiments, a variant V protein comprises at least one amino acid mutation of a least one residue corresponding to an amino acid residue in at least one of the domains, more preferably in more than one of the domains.

In an embodiment, the V protein comprises one or more amino acid substitutions or deletions at or between residues corresponding to positions 67, 68, 69, 70, 71, 72, 105, 106, 107, 108, 121, 122, 123, 124, 125, 126, 127, 130, 131, 132, 133, 134, 135, 136, 137, 138, 139, 140, 167, 168, 169, 170, 171, 172, or any one of amino acids 174-225 of SEQ ID NO:4. Preferably, the nucleotide changes that encode a mutation comprise at least two nucleotide changes compared to the codon encoding the wild type amino acid at that position to increase the stability of the mutation. Preferably, the variant V protein has at least 80% sequence identity to that of a reference sequence.

The monocistronic polynucleotide encoding a V protein includes an mRNA editing site. Preferably the editing site includes a heptaguanosine run. In an embodiment, the editing site comprises a nucleotide sequence of SEQ ID NO:8. In an embodiment, the heptaguanosine run is substituted such that editing of nucleotide sequence encoding V protein is inhibited. Nucleotide deletion, insertion, or substitution mutagenesis can be used to inhibit mRNA editing. For example, in V94 HPIV2, mRNA editing of the nucleotide sequence encoding V protein can be inhibited by substituting the nucleotide corresponding to G9 of the editing site (SEQ ID NO:8) with A and the nucleotide corresponding to G12 of the editing site (SEQ ID NO:8) with C. Nucleotide deletions or insertions must conform to the "rule of six", as described herein and in WO 04027037.

The variant polynucleotide encoding a P protein includes a nucleotide sequence encoding a P protein. The variant polynucleotide encoding the P protein is altered so that it does not encode a V protein. The amino acid sequence of the P protein may also be a variant sequence. The P protein can be from a heterologous paramyxovirus of the *Rubulavirus* genus, including but not limited to, SV5, SV41, HPIV4A and HPIV4B. In an embodiment, the nucleotide sequence encoding P protein comprises at least 80% sequence identity, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to a nucleotide sequence encoding P protein in a reference sequence. In an embodiment, the reference sequence is HPIV2 strain V94 (SEQ ID NO:4; Table 6), HPIV2 strain V98 (SEQ ID NO:5; Table 7), or HPIV2 strain Greer (SEQ ID NO:6; Table 8). In an embodiment, an antigenomic cDNA sequence encoding a P protein has a sequence of SEQ ID NO:2.

The variant polynucleotide encoding a P protein includes a P coding sequence or open reading frame (ORF). Preferably the P ORF includes one or more nucleotide substitution(s) that introduce one or more stop codons in an overlapping V ORF reading frame but does not alter the amino acid sequence of P protein encoded by the P ORF. In an embodiment, third base codon substitutions encoding stop codons in the V ORF reading frame at codon positions 167, 176, 184, and/or 186 are introduced into the P ORF (SEQ ID NO:2). In another embodiment, the P ORF comprises a nucleotide sequence of SEQ ID NO:2. In some embodiments, insertion of one or more stop codons in a V ORF may be preferably utilized when it may be undesirable to make modifications to the mRNA editing site in the coding sequence for the P ORF.

The variant polynucleotide encoding a P protein includes an mRNA editing site. Preferably the editing site includes a heptaguanosine run. In an embodiment, the editing site comprises a nucleotide sequence of SEQ ID NO:8. In an embodiment, the heptaguanosine run is substituted such that editing of the nucleotide sequence encoding P protein is inhibited. Nucleotide deletion, insertion, or substitution mutagenesis can be used to inhibit mRNA editing. Preferably, the insertions and/or substitutions destroy the heptaguanosine stretch in the editing site but do not alter the reading frame encoding the carboxy-terminal portion of P protein. In HPIV2, for example, 2 guanosines are inserted into the mRNA editing site such that the nucleotide sequence encoding the carboxy-terminal portion of P protein is shifted in frame. In an embodiment, the number of guanosines necessary to shift the reading frame to the nucleotide sequence encoding the carboxy terminal portion of P protein are inserted in the mRNA editing site and 2 or more guanosines in the heptaguanosine run are substituted with A or T. See, for example, FIG. 6. In another embodiment, A, T, or a combination thereof corresponding to the number of guanosines necessary to shift the reading frame to the nucleotide sequence encoding the carboxy terminal portion of P protein are inserted into the heptaguanosine run of the mRNA editing site. See, for example, FIG. 6. Nucleotide deletions or insertions must conform to the "rule of six", as described herein and in WO 04027037, and maintain the correct P ORF reading frame.

A paramyxovirus or polynucleotide of the invention including a variant polynucleotide encoding a P protein and monocistronic polynucleotide encoding a V protein can be made using known recombinant methods such as oligonucleotide-mediated (site-directed) mutagenesis, alanine scanning, PCR mutagenesis, site-directed mutagenesis (Zoller et al., 1987, *Nucl. Acids Res.*, 10: 6487-6500), cassette mutagenesis (Wells et al., 1985, *Gene*, 34:315), restriction selection mutagenesis (Wells et al., 1986, *Philos. Trans. R. Soc. London SerA*, 317:415), and the like.

B. Combinations of Mutations

A paramyxovirus of the invention, including a partial or complete polyhexameric genome or antigenome having a variant polynucleotide encoding a P protein and a monocistronic polynucleotide encoding a V protein, can include any of the attenuating mutations in the L polymerase and/or 3' leader described herein or other known attenuating mutations. Recombinant viral variants having more than one mutation are likely to have increased stability over those variants having a single mutation or a small number of mutations (e.g., less than 3 mutations). The paramyxovirus of the invention can also include any of the attenuating L polymerase mutations described in WO 04/027037. Preferably, the attenuating effect of the mutations in the L polymerase and/or 3' leader are additive and serve to further increase the attenuation of the paramyxovirus of the invention including a variant polynucleotide encoding a protein and a monocistronic polynucleotide encoding a V protein. In some embodiments, it is desirable to balance the level of attenuation with the immunogenicity. In preferred embodiments, the variant paramyxoviruses have about 100 fold to 5000 fold decrease in viral titer in a mammal. In some embodiments, a decrease of viral replication greater than about 100,000 fold may result in a loss of immunogenicity or an inability to produce the virus on a large scale.

In some embodiments, the variant paramyxoviruses of the invention have at least one temperature sensitive mutation and at least one non-temperature sensitive mutation. In a preferred embodiment, the recombinant variant paramyxoviruses of the invention have at least one temperature sensitive mutation due to insertion of monocistronic polynucleotide encoding a V gene or a mutation in a polynucleotide encoding a L polymerase, wherein the change in the amino acid is due to at least two nucleotide changes to the codon encoding the wild type amino acid. In another embodiment, the recombinant variant paramyxoviruses of the invention comprise a mutation that provides a host range restriction phenotype. In a preferred embodiment, the variant virus having a host range restriction comprises a mutation at position 15 of the 3' terminus of the viral genome.

C. Vectors including Heterologous Antigens

The paramyxoviruses of the invention are also useful as vectors for expressing heterologous antigens in an immunogenic composition. One or more supernumerary genes encoding one or more heterologous polypeptides can be cloned into and expressed by the paramyxovirus of the invention. For example, an immune response against multiple PIV serotypes or strains can be elicited by engineering protective epitopes of multiple PIV serotypes and strains into a single paramyxovirus. The supernumerary genes can be cloned and expressed in a recombinant virus encoding a separate P and V proteins as described herein, as well as recombinant virus comprising one or more mutations in L polymerase and/or a mutation in the 3' leader region. Insertion of additional heterologous genes may also result in an attenuated phenotype. Preferably, the paramyxovirus comprising a polynucleotide encoding a heterologous gene is attenuated about 100 to 5000 fold or more in a cell or mammal.

In an embodiment, the genome or antigenome includes one or more heterologous genes or genome segments encoding one or more antigenic determinants of a heterologous pathogen. For example, one or more heterologous antigenic determinant(s) from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumovituses, or influenza viruses can be expressed by the paramyxovirus of the invention. Examples of useful antigenic determinants include, but are not limited to, measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus preE, and NS1 proteins, human metapneuomovirus (HMPV) G and F proteins, and alphavirus E protein, and antigenic domains, fragments and epitopes thereof.

In an embodiment, a polynucleotide encoding an open reading frame (ORF) of a measles virus HA gene is incorporated into a HPIV2 vector genome or antigenome to yield a chimeric candidate useful to immunize against measles and/or HPIV2 or another HPIV. In another embodiment, a polynucleotide comprising genes or genome segments encoding one or more heterologous PIV(s) (e.g., HPIV1, HPIV3, and/or HPIV4) HPIV2 N, P, V, F, HN and/or L protein(s) or fragment(s) thereof is incorporated into a HPIV2 vector genome or antigenome. In another embodiment, one or more supernumerary heterologous gene(s) or genome segment(s) selected from HPIV1 HN, HPIV2 F, HP1V3 HN, HPIV3 F, measles HA and F, HMPV G and F proteins, and/or RSV subgroup A or B G and F proteins are cloned into a paramyxovirus of the invention.

Figure 5C:
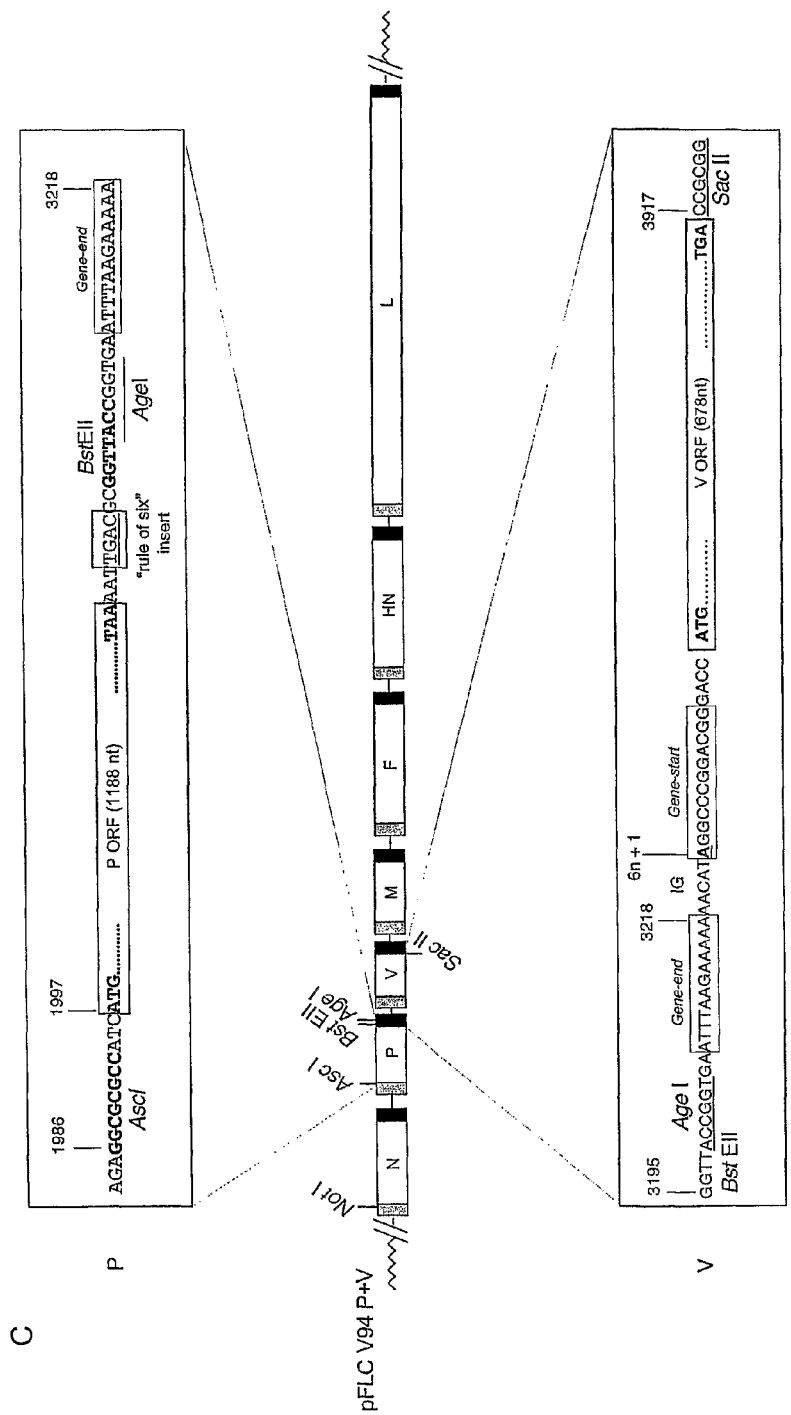
FIG. 5C shows the details of the construction of separate polynucleotides encoding P protein and V protein in the mutant rV94 P+V genome (SEQ ID NO: 1). Sequences are in antigenomic sense and numbered according to their position in the rV94 P+V antigenomic sequence. The exploded view of the polynucleotide encoding P protein (top) shows the P ORF and flanking sequence showing the positions of the introduced AscI, BstEII and AgeI sites, a 4-nucleotide insert introduced to maintain the "rule of six", and the naturally-occurring P gene-end signal. The exploded view of the polynucleotide encoding the V protein (bottom) shows the V ORF and flanking sequence showing the positions of the introduced BstEII and SacII sites, as well as a gene junction including a gene-end signal, intergenic, and gene-start signal positioned with 6n+1 phasing. The "rule of six" refers to the finding that replication of the genomes of most or all members of Paramyxovirinae is efficient only if the nucleotide length of the genome is an even multiple of six, a requirement that is thought to reflect the intimate association of each N protein monomer with exactly six nucleotides (Kolakofsky et al, J. Virol. 72, 891-899, 1998).

Some methods of inserting one or more supernumerary genes or transcriptional units into a paramyxovirus viral genome or antigenome are described in WO04/027037, hereby incorporated by reference. Supernumerary heterologous gene(s) or genome segment(s) can be inserted at various sites within the recombinant genome or antigenome, for example at a position 3' to N, between the N/P, P/M, and/or HN/L genes, or at another intergenic junction or non-coding region of a HPIV2 vector genome or antigenome. Preferably, the heterologous or supernumery gene or transcriptional unit is inserted at a restriction site, for example, AscI, BstEII, AgeI, or SacII as shown in FIG. 5C. Any insertions or deletions of the viral genome, preferably, conform to the rule of six.

D. Recombinant Methods, Vectors, and Host Cells

The infectious paramyxoviruses and polynucloetides of the invention are produced by synthetic and recombinant methods. Accordingly, the invention relates to polynucleotides encoding infectious paramyxovirus clones of the invention and host cells including the infectious clone, as well as methods of making such vectors and host cells by recombinant methods.

The paramyxovirus or polynucleotides of the invention may be synthesized or prepared by techniques well known in the art. See, for example, WO 94/027037. Nucleotide sequences for wild type paramyxovirus genomes are known and readily available, for example, on the Internet at GenBank (accessible at www-ncbi-nlm-nihgov/entrez). The nucleotide sequences encoding the paramyxovirus of the invention may be synthesized or amplified using methods known to those of ordinary skill in the art including utilizing DNA polymerases in a cell free environment.

Amino acid substitutions, insertions, and deletions can be made using known recombinant methods such as oligonucleotide-mediated (site-directed) mutagenesis, alanine scanning, PCR mutagenesis, site-directed mutagenesis (Zoller et al., 1987, *Nucl. Acids Res.,* 10: 6487-6500), cassette mutagenesis (Wells et al., 1985, *Gene,* 34:315), restriction selection mutagenesis (Wells et al., 1986, *Philos. Trans. R. Soc. London SerA,* 317:415), and the like. Examples of PCR primers suitable for use in generating the attenuating mutations of the invention are described in Examples 1, 2, and 3

The paramyxovirus of the invention can be produced from virus isolated from biological samples. The polynucleotides and vectors may be produced by standard recombinant methods known in the art, such as polymerase chain reaction (Sambrook, et al., 1989, Molecular Cloning, A Laboratory Manual, Vols. 1-3, Cold Spring Harbor Press, Cold Spring Harbor, N.Y.). Methods of altering or modifying nucleic acid sequences are also known to those of skill in the art.

The paramyxovirus genome may be assembled from polymerase chain reaction cassettes sequentially cloned into a vector including a selectable marker for propagation in a host. Such markers include dihydrofolate reductase or neomycin resistance for eukaryotic cell culture and tetracycline or ampicillin resistance genes for culturing in *E. coli* and other bacteria.

The polynucleotide may be inserted into a replicable vector for cloning using standard recombinant methods. Various vectors are publicly available. The vector may, for example, be in the form of a plasmid, cosmid, viral particle, or phage. The appropriate nucleic acid sequence may be inserted into the vector by a variety of procedures. In general, a nucleic acid is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors including one or more of these components employs standard ligation techniques that are known to the skilled artisan.

Examples of suitable replicable vectors include, without limitation, pUC19 or pTM1. The polynucleotide can be operably linked to an appropriate promoter such as, for example, T7 polymerase promoter, cytomegalovirus promoter, cellular polymerase II promoter, or SP1 promoter. The replicable vectors may further include sites for transcription initiation, transcription termination, and a ribosome binding site for translation.

In an embodiment, a paramyxovirus of the invention including a variant polynucleotide encoding a P protein and a monocistronic polynucleotide encoding a V protein are cloned by introducing unique restriction enzyme recognition sequences into paramyxovirus cDNA such that the recognition sequences flank the bicistronic polynucleotide encoding the P/V proteins, digesting the genome with one or more restriction enzymes that cut the genome at the restriction sites flanking the bicistronic polynucleotide encoding P/V proteins, inserting the variant polynucleotide encoding a P protein and/or monocistronic polynucleotide encoding a V protein at the cleaved restriction sites, and religating the genome. Examples of suitable restriction enzyme recognition sequences, include but are not limited to, NoI, AscI, BstEII, AgeI, and Sac II. In some embodiments, the restrictions sites are introduced into the non-coding regions upstream or downstream of the bicistronic P/V ORFs. In an embodiment, an AscI site is upstream of the bicistronic P/V ORFs and BstEII, AgeI, and SacH sites are downstream of the bicistronic P/V ORFs (FIGS. 5A and 5B). In an embodiment, the variant polynucleotide encoding a P protein is introduced into the genome using the AscI and BstEII restriction sites. In an embodiment, the monocistronic polynucleotide encoding a V protein is introduced into the genome using the AgeI and SacII restrictions sites.

Introduction of a recombinant vector composed of a paramyxovirus genome or polynucleotide encoding a paramyxovirus protein into a host cell, such as for example a bacterial cell or eukaryotic cell, can be affected by calcium phosphate transfection, DEAE-dextran mediated transfection, cationic lipid-mediated transfection, electroporation, electrical nuclear transport, chemical transduction, electrotransduction, infection, or other methods. Such methods are described in standard laboratory manuals such as Sambrook, et al., 1989, Molecular Cloning, A Laboratory Manual, Vols. 1-3, Cold Spring Harbor Press, Cold Spring Harbor, N.Y. or Davis et al., 1986, *Basic Methods in Molecular Biology*. Commercial transfection reagents, such as Lipofectamine (Invitrogen, Carlsbad, Calif.) and FuGENE 6™ (Roche Diagnostics, Indianapolis, Ind.), are also available. In some embodiments, transfection efficiency of the host cells is about 15% or greater, about 20% or greater, about 30% or greater, about 40% or greater, or about 50% or greater. Suitable host cells include, but are not limited to, HEp-2 cells, FRhL-DBS2 cells, LLC-MK2 cells, MRC-5 cells, and Vero cells.

E. Immunogenic Compositions

The invention provides isolated, infectious, recombinant paramyxovirus including one or more attenuating mutations for use in immunogenic compositions, including live attenuated virus vaccines. The paramyxoviruses of the invention are useful in immunogenic compositions for eliciting an immune response in a mammal. Preferably, the attenuated paramyxovirus includes a variant polynucleotide encoding a P protein and a monocistronic polynucleotide encoding a V protein. In an embodiment, the V gene comprises a nucleotide sequence encoding a V protein having a mutation that inhibits the ability of the V protein to interrupt production and/or signaling of interferon in an infected host. In an embodiment, the attenuated virus is HPIV2.

Recombinant HPIV2 of the invention can be combined with viruses of other PIV serotypes or strains and paramyxoviruses from multiple genera in a composition to elicit an immune response against multiple genera, serotypes, and strains. The immunogenic composition can comprise paramyxoviruses from two or more serotypes. In an embodiment, at least one of the serotypes is HPIV1, HPIV2, HPIV3, or HPIV4. The immunogenic composition can comprise paramyxovirus from two or more strains. In an embodiment, at least one of the strains is an HPIV2 strain, such as for example, V94, V98, or Greer. The immunogenic composition can comprise paramyxovirus from two of more genera. In an embodiment, one genus is *Rubulavirus* genus.

The paramyxoviruses of the invention are also useful as vectors for expressing heterologous antigens in an immunogenic composition. One or more supernumerary genes encoding one or more heterologous polypeptides can be cloned into and expressed by the paramyxovirus of the invention. For example, an immune response against multiple PIV serotypes or strains can be elicited by engineering protective epitopes of multiple PIV serotypes and strains into a single paramyxovirus. In an embodiment, the genome or antigenome includes one or more heterologous genes or genome segments encoding one or more antigenic determinants of a heterologous pathogen.

For example, one or more heterologous antigenic determinant(s) from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumovituses, or influenza viruses can be expressed by the paramyxovirus of the invention. Examples of useful antigenic determinants include, but are not limited to, measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre E, and NS1 proteins, human metapneuomovirus (HMPV) G and F proteins, and alphavirus E protein, and antigenic domains, fragments and epitopes thereof.

In an embodiment, a polynucleotide encoding an open reading frame (ORF) of a measles virus HA gene is incorporated into a HPIV2 vector genome or antigenome to yield a chimeric candidate useful to immunize against measles and/or HPIV2 or another HPIV. In another embodiment, a polynucleotide comprising genes or genome segments encoding one or more heterologous PIV(s) (e.g., HPIV1, HPIV3, and/or HPIV4) HPIV2 N, P, V, F, HN and/or L protein(s) or fragment(s) thereof is incorporated into a HPIV2 vector genome or antigenome. In another embodiment, one or more supernumerary heterologous gene(s) or genome segment(s) selected from HPIV1 HN, HPIV2 F, HP1V3 HN, HPIV3 F, measles HA and F, HMPV G and F proteins, and/or RSV subgroup A or B G and F proteins are cloned into a paramyxovirus of the invention.

Some methods of inserting one or more supernumerary genes or transcriptional units into a paramyxovirus viral genome or antigenome are described in WO04/027037, hereby incorporated by reference. Supernumerary heterologous gene(s) or genome segment(s) can be inserted at various sites within the recombinant genome or antigenome, for example at a position 3' to N, between the N/P, P/M, and/or HN/L genes, or at another intergenic junction or non-coding region of a HPIV2 vector genome or antigenome.

Candidate viruses for use in an immunogenic composition, such as for example a vaccine, are selected based on their attenuation and immunogenicity. These vaccine selection criteria are determined according to well-known methods. Preferably, candidate viruses have a stable attenuation phenotype, exhibit replication in an immunized host, and effectively elicit production of an immune response in a recipient, preferably a protective immune response. Preferably, the candidate viruses stimulate and expand the immune response, e.g., induce an immune response against different viral strains or subgroups and/or stimulate an immune response mediated by a different immunologic basis (e.g., secretory versus serum immunoglobulins, cellular immunity, and the like).

Recombinant paramyxoviruses of the invention can be tested in well-known and in vitro and in vivo models to confirm adequate attenuation, resistance to phenotypic reversion, and immunogenicity. In in vitro assays, the modified virus paramyxovirus of the invention is tested for one or more desired phenotypes, such as, for example, temperature sensitive replication. Paramyxovirus of the invention can also be tested in animal models of PIV infection. A variety of animal models are known. For example, PIV model systems, including rodents and non-human primates, for evaluating attenuation and immunogenic activity of PIV vaccine candidates, are known, and the data obtained therefrom are known to correlate with PIV infection, attenuation, and immunogenicity in humans.

In some embodiments, recombinant variant paramyxoviruses have at least one attenuating mutation with a is phenotype and at least one mutation with a non-ts phenotype. The recombinant attenuated paramyxoviruses are preferably attenuated about 100 to 5000 fold in a cell or mammal compared to wild type paramyxovirus. In some embodiments, attenuation of greater than 100,000 fold may result in reduced immunogenicity. In some embodiments, it is preferred that the level of viral replication in vitro is sufficient to provide for production of viral vaccine for use on a wide spread scale. In some embodiments, it is preferred that the level of viral replication of attenuated paramyxovirus in vitro is at least $10^6$, more preferably at least $10^7$, and most preferably at least $10^8$ per ml. The attenuating mutation is preferably one that is stable. For example, for mutations in L polymerase, it is preferable that a change in amino acid at a position requires at least two nucleotide changes in the codon as compared to the codon encoding the wild type amino acid at that position. A recombinant paramyxovirus with at least two, three, four or ever more attenuating mutations is likely to be more stable. Insertion of a supernumerary gene whose total length conforms to the rule of six, such as a polynucleotide encoding a separate V gene, can also provide a stable phenotype.

Immunogenicity of a recombinant attenuated paramyxovirus can be assessed in an animal model by determining the number of animals that form antibodies to the paramyxovirus after one immunization and after a second immunization. In some embodiments, a recombinant paramyxovirus has sufficient immunogenicity if about 60 to 80% of the animals develop antibodies after the first immunization and about 80 to 100% of the animals develop antibodies after the second immunization. The preferred animal for a determination of immunogenicity is African green monkey. Preferably, the immune response protects against infection with a paramyxovirus of the same strain or multiple strains.

The invention also provides for immunogenic compositions comprising isolated polynucleotides or polypeptides of the invention. For example, an immunogenic composition can include a polynucleotide encoding a polypeptide that has at least 80% sequence identity to a V polypeptide having a sequence of SEQ ID NO:45 or a polypeptide having a sequence at least 80% sequence identity to a V polypeptide having an sequence of SEQ ID NO:45. In other embodiments, an immunogenic composition can include a polynucleotide encoding a polypeptide that has at least 80% sequence identity to a L polypeptide having a sequence of SEQ ID NO:17 or a polypeptide having a sequence at least 80% sequence identity to a L polypeptide having an sequence of SEQ ID NO:17. In other embodiments, an immunogenic compositions can include a nucleic acid comprising a polynucleotide of SEQ ID NO:2.

Recombinant paramyxoviruses of the invention are preferably present in the immunogenic composition in an immunogenic effective amount. An immunogenic effective amount is an amount of recombinant paramyxovirus that induces an immune response in an animal. The actual amount of the recombinant paramyxovirus may vary depending on the animal to be immunized, the route of administration and adjuvants. The actual amount of recombinant paramyxovirus necessary to elicit an immune response, and the timing and repetition of administration, can be determined using conventional methods based on the state of health and weight of the host, mode of administration, nature of formulation, etc. Immunogenic dosages can be determined by those of skill in the art. Dosages will generally range from about $10^3$ to about $10^7$ plaque forming units (PFU) or more of virus per host, more commonly from about $10^4$ to $10^6$ PFU virus per host. In any event, the formulations should provide a quantity of attenuated recombinant paramyxovirus of the invention sufficient to effectively stimulate or induce an anti-PIV or other anti-pathogenic immune response.

The immune response may be indicated by T and/or B cell responses. Typically, the immune response is detected by the presence of antibodies that specifically bind to a particular antigen. Methods of detecting antibodies to a particular antigen are known to those of skill in the art and include such assays as ELISA assays, western blot assays, hemagglutination-inhibition assays, and infectivity neutralization assays. Host receiving immunogenic compositions of the invention are preferably monitored for signs and symptoms of upper and lower respiratory tract illness. Preferably, attenuated virus administered intranasally grows in the nasopharynx of recipients at levels about 10-fold or more lower than wild-type virus, or about 10-fold or more lower when compared to levels of incompletely attenuated virus.

In neonates and infants, multiple administrations may be required to elicit sufficient levels of immunity. Administration could begin within the first month of life, and at intervals throughout the first several years of childhood, such as at two months, six months, one year and two years, as necessary to maintain an immune response against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain immune responses. Levels of induced immunity can be monitored by measuring amounts of neutralizing secretory and serum antibodies, and dosages adjusted or immunizations repeated as necessary to maintain desired levels of immune response.

Recombinant paramyxoviruses, polynucleotides, and polypeptides of the invention can be used directly in formulations, or lyophilized, as desired, using well known methods. Lyophilized virus is typically maintained at about 4° C. When ready for use, the lyophilized virus is reconstituted in an appropriate stabilizing solution. Many stabilizing solutions are known.

Immunogenic compositions including paramyxovirus of the invention can include a physiologically acceptable carrier and/or adjuvant. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. Lyophilized preparations are generally combined with a sterile solution prior to administration.

The compositions may include pharmaceutically acceptable auxiliary substances as required to approximate physiological conditions, such as pH adjusting and buffering agents, tonicity adjusting agents, wetting agents and the like, such as for example, sodium acetate, sodium lactate, sodium chloride, potassium chloride, calcium chloride, sorbitan monolaurate, triethanolamine oleate, and the like. Acceptable adjuvants include, but are not limited to, Freund's adjuvant (incomplete or complete), MPL™ (3-O-deacylated monophosphoryl lipid A; Corixa, Hamilton IN) and IL-12 (Genetics Institute, Cambridge Mass.), CpG oligonucleotides, immunostimulating compositions and alum salts.

The immunogenic compositions of the invention can be administered nasally in droplet, aerosol, or nebulizer form, orally, or parentally, including subcutaneous injection, intravenous, intramuscular, intrasternal or infusion techniques, in dosage unit formulations including conventional non-toxic pharmaceutically acceptable carriers, adjuvants or vehicles. Compositions of the invention can be in the form of suspensions or tablets suitable for oral administration or sterile injectable preparations, such as sterile injectable aqueous or oleagenous suspensions.

For administration as injectable solutions or suspensions, the immunogenic compositions of the invention can be formulated according to techniques well-known in the art, using suitable dispersing or wetting and suspending agents, such as sterile oils, including synthetic mono- or diglycerides, and fatty acids, including oleic acid.

Immunization by the nasal route may be more effective compared with intramuscular or subcutaneous injection because the production of local secretory IgA in the upper respiratory tract can protect against PIV infection. For example, PIV specific secretory IgA can show a broader cross-reactivity for variant strains of PIV and thus may offer a greater degree of protection against mutant PIV. In contrast, injectable vaccines are inefficient at inducing mucosal IgA. In particular, nasal administration of the immunogenic compositions of the invention may be more effective in the elderly since, unlike the systemic immune system, mucosal immune responses do not deteriorate with age. Immunogenic compositions of the invention that also stimulate systemic immune responses may protect the lower respiratory tract (lungs) due to transudation of antibodies from the serum. In addition, PIV-specific cytotoxic T cells (CTL) in nasal associated lymphoid tissue can contribute to recovery from infection.

Immunogenic compositions for nasal administration are preferably formulated so that they are similar to nasal secretions in regard to toxicity, pH, and viscosity so that normal ciliary action is maintained. In an embodiment, the immunogenic compositions of the invention are formulated in an aqueous solution that is isotonic and slightly buffered to maintain a pH of about 5.5 to about 6.5. Antimicrobial preservatives and appropriate stabilizers, if required, are included in the formulation.

F. Methods of Use

The invention also provides methods of making and using the recombinant paramyxovirus of the invention. In one embodiment, the invention relates to methods of generating an infectious, self-replicating paramyxovirus as have been described herein. The methods generally include the steps of removing or altering a bicistronic polynucleotide encoding a P and V protein from the viral genome or antigenome of a paramyxovirus and inserting a variant polynucleotide encoding a P protein and/or a monocistronic polynucleotide encoding a V protein. In an alternative embodiment, the variant polynucleotide encoding the P gene in the paramyxovirus can be altered in situ to no longer encode the V protein using the standard methods and the monocistronic polynucleotide encoding the V protein can be inserted into the paramyxovirus genome or antigenome. Preferably, the variant polynucleotide encoding a P protein includes a mutated mRNA editing site such that editing of mRNA encoding P protein is inhibited and the monocistronic polynucleotide encoding a V protein includes a mutated mRNA editing site such that editing of mRNA encoding V protein is inhibited. More preferably, the V protein has at least one mutation that reduces the ability of the V protein to inhibit production and/or signaling of interferon.

In an embodiment, the removing step includes introducing unique restriction enzyme recognition sequences into the genome or antigenome such that the recognition sequences flank the bicistronic polynucleotide encoding P and V proteins and digesting the genome or antigenome with one or more restriction enzymes that cut the genome or antigenome at the restriction sites flanking the bicistronic polynucleotide. In an embodiment, the inserting step includes inserting the variant polynucleotide encoding a P protein and a monocistronic polynucleotide encoding a V protein at the cleaved restriction sites and religating the genome or antigenome.

In another embodiment, the invention relates to methods of producing infectious, self-replicating, recombinant paramyxovirus. The methods of the invention include transfecting a population of cells with an expression vector comprising a partial or complete polyhexameric genome or antigenome sequence and one or more supporting vectors including one or more polynucleotides encoding N protein, P protein, and L polymerase, and incubating the transfected cells under conditions to allow for viral replication. Preferably, the paramyxoviruses have a variant polynucleotide encoding a P protein and/or a monocistronic polynucleotide encoding a V protein.

In another embodiment, the invention relates to methods of eliciting an immune response in a mammal. The methods of the invention include administering an immunogenic composition of the invention. Preferably, the immune response produces antibodies that are protective (e.g. inhibit infection or reduce the severity of infection). In an embodiment, the antibodies are anti-PIV antibodies. In an embodiment, the anti-PIV antibodies are IgA. In some embodiments, the immune response produces antibodies that bind one or more antigenic determinants of a heterologous pathogen encoded by supernumerary genes or genome segments. Examples of heterologous pathogens include, but are not limited to, HPIV1, HPIV3, measles virus, subgroup A or subgroup B respiratory syncytial virus, mumps virus, human papilloma virus, type 1 or type 2 human immunodeficiency virus, herpes simplex virus, cytomegalovirus, rabies virus, Epstein Barr virus, filovirus, bunyavirus, flavivirus, alphavirus, human metapneumovirus, or influenza virus. In an embodiment, the antigenic determinants include measles virus HA, HPIV1 HN, and/or HPIV3 HN.

In another embodiment, the invention relates to methods of inhibiting a paramyxovirus infection including, but not limited to, PIV infection. The methods of the invention include administering an immunogenic composition of the invention comprising an attenuated paramyxovirus of the invention. Preferably the paramyxovirus of the invention includes a variant polynucleotide encoding a P protein and a monocistronic polynucleotide encoding a V protein. In an embodiment, the paramyxovirus is PIV. In an embodiment, the PIV is HPIV2. Preferably the immunogenic composition elicits antibodies that are protective (e.g. inhibit infection or reduce the severity of infection). In an embodiment, the antibodies are anti-PIV antibodies. In an embodiment, the anti-PIV antibodies are IgA.

All publications, patents and patent applications are hereby incorporated by reference. The following examples are provided for illustrative purposes only, and are in no way intended to limit the scope of the present invention.

EXAMPLE 1

Level of Attenuation and Stability Conferred by L Protein Mutations Enhanced by Alternative Codon Substitution Attenuated HPIV1 and HPIV2 vaccine candidates were previously generated by amino acid substitutions at loci in the L protein (WO04/027037; (McAuliffe et al., 2004)). In this example, the level of attenuation conferred by alternative codon substitutions at mutant loci in the L protein was studied. Codon substitution mutations were designed so that at least two nucleotide changes would be required to regenerate a codon specifying the wild type amino acid at each position, thereby reducing the chance of spontaneous reversion to a codon specifying the wild type amino acid. For example, taking the commonly cited value of $10^{-4}$ for the mutation rate for a RNA virus, reversion that requires a single nucleotide substitution would occur at a frequency of $\sim 10^{-4}$ whereas reversion requiring two or three substitutions would occur at the greatly reduced frequencies of $\sim 10^{-8}$ and $\sim 10^{-12}$, respectively.

Material and Methods

Preparation of Plasmids and Generation of Mutants

HPIV2 V94 strain antigenomic sense cDNA (SEQ ID NO:4), which is 15,654 nucleotides in length and conforms to the "rule of six" (Calain and Roux, 1993; Kolakofsky et al., 1998; Vulliemoz and Roux, 2001), was modified by PCR mutagenesis and standard molecular cloning techniques to include a NotI site (GCGGCCGC (SEQ ID NO:11)) at nucleotide sequence positions 149 to 156 in the HPIV2 genome, which is within the N gene and upstream of the N ORF. The NotI restriction site was introduced to aid in subsequent cloning steps and as a site for the subsequent insertion of supernumerary genes. Unless otherwise noted, each of the recombinant mutant HPIV2s described includes this NotI site.

The original biologically derived wild-type clinical HPIV2 isolate is designated V94 (SEQ ID NO:4); its recombinant wild-type counterpart lacking the NotI site is designated rV94 (SEQ ID NO:12), and the version including the NotI site is designated rV94Not (SEQ ID NO:13). Wild-type and recombinant HPIV2 were assembled and recovered as described in WO04/027037 and Skiadopoulos et al., 2003, *J. Virol.*, 77:270-279.

Four L protein mutations conferring is attenuation (att) phenotypes were previously identified in several heterologous paramyxoviruses (WO04/027037). These mutations were imported into HPIV2 as follows: F460L, imported from the RSVcpts530 L protein, F521L (Juhasz et al., 1999; Whitehead et al., 1999; Skiadopoulos et al., 1999c; Juhasz, Murphy, and Collins, 1999)); Y948H and L1566I, imported from the HPIV3 cp45 L protein, Y942H and L1558I, respectively (Skiadopoulos et al., 1998; Skiadopoulos et al., 1999a)); and S1724I, imported from the bovine PIV3 (BPIV3) L protein, T1711I (Skiadopoulos et al., 2003a).

In the present example, the L protein mutations were designed to involve more than one nucleotide change including two mutations at the codons specifying amino acid position 460 (F460A and F460P) and three at amino acid position 948 (Y948A, Y948G, and Y948L). A codon substitution at position 1724 (S1724I) specifying the mutation originally identified in the BPIV3 L ORF (T1711I) was also generated, although this mutant codon differed from wild type by only a single nucleotide substitution. The codons at positions 1724 and 1725 were both deleted in order to maintain a polyhexameric genome length, i.e. to conform the genome length to the rule of six. Thus, six mutations, including novel mutations at codon positions encoding amino acids at positions 460, 948, 1566, 1724, and 1725, were generated by PCR mutagenesis (Moeller et al., 2001) and standard molecular cloning techniques (Skiadopoulos et al., 2003, *J. Virol.*, 77:270-279; Newman et al., 2004) using mutagenic PCR primers designed to achieve the nucleotide sequence indicated in Table 2.

Table 2 summarizes the substitution mutations introduced into the L ORF of HPIV2. Mutants bearing a mutation in the L protein were designated by the amino acid substitution generated (e.g., rF460A, recombinant V94 with the F-460 to A mutation).

TABLE 2

| Virus | Amino acid | | Codon | | Number of nucleotide changes to revert to wild type[a] |
|---|---|---|---|---|---|
| | Wild type | Mutant | Wild type | Mutant | |
| rF460L[b] | Phe | Leu | TTT | CTG | 2 |
| rF460A[c] | | Ala | TTT | GCA | 3 |
| rF460P[c] | | Pro | TTT | CCA | 3 |
| rY948H[b] | Tyr | His | TAC | CAC | 1 |
| rY948A[c] | | Ala | TAC | GCA | 3 |
| rY948L[c] | | Leu | TAC | CTA | 3 |
| rY948G[c] | | Gly | TAC | GGA | 3 |
| rL1566I[b] | Leu | Ile | TTG | ATC | 1 |
| rS1724I[b, c] | Ser | Ile | TCT | ATT | 1 |
| r1724del | Ser-Thr | deletion | TCT-ACT | deletion | 6[d] |

[a]Number of nucleotide changes required to revert the codon to any possible codon specifying the indicated wild type amino acid.
[b]Original imported mutations corresponding the RSV L protein F521L, HPIV3 L protein Y942H and L1558I, or BPIV3 L protein T1711I mutations.
[c]Novel recombinant HPIV2 mutants.
[d]Six nucleotides would need to be inserted to restore the codons encoding Ser and Thr.

Additional codon substitution mutations not shown in Table 2 were introduced into the HPIV2 full-length antigenomic cDNA, but rHPIV2 could not be recovered from these constructs after 1 or 2 attempts, suggesting that these mutations may specify a lethal phenotype. These mutations included Ala-998 to Phe or Cys, Leu-1566 to Ala, Gly, Lys, and Asn, and Tyr-948 to Thr.

rV94Not comprising the indicated L gene mutations (Table 2) was recovered from cDNA using a reverse genetics system that employed a full length HPIV2/rV94Not plasmid and three HPIV2 support plasmids as described in WO04/027037 and below.

A support plasmid encoding the N protein of HPIV2/V94 (pTM-N2) was derived from vRNA using the Thermoscript RT-PCR System (Invitrogen, Inc.) and the Advantage-HF PCR kit (Clontech) using an antigenomic sense oligonucleotide that included an AflIII site spanning the N ORF ATG translation initiation codon site and an anti-sense oligo including an EcoRI site. The PCR product was digested with AflIII and EcoRI and cloned into pTM1 (Durbin et al., Virology 235: 323-332, 1997; Durbin et al., Virology 234: 74-83, 1997; Elroy-Stein et al., Proc. Natl. Acad. Sci. USA. 86: 6126-30, 1989), that was digested with Nco I and EcoRI.

A support plasmid encoding the P protein of HPIV2/V94 (pTM-P2) was generated from two overlapping PCR fragments (Moeller et al., J. Virol. 75: 7612-20, 2001, incorporated herein by reference) and engineered to include a two guanosine nucleotide insertion within the HPIV2 P gene editing site (nt 2481-2487) to generate the complete P ORF (as distinguished thereby from the V ORF) which was subcloned into pTM1 as an Nco I to EcoRI fragment.

A support plasmid encoding the L polymerase of HPIV2 (pTM-L2) was made by PCR amplification with a sense oligo including an Nco I site spanning the L gene ATG translation initiation codon, and an antisense oligo downstream of a unique Aat II site (nt 10342) in the L ORF. The remainder of the L ORF was derived from a subclone used to construct the HPIV2 full-length clone. The PCR product was digested with Asp718 and Aat II and was cloned into a pUC19 plasmid including the HPIV2 nts 10342 to 15654 followed by the unique extragenomic Rsr II site. The complete HPIV2/V94 L ORF was then subcloned into a modified pTM1 as an Nco I to Rsr II fragment.

HEp-2 cells (ATCC CCL 23) in 6-well plates (Costar, Coming Inc., Coming, N.Y.) were co-transfected with a cDNA plasmid encoding the mutant HPIV2 of the invention and the three HPIV2 support plasmids (pTM-N2, pTM-P2, pTM-L2), using Lipofectamine-2000 reagent (Invitrogen, Inc.). The HEp-2 cells were simultaneously infected with MVA-T7 as described previously (Durbin et al., Virology 235: 323-332, 1997; Schmidt et al., J. Virol. 74: 8922-9, 2000). Supernatant was harvested on day three or four post-transfection and was passaged two times on LLC-MK2 (ATCC CCL 7.1) monolayers.

To confirm that viruses were derived from cDNA, rather than representing contamination by biologically derived virus, RT was performed and segments of the viral genome were amplified by PCR. Sequence analysis of the PCR products revealed the presence of the two point mutations that are present in the F and L genes of the recombinant virus, designated rHPIV2/V94, but that are not present in the wild type parental virus. Each rHPIV2/V94 was then cloned by plaque to plaque purification on LLC-MK2 monolayers and passaged 6 to 8 times on LLC-MK2 cells using standard techniques (Skiadopoulos et al., 1999, Virology, 260:125-35).

The HEp-2 and LLC-MK2 cells were maintained in Opti-MEM I (LifeTechnologies, Gaithersburg, Md.) supplemented with 5% FBS and gentamicin sulfate (50 ug/mL). Recombinant and biologically derived HPIV2s were propagated in LLC-MK2 cells and were quantified by limiting dilution with virus-infected cultures identified by hemadsorption with guinea pig erythrocytes using standard techniques (Hall et al., 1992, Virus Res., 22:173-184).

Replication of Recombinant and Mutant rHPIV2 In Vitro

Replication of recombinant wild type and mutant rHPIV2 at permissive (32° C.) and restrictive (37-40° C.) temperatures was tested in vitro. Recombinant or biologically derived HPIV2 was inoculated in triplicate onto LLC-MK2 cell monolayers in six-well plates at a multiplicity of infection of 0.01, and cultures were incubated at 32° C. with and without 5 µg of porcine trypsin/ml added to the culture medium (Skiadopoulos et al., 1999, Vaccine, 18:503-510). Medium (0.5 ml) from each well was harvested and replaced with 0.5 ml of fresh medium at 0 h and at 1 to 6 days postinfection. Virus present in the samples was quantified by titration on LLC-MK2 monolayers in 96-well plates that were incubated for 6 days at permissive (32° C.) or restrictive (37-40° C.) temperatures (Skiadopoulos et al., 1999, Vaccine, 18:503-510). Virus grown in the presence of trypsin was titered with trypsin in the medium. Virus was detected by hemadsorption with guinea pig erythrocytes (Skiadopoulos et al., 1999, Vaccine, 18:503-510).

Replication of HPIV2 In Vitro (Multi-Cycle Growth Curves)

Recombinant or biologically derived HPIV2 was inoculated in triplicate onto LLC-MK2 cell monolayers in 6-well plates at a multiplicity of infection (m.o.i.) of 0.01, and cultures were incubated at 32° C. 0.5 ml of medium from each well was harvested and replaced with 0.5 ml of fresh medium at 0 hr and at 1 to 7 days post-infection. Virus present in the samples was quantified by titration on LLC-MK2 monolayers in 96-well plates that were incubated for 6-7 days at 32° C. Virus was detected by hemadsorption and the titer is reported as $\log_{10} TCID_{50}/ml$ (50% tissue culture infectious dose/ml).

Replication of Recombinant HPIV2 L Protein Mutants In vivo

Golden Syrian hamsters (*Mesocricetus auratus*) have been demonstrated to be an appropriate small animal model for evaluating the level of replication of human parainfluenza viruses. Therefore, the level of replication of wild type and recombinant mutant HPIV2 in the upper and lower respiratory tract of hamsters was examined, as described previously (Skiadopoulos et al., 2003b). Briefly, four week-old Golden Syrian hamsters (Charles River Laboratories, NY) in groups of 6 were inoculated intranasally (IN) with 0.1 ml of L15 medium including $10^{6.0} TCID_{50}$ of HPIV2. On day 4 post-infection, the lungs and nasal turbinates were harvested, and the virus was quantified by serial dilution of tissue homogenates on LLC-MK2 monolayers, as previously described (Newman et al., 2002). The mean virus titer was calculated for each group of hamsters and is expressed as $\log_{10} TCID_{50}$ per gram of tissue.

African green monkeys (*Cercopithecus aethiops*) have been previously demonstrated to be an appropriate non-human primate animal model for HPIV2 replication (Durbin, Elkins, and Murphy, 2000). Monkeys that lacked serum antibodies to HPIV2 (hemagglutination inhibition (HAI) titer of ≤1 $\log_2$) were inoculated simultaneously by the IN and intratracheal (IT) routes using a one ml inoculum per site including $10^6 TCID_{50}$ of virus in L15 medium, as described previously (Durbin, Elkins, and Murphy, 2000). Nasopharyngeal (NP) swab samples were collected on days 1-10, and tracheal lavage (TL) samples were collected on days 2, 4, 6, 8, and 10 post-infection. Virus present in NP and TL specimens was quantified by titration on LLC-MK2 cell monolayers, and the mean peak virus titer obtained was expressed as $\log_{10} TCID_{50}/ml$. The monkeys were challenged IN and IT with one ml per site including $10^6 TCID_{50}$ of the biologically-derived V94 HPIV2 strain 28 or 31 days after the first infection, and NP and TL samples were collected on days 2, 4, 6, 8 and 10 post-challenge. HPIV2 present in the samples was quantified as described above. Serum samples were collected to determine the serum antibody titer before immunization (on day 0), post-immunization (on day 28 or 31), and 28 days post-challenge (day 56 or 59 post first infection).

Results and Discussion

The L protein mutants shown in Table 2 were found to grow to high titer at 32° C. on LLC-MK2 cell monolayers ($\geq 10^{6.8}$ $\log_{10}$ TCID$_{50}$/ml), indicating the mutations in the L protein are not attenuating for replication at permissive temperature (32° C.) in vitro (Table 3). The shut-off temperature of a rHPIV2 mutant is defined as the lowest temperature at which the reduction in virus titer compared to its titer at 32° C. was 100-fold greater than the difference of HPIV2/V94 between the same two temperatures.

Mutant recombinants rF460A, rF460P, rY948A, rY948G, rY948L, rS1724I, and rdel1724 were designated as having a ts phenotype (Table 3).

TABLE 3

| Virus[a] | Mean titer at 32° C. | Mean log$_{10}$ reduction in virus titer at the indicated temperature (° C.)[b] | | | |
|---|---|---|---|---|---|
| | | 37 | 38 | 39 | 40 |
| V94 | 7.2 | 0.0 | 0.3 | 0.4 | 0.5 |
| rV94Not | 7.5 | −0.2 | −0.1 | 0.3 | 0.5 |
| rV94 | 7.8 | nd[c] | −0.1 | 0.8 | 0.7 |
| rV94 N/A/B | 7.3 | nd | −0.4 | 0.4 | 0.7 |
| r F460L | 7.5 | 0.0 | −0.3 | 0.6 | 1.1 |
| rF460A | 7.0 | 0.7 | 1.1 | 2.1 | 5.0 |
| rF460P | 6.8 | 1.3 | 1.1 | 2.2 | 5.1 |
| rY948H | 8.1 | 0.2 | 0.5 | 1.0 | 1.8 |
| rY948A | 7.2 | 0.1 | 0.6 | 3.0 | 5.7 |
| rY948G | 7.4 | −0.1 | 0.5 | 0.9 | 3.1 |
| rY948L | 7.1 | 1.1 | 1.9 | 5.5 | 5.7 |
| rL1566I | 7.6 | 0.4 | 0.6 | 0.8 | 0.9 |
| rS1724I | 7.6 | −0.3 | 0.5 | 2.9 | 5.8 |
| rdel1724 | 7.3 | 1.0 | 1.5 | 4.0 | 6.2 |
| rV94 P + V | 7.3 | nd | 2.8 | 4.8 | 6.0 |
| rV94 RSV-F | 5.7 | nd | 0.3 | 0.6 | 1.0 |

[a] See Table 2. V94 is the original HPIV2 clinical isolate; rV94 is its recombinant counterpart; rV94Not is rV94 including the pre-N ORF NotI site. rV94 N/A/B is rV94Not including additional unique restriction sites flanking the P/V ORFs.
[b] Values are the mean of at least two experiments. Values in bold type indicate temperatures at which the mean log$_{10}$ reduction versus 32° C. was ≥2.0 log$_{10}$ compared to wild type rHPIV2. The lowest temperature in bold is the shut-off temperature. Viruses in bold have a ts phenotype.
[c] nd = Not determined.

Figure 1:
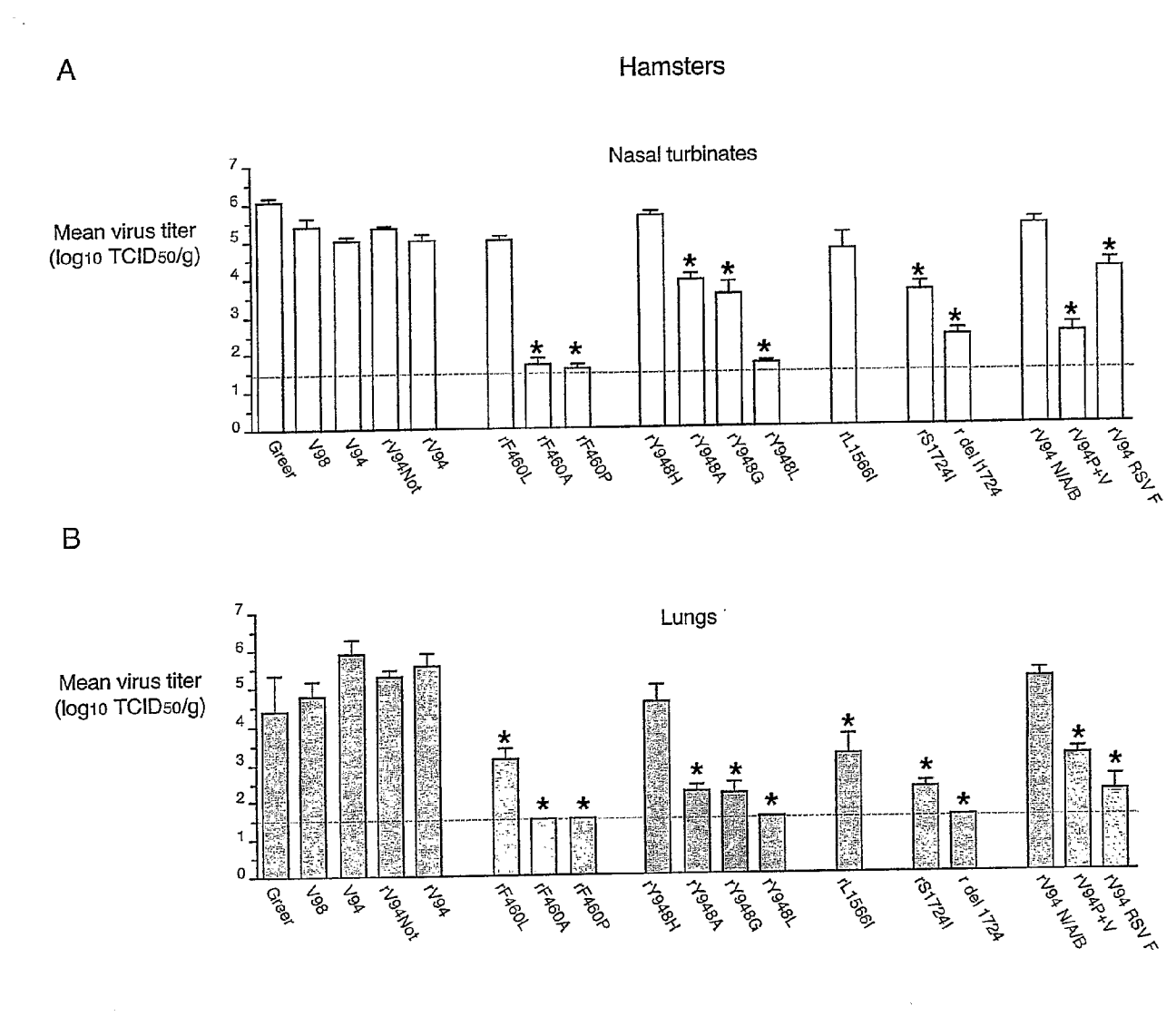

As shown in FIG. 1 and Table 4, recombinant HPIV2 (rF460A, rF460P, rY948A, rY948G and rY948L) comprising an alternative codon substitution were more attenuated than the rV94Not parent virus. rF460A and rF460P were more attenuated in both the upper and lower respiratory tract than F460L which bears the original imported mutation. Similarly, rY948A, rY948G, and rY948L were more attenuated in both the upper and lower respiratory tract than rY948H, which bears the original imported mutation. Thus, the codon substitution mutants exhibited increased attenuation, a desirable property for a vaccine virus.

Both the newly derived rS1724I and the previously derived rdel1724 (WO04/027037) recombinants were more attenuated in the upper and lower respiratory tract of hamsters than the rV94Not parent virus. These results indicated that amino acid 1724 in the HPIV2 L protein is a susceptible site for yielding an attenuation phenotype. Importantly, the rdel1724, which is highly attenuated in hamsters, includes a two amino acid deletion and thus would require the insertion of six specific nucleotides to revert to wild type, whereas rS1724I includes a single nucleotide substitution and would be much more susceptible to reversion. Therefore, the deletion mutation is a preferred mutation for inclusion in a HPIV2 vaccine, because it specifies an att phenotype that should be stable in vivo.

TABLE 4

| Virus[a] | No. of animals | Mean virus titer ($\log_{10}$ TCID$_{50}$/g ± S.E.[c]) | |
|---|---|---|---|
| | | Nasah Turbinates | Lungs |
| V94 | 6 | 4.9 ± 0.1 | 5.9 ± 0.4 |
| rV94Not | 18[b] | 5.3 ± 0.1 | 5.3 ± 0.2 |
| rV94 | 6 | 5.0 ± 0.2 | 5.5 ± 0.4 |
| rV94 N/A/B | 6 | 5.3 ± 0.2 | 5.1 v 0.2 |
| r F460L | 6 | 5.0 ± 0.1 | 3.1 ± 0.3 |
| rF460A | 6 | 1.7 ± 0.2 | ≤1.5 ± 0.0 |
| rF460P | 6 | 1.6 ± 0.1 | ≤1.5 ± 0.0 |
| rY948H | 6 | 5.6 ± 0.1 | 4.5 ± 0.4 |
| rY948A | 6 | 3.9 ± 0.2 | 2.2 ± 0.2 |
| rY948G | 6 | 3.5 ± 0.3 | 2.2 ± 0.3 |
| rY948L | 6 | 1.7 ± 0.1 | ≤1.5 ± 0.0 |
| rL1566I | 6 | 4.6 ± 0.4 | 3.1 ± 0.5 |
| rS1724I | 6 | 3.5 ± 0.3 | 2.2 ± 0.2 |
| rdel1724 | 6 | 2.4 ± 0.2 | ≤1.5 ± 0.0 |
| rV94 P + V | 6 | 2.4 ± 0.2 | 3.1 ± 0.1 |
| rV94 RSV-F | 6 | 4.1 ± 0.2 | 2.1 ± 0.4 |

[a] Hamsters in groups of 6 were inoculated IN with 10$^6$ TCID$_{50}$ of the indicated virus. Nasal turbinates and lung tissues were harvested on day 4. Virus present in the tissues was quantified by serial dilution on LLC-MK2 monolayers at 32° C.
[b] Total number of animals from three independent experiments.
[c] Data shown were compiled from multiple experiments. The mean virus titer per gram of tissue for each group of animals receiving the same inoculum is shown. S.E., standard error. A statistical analysis of the level of reduction of replication of mutant virus versus wild-type viruses is presented in FIG. 1.

The Y948L mutation attenuated HPIV2 replication to the greatest extent in the respiratory tract of hamsters (4000 and 6000-fold reduction of replication in the upper and lower respiratory tract, respectively, compared to rV94Not). We therefore examined the ability of the Y948L mutant to replicate in the respiratory tract of non-human primates.

As shown in FIG. 2 and Table 5, the novel HPIV2 L protein Y948L mutation conferred an additional 160-fold reduction in the mean peak level of virus replication in the lower respiratory tract of African green monkeys compared to its rV94Not parent, as well as a significant reduction in the mean sum of daily virus shed in the lower respiratory tract. Furthermore, infection with rY948L protected animals from challenge with the biologically derived V94 (Table 5). These results indicate the rY948L mutant is appropriately attenuated and efficacious in non-human primates. In addition, the Y948L codon substitution would require 3 nucleotide changes to revert to the wild type Tyr codon thereby rendering this mutation genetically more stable. Thus, the use of alternative codon substitutions at positions known to confer an attenuation phenotype in a heterologous virus is an effective means of enhancing the level of HPIV2 attenuation for non-human primates.

The HPIV2 mutant bearing a deletion of amino acids 1724-1725 was also highly attenuated and efficacious in African green monkeys (FIG. 2 and Table 5). rV94 del1724 has a greater level of stability than rV94 Y948L, since rV94 del1724 requires insertion of 6 nucleotides to revert to the wild type.

TABLE 5

| Immunizing virus[a] | Group size[b] | Mean peak titer of immunizing virus ($\log_{10}TCID_{50}$/ml ± S.E.)[c] | | Mean of sum of daily virus titers of immunizing virus ($\log_{10}TCID_{50}$/ml ± S.E.)[d] | | Post-immunization serum HPIV2 HAI antibody titer (recip. $\log_2$ ± S.E.)[e] | Mean peak challenge HPIV2 titer[f] ($\log_{10}TCID_{50}$/ml ± S.E.) | | Post-challenge serum HPIV2 HAI antibody titer (recip. $\log_2$ ± S.E.)[g] |
|---|---|---|---|---|---|---|---|---|---|
| | | NP | TL | NP | TL | | NP | TL | |
| V94 | 8 | 2.6 ± 0.3 | 4.8 ± 0.3 | 11.7 ± 1.0 | 14.5 ± 1.3 | 1.3 ± 0.3 | 0.7 ± 0.2 | 0.8 ± 0.3 | 3.1 ± 0.6 |
| V98 | 4 | 2.6 ± 0.6 | 4.6 ± 0.5 | 11.5 ± 2.5 | 14.5 ± 2.7 | 6.3 ± 0.3[j] | ≤0.5 ± 0.0 | 0.6 ± 0.1 | 7.3 ± 0.3[j] |
| Greer | 4 | 2.7 ± 0.6 | 3.7 ± 0.5 | 11.8 ± 2.6 | 12.9 ± 2.1 | 6.0 ± 0.4[j] | 1.4 ± 0.1 | 1.1 ± 0.4 | 8.8 ± 0.5[j] |
| RV94 Not | 7 | 2.3 ± 0.5 | 3.2 ± 0.2[A] | 8.8 ± 1.2 | 9.0 ± 0.7[A] | 2.0 ± 0.6 | 0.6 ± 0.1 | ≤0.5 ± 0.0 | 3.7 ± 0.4 |
| RV94 | 6 | 3.1 ± 0.4 | 2.7 ± 0.5[A] | 13.6 ± 1.4 | 5.9 ± 0.8[A] | 3.7 ± 1.0 | 0.6 ± 0.1 | 1.1 ± 0.3 | 5.0 ± 0.4 |
| RV94 del1724 | 8 | 2.0 ± 0.4 | 2.0 ± 0.1[A] | 10.8 ± 1.9 | 6.2 ± 0.3[A] | 1.5 ± 0.2[h] | 0.6 ± 0.1 | 1.1 ± 0.2 | 3.1 ± 0.6[i] |
| RV94 Y948L | 4 | 2.9 ± 0.4 | 1.0 ± 0.5[A, B] | 13.5 ± 2.2 | 3.0 ± 0.5[A, B] | 2.8 ± 0.8 | ≤0.5 ± 0.0 | 0.8 ± 0.3 | 4.8 ± 0.9 |
| RV94 P + V | 4 | 2.2 ± 0.3 | 2.4 ± 0.6[A] | 11.1 ± 0.7 | 6.2 ± 0.7[A] | 1.0 ± 0.0 | ≤0.5 ± 0.0 | ≤0.5 ± 0.0 | 3.8 ± 0.8 |

[a]Animals were inoculated IN and IT on day 0 with $10^6$ TCID$_{50}$ per site of the indicated virus.
[b]Includes data collected from similarly infected and sampled African green monkeys from three studies.
[c]Nasopharyngeal (NP) swab samples were collected on days 1 to 10 post-infection. Tracheal lavage (TL) samples were collected on days 2, 4, 6, 8 and 10 post-infection. The mean of the peak virus titer for each animal in its group irrespective of sampling day is shown. S.E. = standard error. The limit of detection of virus titer was 10 TCID$_{50}$/ml. Values indicated by A differ significantly from the group that received V94 (P < 0.05). Values indicated by B differ significantly from the group that received rV94Not.
[d]The sum of the viral titers obtained for each animal on all sampling days (days 1-10 for NP and days 2, 4, 6, 8 and 10 for TL) was calculated and the mean ($\log_{10}$) ± S.E. for each group is shown. The lower limit of detection is 5.0 $\log_{10}TCID_{50}$/ml for NP swab and 2.5 $\log_{10}TCID_{50}$/ml for TL samples. Values indicated with A differed significantly from the group that received V94. Values indicated with B differed significantly from the group that received rV94Not.
[e]Sera were collected 28 to 31 days post-challenge and were titered in the same HPIV2 hemagglutination inhibition assay.
[f]Animals were challenged IN and IT on day 28 or 31 post-first immunization with $10^6$ TCID$_{50}$ per site of the V94 strain of HPIV2. NP swab and TL samples were collected on days 2, 4, 6, and 8 post-infection. Virus titrations were performed on LLC-MK2 cells at 32° C. Mean of the peak virus titers ± S.E. for each animal in its group irrespective of sampling day is shown. The limit of detection of virus titer was 10 TCID$_{50}$/ml. Compare to mean peak virus titer values obtained in HPIV2 naïve monkeys that received V94.
[g]Post-challenge antibody titers were obtained 28 days post-challenge and were titered in the same HPIV2 hemagglutination inhibition assay.
[h]Quantity of serum not sufficient from 2 AGMs; mean was calculated from 6 animals
[i]Quantity of serum not sufficient from 1 AGM; mean was calculated from 7 animals.
[j]HAI data from previous study, samples not tested at the same time as other samples.

Analysis of the replicative properties of these mutants in vivo and in animal models demonstrated that the F460L and L1566I mutations each conferred approximately a 250 fold reduction of replication in the lower respiratory track of hamsters, and the 1724-1725 deletion mutation conferred a 4 to 25 fold reduction in replication in the respiratory tract of African Green monkeys. Interestingly, while the Y942H mutation conferred ts and att phenotypes in HPIV3 and HPIV1, the analogous mutant did not attenuate HPIV2. This shows that the importation strategy frequently, but not always, results in an att phenotype in a recipient virus.

EXAMPLE 2

Identification of a Putative Non-ts, Host-Range att Mutation in the 3' Leader Sequence of HPIV2/V94

In African green monkeys, we noted a significant and unexpected difference between the level of replication of the rV94 bearing the pre-N ORF NotI restriction site (rV94Not) versus the biologically derived V94 in the lower respiratory tract (Table 5 and FIG. 2). With the exception of the introduced pre-N ORF NotI restriction site and a translationally silent nucleotide substitution in the F ORF, the recombinant V94 sequence was identical to that determined for the biologically derived virus (Skiadopoulos et al., 2003b). To establish whether the introduced NotI site was responsible for the attenuation phenotype, we compared the level of replication of biologically derived V94 to that of a recombinant V94 (rV94) that does not includes the pre-N ORF NotI site. We found that rV94 was also significantly attenuated in the lower respiratory tract of African green monkeys (FIG. 2 and Table 5). These results indicated that another factor was responsible for the difference in the observed level of replication of recombinant and biologically derived V94 in the lower respiratory tract of African green monkeys and that the NotI site likely did not specify an att phenotype.

Materials and Methods

Passaging and Sequencing

The uncloned, biologically derived HPIV2 V94 clinical isolate administered to the monkeys in Example 1 was sequentially passaged nine times on Vero cell monolayers and then passaged once on LLC-MK2 cell monolayers to generate a virus preparation (V94(a)).

Figure 3:
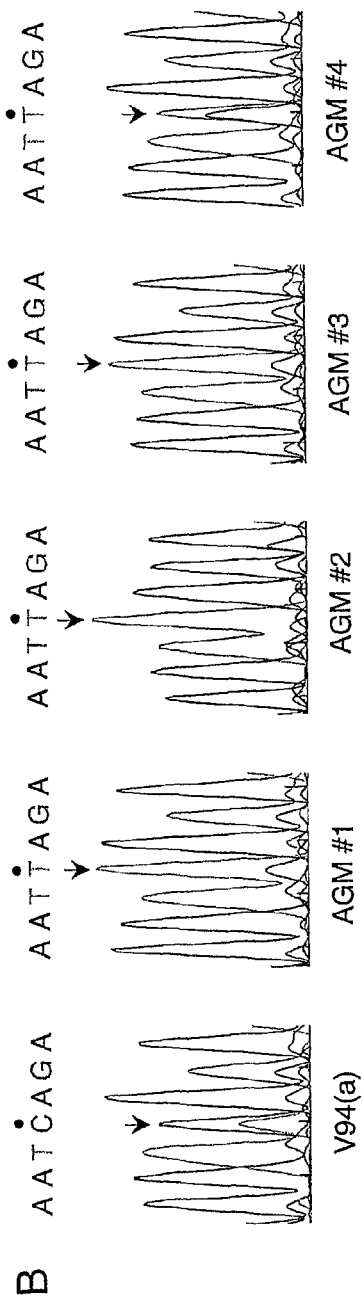
FIG. 3A shows a partial nucleotide sequence comparison (antigenomic-sense) of the 3' leader (nt 1-30) of a biologically derived, low-passage HPIV2 V98 (SEQ ID NO:18) strain, two different preparations (V94(a) (SEQ ID NO:19) and V94 (b) (SEQ ID NO:20) of the biologically derived V94 strain of HPIV2, and the recombinant V94 consensus cDNA sequence (SEQ ID NO:12). Nucleotide position 15 (bolded and underlined) is the only position found to vary in these virus preparations.
FIG. 3B shows sequence electropherograms from uncloned RT-PCR products derived from primary isolates of virus recovered from the lower respiratory tract of four African green monkeys infected with V94 (preparation a). The sequence obtained from V94(a) passaged in LLC-MK2 cells was used as a control.

The virus preparation used to determine HPIV2/V94 consensus sequence, however, was prepared from V94 that was first passaged nine times on Vero cells and then passaged multiple times on LLC-MK2 cells (V94(b)). Therefore, the possibility existed that V94(a) and V94(b) were not genetically identical. We determined the sequence of V94(a) and compared it to the V94(b) consensus sequence (FIG. 3A). Sequence was determined by sequencing overlapping RT-PCR cDNA fragments spanning the entire genome as described previously (WO04/027037; Skiadopoulos et al., 2003, *J. Virol.*, 77:270-279). Sequence electropherograms from uncloned RT-PCR products derived from primary isolates of virus recovered from the lower repsiratory tracts of four African green monkeys infected with V94(a) are shown in FIG. 3b. V94(a) passaged in LLC-MK2 cells is shown as a control. The electorpherograms were generated by ABI Prism Sequencing Analysis software (version 3.0) (Perkin-Elmer, UK) on a Perkin-Elmer ABI 3100 sequencer with a Big Dye sequencing kit (Perkin-Elmer Applied Biosystems, Warrington, UK).

Sequencing of Viral Isolates of Tracheal Lavage of African Green Monkeys

Tracheal lavage samples collected from four African green monkeys that were infected with V94(a) (including a mixed population of T or C at nucleotide position 15) were amplified by a single passage on LLC-MK2 monolayers. As a control, the original V94(a) inoculum was also passaged once on LLC-MK2 cells. Primary isolates were similarly prepared from tracheal lavage samples from animals that were administered rV94 (including exclusively C at position 15). These primary isolates were harvested after incubation at 32° C. for six days and vRNA was prepared and used in 3' RACE (Rapid Amplification of cDNA Ends) reactions to generate RT-PCR products spanning the 3' end of the viral genome. The PCR products were sequenced in the vicinity of nucleotide position 15.

Results and Discussion

The sequences of V94 (a) and V94 (b) were found to be completely identical except for a single position in the 3' leader. While the sequence at nucleotide position 15 of V94 (b) is a cytosine (C, antigenomic cDNA sense), the sequence determined for the V94(a) preparation administered to the monkeys was a mixture of cytosine and thymidine (T). This difference in sequence is likely a spontaneous change that arose during passage of V94 in Vero cells and was selected for by multiple passage on LLC-MK2 cells. The sequences of the recombinant versions of V94 (rV94 and rV94Not) had a C at position 15. Because this is the only sequence difference observed between the biologically derived V94 (V94(a)) and the recombinant V94 (V94(b)), we conclude that a C at position 15 has an attenuating effect on replication of the virus in the lower respiratory tract of African green monkeys.

Interestingly, there was no difference between the level of replication of the biologically derived V94 and the rV94 in the respiratory tract of hamsters. Moreover, the growth characteristics of the biologically derived and recombinant viruses in vitro were also identical (Table 3), indicating that this nucleotide substitution specifies a host-range att phenotype, i.e., attenuated in African green monkeys but is a wild type phenotype in hamsters. The results in nonhuman primates are likely predictive of results in humans. Therefore, T15C constitutes another novel attenuating mutation available for producing a live-attenuated HPIV2 vaccine.

In the sequence electropherogram of the V94(a) preparation used to inoculate the monkeys, the relative signal strengths of the C and T nucleotides at position 15 were approximately the same (not shown), suggesting that the preparation included populations of viruses bearing C or T that were nearly equivalent in abundance. Based on this observation, we suggest that the population of T-including virus might account for the higher level of V94 replication observed in the monkeys that received V94 (a). If this was indeed the case, then the virus that replicated in the lungs of these animals should predominately have a T at position 15.

To test this hypothesis, tracheal lavage samples collected from four African green monkeys that were infected with V94(a) (including a mixed population of T or C at nucleotide position 15) were amplified by a single passage on LLC-MK2 monolayers. As shown in FIG. 3B, the original V94(a) inoculum passaged once on LLC-MK2 cells maintained a mixed population (C+T) at the position-15 locus. Significantly, each of the isolates obtained from animals that had been administered the same V94(a) inoculum now had a predominantly homogeneous population (T15) at the same locus. This indicates that the virus population including a T at position 15 is the predominant replicating population in the respiratory tract of the monkeys.

Primary isolates were similarly prepared from tracheal lavage samples from animals that were administered rV94 (including exclusively C at position 15). Sequence analysis of RT-PCR products prepared from vRNA purified from these isolates verified that the input virus sequence at this position (C-15) was unchanged (data not shown), indicating that it is genetically stable following in vivo replication. Thus, a C at position 15 of the V94 genome is associated with attenuation in the lower respiratory tract of African green monkeys, but not in hamsters. Since rV94 is not restricted for replication at 39° C. or 40° C. (Table 3), this change does not confer a ts phenotype.

Because T15C confers a non-ts, host-range att phenotype, it is a useful component to include in a live-attenuated HPIV2 vaccine. FIG. 2 indicated that the attenuation specified by the Y948L mutation is additive with the 3' leader T15C mutation, indicating that ts and non-ts att mutations are compatible and additive. These mutations provide a method to incrementally adjust the level of attenuation of an HPIV2 vaccine virus.

EXAMPLE 3

Recombinant HPIV2 Including Separate Polynucleotides Encoding P or V Protein

The bicistronic P/V gene of HPIV2 encodes the nucleocapsid-associated P phosphoprotein (395 amino acids) and the accessory V protein (225 amino acids) from two overlapping reading frames (Ohgimoto et al., 1990). Since the V protein is not absolutely required for virus replication (Kato et al., 1997; Fukuhara et al., 2002; He et al., 2002; Sun et al., 2004), it is an attractive target for the introduction of mutations that do not interfere with the replication of a vaccine virus in cell culture but attenuate the virus for replication in a human host. The overlapping nature of the P and V ORFs, however, greatly restricts the number and types of mutations that can be introduced into the V protein without also affecting the P protein (and vice versa). To overcome this obstacle we have undertaken a novel approach and modified the HPIV2 V94 strain antigenomic cDNA such that the P and V proteins are encoded by a separate polynucleotide encoding a P protein and a monocistronic polynucleotide encoding a V protein, respectively. This will allow the introduction of a variety of substitution and deletion mutations in the V protein without compromising the integrity of the P protein.

The alternative reading frames of the P/V gene are accessed by an unusual cotranscriptional editing of the P/V gene mRNA (Ohgimoto et al., 1990), a feature unique to most members of the Paramyxovirinae subfamily of Paramyxoviruses (Kawano et al., 1993; Chanock, Murphy, and Collins, 2001). The HPIV2 P protein is translated from a P/V gene mRNA, which has had two additional guanosine residues, inserted into the heptaguanosine stretch (underlined) (TT-TAAGAGGGGGGG, V94 nucleotide 2474-2487; SEQ ID NO:8) of the mRNA editing site. This editing site, which shares common features with the editing sites of other paramyxoviruses, includes the uninterrupted heptaguanosine tract (Jacques and Kolakofsky, 1991; Chanock, Murphy, and Collins, 2001) (FIGS. 4A and B). During mRNA synthesis, the viral polymerase is believed to insert one or more guanosine residues by stuttering at the heptaguanosine tract. In the case of HPIV2, two guanosine residues are inserted. The inserted residues shift the translational reading frame at codon 164 and the translation machinery subsequently accesses an alternative ORF specifying the carboxy-terminal half of the P protein (aa 165-395). The shorter V protein is generated from an unedited P/V gene mRNA. Thus the P and V proteins have a common amino-terminal sequence (aa 1-164) and unique carboxy-termini (FIG. 4C).

Paramyxovirus V proteins have a range of functions from activities affecting virus morphogenesis to counteracting host cell innate immune response (Parisien et al., 2001; Andrejeva et al., 2002a; Parisien, Lau, and Horvath, 2002). Analogous to *Rubulavirus* V proteins, putative HPIV2 V protein activities include RNA binding (Lin, Paterson, and Lamb, 1997), viral nucleoprotein (N) binding (Precious et al., 1995; Randall and Bermingham, 1996; Watanabe et al., 1996a), subcellular localization activities (Watanabe et al., 1996b; Rodriguez, Cruz, and Horvath, 2004), E2- or E3-like ubiquitin ligase activity (Ulane and Horvath, 2002), induction of ubiquitination, STAT binding and degradation (Andrejeva et al., 2002a; Kozuka et al., 2003), binding to the damage specific DNA binding protein (DDBP) (Lin et al., 1998; Andrejeva et al., 2002b), blocking apoptosis (Sun et al., 2004), and zinc ion binding via a highly conserved cysteine rich carboxy-terminal domain (Liston and Briedis, 1994; Paterson et al., 1995; Huang et al., 2000). The active sites for many of these functions are thought to localize to separate domains of the V protein, while some activities likely overlap.

Since the V protein is not absolutely required for virus replication (Kato et al., 1997; Fukuhara et al., 2002; He et al., 2002; Sun et al., 2004), it is an attractive target for the introduction of mutations that do not interfere with the replication of a vaccine virus in cell culture but attenuate the virus for replication in a human host. Paramyxoviruses that express a V protein with a carboxy-terminal deletion were found to be defective for replication in vivo and sometimes in vitro, including in Vero cells which do not express antiviral interferons α and β (Kato et al., 1997; Delenda et al., 1997; Durbin et al., 1999; Kawano et al., 2001; He et al., 2002; Park et al., 2003). Thus, it is important to determine the protein domains of the HPIV2 V protein that are responsible for the growth promoting function in vitro and for the anti-innate immune response activities in vivo. However, the overlapping nature of the P and V ORFs greatly restricts the number and types of mutations that can be introduced into the V protein without also affecting the P protein (and vice versa).

Materials and Methods
Generation and Recovery of Recombinant HPIV2 Including a Genetic Rearrangement of the P/V Gene.

To facilitate subsequent cloning steps, unique endonuclease restriction recognition sequences [AscI (nt 1986-1993); BstEII (nt 3188-3194); AgeI (nt 3192-3197); SacII (nt 3221-3226)] were introduced into rV94Not cDNA (FIG. 5A). The restriction sites were introduced by nucleotide substitution PCR mutagenesis in the non-coding regions upstream (AscI) or downstream (BstEII, AgeI, and SneII) of the P/V ORFs using mutagenic PCR primers designed to achieve the sequence indicated in FIG. 5B or 5C. The restrictions sites were translationally silent because they occurred outside of the ORFs. Recombinant V94 comprising the introduced restrictions sites (termed rV94N/A/B) was recovered as described in Example 1.

The naturally occurring P/V ORF in rV94N/A/B was replaced by a modified P ORF (SEQ ID NO:2) encoding only the P protein. In the P gene unit, the editing site was modified by the insertion of two nucleotides, which serve to access the appropriate P reading frame specifying the carboxy-terminal half of the P protein, and the translationally-silent substitution of 3 guanosines to prevent editing of the mRNA encoding P protein. Four additional nucleotides (TGAC; SEQ ID NO:14) were inserted in the non-coding region flanking the P ORF (FIG. 5C) so that the genome length of the final construct conformed to the "rule of six" (Calain and Roux, 1993; Kolakofsky et al., 1998; Vulliemoz and Roux, 2001). The editing sites were modified by PCR mutagenesis (Moeller et al., 2001) using mutagenic PCR primers designed to achieve the sequences indicated in FIG. 6. Silent third base codon substitutions in the editing site are bolded and underlined. The two nucleotides (TG) inserted to access the 3'-terminal half of the P ORF are indicated by arrows. Parainfluenza viruses generated from cDNAs that do not conform to the rule of six accumulate spontaneous nucleotide deletion or insertion mutations at positions that cannot be predicted (Skiadopoulos et al., 2003b), and therefore cannot be reliably used for live-vaccine production.

Figure 6:
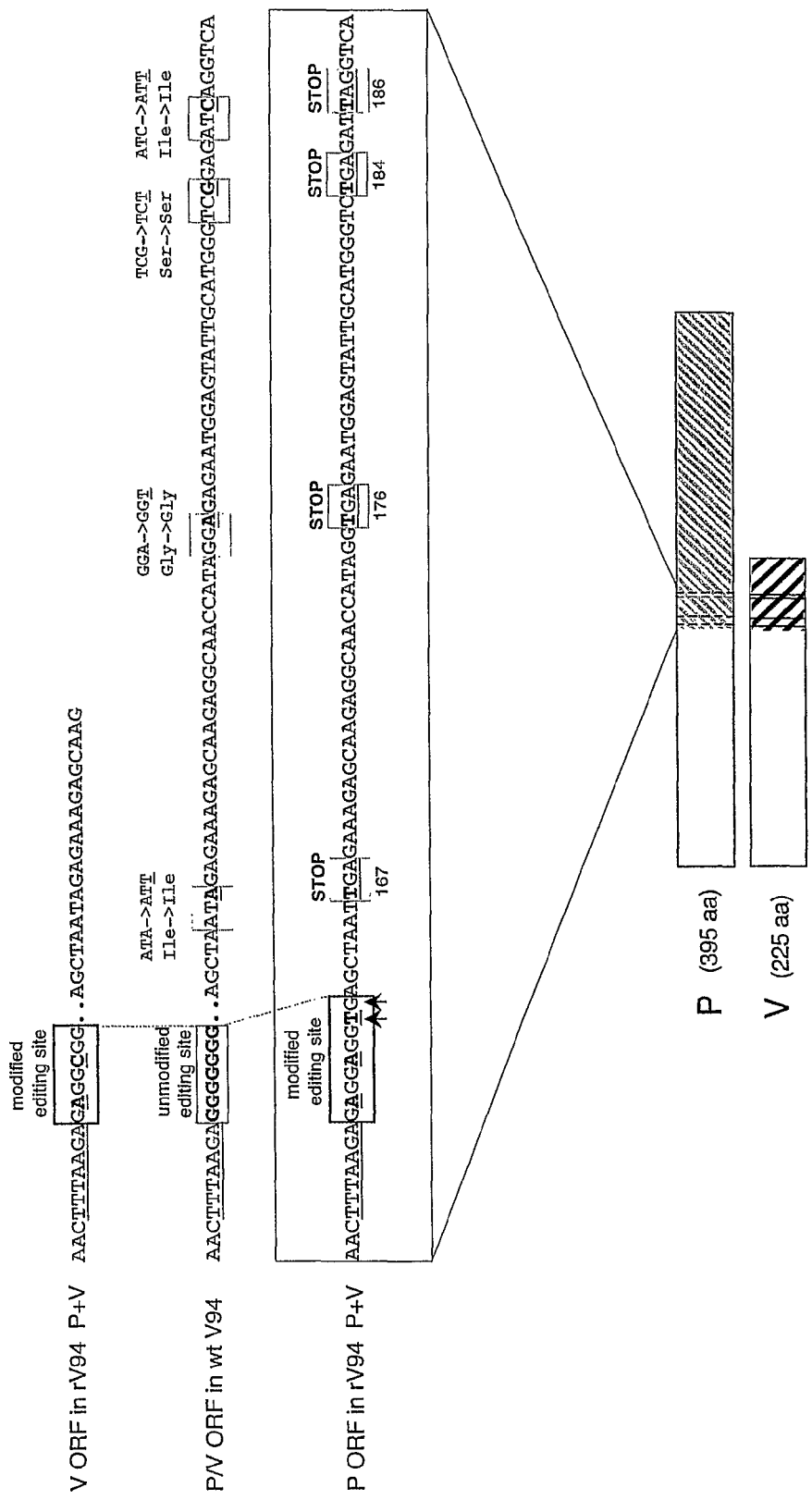
FIG. 6 shows the common amino acid domains (white box) and distinct carboxy-terminal domains (hatched boxes) of P protein and V protein. The exploded view shows the sequence modifications introduced into the wild type P/V ORF to create a V ORF that expresses only V protein and a P ORF that expresses only P protein. Silent third base codon substitutions in the editing site are underlined and in bold type. The top sequence (V ORF in rV94 P+V) shows modifications introduced into the editing site of the modified V gene that inactivate the editing site and allow for expression of V protein only (SEQ ID NO:9). The middle sequence (P/V ORF in wt V94) shows unedited wild type P/V sequence, including the wild type editing site (SEQ ID NO:8). The bottom sequence (P ORF in V94 P+V) shows modifications introduced into the wild type P/V ORF that allow for expression of P protein and not the V protein. The 2 nucleotides (TG) inserted into the editing site to access the 3'-terminal half of the P ORF are indicated by the arrows (↑; SEQ ID NO: 10). Proposed third base codon substitution mutations (underlined and in bold type) that introduce stop codons in the V ORF reading frame (V ORF codon positions 167, 176, 184, and 186 are boxed) but do not alter the P protein sequence are shown. Dashed lines show the relative positions of the silent third codon mutations in P protein. Solid lines show the relative positions of the stop codons in V protein.

To further ensure that a V protein could not be generated from the polynucleotide encoding P protein, silent third base codon substitution mutations were introduced into the P ORF downstream of the ablated editing site by PCR (Moeller et al., 2001) using mutagenic primers designed to achieve the nucleotide sequence indicated in FIG. 6. These nucleotide substitutions encoded stop codons in the overlapping V reading frame. Thus, in the unlikely event that the translation apparatus shifts translation back into the V reading frame, translation termination codons would be encountered at codon positions 167, 176, 184 and 186 of the V ORF remnant. The modified P ORF was subcloned into rV94N/A/B cDNA between the AscI and BstEII sites, as indicated in FIG. 5C, using standard methods.

A modified V ORF designed to encode only the V protein (SEQ ID NO:3). The P and V genes were separated by a non-coding polynucleotide spacer sequence. The spacer sequence was located upstream of the modified V ORF (FIG. 5C). The spacer sequence included an AgeI site and upstream gene end (GE), intergenic (IG), and gene start (GS) transcription signals that served to terminate P gene transcription and initiate V gene transcription, respectively.

The editing site in the V gene unit was engineered so that the heptaguanosine run in the mRNA editing site was mutated by the substitution of 2 guanosines to either adenosine or cytosine (FIG. 6) using PCR mutagenesis and standard molecular cloning techniques (Moeller et al., 2001; Skiadopolous et al., 2003, *J. Virol.*, 77:270-279). This mutation eliminated RNA editing so that the gene unit encoded only the V protein, and was silent at the level of translation. Four additional nucleotides (TGAC) were inserted in the non-coding region flanking the V ORF (FIG. 5C) so that the genome length of the final construct conformed to the "rule of six" (Calain and Roux, 1993; Kolakofsky et al., 1998; Vulliemoz and Roux, 2001).

It is believed that the phasing of the first adenosine in the transcription gene start sequence, with respect to its position in the polyhexameric genome, may be important for the appropriate production of the viral mRNA of all members of the Paramyxovirinae subfamily (Kolakofsky et al., 1998). Therefore, the cis-acting transcription gene start sequence of the inserted polynucleotide encoding V protein was designed so that the phasing of the first adenosine (antigenomic cDNA sequence) in the signal sequence was in a 6n+1 position (FIG. 5C), similar to that of the naturally occurring P/V gene start cis-acting transcription control regions.

The modified V ORF was subcloned into pFLC V94 using the AgeI and SacII restrictions sites, as indicated in FIG. 5c, using standard methods. The transcription control sequences upstream of the P ORF and downstream of the V ORF were not affected by the cis-acting transcription gene start sequence in the V gene unit and the phasing of the polynucleotide encoding P protein in rV94 P+V remained unaltered.

Figure 10A:
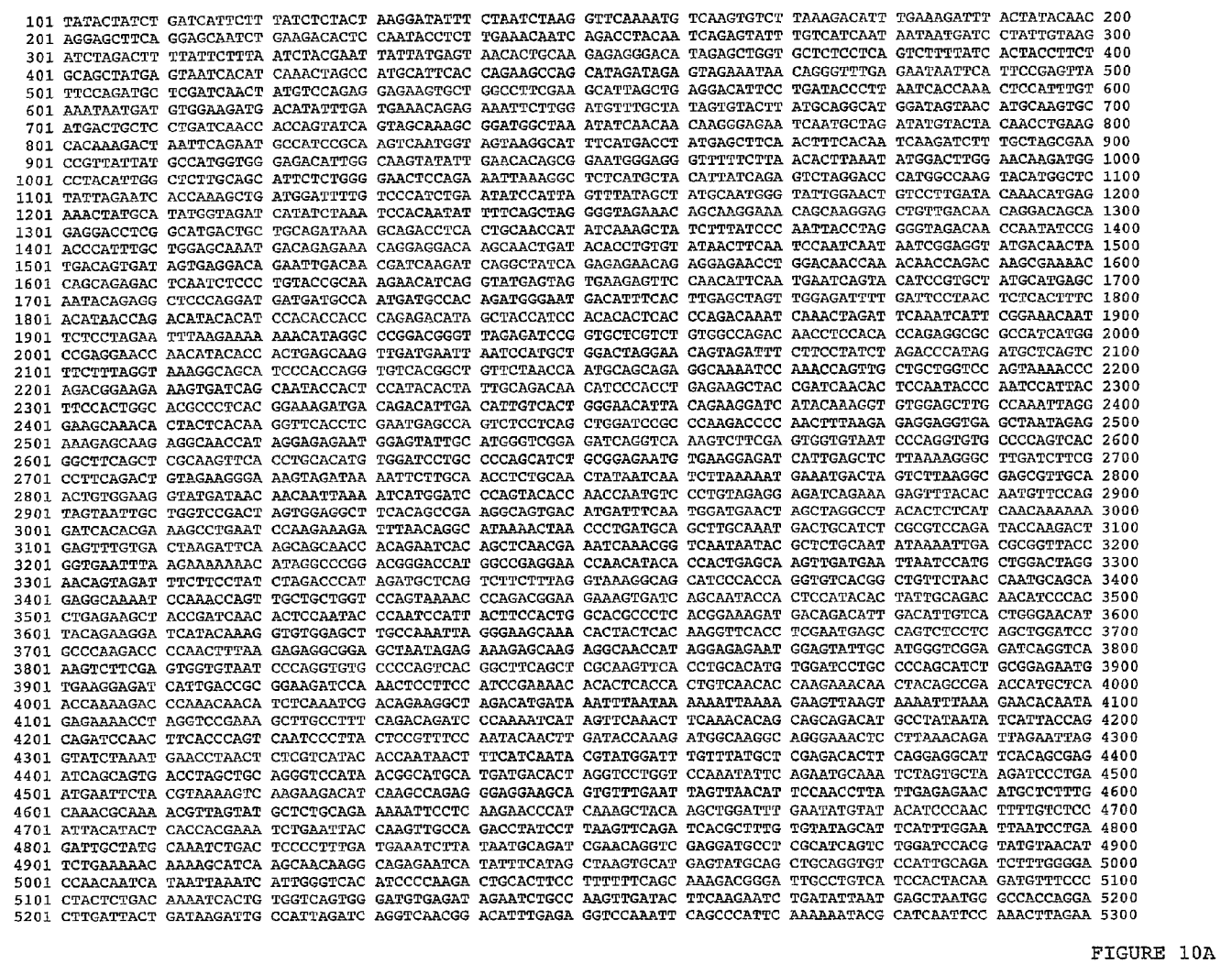
Figure 10B:
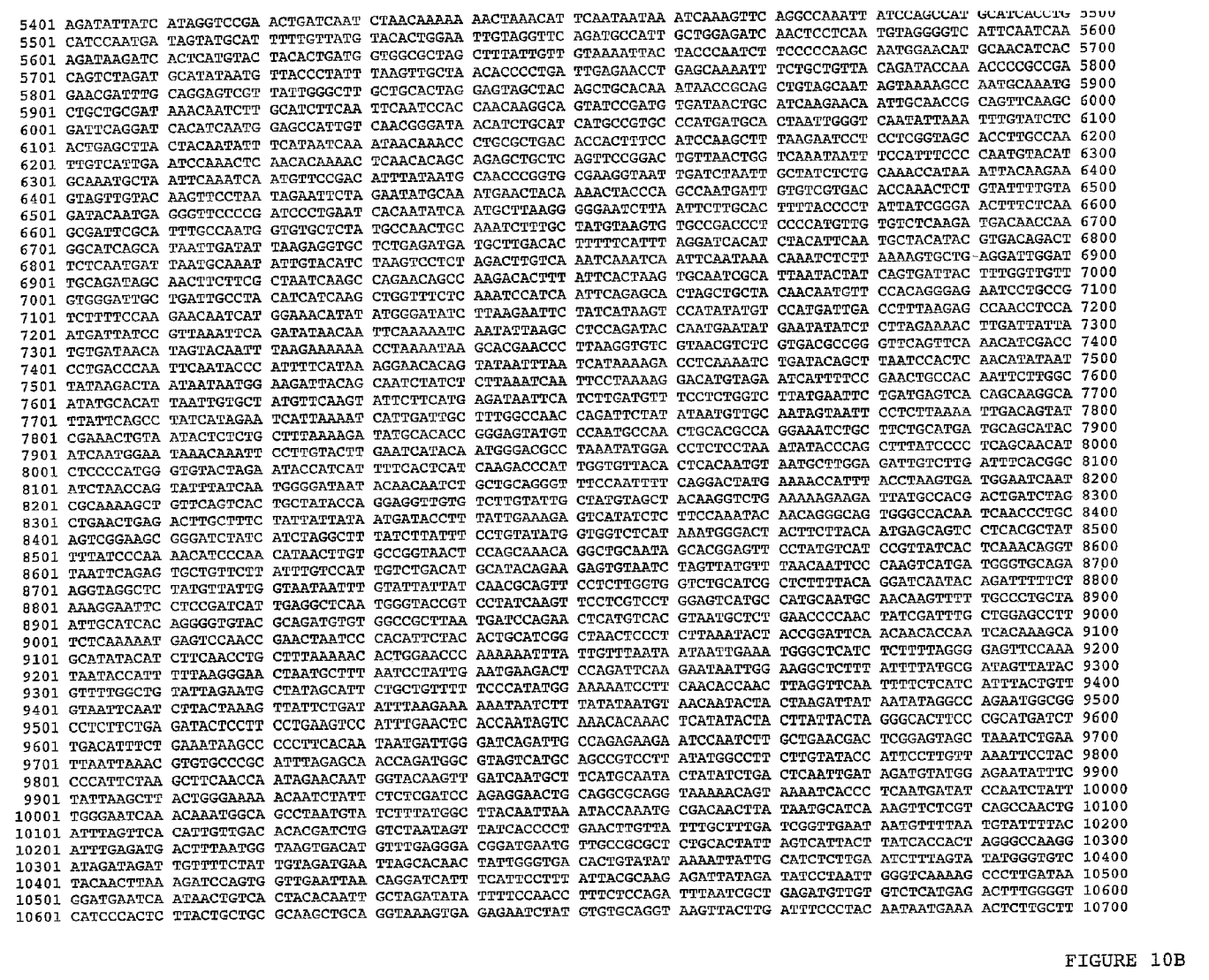
Figure 10C:
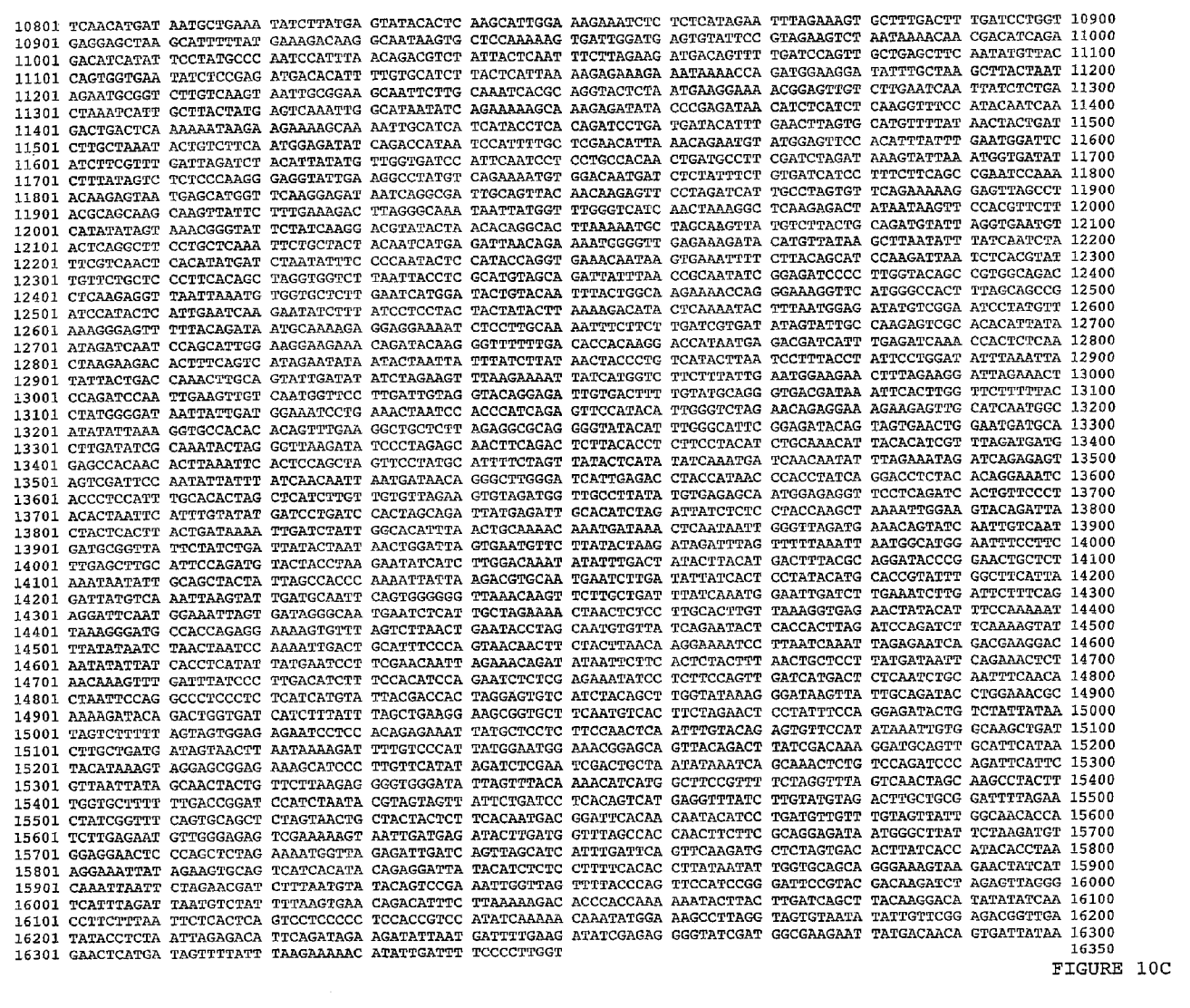

The final full-length antigenomic cDNA plasmid (pFLC V94 P+V) was sequenced using standard methods. HPIV2 P+V cDNA (SEQ ID NO:1) was 16,350 nucleotides in length and is shown in FIG. 10. The supernumerary polynucleotide encoding V protein increased the number of encoded mRNAs to 7, which is one mRNA more than that of wild type HPIV2.

Recovery and sequencing of a recombinant V94 P+V.

Recombinant HPIV2 expressing the P and V proteins from separated polynucleotide (rV94 P+V) was recovered in HEp-2 cells using the full-length antigenomic HPIV2 plasmid pFLC V94 P+V and the HPIV2 N, P and L support plasmids in the reverse genetics system described in Example 1. Virus recovered from transfected HEp-2 cells was passaged onto Vero cell monolayer culture or onto LLC-MK2 cells. The recovered virus, rV94 P+V, grew to high titer in LLC-MK2 ($1.3 \times 10^8$ $\log_{10}$ $TOD_{50}$/ml) and in Vero cell culture ($5 \times 10^8$ $\log_{10}$ $TCID_{50}$/ml).

Figure 7:
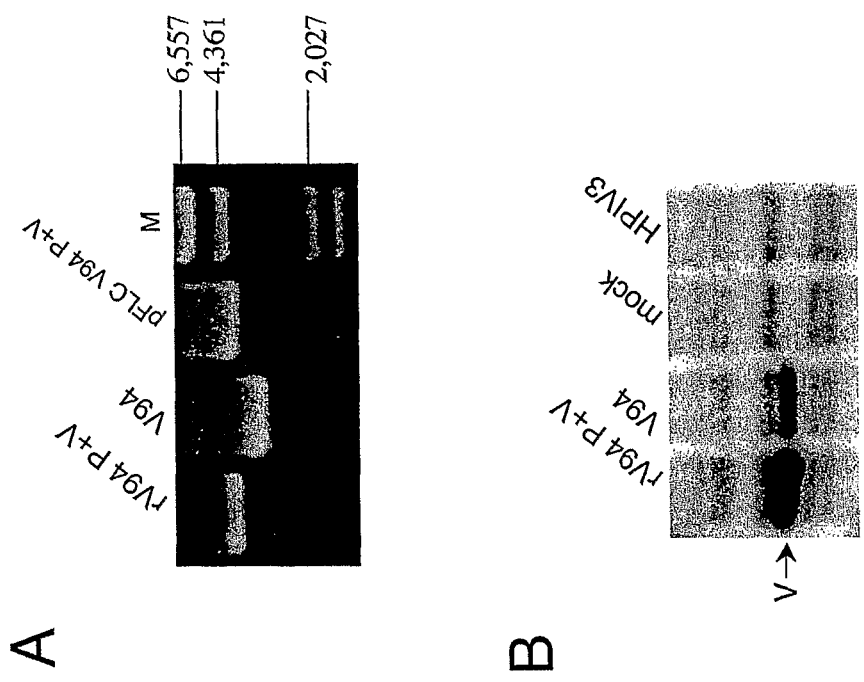
FIG. 7A shows agarose gel electrophoresis analysis of RT-PCR products obtained from vRNA purified from V94 or rV94 P+V infected cells, or PCR product generated from the antigenomic V94 P+V cDNA (pFLC V94 P+V) using a sense oligonucleotide (V94, nucleotides 395-425) and an antisense oligonucleotide (V94, nucleotides 3567-3598). The predicted size for the PCR product obtained from wild type V94 is 3203 bp. The predicted size of the PCR product obtained from the P+V gene rearrangement for both rV94 P+V and pFLC V94 P+V is 3899 bp.
FIG. 7B shows a Western blot analysis demonstrating the production of V protein in wild type V94 or rV94 P+V infected Vero cells.

The identity of the recovered virus was confirmed by RT-PCR amplification from purified viral RNA (vRNA) of a subgenomic fragment including a polynucleotide encoding P or V protein (FIG. 7A). Oligonucleotide primers approximately 25-30 nucleotides in length, in both sense and anti-sense orientation, spanning the HPIV2 genome were used as sequencing primers. A PCR product was not obtained from similar RT-PCR reactions that did not have the RT enzyme added to them (data not shown), indicating that the RT-PCR product was generated from an RNA template rather than from contaminating plasmid DNA. The size of the PCR product obtained from rV94 P+V was compared to that of the biologically derived V94 virus and to a PCR product obtained with the pFLC V94 P+V cDNA.

Western Blot of Protein Extracts

To demonstrate that the V protein was produced by rV94 P+V, total cellular protein was purified from Vero cells infected with rV94 P+V or wild type V94. Uninfected Vero cells and Vero cells infected with HPIV3 were used as controls. Forty-eight hours after infection Vero cell monolayers were harvested and washed once with PBS. Cell pellets were disrupted with 2× sample buffer (100 mM Tris-Cl [pH 6.8], 4% sodium dodecylsulfate, 20% glycerol, 0.2% bromophenol blue, 200 mM dithiothreitol) and centrifuged through Qiashredders (Qiagen). Five µl of each sample was electrophoresed through sodium dodecylsulfate –4 to 20% polyacrylamide gels (Invitrogen) and transferred to a nitrocellulose membrane. Membranes were incubated with rabbit polyclonal antisera raised against a V protein specific peptide representing amino acids 186 to 201 of HPIV2 V protein (SEQ ID NO:45). Bound antibodies were visualized by incubation with horseradish peroxidase-coupled goat anti-rabbit immunoglobulin G antibodies and chemilluminescence (Pierce). Western blot analysis of protein extracts from the infected cells confirmed that V protein was produced by rV94 P+V (FIG. 7B).

Replication of rV94 P+V In Vitro at Permissive and Restrictive Temperatures.

The kinetics of replication of rV94 P+V was determined by inoculation of HPIV2 onto LLC-MK2 monolayers on 6-well plates at a multiplicity of infection (m.o.i.) of 0.01. rV94Not and the ts and att recombinant rdel1724 were used as control viruses and the cultures were incubated at 32° C. 0.5 ml of medium from each well was harvested and replaced with 0.5 ml of fresh OptiMEM medium at 0 hr and at 24 hour intervals for up to 7 days post-infection. Virus present in the daily harvest was quantified by titration on LLC-MK2 monolayers in 96-well plates incubated at 32° C.

Recombinant HPIV2 Expressing RSV F Protein (rV94 RSV-F)

Recombinant HPIV2 expressing RSV F protein were constructed as described in WO04/027037. Briefly, a polynucleotide expressing RSV subtype A fusion (F) protein ORF as a supernumerary HPIV2 gene unit was cloned into V94Not cDNA upstream of the N coding sequence and under the control of the cis-acting HPIV2 transcription signals. Recombinant V94Not vector viruses expressing RSV F protein were recovered using a reverse genetics system that employed a full length HPIV2/rV94Not plasmid and three HPIV2 support plasmids as described in WO04/027037 and Example 1.

Results and Discussion

A modified HPIV2 V94 strain antigenomic cDNA comprising separate polynucleotides encoding P and V proteins was prepared and designated rV94 P+V. The identity of the recombinant V94 P+V virus was confirmed by RT-PCR amplification from purified viral RNA (vRNA) of a subgenomic fragment including the P and V genes (FIG. 7A). As shown in FIG. 7A, the RT-PCR product obtained from rV94 P+V vRNA is approximately 700 bp larger than that obtained from wild type V94 and is the same size as that obtained from the pFLC V94 P+V cDNA.

The genomic sequence of rV94 P+V was determined by sequencing of the RT-PCR products spanning the entire genome generated from purified vRNA, with the exception of nucleotides 16287 to 16350 from the 5' end which were not sequenced. The genetic structure of the monocistronic polynucleotides was confirmed by sequence analysis. Several spontaneous point mutations were also identified. These nucleotide substitutions were not encoded in the pFLC P+V cDNA and thus arose during propagation of the virus in cell culture. Coding substitutions identified included mutations Phe25Leu and Leu27Pro in the V protein, and Asn1120His and Asp1892Asn in the L protein. Western blot analysis of protein extracts from the infected cells confirmed that V protein was produced by rV94 P+V (FIG. 7B).

Figure 8:
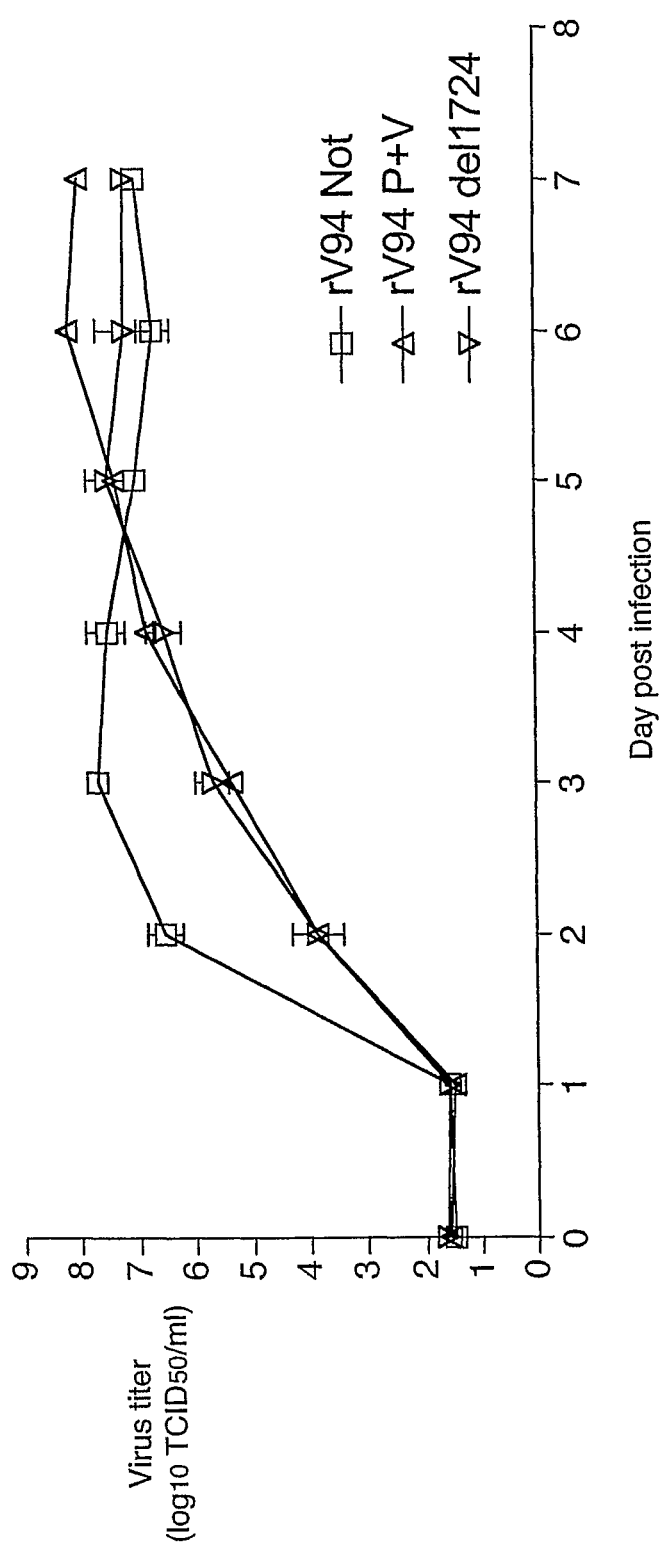
FIG. 8 shows the growth of recombinant V94 in Vero cell culture. Virus titers are shown as mean $\log_{10}$ TCID$_{50}$/ml of triplicate samples. Error bars indicate standard error.

The growth kinetics of rV94 P+V in Vero cells was similar to that of rdel1724 (FIG. 8), which grew at a moderately slower rate than rV94Not. However, the peak virus titers of rV94 P+V and rdel1724, which are an important consideration for the manufacture of live-vaccine viruses, were comparable to that of rV94Not.

The ability of rV94 P+V to replicate at higher temperatures (37-40° C.) was also examined. rV94 P+V was found to be highly ts with a shut-off temperature of 38° C. (Table 3). In contrast, rV94 and rV94 N/A/B did not exhibit significant shut off even at 40° C. Replication of a previously described recombinant HPIV2 expressing the RSV fusion F protein from a supernumerary gene unit inserted upstream of the HPIV2 N ORF (rV94 RSV-F; WO 04/027037) was found to not be restricted at 39 or 40° C. (Table 3). This data indicated an increase in the number of inserted supernumerary gene units or an increase in genome length was not responsible for the ts phenotype of rV94 P+V. Recombinant HPIV3 with gene unit insertions has been shown to exhibit a moderate level of temperature sensitivity (Skiadopoulos et al., 2000; Skiadopoulos et al., 2002). The basis for this phenomenon, however, is not known.

Replication of rV94 P+V in hamsters was examined as described in Example 1. rV94 P+V was approximately 800-fold restricted in replication in the upper respiratory tract and approximately 100-fold restricted in lower respiratory tract of hamsters (FIG. 1 and Table 3) compared to parent viruses rV94Not and rV94 N/A/B. Similarly, recombinant HPIV2 expressing RSV F protein (rV94 RSV-F) was attenuated for replication in the upper and lower respiratory tract of hamsters. The basis for the high level of attenuation conferred by these supernumerary gene unit insertions is not known. The level of attenuation, however, is more pronounced than that observed in other recombinant paramyxoviruses including additional gene units (e.g., HPIV3 and HPIV1) (Skiadopoulos et al., 2000; Skiadopoulos et al., 2002).

Figure 4:
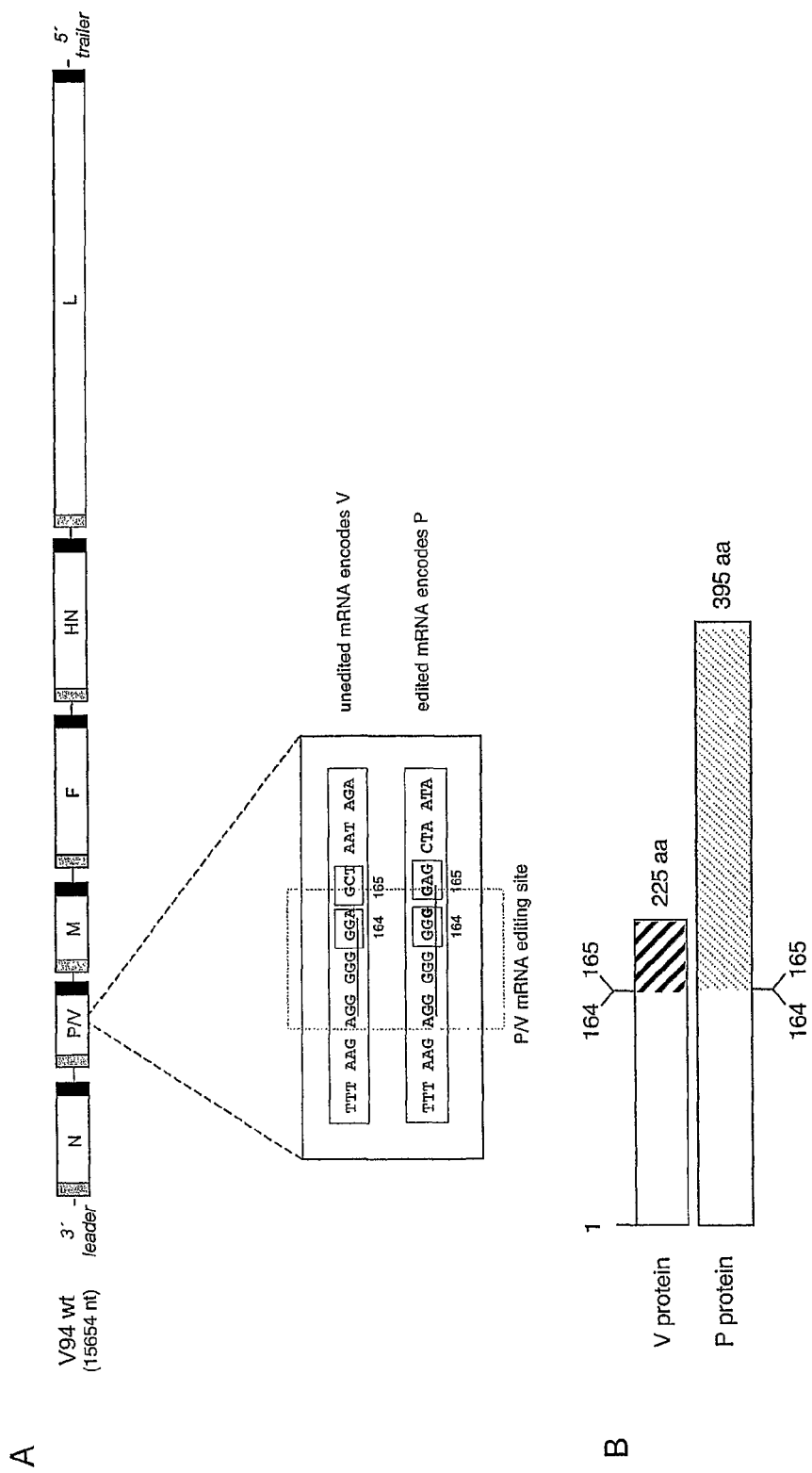
FIGS. 4A-B show a diagrammatic representation of the genomic organization of wild type HPIV2 V94.

Replication of rV94 P+V in African green monkeys was examined as described in Example 1. As shown in FIG. 4 and Table 4, rV94 P+V was approximately 250-fold restricted for replication in the lower respiratory tract of African green monkeys compared to biologically derived V94. rV94 P+V was approximately 6-fold restricted for replication in the upper respiratory tract of African green monkeys compared to parent rV94Not virus. This difference, however, is not statistically significant. It remains to be determined whether attenuation in monkeys conferred by the T15C substitution in the 3' leader is additive to attenuation conferred by the P/V gene rearrangement. Attenuation of rV94 P+V in hamsters was independent of the T15C mutation as both rV94Not and rV94 P+V possessed the mutation and rV94 P+V was significantly more restricted in replication than rV94Not. The independent contribution of the P+V rearrangement to attenuation for African green monkeys will be determined by constructing and characterizing V94 P+V lacking the T15 C mutation.

Although the rV94 P+V vaccine candidate is highly attenuated for replication in monkeys, it conferred a high level of protection against the wild type HPIV2 challenge virus (Table 5). Thus, the P/V ORF rearrangement and supernumerary polynucleotide insertion are useful as a method of conferring an attenuation phenotype to HPIV2. Importantly, the attenuating effect of the gene rearrangement, similar to that of the codon substitutions and deletion mutations described in Examples 1 and 2, should be genetically and phenotypically stable following replication in vivo.

The ability to recover recombinant HPIV2 encoding P and V proteins from separate genes will be valuable in examining the domain structure of the V protein and for introducing attenuating V protein mutations. Candidate sites for mutations in V protein are summarized in FIG. 9. These include mutations in the highly conserved cysteine-rich carboxy-terminal domain, a critical domain of the V protein shown to bind zinc ions and to play a major role in several V protein activities in other paramyxoviruses. Mutations in the N-terminal half of V protein directly affect RNA binding or STAT binding and degradation may be used to attenuate HPIV2. Useful mutations will minimally impact virus replication in vitro, disable the ability of the virus to block interferon response resulting in virus that are more immunogenic, and/or attenuate virus replication in a human host. Mutations at the indicated sites include, but are not limited to, amino acid substitutions or deletion of the indicated residues.

TABLE 6

ACCAAGGGGAGAATCAGATGGCATCGTTATATGACGAATTGCAAAAAGATTACGTAGGTCCGGA

ACCACTAGATTCCGGTGCCGGTAACGATCTCAGTTTTATACTATCTGATCATTCTTTATCTCTA

CTAAGGATATTTCTAATCTAAGGTTCAAAATGTCAAGTGTCTTAAAGACATTTGAAAGATTTAC

TATACAACAGGAGCTTCAGGAGCAATCTGAAGACACTCCAATACCTCTTGAAACAATCAGACCT

ACAATCAGAGTATTTGTCATCAATAATAATGATCCTATTGTAAGATCTAGACTTTTATTCTTTA

ATCTACGAATTATTATGAGTAACACTGCAAGAGAGGGACATAGAGCTGGTGCTCTCCTCAGTCT

TTTATCACTACCTTCTGCAGCTATGAGTAATCACATCAAACTAGCCATGCATTCACCAGAAGCC

AGCATAGATAGAGTAGAAATAACAGGGTTTGAGAATAATTCATTCCGAGTTATTCCAGATGCTC

GATCAACTATGTCCAGAGGAGAAGTGCTGGCCTTCGAAGCATTAGCTGAGGACATTCCTGATAC

CCTTAATCACCAAACTCCATTTGTAAATAATGATGTGGAAGATGACATATTTGATGAAACAGAG

AAATTCTTGGATGTTTGCTATAGTGTACTTATGCAGGCATGGATAGTAACATGCAAGTGCATGA

CTGCTCCTGATCAACCACCAGTATCAGTAGCAAAGCGGATGGCTAAATATCAACAACAAGGGAG

AATCAATGCTAGATATGTACTACAACCTGAAGCACAAAGACTAATTCAGAATGCCATCCGCAAG

TCAATGGTAGTAAGGCATTTCATGACCTATGAGCTTCAACTTTCACAATCAAGATCTTTGCTAG

CGAACCGTTATTATGCCATGGTGGGAGACATTGGCAAGTATATTGAACACAGCGGAATGGGAGG

GTTTTTCTTAACACTTAAATATGGACTTGGAACAAGATGGCCTACATTGGCTCTTGCAGCATTC

TCTGGGGAACTCCAGAAATTAAAGGCTCTCATGCTACATTATCAGAGTCTAGGACCCATGGCCA

AGTACATGGCTCTATTAGAATCACCAAAGCTGATGGATTTTGTCCCATCTGAATATCCATTAGT

TTATAGCTATGCAATGGGTATTGGAACTGTCCTTGATACAAACATGAGAAACTATGCATATGGT

AGATCATATCTAAATCCACAATATTTTCAGCTAGGGGTAGAAACAGCAAGGAAACAGCAAGGAG

CTGTTGACAACAGGACAGCAGAGGACCTCGGCATGACTGCTGCAGATAAAGCAGACCTCACTGC

AACCATATCAAAGCTATCTTTATCCCAATTACCTAGGGGTAGACAACCAATATCCGACCCATTT

GCTGGAGCAAATGACAGAGAAACAGGAGGACAAGCAACTGATACACCTGTGTATAACTTCAATC

CAATCAATAATCGGAGGTATGACAACTATGACAGTGATAGTGAGGACAGAATTGACAACGATCA

AGATCAGGCTATCAGAGAGAACAGAGGAGAACCTGGACAACCAAACAACCAGACAAGCGAAAAC

CAGCAGAGACTCAATCTCCCTGTACCGCAAAGAACATCAGGTATGAGTAGTGAAGAGTTCCAAC

TABLE 6-continued

```
ATTCAATGAATCAGTACATCCGTGCTATGCATGAGCAATACAGAGGCTCCCAGGATGATGATGC
CAATGATGCCACAGATGGGAATGACATTTCACTTGAGCTAGTTGGAGATTTTGATTCCTAACTC
TCACTTTCACATAACCAGACATACACATCCACACCACCCAGAGACATAGCTACCATCCACACAC
TCACCCAGACAAATCAAACTAGATTCAAATCATTCGGAAACAATTCTCCTAGAATTTAAGAAAA
AAACATAGGCCCGGACGGGTTAGAGATCCGGTGCTCGTCTGTGGCCAGACAACCTCCACACCAG
AGCCACACAATCATGGCCGAGGAACCAACATACACCACTGAGCAAGTTGATGAATTAATCCATG
CTGGACTAGGAACAGTAGATTTCTTCCTATCTAGACCCATAGATGCTCAGTCTTCTTTAGGTAA
AGGCAGCATCCCACCAGGTGTCACGGCTGTTCTAACCAATGCAGCAGAGGCAAAATCCAAACCA
GTTGCTGCTGGTCCAGTAAAACCCAGACGGAAGAAAGTGATCAGCAATACCACTCCATACACTA
TTGCAGACAACATCCCACCTGAGAAGCTACCGATCAACACTCCAATACCCAATCCATTACTTCC
ACTGGCACGCCCTCACGGAAAGATGACAGACATTGACATTGTCACTGGGAACATTACAGAAGGA
TCATACAAAGGTGTGGAGCTTGCCAAATTAGGGAAGCAAACACTACTCACAAGGTTCACCTCGA
ATGAGCCAGTCTCCTCAGCTGGATCCGCCCAAGACCCCAACTTTAAGAGGGGGGAGCTAATAG
AGAAAGAGCAAGAGGCAACCATAGGAGAGAATGGAGTATTGCATGGGTCGGAGATCAGGTCAAA
GTCTTCGAGTGGTGTAATCCCAGGTGTGCCCCAGTCACGGCTTCAGCTCGCAAGTTCACCTGCA
CATGTGGATCCTGCCCCAGCATCTGCGGAGAATGTGAAGGAGATCATTGAGCTCTTAAAAGGGC
TTGATCTTCGCCTTCAGACTGTAGAAGGGAAAGTAGATAAAATTCTTGCAACCTCTGCAACTAT
AATCAATCTTAAAAATGAAATGACTAGTCTTAAGGCGAGCGTTGCAACTGTGGAAGGTATGATA
ACAACAATTAAAATCATGGATCCCAGTACACCAACCAATGTCCCTGTAGAGGAGATCAGAAAGA
GTTTACACAATGTTCCAGTAGTAATTGCTGGTCCGACTAGTGGAGGCTTCACAGCCGAAGGCAG
TGACATGATTTCAATGGATGAACTAGCTAGGCCTACACTCTCATCAACAAAAAAGATCACACGA
AAGCCTGAATCCAAGAAAGATTTAACAGGCATAAAACTAACCCTGATGCAGCTTGCAAATGACT
GCATCTCGCGTCCAGATACCAAGACTGAGTTTGTGACTAAGATTCAAGCAGCAACCACAGAATC
ACAGCTCAACGAAATCAAACGGTCAATAATACGCTCTGCAATATAAAATGCGGTGCAATCACAC
AAGAGACATTCAACATGCATCCGATCAAGATCCAAACTCCTTCCATCCGAAAACACACTCACCA
CTGTCAACACCAAGAAACAACTACAGCCGAACCATGCTCAACCAAAAGACCCAAACAACATCTC
AAATCGACAGAAGGCTAGACATGATAAATTTAATAAAAAATTAAAAGAAGTTAAGTAAAATTTA
AAGAACACAATAGAGAAAACCTAGGTCCGAAAGCTTGCCTTTCAGACAGATCCCAAAATCATAG
TTCAAACTTCAAACACAGCAGCAGACATGCCTATAATATCATTACCAGCAGATCCAACTTCACC
CAGTCAATCCCTTACTCCGTTTCCAATACAACTTGATACCAAAGATGGCAAGGCAGGGAAACTC
CTTAAACAGATTAGAATTAGGTATCTAAATGAACCTAACTCTCGTCATACACCAATAACTTTCA
TCAATACGTATGGATTTGTTTATGCTCGAGACACTTCAGGAGGCATTCACAGCGAGATCAGCAG
TGACCTAGCTGCAGGGTCCATAACGGCATGCATGATGACACTAGGTCCTGGTCCAAATATTCAG
AATGCAAATCTAGTGCTAAGATCCCTGAATGAATTCTACGTAAAAGTCAAGAAGACATCAAGCC
AGAGGGAGGAAGCAGTGTTTGAATTAGTTAACATTCCAACCTTATTGAGAGAACATGCTCTTTG
CAAACGCAAAACGTTAGTATGCTCTGCAGAAAAATTCCTCAAGAACCCATCAAAGCTACAAGCT
GGATTTGAATATGTATACATCCCAACTTTTGTCTCCATTACATACTCACCACGAAATCTGAATT
ACCAAGTTGCCAGACCTATCCTTAAGTTCAGATCACGCTTTGTGTATAGCATTCATTTGGAATT
AATCCTGAGATTGCTATGCAAATCTGACTCCCCTTTGATGAAATCTTATAATGCAGATCGAACA
GGTCGAGGATGCCTCGCATCAGTCTGGATCCACGTATGTAACATTCTGAAAAACAAAAGCATCA
```

TABLE 6-continued

```
AGCAACAAGGCAGAGAATCATATTTCATAGCTAAGTGCATGAGTATGCAGCTGCAGGTGTCCAT
TGCAGATCTTTGGGGACCAACAATCATAATTAAATCATTGGGTCACATCCCCAAGACTGCACTT
CCTTTTTTCAGCAAAGACGGGATTGCCTGTCATCCACTACAAGATGTTTCCCCTACTCTGACAA
AATCACTGTGGTCAGTGGGATGTGAGATAGAATCTGCCAAGTTGATACTTCAAGAATCTGATAT
TAATGAGCTAATGGGCCACCAGGACTTGATTACTGATAAGATTGCCATTAGATCAGGTCAACGG
ACATTTGAGAGGTCCAAATTCAGCCCATTCAAAAAATACGCATCAATTCCAAACTTAGAAGCCA
TCAACTGAATGCTCCAGCATCTAGGAATAGAACAACAACTAAGTCATACCATTATTGACCATAC
AATAATCAACAATTTTAGCCAACTGATTACTAAGATATTATCATAGGTCCGAACTGATCAATCT
AACAAAAAAACTAAACATTCAATAATAAATCAAAGTTCAGGCCAAATTATCCAGCCATGCATCA
CCTGCATCCAATGATAGTATGCATTTTTGTTATGTACACTGGAATTGTAGGTTCAGATGCCATT
GCTGGAGATCAACTCCTCAATGTAGGGGTCATTCAATCAAAGATAAGATCACTCATGTACTACA
CTGATGGTGGCGCTAGCTTTATTGTTGTAAAATTACTACCCAATCTTCCCCCAAGCAATGGAAC
ATGCAACATCACCAGTCTAGATGCATATAATGTTACCCTATTTAAGTTGCTAACACCCCTGATT
GAGAACCTGAGCAAAATTTCTGCTGTTACAGATACCAAACCCCGCCGAGAACGATTTGCAGGAG
TCGTTATTGGGCTTGCTGCACTAGGAGTAGCTACAGCTGCACAAATAACCGCAGCTGTAGCAAT
AGTAAAAGCCAATGCAAATGCTGCTGCGATAAACAATCTTGCATCTTCAATTCAATCCACCAAC
AAGGCAGTATCCGATGTGATAACTGCATCAAGAACAATTGCAACCGCAGTTCAAGCGATTCAGG
ATCACATCAATGGAGCCATTGTCAACGGGATAACATCTGCATCATGCCGTGCCCATGATGCACT
AATTGGGTCAATATTAAATTTGTATCTCACTGAGCTTACTACAATATTTCATAATCAAATAACA
AACCCTGCGCTGACACCACTTTCCATCCAAGCTTTAAGAATCCTCCTCGGTAGCACCTTGCCAA
TTGTCATTGAATCCAAACTCAACACAAAACTCAACACAGCAGAGCTGCTCAGTTCCGGACTGTT
AACTGGTCAAATAATTTCCATTTCCCCAATGTACATGCAAATGCTAATTCAAATCAATGTTCCG
ACATTTATAATGCAACCCGGTGCGAAGGTAATTGATCTAATTGCTATCTCTGCAAACCATAAAT
TACAAGAAGTAGTTGTACAAGTTCCTAATAGAATTCTAGAATATGCAAATGAACTACAAAACTA
CCCAGCCAATGATTGTGTCGTGACACCAAACTCTGTATTTTGTAGATACAATGAGGGTTCCCCG
ATCCCTGAATCACAATATCAATGCTTAAGGGGGAATCTTAATTCTTGCACTTTTACCCCTATTA
TCGGGAACTTTCTCAAGCGATTCGCATTTGCCAATGGTGTGCTCTATGCCAACTGCAAATCTTT
GCTATGTAAGTGTGCCGACCCTCCCCATGTTGTGTCTCAAGATGACAACCAAGGCATCAGCATA
ATTGATATTAAGAGGTGCTCTGAGATGATGCTTGACACTTTTTCATTTAGGATCACATCTACAT
TCAATGCTACATACGTGACAGACTTCTCAATGATTAATGCAAATATTGTACATCTAAGTCCTCT
AGACTTGTCAAATCAAATCAATTCAATAAACAAATCTCTTAAAAGTGCTGAGGATTGGATTGCA
GATAGCAACTTCTTCGCTAATCAAGCCAGAACAGCCAAGACACTTTATTCACTAAGTGCAATCG
CATTAATACTATCAGTGATTACTTTGGTTGTTGTGGGATTGCTGATTGCCTACATCATCAAGCT
GGTTTCTCAAATCCATCAATTCAGAGCACTAGCTGCTACAACAATGTTCCACAGGGAGAATCCT
GCCGTCTTTTCCAAGAACAATCATGGAAACATATATGGGATATCTTAAGAATTCTATCATAAGT
CCATATATGTCCATGATTGACCTTTAAGAGCCAACCTCCAATGATTATCCGTTAAATTCAGATA
TAACAATTCAAAAATCAATATTAAGCCTCCAGATACCAATGAATATGAATATATCTCTTAGAAA
ACTTGATTATTATGTGATAACATAGTACAATTTAAGAAAAAACCTAAAATAAGCACGAACCCTT
AAGGTGTCGTAACGTCTCGTGACGCCGGGTTCAGTTCAAACATCGACCCCTGACCCAATTCAAT
ACCCATTTTCATAAAGGAACACAGTATAATTTAATCATAAAAGACCTCAAAATCTGATACAGCT
```

TABLE 6-continued

```
TAATCCACTCAACATATAATTATAAGACTAATAATAATGGAAGATTACAGCAATCTATCTCTTA
AATCAATTCCTAAAAGGACATGTAGAATCATTTTCCGAACTGCCACAATTCTTGGCATATGCAC
ATTAATTGTGCTATGTTCAAGTATTCTTCATGAGATAATTCATCTTGATGTTTCCTCTGGTCTT
ATGAATTCTGATGAGTCACAGCAAGGCATTATTCAGCCTATCATAGAATCATTAAAATCATTGA
TTGCTTTGGCCAACCAGATTCTATATAATGTTGCAATAGTAATTCCTCTTAAAATTGACAGTAT
CGAAACTGTAATACTCTCTGCTTTAAAAGATATGCACACCGGGAGTATGTCCAATGCCAACTGC
ACGCCAGGAAATCTGCTTCTGCATGATGCAGCATACATCAATGGAATAAACAAATTCCTTGTAC
TTGAATCATACAATGGGACGCCTAAATATGGACCTCTCCTAAATATACCCAGCTTTATCCCCTC
AGCAACATCTCCCCATGGGTGTACTAGAATACCATCATTTTCACTCATCAAGACCCATTGGTGT
TACACTCACAATGTAATGCTTGGAGATTGTCTTGATTTCACGGCATCTAACCAGTATTTATCAA
TGGGGATAATACAACAATCTGCTGCAGGGTTTCCAATTTTCAGGACTATGAAAACCATTTACCT
AAGTGATGGAATCAATCGCAAAAGCTGTTCAGTCACTGCTATACCAGGAGGTTGTGTCTTGTAT
TGCTATGTAGCTACAAGGTCTGAAAAAGAAGATTATGCCACGACTGATCTAGCTGAACTGAGAC
TTGCTTTCTATTATTATAATGATACCTTTATTGAAAGAGTCATATCTCTTCCAAATACAACAGG
GCAGTGGGCCACAATCAACCCTGCAGTCGGAAGCGGGATCTATCATCTAGGCTTTATCTTATTT
CCTGTATATGGTGGTCTCATAAATGGGACTACTTCTTACAATGAGCAGTCCTCACGCTATTTTA
TCCCAAAACATCCCAACATAACTTGTGCCGGTAACTCCAGCAAACAGGCTGCAATAGCACGGAG
TTCCTATGTCATCCGTTATCACTCAAACAGGTTAATTCAGAGTGCTGTTCTTATTTGTCCATTG
TCTGACATGCATACAGAAGAGTGTAATCTAGTTATGTTTAACAATTCCCAAGTCATGATGGGTG
CAGAAGGTAGGCTCTATGTTATTGGTAATAATTTGTATTATTATCAACGCAGTTCCTCTTGGTG
GTCTGCATCGCTCTTTTACAGGATCAATACAGATTTTTCTAAAGGAATTCCTCCGATCATTGAG
GCTCAATGGGTACCGTCCTATCAAGTTCCTCGTCCTGGAGTCATGCCATGCAATGCAACAAGTT
TTTGCCCTGCTAATTGCATCACAGGGGTGTACGCAGATGTGTGGCCGCTTAATGATCCAGAACT
CATGTCACGTAATGCTCTGAACCCCAACTATCGATTTGCTGGAGCCTTTCTCAAAAATGAGTCC
AACCGAACTAATCCCACATTCTACACTGCATCGGCTAACTCCCTCTTAAATACTACCGGATTCA
ACAACACCAATCACAAAGCAGCATATACATCTTCAACCTGCTTTAAAAACACTGGAACCCAAAA
AATTTATTGTTTAATAATAATTGAAATGGGCTCATCTCTTTTAGGGGAGTTCCAAATAATACCA
TTTTTAAGGGAACTAATGCTTTAATCCTATTGAATGAAGACTCCAGATTCAAGAATAATTGGAA
GGCTCTTTATTTTATGCGATAGTTATACGTTTTGGCTGTATTAGAATGCTATAGCATTCTGCTG
TTTTTCCCATATGGAAAAATCCTTCAACACCAACTTAGGTTCAATTTTCTCATCATTTACTGTT
GTAATTCAATCTTACTAAAGTTATTCTGATATTTAAGAAAAAATAATCTTTATATAATGTAACA
ATACTACTAAGATTATAATATAGGCCAGAATGGCGGCCTCTTCTGAGATACTCCTTCCTGAAGT
CCATTTGAACTCACCAATAGTCAAACACAAACTCATATACTACTTATTACTAGGGCACTTCCCG
CATGATCTTGACATTTCTGAAATAAGCCCCCTTCACAATAATGATTGGGATCAGATTGCCAGAG
AAGAATCCAATCTTGCTGAACGACTCGGAGTAGCTAAATCTGAATTAATTAAACGTGTGCCCGC
ATTTAGAGCAACCAGATGGCGTAGTCATGCAGCCGTCCTTATATGGCCTTCTTGTATACCATTC
CTTGTTAAATTCCTACCCCATTCTAAGCTTCAACCAATAGAACAATGGTACAAGTTGATCAATG
CTTCATGCAATACTATATCTGACTCAATTGATAGATGTATGGAGAATATTTCTATTAAGCTTAC
TGGGAAAAACAATCTATTCTCTCGATCCAGAGGAACTGCAGGCGCAGGTAAAAACAGTAAAATC
ACCCTCAATGATATCCAATCTATTTGGGAATCAAACAAATGGCAGCCTAATGTATCTTTATGGC
```

TABLE 6-continued

```
TTACAATTAAATACCAAATGCGACAACTTATAATGCATCAAAGTTCTCGTCAGCCAACTGATTT
AGTTCACATTGTTGACACACGATCTGGTCTAATAGTTATCACCCCTGAACTTGTTATTTGCTTT
GATCGGTTGAATAATGTTTTAATGTATTTTACATTTGAGATGACTTTAATGGTAAGTGACATGT
TTGAGGGACGGATGAATGTTGCCGCGCTCTGCACTATTAGTCATTACTTATCACCACTAGGGCC
AAGGATAGATAGATTGTTTTCTATTGTAGATGAATTAGCACAACTATTGGGTGACACTGTATAT
AAAATTATTGCATCTCTTGAATCTTTAGTATATGGGTGTCTACAACTTAAAGATCCAGTGGTTG
AATTAACAGGATCATTTCATTCCTTTATTACGCAAGAGATTATAGATATCCTAATTGGGTCAAA
AGCCCTTGATAAGGATGAATCAATAACTGTCACTACACAATTGCTAGATATATTTTCCAACCTT
TCTCCAGATTTAATCGCTGAGATGTTGTGTCTCATGAGACTTTGGGGTCATCCCACTCTTACTG
CTGCGCAAGCTGCAGGTAAAGTGAGAGAATCTATGTGTGCAGGTAAGTTACTTGATTTCCCTAC
AATAATGAAAACTCTTGCTTTTTTCCACACAATTTTAATCAATGGTTATCGTAGAAAGAAGAAT
GGAATGTGGCCTCCACTTATACTTCCTAAAAATGCATCAAAAAGCTTAATAGAGTTTCAACATG
ATAATGCTGAAATATCTTATGAGTATACACTCAAGCATTGGAAAGAAATCTCTCTCATAGAATT
TAGAAAGTGCTTTGACTTTGATCCTGGTGAGGAGCTAAGCATTTTTATGAAAGACAAGGCAATA
AGTGCTCCAAAAAGTGATTGGATGAGTGTATTCCGTAGAAGTCTAATAAAACAACGACATCAGA
GACATCATATTCCTATGCCCAATCCATTTAACAGACGTCTATTACTCAATTTCTTAGAAGATGA
CAGTTTTGATCCAGTTGCTGAGCTTCAATATGTTACCAGTGGTGAATATCTCCGAGATGACACA
TTTTGTGCATCTTACTCATTAAAAGAGAAAGAAATAAAACCAGATGGAAGGATATTTGCTAAGC
TTACTAATAGAATGCGGTCTTGTCAAGTAATTGCGGAAGCAATTCTTGCAAATCACGCAGGTAC
TCTAATGAAGGAAAACGGAGTTGTCTTGAATCAATTATCTCTGACTAAATCATTGCTTACTATG
AGTCAAATTGGCATAATATCAGAAAAAGCAAAGAGATATACCCGAGATAACATCTCATCTCAAG
GTTTCCATACAATCAAGACTGACTCAAAAAATAAGAAGAAAAGCAAAATTGCATCATCATACCT
CACAGATCCTGATGATACATTTGAACTTAGTGCATGTTTTATAACTACTGATCTTGCTAAATAC
TGTCTTCAATGGAGATATCAGACCATAATCCATTTTGCTCGAACATTAAACAGAATGTATGGAG
TTCCACATTTATTTGAATGGATTCATCTTCGTTTGATTAGATCTACATTATATGTTGGTGATCC
ATTCAATCCTCCTGCCACAACTGATGCCTTCGATCTAGATAAAGTATTAAATGGTGATATCTTT
ATAGTCTCTCCCAAGGGAGGTATTGAAGGCCTATGTCAGAAAATGTGGACAATGATCTCTATTT
CTGTGATCATCCTTTCTTCAGCCGAATCCAAAACAAGAGTAATGAGCATGGTTCAAGGAGATAA
TCAGGCGATTGCAGTTACAACAAGAGTTCCTAGATCATTGCCTAGTGTTCAGAAAAAGGAGTTA
GCCTACGCAGCAAGCAAGTTATTCTTTGAAAGACTTAGGGCAAATAATTATGGTTTGGGTCATC
AACTAAAGGCTCAAGAGACTATAATAAGTTCCACGTTCTTCATATATAGTAAACGGGTATTCTA
TCAAGGACGTATACTAACACAGGCACTTAAAAATGCTAGCAAGTTATGTCTTACTGCAGATGTA
TTAGGTAATGTACTCAGGCTTCCTGCTCAAATTCTGCTACTACAATCATGAGATTAACAGAAA
ATGGGGTTGAGAAAGATACATGTTATAAGCTTAATATTTATCAATCTATTCGTCAACTCACATA
TGATCTAATATTTCCCCAATACTCCATACCAGGTGAAACAATAAGTGAAATTTTCTTACAGCAT
CCAAGATTAATCTCACGTATTGTTCTGCTCCCTTCACAGCTAGGTGGTCTTAATTACCTCGCAT
GTAGCAGATTATTTAACCGCAATATCGGAGATCCCCTTGGTACAGCCGTGGCAGACCTCAAGAG
GTTAATTAAATGTGGTGCTCTTGAATCATGGATACTGTACAATTTACTGGCAAGAAAACCAGGG
AAAGGTTCATGGGCCACTTTAGCAGCCGATCCATACTCATTGAATCAAGAATATCTTTATCCTC
CTACTACTATACTTAAAAGACATACTCAAAATACTTTAATGGAGATATGTCGGAATCCTATGTT
```

TABLE 6-continued

```
AAAGGGAGTTTTTACAGATAATGCAAAAGAGGAGGAAAATCTCCTTGCAAAATTTCTTCTTGAT
CGTGATATAGTATTGCCAAGAGTCGCACACATTATAATAGATCAATCCAGCATTGGAAGGAAGA
AACAGATACAAGGGTTTTTTGACACCACAAGGACCATAATGAGACGATCATTTGAGATCAAACC
ACTCTCAACTAAGAAGACACTTTCAGTCATAGAATATAATACTAATTATTTATCTTATAACTAC
CCTGTCATACTTAATCCTTTACCTATTCCTGGATATTTAAATTATATTACTGACCAAACTTGCA
GTATTGATATCTAGAAGTTTAAGAAAATTATCATGGTCTTCTTTATTGAATGGAAGAACTTT
AGAAGGATTAGAAACTCCAGATCCAATTGAAGTTGTCAATGGTTCCTTGATTGTAGGTACAGGA
GATTGTGACTTTTGTATGCAGGGTGACGATAAATTCACTTGGTTCTTTTTACCTATGGGGATAA
TTATTGATGGAAATCCTGAAACTAATCCACCCATCAGAGTTCCATACATTGGGTCTAGAACAGA
GGAAAGAAGAGTTGCATCAATGGCATATATTAAAGGTGCCACACACAGTTTGAAGGCTGCTCTT
AGAGGCGCAGGGGTATACATTTGGGCATTCGGAGATACAGTAGTGAACTGGAATGATGCACTTG
ATATCGCAAATACTAGGGTTAAGATATCCCTAGAGCAACTTCAGACTCTTACACCTCTTCCTAC
ATCTGCAAACATTACACATCGTTTAGATGATGGAGCCACAACACTTAAATTCACTCCAGCTAGT
TCCTATGCATTTTCTAGTTATACTCATATATCAAATGATCAACAATATTTAGAAATAGATCAGA
GAGTAGTCGATTCCAATATTATTTATCAACAATTAATGATAACAGGGCTTGGGATCATTGAGAC
CTACCATAACCCACCTATCAGGACCTCTACACAGGAAATCACCCTCCATTTGCACACTAGCTCA
TCTTGTTGTGTTAGAAGTGTAGATGGTTGCCTTATATGTGAGAGCAATGGAGAGGTTCCTCAGA
TCACTGTTCCCTACACTAATTCATTTGTATATGATCCTGATCCACTAGCAGATTATGAGATTGC
ACATCTAGATTATCTCTCCTACCAAGCTAAAATTGGAAGTACAGATTACTACTCACTTACTGAT
AAAATTGATCTATTGGCACATTTAACTGCAAAACAAATGATAAACTCAATAATTGGGTTAGATG
AAACAGTATCAATTGTCAATGATGCGGTTATTCTATCTGATTATACTAATAACTGGATTAGTGA
ATGTTCTTATACTAAGATAGATTTAGTTTTTAAATTAATGGCATGGAATTTCCTTCTTGAGCTT
GCATTCCAGATGTACTACCTAAGAATATCATCTTGGACAAATATATTTGACTATACTTACATGA
CTTTACGCAGGATACCCGGAACTGCTCTAAATAATATTGCAGCTACTATTAGCCACCCAAAATT
ATTAAGACGTGCAATGAATCTTGATATTATCACTCCTATACATGCACCGTATTTGGCTTCATTA
GATTATGTCAAATTAAGTATTGATGCAATTCAGTGGGGGGTTAAACAAGTTCTTGCTGATTTAT
CAAATGGAATTGATCTTGAAATCTTGATTCTTTCAGAGGATTCAATGGAAATTAGTGATAGGGC
AATGAATCTCATTGCTAGAAAACTAACTCTCCTTGCACTTGTTAAAGGTGAGAACTATACATTT
CCAAAAATTAAAGGGATGCCACCAGAGGAAAAGTGTTTAGTCTTAACTGAATACCTAGCAATGT
GTTATCAGAATACTCACCACTTAGATCCAGATCTTCAAAAGTATTTATATAATCTAACTAATCC
AAAATTGACTGCATTTCCCAGTAACAACTTCTACTTAACAAGGAAAATCCTTAATCAAATTAGA
GAATCAGACGAAGGACAATATATTATCACCTCATATTATGAATCCTTCGAACAATTAGAAACAG
ATATAATTCTTCACTCTACTTTAACTGCTCCTTATGATAATTCAGAAACTCTAACAAAGTTTGA
TTTATCCCTTGACATCTTTCCACATCCAGAATCTCTCGAGAAATATCCTCTTCCAGTTGATCAT
GACTCTCAATCTGCAATTTCAACACTAATTCCAGGCCCTCCCTCTCATCATGTATTACGACCAC
TAGGAGTGTCATCTACAGCTTGGTATAAAGGGATAAGTTATTGCAGATACCTGGAAACGCAAAA
GATACAGACTGGTGATCATCTTTATTTAGCTGAAGGAAGCGGTGCTTCAATGTCACTTCTAGAA
CTCCTATTTCCAGGAGATACTGTCTATTATAATAGTCTTTTTAGTAGTGGAGAGAATCCTCCAC
AGAGAAATTATGCTCCTCTTCCAACTCAATTTGTACAGAGTGTTCCATATAAATTGTGGCAAGC
TGATCTTGCTGATGATAGTAACTTAATAAAAGATTTTGTCCCATTATGGAATGGAAACGGAGCA
```

TABLE 6-continued

```
GTTACAGACTTATCGACAAAGGATGCAGTTGCATTCATAATACATAAAGTAGGAGCGGAGAAAG
CATCCCTTGTTCATATAGATCTCGAATCGACTGCTAATATAAATCAGCAAACTCTGTCCAGATC
CCAGATTCATTCGTTAATTATAGCAACTACTGTTCTTAAGAGGGTGGGATATTAGTTTACAAA
ACATCATGGCTTCCGTTTTCTAGGTTTAGTCAACTAGCAAGCCTACTTTGGTGCTTTTTTGACC
GGATCCATCTAATACGTAGTAGTTATTCTGATCCTCACAGTCATGAGGTTTATCTTGTATGTAG
ACTTGCTGCGGATTTTAGAACTATCGGTTTCAGTGCAGCTCTAGTAACTGCTACTACTCTTCAC
AATGACGGATTCACAACAATACATCCTGATGTTGTTTGTAGTTATTGGCAACACCATCTTGAGA
ATGTTGGGAGAGTCGAAAAGTAATTGATGAGATACTTGATGGTTTAGCCACCAACTTCTTCGC
AGGAGATAATGGGCTTATTCTAAGATGTGGAGGAACTCCCAGCTCTAGAAAATGGTTAGAGATT
GATCAGTTAGCATCATTTGATTCAGTTCAAGATGCTCTAGTGACACTTATCACCATACACCTAA
AGGAAATTATAGAAGTGCAGTCATCACATACAGAGGATTATACATCTCCTTTTCACACCTTA
TAATATTGGTGCAGCAGGGAAAGTAAGAACTATCATCAAATTAATTCTAGAACGATCTTTAATG
TATACAGTCCGAAATTGGTTAGTTTTACCCAGTTCCATCCGGGATTCCGTACGACAAGATCTAG
AGTTAGGGTCATTTAGATTAATGTCTATTTTAAGTGAACAGACATTTCTTAAAAAGACACCCAC
CAAAAAATACTTACTTGATCAGCTTACAAGGACATATATATCAACCTTCTTTAATTCTCACTCA
GTCCTCCCCCTCCACCGTCCATATCAAAAACAAATATGGAAAGCCTTAGGTAGTGTAATATATT
GTTCGGAGACGGTTGATATACCTCTAATTAGAGACATTCAGATAGAAGATATTAATGATTTTGA
AGATATCGAGAGGGGTATCGATGGCGAAGAATTATGACAACAGTGATTATAAGAACTCATGATA
GTTTTATTTAAGAAAAACATATTGATTTTCCCCTTGGT
```

TABLE 7

```
ACCAAGGGGAGAATTAGATGGCATCGTTATATGACGAATTGCAAAAAGATTACGTAGGTCCGGA
ACCACTAGATTCCGGTGCCGGTAACGATTCCATTTTTATACTATCTGATCATTCTCTATCTCTA
CTAAGGATATTTCTAGTCTAAAGTTCAAAATGTCAAGTGTCTTAAAGACATTTGAAAGGTTTAC
TATACAACAAGAGCTTCAGGAGCAATCTGATGACACTCCAGTACCTCTTGAGACAATCAAACCT
ACAATAAGGGTATTTGTCATCAATAATAATGATCCTGCCATAAGGTCTAGACTTTTATTCTTTA
ATCTACGAATTATTATGAGTAACACCGCAAGAGAGGGACATAGAGCTGGTGCTCTCCTCAGTCT
CTTATCACTACCTTCTGCAGCTATGAGTAATCACATCAAACTAGCCATGCATTCACCAGAAGCC
AGCATAGATAGAGTAGAGATAACAGGGTTTGAGAATAATTCATTCCGAGTTATTCCAGATGCTC
GATCAACTATGTCCAGAGGAGAGGTGCTGGCCTTTGAAGCATTAGCTGAAGACATTCCTGATAC
CCTTAATCACCAAACTCCATTTGTAAATAATGATGTAGAAGATGACATGTTTGATGAAACAGAG
AAATTCTTAGATGTTTGCTACAGTGTACTTATGCAGGCATGGATAGTAACATGCAAGTGTATGA
CTGCTCCTGATCAGCCGCCAGTATCAGTAGCAAAGCGGATGGCTAAATATCAACAACAAGGGAG
AATCAATGCTAGGTATGTACTACAGCCTGAAGCACAAAGACTAATTCAGAATGCCATCCGCAAG
TCAATGGTAGTGAGGCATTTCATGACTTATGAGCTTCAACTTTCACAATCAAGATCTTTGCTAG
CAAACCGCTACTATGCTATGGTGGGAGACATTGGCAAGTACATTGAACACAGCGGAATGGGAGG
TTTTTTCTTAACACTTAAATATGGACTTGGAACAAGATGGCCTACATTGGCTCTTGCAGCATTC
TCTGGGGAACTCCAGAAATTAAAAGCTCTCATGCTACATTATCAGAGCCTAGGACCCATGGCCA
AGTACATGGCTCTATTAGAATCACCAAAGCTGATGGATTTTGTCCCATCTGAATATCCATTAGT
TTATAGTTATGCAATGGGTATTGGAACTGTCCTTGATACAAATATGAGAAACTATGCATATGGT
```

TABLE 7-continued

```
AGATCATATTTAAATCCGCAATATTTTCAGCTAGGAGTAGAAACAGCAAGGAAACAGCAGGGAG
CTGTTGACAACAGGACAGCAGAGGACCTCGGCATGACTGCTGCAGACAAAGCAGACCGCACTGC
AACCATATCAAAGCTATCTTTGTCCCAATTACCTAGGGGTAGACAACCAATATCTGACCCATTT
GCTGGAGCAAATGACAGAGAAATAGGAGGCCAAGCAAATGATACACCTGTATACAACTTCAATC
CAATCAATACTCGGAGGTATGACAACTATGACAGTGATGGTGAGGACAGAATTGACAACGATCA
AGATCAAGCTATCAGAGAGAACAGAGGAGAGCCTGGACAACTAAACAACCAGACAAGTGACAAC
CAGCAGAGACTCAATCTCTCCATACCGCAAAGAACATCAGGTATGAGCAGTGAAGAGTTCCAAC
ATTCAATGAATCAGTACATCCGTGCCATGCATGAGCAATACAGAGGACCCCAGGATGATGATAC
CAATGATGCCGCAGATGGGAATGACATTTCTCTTGAGCTAGTTGGGGATTTTGATTCCTAATTC
TCAATGTCATACAACCAGATATACACATCCACATCACTTAAAGATACAGCTGCCACCCACACAC
TCATCCAGACAAATCAAACCAGACTCACATCATTCAGAAACAATTCTCTCATAATTTAAGAAAA
AAACATAGGCCCGGACGGGTTTAAAATCTGGTGCTCGTTCGTGGTCTGACAACCTCCAAACCAG
AATCACACAATTATGGCCGAGGAACCAACATACACCACTGAGCAAGTTGATGAACTAATCCATG
CTGGACTGGGAACAGTAGATTTCTTCCTATCTAGACCCATAGATGCTCAATCTTCCCTAGGCAA
GGGCAGCATCCCACCAGGTGTCACAGCTGTTCTAACTAGTGCAGCAGAGGCAAAATCCAAACCA
GTTGCCGCTGGTCCAGTGAAACCCAGGCGGAAGAAAGTGATCAGCAATGCTACCCCATACACTG
TTGCAGACAATACTCCACCTGAGAAGCTACCAATCAACACCCCAATACCCAATCCATTACTTCC
ACTGGCACGCCCCCAAGGAAAGATGACAGACATTGACATTGTCACTGGGACCATTACAGAAGGA
TCGTACAAAGGTGTGGAGCTTGCTAAATTAGGGAAGCAAACACTACTCACAAGGTTCACCTCGA
ACGAGCCAGTCTCCTCAGCTGGATCCGCCCAAGACCCCAACTTTAAGAGGGGGGAGCTAATAG
AGAAAGAGCAAGAGGCAACCATAGGAGAGAATGGAGTATTGCATGGGTCGGAGATCAGGTCAAA
GTCTTCGAGTGGTGTAATCCCAGGTGTGCCCCAGTCACGGCCTCAGCTCGCAAGTTCACCTGCA
CATGCGGATCCTGCCCCAGCATCTGCGGAGAATGTGAAGGAGATCATTGAGCTCTTAAAGGGGC
TTGATCTTCGCCTTCAGACTGTAGAAGGGAAGGTAGATAAAATTCTTGCAACTTCCGCAACTAT
AATCAATCTTAAAAATGAAATGACTAGTCTCAAGGCGAGCGTTGCAACTGTGGAAGGTATGATA
ACAACAATTAAAATCATGGATCCCAGCACACCAACCAATGTCCCTGTAGAGGAGATCAGAAAGA
GCTTACACAATGCTCCAGTAGTAATTGCCGGTCCAACTAGTGGAGGCTTCACAGCCGAAGGCAG
TGATATGATTTCAATGGATGAACTAGCTAGACCTACACTCTCATCAACAAAAAAGATCACACGA
AAGCCTGAATCCAAGAAAGACTTAACAGGCACAAAACTAACCTTGATGCAGCTTGCAAATGACT
GCATCTCGCGTCCAGATACCAAGACTGAGTTCGTGACTAAGATTCAAGCAGCAACCACAGAATC
ACAGCTTAATGAAATCAAGCGGTCAATAATACGCTCTGCAATATAAAATGAGGTGCAATCACAC
AAGAGACACTCAACATGCATCCAATCAAGATCCAAATTCTGTCCATCCGAAAACACACCCACAA
TTGTTAACACCAAGAAACAACCACAGCCGAACCATGCTTAATCAAAAGATCCAAACAACATCTC
ACATCGACAGAAGGCTGGACATGATAAATTTAATAAAAAAGAAAAAAAGTCAAGTAAAATTTA
AAGGACACAATAGAGAAAATCTAGGTCCGAAAGCTTGCTTCCCGGACAGATCTCAAAATCATAG
TCTAAACCTCAAACACAGCAGCAGACATGCCCATAATATCATTACCAGCAGATCCAACTTCACC
CAGTCAATCCCTTACTCCGTTTCCAATACAACTTGACACCAAAGATGGCAAGGCAGGGAAACTC
CTTAAACAGATTCGAATTAGGTATCTAAATGAGCCTAATTCTCGCCATACACCAATAACTTTCA
TCAATACGTATGGATTTGTTTATGCTCGAGACACTTCAGGGGGCATTCACAGTGAGCTTAGTAG
TGACCTAGCTGCAGGGTCTATAACAGCATGCATGATGACGCTAGGCCCTGGTCCAAATATTCAG
```

TABLE 7-continued

AATGCAAATCTAGTGCTAAGATCTCTGAATGAATTCTACGTGAAAGTCAAGAAGACATCAAGCC

AGAGAGAGGAAGCAGTGTTTGAATTAGTTAACATTCCAACTTTATTGAGAGAACATGCTCTTTG

CAAACGCAAAATGTTAGTTTGCTCTGCAGAAAAGTTCCTCAAGAACCCGTCAAAGCTACAAGCT

GGATTTGAGTATGTATACATACCAACTTTTGTCTCCATTACATACTCACCACGAAATCTGAATT

ACCAAGTTGCCAGACCTATCCTTAAGTTCAGATCACGTTTTGTGTATAGCATTCATTTGGAATT

AATTCTGAGATTGCTATGCAAATCTGAATCCCCCTTAATGAAATCCTACAATGCAGACAAAACA

GGTCGGGGATGCCTTGCATCAGTCTGGATCCATGTATGTAACATTCTGAAAAACAAAAGCATCA

AGCAACAAGGCAGAGAATCATATTTCATAGCCAAGTGCATGAGCATGCAGCTGCAGGTGTCCAT

TGCAGATCTTTGGGGACCAACAATCATAATCAAATCATTGGGTCACATCCCCAAGACTGCACTT

CCTTTTTTCAGCAAAGATGGGATTGCCTGTCATCCATTACAAGATGTTTCCCCCACTCTGACAA

AATCACTGTGGTCAGTTGGATGTGAGATAGAATCTGCCAAGTTGATACTTCAAGAATCTGATCT

TAATGAGCTAATGGGCCACCAGGACCTTATCACTGATAAGATTGCCATCAGATCAGGTCAACGG

ACATTTGAGAGGTCCAAATTCAGCCCATTTAAAAAATATGCATCAATTCCAAACTTGGAAGCCA

TCAACTGAATGCTCCAGCATCTGAGAATAGAACCACAATTAAATCATACTATTAGTAACTATAC

AATAATAAACAATTTTAGTCAACAGATTACCAAGATGTTATCATAGGTCCGAACTGATCAATCT

AACAAAAAAACTAAACGTTCCATAATAAATCAACGTTCAGGTCAAAATACTCAACCATGCATCA

CCTACATCCAATGATAGTATGCATCTTTGTTATGTACACTGGAATTGTAGGTTCAGGTGCCATT

GCCGGAGACCAACTACTTAATATAGGGGTCATTCAATCAAAGATAAGATCACTCATGTACTATA

CTGATGGTGGTGCTAGCTTTATTGTTGTTAAATTGCTACCTAATCTTCCCCCAAGCAATGGAAC

ATGCAACATTACCAGTCTAGATGCATACAATGTTACCCTATTTAAATTACTGACACCCCTGATT

GAGAACCTGAGCAAAATCTCCGCTGTTACAGATACCAAAACCCGCCAAGAACGATTTGCAGGAG

TCGTTGTTGGACTTGCTGCATTAGGAGTAGCCACAGCTGCACAAATAACCGCAGCTGTAGCAAT

AGTTAAAGCTAATGCAAATGCTGCCGCGATTAATAATCTTGCATCTTCAATTCAATCAACAAAC

AAGGCAGTATCCGATGTGATAGATGCATCAAAAACAATTGCAACTGCAGTTCAAGCAATCCAGG

ATCATATCAATGGAGCTATTGTTAATGGGATAACATCTGCATCATGCCGTGCCCATGATGCACT

CATTGGGTCAATATTAAATCTTTATCTCACTGAGCTTACCACAATATTTCACAATCAAATAACA

AACCCTGCGCTGACACCGCTCTCCATCCAAGCTTTAAGAATTCTCCTCGGTAGCACCTTGCCAA

TTGTCATTGAGTCCAAACTCAACACAAACCTCAACACAGCAGAGCTGCTCAGCTCCGGACTGTT

AACTGGTCAAATAATTTCAATTTCCCCAATGTACATGCAAATGCTAATTCAAATCAATGTTCCG

ACATTTATAATGCAACCCGGTGCGAAGGTAATTGATCTAATTGCTATCTCTGCAAACCATAAAT

TGCAAGAAGTAGTTGTACAAGTTCCGAATAGGATTCTAGAGTATGCAAATGAACTACAAAATTA

TCCAGCCAATGACTGTGTTGTGACACCGAACTCTGTATTCTGTAGATACAATGAGGGTTCCCCT

ATCCCTGAATCACAATACCAATGCTTGAGGGGGAATCTTAATTCTTGCACTTTTACCCCTATTA

TCGGGAACTTTCTTAAGCGATTTGCATTTGCCAATGGTGTGCTCTATGCCAACTGCAAATCTTT

GCTATGTAAGTGTGCCGACCCTCCCCATGTGGTGTCCCAAGATGATACCCAAGGCATCAGCATA

ATTGATATTAAGAGATGCTCTGAGATGATGCTTGACACTTTCTCATTTAGGATCACATCTACGT

TCAATGCTACATACGTGACAGACTTCTCAATGATTAATGCAAATATTGTACATCTAAGTCCTCT

AGATTTGTCAAACCAAATCAATTCAATAAACAAATCTCTTAAAAGTGCTGAGGATTGGATTGCA

GATAGCAACTTCTTTGCTAATCAAGCCAGGACAGCCAAGACACTTTATTCATTAAGTGCAATAG

CATTAATACTATCAGTGATTACCTTGGTTGTTGTGGGATTGCTGATTGCCTACATCATCAAACT

TABLE 7-continued

```
AGTTTCCCAAATCCATCAATTCAGAGCGCTAGCTGCTACAACAATGTTCCACAGGGAAAATCCT
GCCTTCTTTTCCAAGAACAATCATGGAAACATATATGGGATATCTTAAGAAATCTATCACAAGT
CCATATATGTCCACAATTGATTCTTAAGAACCAACTTCCAATGATTATCCTTTAAACTTAAGTA
TAATAGTTTAAAAATTAACATTAAGCCTCCAGATACCAATGAATATGAATATATCTCTAAGAAA
ACCTGATTATTATGTGATAGTGTAGTACAATTTAAGAAAAAACCTAAAATAAGCACGAACCCTT
AAGGTGTCGTAACGTCTCGTGACACTGGGTTCAGTTCAAAAATCGACTTCTAATCTAATTTAAC
ACCCATTCTTATATAAGAACACAGTATAACTTAATTACAAAAGACCTCAAAAACTGACACAGCT
TAATCCACTCAACATATAATTGTAAGATTAATAATAATGGAAGATTACAGCAATCTATCTCTTA
AATCAATTCCTAAAAGGACATGTAGAATCATTTTCCGAACTGCCAGCCTTCTTGGAATATGCAC
ATTGATTGTTCTATGTTCAAGTATTCTTCATGAAATAATTCATCTTGATGCTTCCTCTGGTCTC
ATGAATTCTGATGATTCACAGCAAGGCATTATTCAGCCTATTGTAGAATCATTAAAATCATTGA
TTGCTTTGGCTAACCAGATTCTGTACAATGTTGCAATAATAATTCCTCTTAAAATTGACAGTAT
TGAGACCGTAATACTCTCTGCTTYAAAGGAYATGCATACTGGGAGCATGTCCAACACCAACTGT
ACACCCGGAAATCTGCTTCTGCATGATGCAGCATACATCAATGGAATAAACAAATTCCTTGTAC
TTAAATCATACAATGGTACGCCTAAATATGGACCTCTCCTAAATATTCCTAGCTTTATCCCCTC
AGCAACATCTCCCCACGGGTGCACTAGAATACCATCATTTTCACTCAGTAAGACTCATTGGTGT
TACACTCACAATGTAATACTTGGAGATTGCCTCGATTTCACGACATCTAATCAGTATTTAGCAA
TGGGGATAATACAACAATCTGCTGCAGCATTTCCAATCTTCAGGACTATGAAAACCATTTACCT
AAGTGATGGAATCAATCGCAAAAGCTGTTCAGTCACTGCCATACCAGGAGGTTGTGTCTTGTAC
TGCTATGTAGCTACAAGATCTGAGAAAGAAGATTATGCCACAACTGATCTAGCTGAACTGAGAC
TTGCTTTCTATTATTATAATGATACCTTTGTTGAAAGAGTCATATCTCTTCCAAATACAACAGG
GCAATGGGCCACAATCAATCCTGCAGTTGGAAGCGGGATCTATCATCTAGGCTTTATTTTATTT
CCTGTATATGGTGGTCTCATAAATGGGACTCCTTCCTACAACGAGCAGTCCTCACGCTATTTTA
TCCCAACACATCCCAACATAACCTGTGCCGGAAACTCCAGTGAACGGGCTGCAGCAGCACGGGG
TTCCTATGTCATCCGTTATCATTCAAACAGGTTGATTCAGAGTGCTATTCTTATTTGCCCATTA
TCTGACATGCAAACAGCAAGGTGTGATCTAGTTATGTTTAACAATTCTCAAGTCATGATGGGTG
CAGAAGGTAGGCTCTATGTTATTGACAACAATTTGTATTATTATCAACGTAGTTCCTCTTGGTG
GTCTGCATCGCTTTTCTACAGGATCAATACAGATTTCTCTAAAGGAATTCCTCCTATCATTGAG
GCTCAATGGGTACCGTCCTATCAAGTTCCCCGCCCTGGAGTCATGCCATGTAATGCAACAAGTT
TTTGCCCTGCTAATTGCATCACAGGAGTGTATGCAGATGTGTGGCCGCTTAACGATCCAGAACT
CACATCACAAAATGCTCTGAATCCCAACTATCGATTTGCTGGAGCCTTTCTAAAAAATGAGTCC
AACCGAACCAATCCCACATTTTACACTGCATCAGCCAACTCCCTACTAAATACTACCGGATTCA
ACAACACCAATCACAAAGCAGCATATACGTCTTCAACCTGCTTTAAGAATACTGGAACTCAGAA
GATTATTGTTTGATAATAATCGAAATGGGCTCATCTCTTTTAGGGGAGTTCCAAATAATACCA
TTTCTAAGGGAACTAATACCTTAATACTATTGAATGAAAACTTAAGATTCAATAATAATTGAAA
GGCTCTCTATCTTATGTAATAGTTATACGTTTTGGCTGTATTAGAATGTTATAGCATTCTGCTG
TGTTTCCCATATGAAGCAAGCCTTCAACACCGACTTAGGTTCAATTTTCTCATCATTTACTGTT
GTAATCCAATCTTACTAAAGTTATTCTGATATTTAAGAAAAAATAACCTTTATATAATATAACA
ATACTATTAAGATTATGATATAGGCCAGAATGGCGGCCTCTTCTGAGATACTCCTTCCTGAAGT
CCACTTGAACTCACCAATAGTCAAACACAAACTCATATACTACTTATTACTAGGGCACTTCCCG
```

TABLE 7-continued

```
CATGATCTTGACATTTCTGAAATAAGCCCTCTTCACAATAATGATTGGGATCAAATTGCCAGAG
AAGAATCCAATCTTGCTGAACGACTTGGAGTAGCTAAATCTGAATTAATTAAACGTGTGCCCGC
ATTTAGAGCAACTAGATGGCGTAGTCATGCAGCTGTCCTTATATGGCCTTCTTGTATACCATTT
CTTGTTAAATTCCTACCTCATTCTAAGCTTCAACCAATAGAACAATGGTACAAGTTGATCAATG
CTTCATGTAATACTATATCTGACTCAATTGATAGATGTATGGAGAATATTTCTATTAAGCTTAC
TGGGAAAAACAATCTATTCTCTCGATCCAGAGGAACTGCAGGTGCAGGTAAAAACAGTAAAATC
ACCCTCAATGATATCCAATCTATTTGGGAATCAAACAAGTGGCAGCCTAATGTATCTTTATGGC
TTACAATTAAATATCAAATGCGACAACTTATAATGCATCAAAGTTCTCGTCAGCCGACTGATTT
AGTTCACATTGTTGACACACGATCTGGTCTAATAGTTATCACCCCTGAACTTGTTATTTGTTTT
GATCGGTTGAATAGTGTTTTAATGTATTTTACATTTGAGATGACTTTAATGGTAAGCGACATGT
TCGAGGGGAGGATGAATGTCACTGCTCTCTGCACTATTAGTCATTACTTATCTCCACTAGGGCC
AAGGATCGATAGATTGTTTTCCATTGTAGATGAATTAGCACAACTATTAGGTGACACTGTATAT
AAAGTTATTGCATCTCTTGAATCTTTAGTATATGGGTGTCTACAACTTAAAGATCCAGTAGTGG
AATTAGCAGGGTCATTTCATTCCTTTATTACACAAGAGATTATAGATATCCTAATTGGTTCAAA
AGCCCTTGATAAGGATGAATCAATAACTGTTACTACACAATTGTTAGATATATTTTCCAACCTT
TCTCCAGATTTAATTGCTGAGATGTTGTGTCTCATGAGACTTTGGGGTCATCCTACTCTTACTG
CTGCGCAAGCTGCAGGTAAAGTGAGAGAATCTATGTGTGCAGGTAAGTTGCTTGATTTCCCTAC
AATAATGAAAACTCTTGCTTTTTTCCACACAATTTTAATTAATGGTTACCGTAGAAAGAAAAAT
GGAATGTGGCCTCCACTTATACTTCCTAAAAATGCATCAAAAAGCTTAATAGAATTTCAACATG
ATAATGCTGAAATATCTTACGAATATACACTCAAGCATTGGAAAGAGATCTCTCTCATAGAATT
TAGAAAGTGCTTTGACTTTGATCCTGGTGAGGAGCTAAGCATTTTTATGAAGGACAAGGCAATA
AGTGCTCCAAAAAGTGATTGGATGAGTGTATTTCGTAGAAGTCTAATAAAACAACGACATCAGA
GACATCATATTCCTATGCCCAATCCATTTAATAGACGTCTATTACTCAATTTCTTAGAAGATGA
CAGTTTTGACCCAGTTGCTGAGCTCCAATATGTTACCAGTGGTGAATACCTCCAAGATGACACA
TTTTGTGCATCTTACTCATTAAAAGAGAAAGAAATAAAACCAGATGGAAGGATATTCGCTAAGC
TTACTAATAGAATGCGGTCCTGTCAAGTAATTGCGGAAGCAATTCTTGCAAATCATGCAGGTAC
TCTAATGAAGGAAAACGGAGTTGTCTTGAATCAATTATCACTGACCAAGTCATTGCTTACTATG
AGTCAAATTGGCATAATATCAGAAAAGGCAAAGAGATATACGCGAGATAACATCTCATCTCAAG
GTTTCCATACAATCAAGACTGACTCTAAAAATAAGAGGAAAAGCAAAACTGCATCATCATACCT
CACAGATCCTGATGATACATTTGAACTTAGTGCATGTTTTATAACTACTGATCTTGCTAAATAC
TGTCTTCAATGGAGATATCAGACCATAATCCATTTTGCTCGAACATTAAACAGAATGTATGGAG
TTCCACATTTATTTGAATGGATTCATCTTCGTTTAATTAGGTCTACATTATATGTTGGTGATCC
ATTCAATCCCCCTGCTGCGACTGATGCTTTCGATCTAGATAAAGTATTAAATGGTGATATCTTT
ATAGTCTCTCCCAAAGGAGGTATTGAAGGCCTATGTCAGAAAATGTGGACAATGATCTCTATTT
CTGTGATCATCCTCTCCTCAGCCGAATCCAAAACAAGAGTAATGAGCATGGTTCAAGGAGATAA
TCAGGCAATTGCAGTTACAACAAGAGTTCCTAGATCATTACCTAGTATTCAGAAAAAGGAGTTA
GCCTATGCAGCAAGCAAGTTATTTTTTGAAAGACTTAGGGCAAATAATTATGGGTTGGGTCATC
AGCTAAAGGCTCAAGAAACTATAATAAGTTCCACATTCTTCATATATAGTAAACGGGTATTTTA
TCAAGGACGTATACTAACACAGGCACTCAAAAACGCTAGCAAGCTATGTCTTACTGCGGATGTA
TTAGGTGAATGTACTCAAGCTTCCTGTTCAAATTCTGCTACTACCATCATGAGATTAACAGAAA
```

TABLE 7-continued

```
ATGGGGTTGAGAAAGATACATGTTATAAGCTTAATATTTATCAGTCCATTCGTCAACTCACATA
TGATCTAATATTTCCCCAATATTCCATACCAGGTGAAACGATAAGTGGGATTTTCCTGCAGCAT
CCAAGACTAATCTCACGTATTGTTCTGCTCCCTTCACAGCTAGGTGGTCTTAATTACCTCGCAT
GCAGCAGATTATTTAACCGCAATATCGGAGATCCTCTTGGTACAGCTGTGGCGGACCTCAAGAG
GTTAATTAAATGTGGTGCTCTTGAATCATGGATACTGTACAATTTACTAGCAAGAAAACCAGGG
AAAGGTTCATGGGCAACTTTAGCAGCCGATCCGTACTCATTGAATCAAGAATATCTTTATCCTC
CTACTACTATACTTAAAAGACATACTCAACATACTTTAATGGAGATATGTAGGAATCCTATGTT
AAAGGGAGTTTTCACAGATAATGCAAAAGAGGAGGAAAATCTCCTTGCAAAATTTCTTCTTGAT
CGTGATATAGTATTGCCAAGAGTTGCGCACATTATAATAGATCAATCTAGCATCGGAAGGAAGA
AACAGATACAAGGATTTTTTGACACCACAAGGACCATTATGAGACGATCATTTGAAATCAAACC
ACTCTCAACTAAGAAGACTCTTTCAGTTATAGAATATAATACAAATTACTTATCTTATAACTAC
CCTGTCATACTTAATCCTTTACCTATTCCCGGATATTTAAATTATATTACTGACCAAACTTGCA
GTATTGATATATCTAGAAGTTTAAGAAAATTATCATGGTCTTCTTTATTGAATGGAAGAACTTT
AGAAGGATTAGAAACTCCAGATCCAATTGAAGTTGTCAATGGTTCCTTGATTGTAGGTACAGGA
GATTGTGATTTTTGTATGCAGGGTGATGACAAATTTACTTGGTTCTTTTTACCTATGGGGATAA
TTATTGATGGAAATCCTGAAACTAATCCACCCATCAGAGTTCCATACATTGGGTCTAGAACAGA
GGAAAGAAGAGTTGCATCAATGGCATATATTAAAGGTGCCACACACAGTTTGAAGGCTGCTCTT
AGGGGTGCAGGGGTATATATTTGGGCATTCGGGGATACTATAGTGAACTGGAATGATGCACTTG
ATATTGCAAATACTAGAGTTAAGATATCCCTAGAGCAACTTCAGACTCTCACACCTCTTCCTAC
ATCTGCAAACATTACACACCGTTTAGATGATGGAGCCACAACACTTAAATTCACTCCAGCTAGT
TCCTATGCATTTTCTAGTTATACTCATATATCAAATGATCAACAATATTTAGAAATAGATCAGA
GAGTAGTTGATTCCAATATTATTTATCAACAATTAATGATAACAGGACTTGGGATTATTGAGAC
CTACCATAACCCACCTATAAGAACTTCTACACAAGAAATCACTCTCCATTTGCACACTAGCTCA
TCTTGTTGTGTTAGAAGTGTAGATGGCTGCCTTATATGTGAAAGCAATGGAGAGGTTCCCCAGA
TCACTGTTCCCTATACTAATACATTTGTATATGATCCTGACCCACTAGCAGATTATGAGATTGC
ACATCTAGATTACCTCTCCTACCAAGCTAAAATTGGAAGTACAGATTACTACTCACTCACTGAT
AAAATTGACCTATTAGCACATTTAACTGCAAAACAAATGATAAACTCAATAATTGGGTTAGATG
AAACAGTATCGATTGTCAATGATGCGGTTATCCTATCTGACTATACTAATAACTGGATTAGTGA
ATGTTCTTATACTAAAATAGATCTAGTTTTTAAATTAATGGCATGGAATTTTCTTCTTGAGCTT
GCATTCCAGATGTACTACTTAAGGATATCATCTTGGACAAATATATTTGACTATACTTACATGA
CTTTACGCAGAATACCCGGAACTGCTCTAAATAATATTGCAGCTACTATTAGCCATCCAAAATT
ACTGAGACGTGCAATGAATCTTGATATTATCACTCCTATACATGCACCGTATCTAGCTTCATTA
GATTATGTCAAATTAAGTATTGATGCAATTCAGTGGGAGTTAAACAAGTTCTTGCTGATTTAT
CAAATGGAATTGATCTTGAAATCTTGATTCTTTCAGAGGATTCAATGGAAATTAGTGATAGGGC
AATGAATCTCATTGCTAGAAAACTAACTCTCCTTGCACTTGTTAAAGGTGAGAACTACACTTTT
CCAAAAATTAAAGGGATGCCACCAGAAGAAAAGTGTTTAGTCTTAACTGAATATCTAGCAATGT
GTTATCAAATACTCACCACTTAGATCCAGATCTTCAAAAGTATTTATATAATCTAACTAATCC
AAAATTGACCGCATTTCCCAGTAACAACTTCTACTTAACTAGGAAAATCCTCAATCAAATTAGA
GAATCAGACGAAGGACAATATATTATCACCTCATATTATGAATCCTTCGAACAATTAGAAACAG
ATATAATTCTTCATTCTACTTTAACTGCTCCTTATGATAATTCAGAAACTCTAACAAAGTTTGA
```

TABLE 7-continued

```
TTTATCCCTTGACATCTTTCCACATCCAGAATCTCTCGAGAAATATCCTCTTCCAGTTGATCAT
GACTCTCAATCTGCAATTTCAACACTAATTCCAGGCCCTCCTTCTCATCATGTATTACGACCAC
TGGGAGTGTCCTCTACAGCTTGGTATAAAGGGATAAGTTATTGTAGGTATCTAGAAACACAAAA
GATACAGACTGGTGATCATCTTTATTTAGCTGAAGGAAGCGGCGCTTCAATGTCACTCCTAGAA
CTCCTATTTCCAGGAGATACTGTCTATTATAATAGTCTTTTTAGTAGTGGAGAGAATCCTCCAC
AGAGAAACTACGCCCCTCTTCCAACTCAATTTGTACAGAGTGTTCCATATAAATTGTGGCAAGC
TGATCTTGCTGATGATAGCAACTTGATAAAAGATTTTGTCCCATTATGGAATGGAAATGGTGCA
GTTACAGACTTATCAACAAAGGATGCAGTTGCATTCATAATACATAAAGTAGGAGCAGAAAAAG
CATCTCTTGTCCATATAGATCTCGAATCGACTGCTAATATAAATCAGCAAACTCTGTCCAGATC
CCAGATTCATTCATTAATTATAGCAACTACTGTTCTTAAGAGGGGTGGGATATTAATTTATAAG
ACATCATGGCTTCCTTTTTCTAGATTTAGTCAACTAGCAAGCCTTCTTTGGTGCTTTTTTGACC
GGATCCATCTAATACGTAGTAGCTATTCTGATCCTCACAGTCATGAGGTTTATCTTGTATGTAG
ACTTGCCGCAGATTTTAGAACTATCGGTTTCAGTGCAGCTCTAGTAACTGCTACTACTCTTCAC
AATGACGGATTCACAACAATACATCCTGATGTTGTTTGTAGTTATTGGCAACACCATCTTGAAA
ATGTTGGGAGAGTCGGAAAAGTAATTGATGAGATACTTGATGGTTTAGCCACCAACTTCTTTGC
AGGAGATAATGGACTTATTCTAAGATGTGGAGGAACTCCCAGCTCCAGAAAATGGTTGGAGATT
GACCAGTTAGCATCATTTGATTTGGTTCAAGATGCTCTGGTGACACTTATCACTATACACCTAA
AGGAAATTATAGAAGTGCAATCATCACATACAGAAGATTATACATCTCTCCTCTTCACACCTTA
TAATATTGGTGCAGCAGGGAAAGTTAGAACTATCATCAAATTAATTCTAGAACGATCTTTAATG
TATACAGTCCGAAATTGGTTAGTGTTACCCAGTTCCATCCGGGATTCTGTACGACAAGATTTGG
AATTAGGGTCATTTAGATTAATGTCTATTTTAAGTGAACAGACATTTCTTAAAAAGACACCCAC
AAAAAAATACTTACTTGATCAGCTTACAAGGACATATATATCAACCTTCTTTAACTCTCACTCA
GTCCTTCCTCTTCACCGTCCATATCAAAAACAAATATGGAAAGCCTTAGGTAGTGTAATATATT
GTTCGGAGACAGTTGATATACCTCTAATTAAAGACATTCAGATAGAAGATATTAATGATTTTGA
GGATATCGAGAGGGGTATCGATGGCGAAGAATTATGACAACAATGATTATAAGAACTCATGATA
GTTTTATTTAAGAAAAACATATTGATTTTCCCCTTGGT
```

TABLE 8

```
ACCAAGGGGAGAATCAGATGGCATCGTTATATGACGAATTGCAAAAAGATTACGTAGGTCCGGA
ACCACTAGATTCCGGTGCCGGTAACGATTCCAGTTTTATACTATCTGATCATTCTCTATCTCTA
TTAAGGATATTTCTAGTCTAAAGTTCAAAATGTCAAGTGTTTTAAAGACATTTGAAAGATTTAC
TATACAACAGGAGCTTCAGGAGCAATCTGATGACACTCCAGTACCTCTTGAGACAATCAAACCT
ACAATCAGGGTATTTGTCATCAATAATAATGATCCTGTCGTAAGATCTAGACTTTTATTCTTTA
ATCTACGAATCATTATGAGTAACACTGCAAGAGAGGGACATAGAGCTGGTGCTCTCCTCAGTCT
TTTATCACTACCTTCTGCAGCTATGAGTAATCACATCAAATTAGCCATGCATTCACCAGAAGCC
AGCATAGATAGAGTAGAGATAACAGGGTTTGAGAATAATTCATTCCGAGTCATTCCAGATGCTC
GATCAACTATGTCCAGAGGAGAGGTGCTGGCTTTTGAAGCATTAGCTGAGGACATTCCTGATAC
CCTTAATCACCAAACTCCATTTGTAAATAATGATGTAGAAGATGACATATTTGATGAAACAGAG
AAATTCTTAGATGTTTGCTACAGTGTGCTTATGCAGGCATGGATAGTAACATGCAAGTGTATGA
```

TABLE 8-continued

```
CTGCTCCTGATCAACCACCAGTATCAGTAGCAAAGCGGATGGCTAAATATCAACAACAAGGGAG
AATCAATGCTAGGTATGTACTACAACCTGAAGCACAAAGACTAATTCAGAATGCCATCCGCAAG
TCAATGGTAGTAAGGCATTTCATGACTTATGAGCTTCAACTTTCACAATCAAGATCTTTGCTAG
CAAACCGCTACTATGCTATGGTGGGAGACATTGGCAAGTACATTGAACACAGCGGAATGGGAGG
ATTTTTCTTAACACTTAAATATGGACTTGGAACAAGATGGCCTACATTGGCTCTTGCAGCATTT
TCTGGGGAACTCCAGAAATTAAAAGCTCTCATGCTACATTATCAGAGTCTAGGACCCATGGCCA
AGTACATGGCTCTATTAGAATCACCAAAACTGATGGATTTTGTCCCATCTGAATATCCATTAGT
TTATAGCTATGCAATGGGTATTGGAACTGTCCTTGATACAAATATGAGAAATTATGCATACGGT
AGATCATATTTAAATCCGCAATATTTTCAGCTAGGAGTAGAAACAGCAAGGAAACAGCAGGGAG
CTGTTGACAACAGGACAGCAGAGGACCTCGGCATGACTGCTGCAGACAAAGCAGACCTCACTGC
AACCATATCAAAGCTATCCTTGTCCCAATTACCTAGGGGTAGACAACCAATATCTGACCCATTT
GCTGGAGCAAATGACAGAGAAATGGGAGGACAAGCAAATGATACACCTGTGTATAACTTCAATC
CAATCAATACTCGGAGGTATGACAACTATGACAGTGATGGTGAGGACAGAATTGACAACGATCA
AGATCAAGCTATCAGAGAGAATAGAGGAGAGCCTGGACAACCAAACAACCAGACAAGTGACAAC
CAGCAGAGATTCAACCCCCCCATACCGCAAAGAACATCAGGTATGAGCAGTGAAGAGTTCCAAC
ATTCAATGAATCAGTACATCCGTGCTATGCATGAGCAATACAGAGGCTCCCAGGATGATGATGC
CAATGATGCCACAGATGGGAATGACATTTCTCTTGAGCTAGTTGGAGATTTTGATTCCTAACTC
TCAATGTCATACAACCAGATATACACATCCACATCACTCAGAGATACAGCTGCCACTCACACAC
TCATCCAGACAAATCAAACTAGACTCACATCATTCGGAAACAATTCTCTCATAATTTAAGAAAA
AATCATAGGCCCGGACGGGTTAGAAATCCGGTGCTTGTTCGTGATCAGATAACCTCCACACCAG
AATCATACAATCATGGCCGAGGAACCAACATACACCACTGAGCAAGTTGATGAATTAATCCATG
CTGGACTGGGAACAGTAGATTTCTTCCTATCTAGACCCATAGATGCTCAGTCTTCTTTAGGCAA
AGGCAGCATCCCACCAGGTGTCACAGCTGTTCTAACTAGTGCAGCGGAGGCAAAATCCAAACCA
GTTGCTGCTGGTCCAGTTAAACCCAGGCGGAAGAAAGTGATCAGCAATACTACTCCATACACTA
TTGCAGACAATATTCCACCTGAGAAGCTACCGATCAACACTCCAATACCCAATCCATTACTTCC
ACTGGCACGCCCTCACGGAAAGATGACAGACATTGACATTGTCACTGGGAACATTACAGAAGGA
TCGTACAAAGGTGTGGAGCTTGCTAAATTAGGGAAGCAGACACTACTCACAAGGTTCACCTCGA
ATGAGCCAGTCTCCTCAGCTGGATCCGCCCAAGACCCCAACTTTAAGAGGGGGGAGCTAATAG
AGAAAGAGCAAGAGGCAACCATAGGAGAGAATGGAGTATTGCATGGGTCGGAGATCAGGTCAAA
GTCTTCGAGTGGTGTAATCCCAGGTGTGCCCCAGTCACGGCCTCAGCTCGCAAGTTCACCTGCA
CATGCGGATCCTGCCCCAGCATCTGCGGAGAATGTGAAGGAGATCATTGAGCTCTTAAAGGGAC
TTGATCTTCGCCTTCAGACTGTAGAAGGGAAAGTAGATAAAATTCTTGCAACTTCTGCAACTAT
AATCAATCTTAAAAATGAAATGACTAGTCTCAAGGCGAGTGTTGCAACTGTGGAAGGTATGATA
ACAACAATTAAAATCATGGATCCCAGTACACCAACTAATGTCCCTGTAGAGGAGATCAGAAAGA
GTTTACACAATGTTCCAGTAGTAATTGCCGGTCCAACTAGTGGAGGCTTCACAGCCGAAGGCAG
TGATATGATTTCAATGGATGAACTAGCTAGACCTACACTCTCATCAACAAAAAGGATCACACGA
AAGCCTGAATCCAAGAAAGATTTAACAGGCATAAAACTAACTTTGATGCAGCTTGCAAATGACT
GCATCTCGCGTCCAGATACCAAGACTGAGTTCGTGACTAAGATTCAGGCAGCAACCACAGAATC
ACAGCTTAACGAAATTAAACGGTCAATAATACGCTCTGCAATATAAAATGAGGTGCAGTCACAC
AAGAGACACTCAACATGCATCCAATCAAGATCCAGACTCCATCCATCCAAAAACACGCCCACAA
```

TABLE 8-continued

```
TTGTCAACACCAAGAAACAACCACAGCCGAACCATGCTCAACCAAAAGACCCAAACAACACCTC

ACATCAATAGAAGGCTGGACATGATAAATTTAATAAAAAAAGAAAAGAAGTTAAGTAAAATTTA

AAGGACACAATAGAGAAAATCTAGGTCCGAAAGCTTGCCTCTCAGACAGATCCCAAAATCATAG

TCCAAACCCCAAACACAGCAGCAGACATGCCTATAATATCATTACCAGCAGATCCAACTTCACC

CAGTCAATCCCTTACTCCGTTTCCAATACAACTTGACACCAAAGATGGCAAGGCAGGGAAACTC

CTTAAACAGATTCGAATTAGGTATCTAAATGAGCCTAATTCTCGCCATACACCAATAACTTTCA

TCAATACGTATGGATTTGTTTATGCTCGAGACACTTCAGGGGGCATTCACAGTGAGATCAGCAG

TGACCTAGCTGCAGGGTCCATAACAGCATGCATGATGACGCTAGGTCCTGGTCCAAATATTCAG

AATGCAAATCTAGTGCTAAGATCTCTGAATGAATTCTACGTAAAAGTCAAGAAGACATCAAGCC

AGAGAGAGGAAGCAGTGTTTGAATTAGTTAACATTCCAACTTTATTGAGAGAACATGCTCTTTG

CAAACGCAAATGTTAGTATGCTCTGCAGAAAAATTCCTCAAGAACCCGTCAAAGCTACAAGCT

GGATTTGAGTATGTATACATACCAACTTTTGTCTCCATTACATACTCACCACGAAATCTGAATT

ACCAAGTTGCCAGACCTATCCTTAAGTTCAGATCACGCTTTGTGTATAGCATTCATTTGGAATT

AATCCTGAGATTGCTATGCAAATCTGACTCCCCCTTGATGAAATCCTACAATGCAGACAGAACA

GGTCGGGATGCCTCGCATCAGTCTGGATCCTTGTATGTAACATTCTGAAAAACAAAAGCATCA

AGCAACAAGGCAGAGAATCATATTTCATAGCTAAGTGCATGAGCATGCAGCTGCAGGTGTCCAT

TGCAGATCTTTGGGGACCAACAATCATAATCAAATCATTGGGTCACATCCCCAAGACTGCACTT

CCTTTTTTCAGCAAAGATGGGATTGCCTGTCATCCATTACAAGATGTTTCCCCTAATCTGACAA

AATCACTGTGGTCAGTTGGATGTGAGATAGAATCTGCCAAGTTGATACTTCAAGAATCTGATCT

TAATGAGCTAATGGGCCACCAGGACCTTATCACTGATAAGATTGCCATTAGATCAGGTCAACGG

ACATTTGAGAGGTCCAAATTCAGCCCATTCAAAAAATATGCATCAATTCCAAACTTGGAAGCCA

TCAACTGAATGCTCCAGCATCTGAGAATAGAACCACAATCAAGTCATACTACTAGTCACTATAC

AATAATCAACAATTTTAGTCAACTGATTACCAAGATGTTATCATAGGTCCGAACTGATCAATCT

AACAAAAAAACTAAACGTTCCACAATAAATCAACGTTCAGGCCAAAATATTCAGCCATGCATCA

CCTGCATCCAATGATAGTATGCATCTTTGTTATGTACACTGGAATTGTAGGTTCAGATGCCATT

GCTGGAGATCAACTACTTAATATAGGGGTCATTCAATCAAAGATAAGATCACTCATGTACTATA

CTGATGGTGGTGCTAGCTTTATTGTTGTAAAATTGCTACCTAATCTTCCCCCAAGCAATGGAAC

ATGCAACATCACCAGTCTAGATGCATATAATGTTACCCTATTTAAGTTACTAACACCCCTGATT

GAGAACCTGAGTAAAATTTCCACTGTTACAGATACCAAAACCCGCCAAGAACGATTTGCAGGAG

TAGTTGTTGGACTTGCTGCATTAGGAGTAGCCACAGCCGCACAAATAACTGCAGCTGTAGCAAT

AGTGAAAGCTAATGCAAATGCTGCTGCGATAAACAATCTTGCATCTTCAATTCAATCCACCAAC

AAGGCAGTATCCGATGTGATAGATGCATCAAGAACAATTGCAACCGCAGTTCAAGCAATTCAGG

ATCACATCAATGGAGCTATTGTTAATGGGATAACATCTGCATCATGCCGTGCCCATGATGCACT

CATTGGGTCAATATTAAATCTTTATCTCACTGAGCTTACCACAATATTTCATAATCAAATAACA

AACCCTGCGCTGACACCACTCTCCATCCAAGCTTTAAGAATCCTCCTCGGTAGCACCTTGCCAA

TTGTCATTGAGTCCAAACTCAACACAAACCTCAACACAGCAGAGCTGCTCAGTTCCGGACTGTT

AACTGGTCAAATAATTTCCATTTCCCCAATGTACATGCAAATGCTAATTCAAATCAATGTTCCG

ACATTTATAATGCAACCCGGTGCGAAGGTAATTGATCTAATTGCTATCTCCGCAAACCATAAAT

TGCAAGAAGTGGTTGTACAAGTTCCGAATAGGATTCTAGAGTATGCAAATGAACTACAAAATTA

CCCAGCCAATGACTGTGTCGTGACACCGAACTCTGTATTTTGTAGATACAATGAGGGTTCCCCT
```

TABLE 8-continued

```
ATCCCTGAATCACAATATCAATGCTTGAGGGGGAATCTTAATTCTTGCACTTTTACCCCTATTA

TCGGGAACTTTCTTAAGCGATTCGCATTTGCTAATGGTGTGCTCTATGCCAACTGCAAATCTTT

GCTATGTAGGTGTGCCGACCCCCCCCATGTTGTATCCCAGGATGATACCCAAGGCATCAGCATA

ATTGATATTAAGAGATGCTCTGAGATGATGCTTGACACTTTTTCATTTAGGATCACATCTACTT

TCAATGCTACGTACGTGACAGACTTCTCAATGATTAATGCAAATATTGTACATCTAAGTCCTCT

AGATTTGTCAAATCAAATCAATTCAATAAACAAATCTCTTAAAAGTGCTGAGGATTGGATTGCA

GATAGCAACTTCTTTGCTAATCAAGCCAGGACAGCCAAGACACTTTATTCACTAAGTGCAATAG

CATTAATACTATCAGTGATTACTTTGGTTGTCGTGGGATTGCTGATTGCCTACATCATCAAGCT

GGTTTCTCAAATCCATCAATTCAGATCGCTAGCTGCTACAACAATGTTCCACAGGGAAAATCCT

GCCTTCTTTTCCAAGAATAACCATGGAAACATATATGGGATATCTTAAGAAATCTATCACAAGT

CTATATATGTCCACAATTGACCCTTAAGAACCAACTTCCAACGATTATCCGTTAAATTTAAGTA

TAATAGTTTAAAAATTAACATTAAGCCTCCAGATACCAATGAATATGAATATATCTCTTAGAAA

ACCTGATTATTATGTGATAGCGTAGTACAATTTAAGAAAAAACCTAAAATAAGCACGAACCCTT

AAGGTGTCGTAACGTCTCGTGACACCGGGTTCAGTTCAAATATCGACCTCTAACCCAATTTAAC

ACCCATTCTTATATAAGAACACAGTATAATTTAATCACAAAAGACCTCAAAAACTGACACAGCT

TGATCCACTCAACATATAATTGTAAGATTAATAATAATGGAAGATTACAGCAATCTATCTCTTA

AATCAATTCCTAAAAGGACATGTAGAATCATTTTCCGAACTGCCACAATTCTTGGAATATGCAC

ATTGATTGTTCTATGTTCAAGTATTCTTCATGAGATAATTCATCTTGATGTTTCCTCTGGTCTC

ATGGATTCCGATGATTCACAGCAAGGCATTATTCAGCCTATTATAGAATCATTAAAATCATTAA

TTGCTTTGGCTAACCAGATTCTGTACAATGTTGCAATAATAATTCCTCTTAAAATTGACAGTAT

CGAGACTGTAATATACTCTGCTTTAAAGGATATGCATACTGGGAGCATGTCCAACACCAACTGT

ACACCCGGAAATCTGCTTCTGCATGATGCAGCGTACATCAATGGAATAAACAAATTCCTTGTAC

TTAAATCATACAATGGGACGCCTAAATATGGACCTCTCCTAAATATTCCCAGCTTTATCCCCTC

AGCAACATCTCCCAACGGGTGCACTAGAATACCATCATTTTCACTCATTAAGACCCATTGGTGT

TACACTCACAATGTAATACTTGGAGATTGCCTCGATTTCACGACATCTAATCAGTATTTAGCAA

TGGGGATAATACAACAATCTGCTGCAGCATTTCCAATCTTCAGGACTATGAAAACCATTTACCT

AAGTGATGGAATCAATCGCAAAAGCTGTTCAGTCACTGCTATACCAGGAGGTTGTGTCTTGTAT

TGCTATGTAGCTACAAGATCTGAGAAAGAAGATTATGCCACAACTGATCTAGCTGAACTGAGAC

TTGCTTTCTATTATTATAATGATACCTTTATTGAAAGAGTCATATCTCTTCCAAATACAACAGG

GCAATGGGCCACAATCAATCCTGCAGTTGGAAGCGGGATCTATCATCTAGGCTTTATTTTATTT

CCTGTATATGGTGGTCTCATAAAGGGGACTCCTTCCTACAACAAGCAGTCCTCACGCTATTTTA

TCCCAAAACATCCCAACATAAACCTGTGCCGGTAAATCCAGCGAACAGGCTGCAGCAGCACGGAG

TTCCTATGTAATCCGTTATCACTCAAACAGGTTGATTCAGAGTGCTGTTCTTATTTGCCCATTG

TCTGACATGCACACAGCAAGGTGTAATCTAGTTATGTTTAACAATTCTCAAGTCATGATGGGTG

CAGAAGGTAGGCTCTATGTTATTGACAATAATTTGTATTATTATCAACGTAGTTCCTCTTGGTG

GGCTGCATCGCTTTTTTACAGGATCAATACAGATTTTTCTAAAGGAATTCCTCCTATCATTGAG

GCTCAATGGGTACCGTCCTATCAAGTTCCCCGTCCTGGAGTCATGCCATGCAATGCAACAAGTT

TTTGCCCTGCTAATTGCATCACAGGGGTGTACGCAGATGTGTGGCCGCTTAACGATCCAGAACC

CACATCACAAAATGCTCTGAATCCCAACTATCGATTTGCTGGAGCCTTTCTCAGAAATGAGTCC

AACCGAACCAATCCCACATTCTACACTGCATCAGCCAGCGCCCTACTAAATACTACCGGATTCA
```

TABLE 8-continued

```
ACAACACCAATCACAAAGCAGCATATACGTCTTCAACCTGCTTTAAGAATACTGGAACTCAAAA

GATTTATTGTTTGATAATAATTGAAATGGGCTCATCTCTTTTAGGGGAGTTCCAAATAATACCA

TTTCTAAGGGAACTAATACCTTAATACTATTGAATGAAGACTCCAGATTCAATAATAATTGAAA

GGCTCTCTATCTTATGCAATAGTTATACGTTTTGGCTGTATTAGAATGTTATAGCATTCTGCTG

TTTTTCCCATATGAAGCAATCCTTCAACACCGACTTAGGTTCAATTTTCTCATCATTTACTGTT

GTAATTCAATCTTACTAAAGTTATTCCGATATTTAAGAAAAAATAACCTTTATATAATGTAACA

ATACTATTAAGATTATGATATAGGCCAGAATGGCGGCCTCTTCTGAGATACTCCTTCCTGAAGT

CCACTTGAACTCACCAATAGTCAAACACAAACTCATATACTACTTATTACTAGGGCACTTCCCG

CATGATCTTGACATTTCTGAAATAAGCCCCCTTCACAATAATGATTGGGATCAAATTGCCAGAG

AAGAATCCAATCTTGCTGAACGACTTGGAGTAGCTAAATCTGAATTAATTAAACGTGTGCCCGC

ATTTAGAGCAACTAGATGGCGTAGTCATGCAGCCGTCCTTATATGGCCTTCTTGTATACCATTT

CTTGTTAAATTCCTACCTCATTCTAAGCTTCAACCAGTAGAACAATGGTACAAGTTGATCAATG

CTTCATGTAATACTATATCTGACTCAATTGATAGATGTATGGAGAATATTTCTATTAAGCTTAC

TGGGAAAAACAATCTATTCTCTCGATCCAGAGGAACTGCAGGTGCAGGTAAAAACAGTAAAATC

ACCCTCAATGATATCCAATCTATTTGGGAATCAAACAAGTGGCAACCTAATGTATCTTTATGGC

TTACAATTAAATACCAAATGCGACAACTTATAATGCATCAAAGTTCTCGTCAGCCGACTGATTT

AGTTCACATTGTTGACACACGATCTGGTCTAATAGTTATCACCCCTGAACTTGTTATTTGTTTT

GATCGGTTAAATAGTGTTTTAATGTATTTTACATTTGAGATGACTTTAATGGTAAGTGACATGT

TTGAGGGAAGGATGAATGTCACCGCTCTCTGCACTATTAGTCATTACTTATCTCCACTAGGGCC

AAGGATAGATAGATTGTTTTCCATTGTAGATGAATTAGCACAACTATTAGGTGACACTGTATAT

AAAGTTATTGCATCTCTTGAATCTTTAGTATATGGGTGTCTACAACTTAAAGATCCAGTAGTGG

AATTAGCAGGGTCATTTCATTCCTTTATTACACAAGAGATTATAGATATCCTAATTGGTTCAAA

AGCCCTTGATAAGGATGAATCAATAACTGTTACTACACAATTGTTAGATATATTTTCCAACCTT

TCTCCAGATTTAATTGCTGAGATGTTGTGTCTCATGAGACTTTGGGGTCATCCCACTCTTACTG

CTGCGCAAGCTGCAGGTAAAGTGAGAGAATCTATGTGTGCAGGTAAGTTACTTGATTTCCCTAC

AATAATGAAAACTCTTGCTTTTTTCCACACAATTTTAATTAATGGTTACCGTAGAAAGAAAAAT

GGAATGTGGCCTCCACTTATACTTCCTAAAAATGCATCAAAAAGCTTAATAGAATTTCAACATG

ATAATGCTGAAATATCTTACGAATATACACTCAAGCATTGGAAAGAGATCTCTCTCATAGAATT

TAGAAAGTGCTTTGACTTTGATCCTGGTGAGGAGCTAAGCATTTTTATGAAAGACAAGGCAATA

AGTGCTCCAAGAAGTGATTGGATGAGTGTATTTCGTAGAAGTCTAATAAAACAACGACATCAGA

GACATCATATTCCTATGCCCAATCCATTTAATAGACGTCTATTACTCAATTTCTTAGAAGATGA

CAGTTTTGATCCAGTTGCCGAGCTTCAATATGTTACCAGTGGTGAATATCTCCAAGATGACACA

TTTTGTGCATCTTACTCATTAAAAGAGAAAGAAATAAAACCAGATGGAAGGATATTTGCTAAGC

TTACTAATAGAATGCGGTCCTGTCAAGTAATTGCGGAAGCAATTCTCGCAAATCATGCAGGTAC

TCTAATGAAGGAAAACGGAGTTGTCTTGAATCAATTATCACTGACTAAATCATTGCTTACTATG

AGTCAAATTGGCATAATATCAGAAAGGCGAAGAGATATACGCGATATAACATCTCATCCCAAG

GTTTCCATACAATCAAGACTGATTCTAAAAATAAGAGGAAAAGCAAAACTGCATCATCATACCT

CACAGATCCTGATGATACATTTGAACTTAGTGCATGTTTTATAACTACTGATCTTGCTAAATAC

TGTCTTCAATGGAGATATCAGACCATAATCCATTTTGCTCGAACATTAAACAGAATGTATGGAG

TTCCACATTTATTTGAATGGATTCATCTTCGTTTAATTAGATCTACATTATATGTTGGTGATCC
```

TABLE 8-continued

```
ATTCAATCCTCCTGCCGCAACTGATGCTTTCGATCTAGATAAAGTATTAAATGGTGATATCTTT
ATAGTCTCTCCCAAGGGAGGTATTGAAGGCCTATGTCAGAAAATGTGGACAATGATCTCTATTT
CTGTGATCATCCTCTCTTCAGCCGAATCCAAAACAAGAGTAATGAGCATGGTTCAAGGAGATAA
TCAGGCGATTGCAGTTACAACAAGAGTTCCTAGATCATTACCTAGTATTCAGAAAAAGGAGTTA
GCCTATGCAGCAAGCAAGTTATTTTTTGAAAGACTTAGGGCAAATAATTATGGGTTGGGTCATC
AGCTAAAGGCTCAAGAAACTATAATAAGTTCCACGTTCTTCATATATAGTAAACGGGTATTTTA
TCAAGGACGTATACTAACACAGGCACTCAAAAATGCTAGCAAGTTATGTCTTACTGCAGATGTA
TTAGGTGAATGTACTCAAGCTTCCTGTTCAAATTCTGCTACTACCATCATGAGATTAACAGAAA
ATGGGGTTGAGAAAGATACATGTTATAAGCTTAATATTTATCAGTCCATTCGTCAACTCACATA
TGATCTAATATTTCCCCAATACTCCATACCAGGTGAAACTATAAGTGAGATTTTCCTACAGCAT
CCAAGACTAATCTCACGTATTGTTCTGCTCCCTTCACAGCTAGGTGGTCTTAATTACCTCGCAT
GTAGCAGATTATTTAACCGCAATATCGGAGATCCTCTTGGTACAGCTGTGGCAGATCTCAAGAG
GTTAATTAAATGTGGTGCTCTTGAATCATGGATACTGTATAATTTACTAGCAAGAAAACCAGGG
AAAGGTTCATGGGCAACTTTAGCAGCCGATCCATACTCATTGAATCAAGAATATCTTTATCCTC
CTACTACTATACTTAAAAGACATACTCAAAATACTTTAATGGAGATATGTCGGAATCCTATGTT
AAAGGGAGTTTTTACAGATAATGCAAAAGAGGAGGAAAATCTCCTTGCAAAATTTCTTCTTGAT
CGTGATATAGTATTGCCAAGAGTTGCACACATTATAATAGATCAATCTAGCATCGGAAGGAAGA
AACAGATACAAGGATTTTTTGACACCACAAGGACCATAATGAGACGATCATTTGAAATCAAACC
ACTCTCAACTAAGAAGACTCTTTCAGTCATAGAATATAATACTAATTACTTATCTTATAACTAC
CCTGTCATACTTAATCCTTTACCTATTCCTGGATATTTAAATTATATTACTGACCAAACTTGCA
GTATTGATATATCTAGAAGTTTAAGAAAATTATCATGGTCTTCTTTATTGAATGGAAGAACTTT
AGAAGGATTAGAAACTCCAGATCCAATTGAAGTTGTCAATGGTTCCTTGATTGTAGGTACAGGA
GATTGTGATTTTGTATGCAGGGTGACGACAAATTTACTTGGTTCTTTTTACCTATGGGGATAA
TTATTGATGGAAATCCTGAAACTAATCCACCCATCAGAGTTCCATACATTGGGTCTAGAACAGA
GGAAAGAAGAGTTGCATCAATGGCATATATTAAAGGTGCCACACACAGTTTGAAGGCTGCTCTT
AGAGGCGCAGGGGTATATATTTGGGCATTCGGGGATACTGTAGTGAACTGGAATGATGCACTTG
ATATCGCAAATACTAGGGTTAAGATATCCCTAGAGCAACTTCAGACCCTTACACCTCTTCCTAC
ATCTGCAAACATTACACACCGTTTAGATGATGGAGCCACAACACTTAAATTCACTCCAGCTAGT
TCCTATGCATTTTCTAGT6ATACTCATATATCAAATGATCAACAATATTTAGAAATAGATCAGA
GAGTAGTCGATTCTAATATTATTTATCAACAATTAATGATAACAGGACTTGGGATTATTGAGAC
CTACCATAACCCACCTATAAGGACTTCTACACAAGAAATCACTCTCCATTTGCACACTAGCTCA
TCTTGTTGTGTTAGAAGTGTAGATGGTTGCCTTATATGTGAGAGCAATGGAGAGGTTCCTCAGA
TCACTGTTCCCTATACTAATACATTTGTATATGATCCTGATCCACTAGCAGATTATGAGATTGC
ACACCTAGATTATCTCTCCTACCAAGCTAAAATTGGAAGTACAGATTACTACTCACTCACTGAT
AAAATTGACCTATTAGCACATTTAACTGCAAAACAAATGATAAACTCAATAATTGGGTTAGATG
AAACAGTATCAATTGTCAATGATGCGGTTATCCTATCTGACTATACTAATAACTGGATTAGTGA
ATGTTCTTATACTAAGATAGATTTAGTTTTTAAATTAATGGCATGGAATTTCCTTCTTGAGCTT
GCATTCCAGATGTACTACTTAAGGATATCATCTTGGACAAATATATTTGACTATACTTATATGA
CTTTACGCAGGATACCCGGAACTGCTCTAAATAATATTGCAGCTACTATTAGCCATCCAAAATT
ATTAAGACGTGCAATGAATCTTGATATTATCACTCCTATACATGCACCGTATTTAGCTTCATTA
```

TABLE 8-continued

```
GATTATGTCAAATTAAGTATTGATGCAATTCAGTGGGGAGTTAAACAAGTTCTTGCTGATTTAT
CAAATGGAATTGATCTTGAAATCTTGATTCTTTCAGAGGATTCAATGGAAATTAGTGATAGGGC
AATGAATCTCATTGCTAGAAAACTAACTCTCCTTGCACTTGTTAAAGGTGAGAACTATACTTTT
CCAAAAATTAAAGGGATGCCACCAGAAGAAAAGTGTTTAGTCTTAACTGAATATCTAGCAATGT
GTTATCAAAATACTCATCACTTAGATCCAGATCTTCAAAAGTATTTATATAATCTAACTAATCC
AAAATTGACTGCATTTCCCAGTAACAACTTCTACTTAACTAGAAAAATCCTTAATCAAATTAGA
GAATCAGACGAAGGACAATATATTATCACCTCATATTATGAATCCTTCGAACAATTAGAAACAG
ATATAATTCTTCACTCTACTTTAACTGCTCCTTATGATAATTCAGAAACTCTAACAAAGTTCGA
TTTATCCCTTGACATCTTTCCACATCCAGAATCTCTCGAGAAATATCCTCTTCCAGTTGATCAT
GACTCTCGATCTGCAATTTCAACACTAATTCCAGGCCCTCCTTCTCATCATGTATTACGACCAC
TAGGAGTGTCATCCACAGCTTGGTATAAAGGGATAAGTTATTGTAGATACCTAGAAACACAAAA
GATACAGACTGGTGATCATCTTTATTTAGCCGAAGGAAGCGGTGCTTCAATGTCACTTCTAGAA
CTCTTATTTCCAGGAGATACTGTCTATTATAATAGTCTTTTTAGTAGTGGAGAGAATCCTCCAC
AGAGAAACTATGCCCCTCTTCCAACTCAATTTGTACAGAGTGTTCCATATAAATTGTGGCAAGC
TGATCTTGCTGATGATAGCAATTTGATAAAAGATTTTGTCCCATTATGGAATGGAAACGGTGCA
GTTACAGACTTATCAACAAAGGATGCAGTTGCATTCATAATACATAAAGTAGGAGCAGAGAAAG
CATCCCTTGTCCATATAGATCTCGAATCAACTGCTAATATAAATCAGCAAACTCTGTCCAGATC
CCAGATTCATTCATTAATTATAGCAACTACTGTTCTTAAGAGGGGTGGGATATTAATTTATAAA
ACATCATGGCTTCCGTTTTCTAGGTTTAGTCAACTAGCAAGTCTACTTTGGTGCTTCTTTGACC
GGATCCATCTAATACGTAGTAGCTATTCTGATCCTCACAGTCATGAGGTTTATCTTGTATGTAG
ACTTGCCGCAGATTTTAGAACTATCGGTTTCAGTGCAGCTCTAGTAACTGCTACTACTCTTCAC
AATGACGGATTCACAACAATACATCCTGATGTTGTTTGTAGTTATTGGCAACACCATCTTGAAA
ATGTTGGGAGAGTCGGAAAAGTAATTGATGAGATACTTGATGGTTTAGCCACCAACTTCTTCGC
AGGAGATAATGGGCTTATTCTAAGATGTGGAGGAACTCCCAGCTCCAGAAAATGGTTAGAGATT
GACCAGTTAGCATCATTTGATTTGGTTCAAGATGCTCTGGTTACACTTATCACTATACACCTAA
AGGAAATTATAGAAGTGCAGTCATCACATACAGAGGATTATACATCTCTCCTCTTCACACCTTA
TAATATTGGTGCAGCAGGGAAAGTCAGAACTATCATCAAATTAATTCTAGAACGATCTTTAATG
TATACAGTCCGAAATTGGTTAGTTTTACCCAGTTCCATCCGGGATTCTGTACGACAAGATTTAG
AATTAGGGTCATTTAGATTAATGTCTATTTTAAGTGAACAGACATTTCTTAAAAAGACACCCAC
AAAAAAATACTTACTTGATCAGCTTACAAGGACATATATATCAACCTTCTTTAACTCTCACTCA
GTCCTTCCCCTCCACCGTCCATATCAAAAACAAATATGGAAAGCCTTAGGTAGTGTAATATATT
GTTCGGAGACAGTTGATATACCTCTAATTAAAGACATTCAGATAGAAGATATTAATGATTTTGA
AGATATCGAGAGGGGTATCGATGGCGAAGAATTATGACAACAATGATTATAAGAACTCATGATA
GTTTTATTTAAGAAAAACATATTGATTTTCCCCTTGGT
```

TABLE 9

```
MSSVLKTFERFTIQQELQEQSEDTPIPLETIRPTIRVFVINNNDPIVRSRLLFFNLRIIMSNTA
REGHRAGALLSLLSLPSAAMSNHIKLAMHSPEASIDRVEITGFENNSFRVIPDARSTMSRGEVL
AFEALAEDIPDTLNHQTPFVNNDVEDDIFDETEKFLDVCYSVLMQAWIVTCKCMTAPDQPPVSV
AKRMAKYQQQGRINARYVLQPEAQRLIQNAIRKSMVVRHFMTYELQLSQSRSLLANRYYAMVGD
```

TABLE 9-continued

IGKYIEHSGMGGFFLTLKYGLGTRWPTLALAAFSGELQKLKALMLHYQSLGPMAKYMALLESPK
LMDFVPSEYPLVYSYAMGIGTVLDTNMRNYAYGRSYLNPQYFQLGVETARKQQGAVDNRTAEDL
GMTAADKADLTATISKLSLSQLPRGRQPISDPFAGANDRETGGQATDTPVYNFNPINNRRYDNY
DSDSEDRIDNDQDQAIRENRGEPGQPNNQTSENQQRLNLPVPQRTSGMSSEEFQHSMNQYIRAM
HEQYRGSQDDDANDATDGNDISLELVGDFDS

TABLE 10

MAEEPTYTTEQVDELIHAGLGTVDFFLSRPIDAQSSLGKGSIPPGVTAVLTNAAEAKSKPVAAG
PVKPRRKKVISNTTPYTIADNIPPEKLPINTPIPNPLLPLARPHGKMTDIDIVTGNITEGSYKG
VELAKLGKQTLLTRFTSNEPVSSAGSAQDPNFKRGGELIEKEQEATIGENGVLHGSEIRSKSSS
GVIPGVPQSRLQLASSPAHVDPAPASAENVKEIIELLKGLDLRLQTVEGKVDKILATSATIINL
KNEMTSLKASVATVEGMITTIKIMDPSTPTNVPVEEIRKSLHNVPVVIAGPTSGGFTAEGSDMI
SMDELARPTLSSTKKITRKPESKKDLTGIKLTLMQLANDCISRPDTKTEFVTKIQAATTESQLN
EIKRSIIRSAI

TABLE 11

MAASSEILLPEVHLNSPIVKHKLIYYLLLGHFPHDLDISEISPLHNNDWDQIAREESNLAERLG
VAKSELIKRVPAFRATRWRSHAAVLIWPSCIPFLVKFLPHSKLQPIEQWYKLINASCNTISDSI
DRCMENISIKLTGKNNLFSRSRGTAGAGKNSKITLNDIQSIWESNKWQPNVSLWLTIKYQMRQL
IMHQSSRQPTDLVHIVDTRSGLIVITPELVICFDRLNNVLMYFTFEMTLMVSDMFEGRMNVAAL
CTISHYLSPLGPRIDRLFSIVDELAQLLGDTVYKIIASLESLVYGCLQLKDPVVELTGSFHSFI
TQEIIDILIGSKALDKDESITVTTQLLDIFSNLSPDLIAEMLCLMRLWGHPTLTAAQAAGKVRE
SMCAGKLLDFPTIMKTLAFFHTILINGYRRKKNGMWPPLILPKNASKSLIEFQHDNAEISYEYT
LKHWKEISLIEFRKCFDFDPGEELSIFMKDKAISAPKSDWMSVFRRSLIKQRHQRHHIPMPNPF
NRRLLLNFLEDDSFDPVAELQYVTSGEYLRDDTFCASYSLKEKEIKPDGRIFAKLTNRMRSCQV
IAEAILANHAGTLMKENGVVLNQLSLTKSLLTMSQIGIISEKAKRYTRDNISSQGFHTIKTDSK
NKKKSKIASSYLTDPDDTFELSACFITTDLAKYCLQWRYQTIIHFARTLNRMYGVPHLFEWIHL
RLIRSTLYVGDPFNPPATTDAFDLDKVLNGDIFIVSPKGGIEGLCQKMWTMISISVIILSSAES
KTRVMSMVQGDNQAIAVTTRVPRSLPSVQKKELAYAASKLFFERLRANNYGLGHQLKAQETIIS
STFFIYSKRVFYQGRILTQALKNASKLCLTADVLGECTQASCSNSATTIMRLTENGVEKDTCYK
LNIYQSIRQLTYDLIFPQYSIPGETISEIFLQHPRLISRIVLLPSQLGGLNYLACSRLFNRNIG
DPLGTAVADLKRLIKCGALESWILYNLLARKPGKGSWATLAADPYSLNQEYLYPPTTILKRHTQ
NTLMEICRNPMLKGVFTDNAKEEENLLAKFLLDRDIVLPRVAHIIDQSSIGRKKQIQGFFDTT
RTIMRRSFEIKPLSTKKTLSVIEYNTNYLSYNYPVILNPLPIPGYLNYITDQTCSIDISRSLRK
LSWSSLLNGRTLEGLETPDPIEVVNGSLIVGTGDCDFCMQGDDKFTWFFLPMGIIIDGNPETNP
PIRVPYIGSRTEERRVASMAYIKGATHSLKAALRGAGVYIWAFGDTVVNWNDALDIANTRVKIS
LEQLQTLTPLPTSANITHRLDDGATTLKFTPASSYAFSSYTHISNDQQYLEIDQRVVDSNIIYQ
QLMITGLGIIETYHNPPIRTSTQEITLHLHTSSSCCVRSVDGCLICESNGEVPQITVPYTNSFV
YDPDPLADYEIAHLDYLSYQAKIGSTDYYSLTDKIDLLAHLTAKQMINSIIGLDETVSIVNDAV

TABLE 11-continued

```
ILSDYTNNWISECSYTKIDLVFKLMAWNFLLELAFQMYYLRISSWTNIFDYTYMTLRRIPGTAL

NNIAATISHPKLLRRAMNLDIITPIHAPYLASLDYVKLSIDAIQWGVKQVLADLSNGIDLEILI

LSEDSMEISDRAMNLIARKLTLLALVKGENYTFPKIKGMPPEEKCLVLTEYLAMCYQNTHHLDP

DLQKYLYNLTNPKLTAFPSNNFYLTRKILNQIRESDEGQYIITSYYESFEQLETDIILHSTLTA

PYDNSETLTKFDLSLDIFPHPESLEKYPLPVDHDSQSAISTLIPGPPSHHVLRPLGVSSTAWYK

GISYCRYLETQKIQTGDHLYLAEGSGASMSLLELLFPGDTVYYNSLFSSGENPPQRNYAPLPTQ

FVQSVPYKLWQADLADDSNLIKDFVPLWNGNGAVTDLSTKDAVAFIIHKVGAEKASLVHIDLES

TANINQQTLSRSQIHSLIIATTVLKRGGILVYKTSWLPFSRFSQLASLLWCFFDRIHLIRSSYS

DPHSHEVYLVCRLAADFRTIGFSAALVTATTLHNDGFTTIHPDVVCSYWQHHLENVGRVEKVID

EILDGLATNFFAGDNGLILRCGGTPSSRKWLEIDQLASGDSVQDALVTLITIHLKEIIEVQSSH

TEDYTSLLFTPYNIGAAGKVRTIIKLILERSLMYTVRNWLVLPSSIRDSVRQDLELGSFRLMSI

LSEQTFLKKTPTKKYLLDQLTRTYISTFFNSHSVLPLHRPYQKQIWKALGSVIYCSETVDIPLI

RDIQIEDINDFEDIERGIDGEEL
```

Bibliography

Winer, B. J. (1971). "Statistical Principles in Experimental Design." McGraw-Hill, New York.

Dunnet, C. W. (1980). Pairwise multiple comparisons in the homogeneous variance, unequal sample size case. *Journal of the American Statistical Association* 75, 789-795.

Ohgimoto, S., Bando, H., Kawano, M., Okamoto, K., Kondo, K., Tsurudome, M., Nishio, M., and Ito, Y. (1990). Sequence analysis of P gene of human parainfluenza type 2 virus: P and cysteine-rich proteins are translated by two mRNAs that differ by two nontemplated G residues. *Virology* 177(1), 116-23.

Jacques, J. P., and Kolakofsky, D. (1991). Pseudo-templated transcription in prokaryotic and eukaryotic organisms. *Genes Dev* 5(5), 707-13.

Calain, P., and Roux, L. (1993). The rule of six, a basic feature for efficient replication of Sendai virus defective interfering RNA. *J Virol* 67(8), 4822-30.

Kawano, M., Tsurudome, M., Oki, N., Nishio, M., Komada, H., Matsumura, H., Kusagawa, S., Ohta, H., and Ito, Y. (1993). Sequence determination of the P gene of simian virus 41: presence of irregular deletions near the RNA-editing sites of paramyxoviruses. *J Gen Virol* 74(Pt 5), 911-6.

Liston, P., and Briedis, D. J. (1994). Measles virus V protein binds zinc. *Virology* 198(1), 399-404.

Paterson, R., Leser, G., Shaughnessy, M., and Lamb, R. (1995). The paramyxovirus SV5 V protein binds two atoms of zinc and is a structural component of virions. *Virology* 208, 121-31.

Precious, B., Young, D. F., Bermingham, A., Fearns, R., Ryan, M., and Randall, R. E. (1995). Inducible expression of the P, V, and NP genes of the paramyxovirus simian virus 5 in cell lines and an examination of NP-P and NP-V interactions. *J Virol* 69(12), 8001-10.

Randall, R. E., and Bermingham, A. (1996). NP:P and NP:V interactions of the paramyxovirus simian virus 5 examined using a novel protein:protein capture assay. *Virology* 224 (1), 121-9.

Watanabe, N., Kawano, M., Tsurudome, M., Nishio, M., Ito, M., Ohgimoto, S., Suga, S., Komada, H., and Ito, Y. (1996a). Binding of the V proteins to the nucleocapsid proteins of human parainfluenza type 2 virus. *Med Microbiol Immunol* (*Berl*) 185(2), 89-94.

Watanabe, N., Kawano, M., Tsurudome, M., Kusagawa, S., Nishio, M., Komada, H., Shima, T., and Ito, Y. (1996b). Identification of the sequences responsible for nuclear targeting of the V protein of human parainfluenza virus type 2. *J Gen Virol* 77 (Pt 2), 327-38.

Kato, A., Kiyotani, K., Sakai, Y., Yoshida, T., and Nagai, Y. (1997). The paramyxovirus, Sendai virus, V protein encodes a luxury function required for viral pathogenesis. *Embo J* 16(3), 578-587.

Lin, G. Y., Paterson, R. G., and Lamb, R. A. (1997). The RNA binding region of the paramyxovirus SV5 V and P proteins. *Virology* 238(2), 460-9.

Delenda, C., Hausmann, S., Garcin, D., and Kolakofsky, D. (1997). Normal cellular replication of Sendai virus without the trans-frame, nonstructural V protein. *Virology* 228(1), 55-62.

Skiadopoulos, M. H., Durbin, A. P., Tatem, J. M., Wu, S. L., Paschalis, M., Tao, T., Collins, P. L., and Murphy, B. R. (1998). Three amino acid substitutions in the L protein of the human parainfluenza virus type 3 cp45 live attenuated vaccine candidate contribute to its temperature-sensitive and attenuation phenotypes. *J Virol* 72(3), 1762-8.

Kolakofsky, D., Pelet, T., Garcin, D., Hausmann, S., Curran, J., and Roux, L. (1998). Paramyxovirus RNA synthesis and the requirement for hexamer genome length: the rule of six revisited. *J Virol* 72(2), 891-9.

Lin, G. Y., Paterson, R. G., Richardson, C. D., and Lamb, R. A. (1998). The V protein of the paramyxovirus SV5 interacts with damage-specific DNA binding protein. *Virology* 249(1), 189-200.

Juhasz, K., Whitehead, S. S., Boulanger, C. A., Firestone, C. Y., Collins, P. L., and Murphy, B. R. (1999). The two amino acid substitutions in the L protein of cpts530/1009, a live-attenuated respiratory syncytial virus candidate vaccine, are independent temperature-sensitive and attenuation mutations. *Vaccine* In press.

Whitehead, S. S., Firestone, C. Y., Karron, R. A., Crowe, J. E., Jr., Elkins, W. R., Collins, P. L., and Murphy, B. R. (1999). Addition of a missense mutation present in the L gene of respiratory syncytial virus (RSV) cpts530/1030 to RSV vaccine candidate cpts248/404 increases its attenuation and temperature sensitivity. *J Virol* 73(2), 871-7.

Skiadopoulos, M. H., Surman, S., Tatem, J. M., Paschalis, M., Wu, S. L., Udem, S. A., Durbin, A. P., Collins, P. L., and Murphy, B. R. (1999a). Identification of mutations contributing to the temperature-sensitive, cold-adapted, and attenuation phenotypes of the live-attenuated cold-passage 45 (cp45) human parainfluenza virus 3 candidate vaccine. *J Virol* 73(2), 1374-81.

Durbin, A. P., McAuliffe, J. M., Collins, P. L., and Murphy, B. R. (1999). Mutations in the C, D, and V open reading frames of human parainfluenza virus type 3 attenuate replication in rodents and primates. *Virology* 261(2), 319-30.

Skiadopoulos, M. H., Tao, T., Surman, S. R., Collins, P. L., and Murphy, B. R. (1999b). Generation of a parainfluenza virus type 1 vaccine candidate by replacing the HN and F glycoproteins of the live-attenuated PIV3 cp45 vaccine virus with their PIV1 counterparts. *Vaccine* 18(5-6), 503-10.

Skiadopoulos, M. H., Surman, S. R., St Claire, M., Elkins, W. R., Collins, P. L., and Murphy, B. R. (1999c). Attenuation of the recombinant human parainfluenza virus type 3 cp45 candidate vaccine virus is augmented by importation of the respiratory syncytial virus cpts530 L polymerase mutation. *Virology* 260(1), 125-35.

Juhasz, K., Murphy, B. R., and Collins, P. L. (1999). The major attenuating mutations of the respiratory syncytial virus vaccine candidate cpts530/1009 specify temperature-sensitive defects in transcription and replication and a non-temperature-sensitive alteration in mRNA termination. *J Virol* 73(6), 5176-80.

Tao, T., Davoodi, F., Cho, C. J., Skiadopoulos, M. H., Durbin, A. P., Collins, P. L., and Murphy, B. R. (2000a). A live attenuated recombinant chimeric parainfluenza virus (PIV) candidate vaccine containing the hemagglutinin-neuraminidase and fusion glycoproteins of PIV1 and the remaining proteins from PIV3 induces resistance to PIV1 even in animals immune to PIV3. *Vaccine* 18(14), 1359-1366.

Durbin, A. P., Elkins, W. R., and Murphy, B. R. (2000). African green monkeys provide a useful nonhuman primate model for the study of human parainfluenza virus types-1, -2, and -3 infection [In Process Citation]. *Vaccine* 18(22), 2462-9.

Skiadopoulos, M. H., Surman, S. R., Durbin, A. P., Collins, P. L., and Murphy, B. R. (2000). Long nucleotide insertions between the HN and L protein coding regions of human parainfluenza virus type 3 yield viruses with temperature-sensitive and attenuation phenotypes. *Virology* 272(1), 225-34.

Tao, T., Skiadopoulos, M. H., Davoodi, F., Riggs, J. M., Collins, P. L., and Murphy, B. R. (2000b). Replacement of the ectodomains of the hemagglutinin-neuraminidase and fusion glycoproteins of recombinant parainfluenza virus type 3 (PIV3) with their counterparts from PIV2 yields attenuated PIV2 vaccine candidates. *J Virol* 74(14), 6448-58.

Huang, C., Kiyotani, K., Fujii, Y., Fukuhara, N., Kato, A., Nagai, Y., Yoshida, T., and Sakaguchi, T. (2000). Involvement of the zinc-binding capacity of Sendai virus V protein in viral pathogenesis. *J Virol* 74(17), 7834-41.

Chanock, R. M., Murphy, B. R., and Collins, P. L. (2001). Parainfluenza Viruses. 4th ed. In "Fields Virology" (D. M. Knipe, P. M. Howley, D. E. Griffin, R. A. Lamb, M. A. Martin, B. Roizman, and S. E. Strauss, Eds.), Vol. 1, pp. 1341-1379. 2 vols. Lippincott Williams&Wilkins, Philadelphia.

Vulliemoz, D., and Roux, L. (2001). "Rule of six": how does the Sendai virus RNA polymerase keep count? *J Virol* 75(10), 4506-18.

Kawano, M., Kaito, M., Kozuka, Y., Komada, H., Noda, N., Nanba, K., Tsurudome, M., Ito, M., Nishio, M., and Ito, Y. (2001). Recovery of infectious human parainfluenza type 2 virus from cDNA clones and properties of the defective virus without V-specific cysteine-rich domain. *Virology* 284(1), 99-112.

Moeller, K., Duffy, I., Duprex, P., Rima, B., Beschorner, R., Fauser, S., Meyermann, R., Niewiesk, S., ter Meulen, V., and Schneider-Schaulies, J. (2001). Recombinant measles viruses expressing altered hemagglutinin (H) genes: functional separation of mutations determining H antibody escape from neurovirulence. *J Virol* 75(16), 7612-20.

Parisien, J. P., Lau, J. F., Rodriguez, J. J., Sullivan, B. M., Moscona, A., Parks, G. D., Lamb, R. A., and Horvath, C. M. (2001). The V protein of human parainfluenza virus 2 antagonizes type I interferon responses by destabilizing signal transducer and activator of transcription 2. *Virology* 283(2), 230-9.

Schmidt, A. C., McAuliffe, J. M., Murphy, B. R., and Collins, P. L. (2001). Recombinant bovine/human parainfluenza virus type 3 (B/HPIV3) expressing the respiratory syncytial virus (RSV) G and F proteins can be used to achieve simultaneous mucosal immunization against RSV and HPIV3. *J Virol* 75(10), 4594-603.

Skiadopoulos, M. H., Surman, S. R., Riggs, J. M., Orvell, C., Collins, P. L., and Murphy, B. R. (2002). Evaluation of the replication and immunogenicity of recombinant human parainfluenza virus type 3 vectors expressing up to three foreign glycoproteins. *Virology* 297(1), 136-52.

Andrejeva, J., Young, D. F., Goodbourn, S., and Randall, R. E. (2002a). Degradation of STAT1 and STAT2 bp the V proteins of simian virus 5 and human parainfluenza virus type 2, respectively: consequences for virus replication in the presence of alpha/beta and gamma interferons. *J Virol* 76(5), 2159-67.

Fukuhara, N., Huang, C., Kiyotani, K., Yoshida, T., and Sakaguchi, T. (2002). Mutational analysis of the Sendai virus V protein: importance of the conserved residues for Zn binding, virus pathogenesis, and efficient RNA editing. *Virology* 299(2), 172-81.

Newman, J. T., Surman, S. R., Riggs, J. M., Hansen, C. T., Collins, P. L., Murphy, B. R., and Skiadopoulos, M. H. (2002). Sequence analysis of the Washington/1964 strain of human parainfluenza virus type 1 (HPIV1) and recovery and characterization of wild-type recombinant HPIV1 produced by reverse genetics. *Virus Genes* 24(1), 77-92.

Parisien, J. P., Lau, J. F., and Horvath, C. M. (2002). STAT2 acts as a host range determinant for species-specific paramyxovirus interferon antagonism and simian virus 5 replication. *J Virol* 76(13), 6435-41.

He, B., Paterson, R. G., Stock, N., Durbin, J. E., Durbin, R. K., Goodbourn, S., Randall, R. E., and Lamb, R. A. (2002). Recovery of Paramyxovirus Simian Virus 5 with a V Protein Lacking the Conserved Cysteine-rich Domain: The Multifunctional V Protein Blocks both Interferon-beta Induction and Interferon Signaling. *Virology* 303(1), 15-32.

Ulane, C. M., and Horvath, C. M. (2002). Paramyxoviruses SV5 and HPIV2 assemble STAT protein ubiquitin ligase complexes from cellular components. *Virology* 304(2), 160-6.

Andrejeva, J., Poole, E., Young, D. F., Goodbourn, S., and Randall, R. E. (2002b). The p127 subunit (DDB1) of the UV-DNA damage repair binding protein is essential for the targeted degradation of STAT1 bp the V protein of the paramyxovirus simian virus 5. *J Virol* 76(22), 11379-86.

Skiadopoulos, M. H., Schmidt, A. C., Riggs, J. M., Surman, S. R., Elkins, W. R., St Claire, M., Collins, P. L., and Murphy, B. R. (2003a). Determinants of the host range restriction of replication of bovine parainfluenza virus type 3 in rhesus monkeys are polygenic. *J Virol* 77(2), 1141-8.

Skiadopoulos, M. H., Vogel, L., Riggs, J. M., Surman, S. R., Collins, P. L., and Murphy, B. R. (2003b). The genome length of human parainfluenza virus type 2 follows the rule of six, and recombinant viruses recovered from non-polyhexameric-length antigenomic cDNAs contain a biased distribution of correcting mutations. *J Virol* 77(1), 270-9.

Park, M. S., Garcia-Sastre, A., Cros, J. F., Basler, C. F., and Palese, P. (2003). Newcastle disease virus V protein is a determinant of host range restriction. *J Virol* 77(17), 9522-32.

Kozuka, Y., Yamashita, Y., Kawano, M., Tsurudome, M., Ito, M., Nishio, M., Komada, H., and Ito, Y. (2003). Identification of amino acids essential for the human parainfluenza type 2 virus V protein to lower the intracellular levels of the STAT2. *Virology* 317(2), 208-19.

McAuliffe, J. M., Surman, S. R., Newman, J. T., Riggs, J. M., Collins, P. L., Murphy, B. R., and Skiadopoulos, M. H. (2004). Codon substitution mutations at two positions in the L polymerase protein of human parainfluenza virus type 1 yield viruses with a spectrum of attenuation in vivo and increased phenotypic stability in vitro. *J Virol* 78(4), 2029-36.

Newman, J. T., Riggs, J. M., Surman, S. R., McAuliffe, J. M., Mulaikal, T. A., Collins, P. L., Murphy, B. R., and Skiadopoulos, M. H. (2004). Generation of recombinant human parainfluenza virus type 1 vaccine candidates by importation of temperature-sensitive and attenuating mutations from heterologous paramyxoviruses. *J Virol* 78(4), 2017-28.

Rodriguez, J. J., Cruz, C. D., and Horvath, C. M. (2004). Identification of the nuclear export signal and STAT-binding domains of the Nipah virus V protein reveals mechanisms underlying interferon evasion. *J Virol* 78(10), 5358-67.

Sun, M., Rothermel, T. A., Shuman, L., Aligo, J. A., Xu, S., Lin, Y., Lamb, R. A., and He, B. (2004). Conserved cysteine-rich domain of paramyxovirus simian virus 5 V protein plays an important role in blocking apoptosis. *J Virol* 78(10), 5068-78.

What is claimed:

1. A recombinant, infectious, self-replicating human parainfluenza virus 2 (HPIV2) comprising a partial or complete polyhexameric genome or antigenome comprising a variant polynucleotide having:

a monocistronic polynucleotide with an open reading frame (ORF) encoding a P protein, which does not encode a V protein, and a monocistronic polynucleotide with an open reading frame (ORF) encoding a V protein, wherein the two monocistronic polynucleotides are separated by a non-coding polynucleotide spacer sequence comprising a gene end transcription signal, intergenic transcription signal, and gene start transcription signal, wherein said P protein and said V protein are encoded by separate polynucleotides.

2. The recombinant, infectious, self-replicating HPIV2 of claim 1, further comprising a major nucleocapsid (N) protein, a nucleocapsid phosphoprotein (P), and a large polymerase protein (L).

3. The recombinant, infectious, self-replicating HPIV2 of claim 1, wherein the recombinant virus has an attenuated phenotype.

4. The recombinant, infectious, self-replicating HPIV2 of claim 1, wherein the P open reading frame (ORF) and spacer sequence are upstream of the V ORF.

5. The recombinant, infectious, self-replicating HPIV2 of claim 1, wherein the gene start transcription signal is cis-acting.

6. The recombinant, infectious, self-replicating HPIV2 of claim 5, wherein the gene start transcription signal comprises a first adenosine at position 6n+1.

7. The recombinant, infectious, self-replicating HPIV2 of claim 1, wherein the monocistronic polynucleotide encoding a V protein comprises a nucleotide sequence encoding a variant V protein.

8. The recombinant, infectious, self-replicating HPIV2 of claim 1, wherein the monocistronic polynucleotide encoding a V protein is located at:

the 3' terminus of the genome immediately adjacent to the N ORF, or a position making it the first ORF after the N ORF.

9. The recombinant, infectious, self-replicating HPIV2 of claim 7, wherein the V protein comprises an amino acid sequence having at least 80% sequence identity with SEQ ID NO:45.

10. The recombinant, infectious, self-replicating HPIV2 of claim 1, wherein said genome or antigenome further comprises at least one amino acid mutation that is an attenuating mutation.

11. The recombinant, infectious, self-replicating HPIV2 of claim 10, wherein said attenuating mutation is stabilized by at least two changes in the codon specifying the mutation.

12. The recombinant, infectious, self-replicating HPIV2 of claim 1, wherein the variant polynucleotide encoding a P protein comprises a P ORF having one or more nucleotide substitutions, wherein the substitution(s) introduces one or more stop codons in an overlapping V ORF but does not alter an amino acid sequence of P protein encoded by the variant polynucleotide encoding a P protein.

13. The recombinant, infectious, self-replicating HPIV2 of claim 7, wherein the encoded variant V protein comprises an amino acid substitution or deletion.

14. The recombinant, infectious, self-replicating HPIV2 of claim 13, wherein the amino acid substitution occurs at or between amino acid residues corresponding to position 67, 68, 69, 70, 71, 72, 105, 106, 107, 108, 121, 122, 123, 124, 125, 126,127, 130, 131, 132, 133, 134, 135, 136, 137, 138, 139, 140, 167, 168, 169, 170, 171, 172, or any one of the amino acids of 174-225 of SEQ ID NO: 45.

* * * * *

SEQUENCE LISTING

```
<160> NUMBER OF SEQ ID NOS: 51

<210> SEQ ID NO 1
<211> LENGTH: 16350
<212> TYPE: DNA
<213> ORGANISM: Artificial Sequence
<220> FEATURE:
<223> OTHER INFORMATION: Description of Artificial Sequence: Synthetic
      antigenomic cDNA

<400> SEQUENCE: 1
accaagggga gaatcagatg gcatcgttat atgacgaatt gcaaaaagat tacgtaggtc      60
cggaaccact agattccggt gccggtaacg atctcagttt tatactatct gatcattctt     120
tatctctact aaggatattt ctaatctaag gttcaaaatg tcaagtgtct taaagacatt     180
tgaaagattt actatacaac aggagcttca ggagcaatct gaagacactc caataacctct    240 tgaaacaatc agacctacaa tcagagtatt tgtcatcaat aataatgatc ctattgtaag     300
atctagactt ttattcttta atctacgaat tattatgagt aacactgcaa gagagggaca     360
tagagctggt gctctcctca gtcttttatc actaccttct gcagctatga gtaatcacat     420
caaactagcc atgcattcac cagaagccag catagataga gtagaaataa cagggtttga     480
gaataattca ttccgagtta ttccagatgc tcgatcaact atgtccagag gagaagtgct     540
ggccttcgaa gcattagctg aggacattcc tgatacccct aatcaccaaa ctccatttgt     600
aaataatgat gtggaagatg acatatttga tgaaacagag aaattcttgg atgtttgcta     660
tagtgtactt atgcaggcat ggatagtaac atgcaagtgc atgactgctc ctgatcaacc     720
accagtatca gtagcaaagc ggatggctaa atatcaacaa caagggagaa tcaatgctag     780
atatgtacta caacctgaag cacaaagact aattcagaat gccatccgca agtcaatggt     840
agtaaggcat ttcatgacct atgagcttca actttcacaa tcaagatctt tgctagcgaa     900
ccgttattat gccatggtgg gagacattgg caagtatatt gaacacagcg gaatgggagg     960 gttttctta acacttaaat atggacttgg aacaagatgg cctacattgg ctcttgcagc    1020
```

```
attctctggg gaactccaga aattaaaggc tctcatgcta cattatcaga gtctaggacc    1080
catggccaag tacatggctc tattagaatc accaaagctg atggattttg tcccatctga    1140
atatccatta gtttatagct atgcaatggg tattggaact gtccttgata caaacatgag    1200
aaactatgca tatggtagat catatctaaa tccacaatat tttcagctag ggtagaaac     1260 agcaaggaaa cagcaaggag ctgttgacaa caggacagca gaggacctcg gcatgactgc    1320
tgcagataaa gcagacctca ctgcaaccat atcaaagcta tctttatccc aattacctag    1380
gggtagacaa ccaatatccg acccatttgc tggagcaaat gacagagaaa caggaggaca    1440
agcaactgat acacctgtgt ataacttcaa tccaatcaat aatcggaggt atgacaacta    1500
tgacagtgat agtgaggaca gaattgacaa cgatcaagat caggctatca gagagaacag    1560
aggagaacct ggacaaccaa acaaccagac aagcgaaaac cagcagagac tcaatctccc    1620
tgtaccgcaa agaacatcag gtatgagtag tgaagagttc caacattcaa tgaatcagta    1680
catccgtgct atgcatgagc aatacagagg ctcccaggat gatgatgcca atgatgccac    1740
agatgggaat gacatttcac ttgagctagt tggagatttt gattcctaac tctcactttc    1800
acataaccag acatacacat ccacaccacc cagagacata gctaccatcc acacactcac    1860
ccagacaaat caaactagat tcaaatcatt cggaaacaat tctcctagaa tttaagaaaa    1920
aaacataggc ccggacgggt tagagatccg gtgctcgtct gtggccagac aacctccaca    1980
ccagaggcgc gccatcatgg ccgaggaacc aacatacacc actgagcaag ttgatgaatt    2040
aatccatgct ggactaggaa cagtagattt cttcctatct agacccatag atgctcagtc    2100
ttctttaggt aaaggcagca tcccaccagg tgtcacggct gttctaacca atgcagcaga    2160
ggcaaaatcc aaaccagttg ctgctggtcc agtaaaaccc agacggaaga agtgatcag     2220 caataccact ccatacacta ttgcagacaa catcccacct gagaagctac cgatcaacac    2280
tccaataccc aatccattac ttccactggc acgccctcac ggaaagatga cagacattga    2340
cattgtcact gggaacatta cagaaggatc atacaaaggt gtggagcttg ccaaattagg    2400
gaagcaaaca ctactcacaa ggttcacctc gaatgagcca gtctcctcag ctggatccgc    2460
ccaagacccc aactttaaga gaggaggtga gctaatagag aaagagcaag aggcaaccat    2520
aggagagaat ggagtattgc atgggtcgga gatcaggtca aagtcttcga gtggtgtaat    2580
cccaggtgtg ccccagtcac ggcttcagct cgcaagttca cctgcacatg tggatcctgc    2640
cccagcatct gcggagaatg tgaaggagat cattgagctc ttaaaagggc ttgatcttcg    2700
ccttcagact gtagaaggga agtagataa aattcttgca acctctgcaa ctataatcaa    2760
tcttaaaaat gaaatgacta gtcttaaggc gagcgttgca actgtggaag gtatgataac    2820
aacaattaaa atcatggatc ccagtacacc aaccaatgtc cctgtagagg agatcagaaa    2880
gagtttacac aatgttccag tagtaattgc tggtccgact agtggaggct tcacagccga    2940
aggcagtgac atgatttcaa tggatgaact agctaggcct acactctcat caacaaaaaa    3000
gatcacacga aagcctgaat ccaagaaaga tttaacaggc ataaaactaa ccctgatgca    3060
gcttgcaaat gactgcatct cgcgtccaga taccaagact gagtttgtga ctaagattca    3120
agcagcaacc acagaatcac agctcaacga aatcaaacgg tcaataatac gctctgcaat    3180
ataaaattga cgcggttacc ggtgaattta agaaaaaaac ataggcccgg acgggaccat    3240
ggccgaggaa ccaacataca ccactgagca agttgatgaa ttaatccatg ctggactagg    3300
aacagtagat ttcttcctat ctagacccat agatgctcag tcttctttag gtaaaggcag    3360
catcccacca ggtgtcacgg ctgttctaac caatgcagca gaggcaaaat ccaaaccagt    3420
```

```
tgctgctggt ccagtaaaac ccagacggaa gaaagtgatc agcaatacca ctccatacac   3480
tattgcagac aacatcccac ctgagaagct accgatcaac actccaatac ccaatccatt   3540
acttccactg gcacgccctc acggaaagat gacagacatt gacattgtca ctgggaacat   3600
tacagaagga tcatacaaag gtgtggagct tgccaaatta gggaagcaaa cactactcac   3660
aaggttcacc tcgaatgagc cagtctcctc agctggatcc gcccaagacc ccaactttaa   3720
gagaggcgga gctaatagag aaagagcaag aggcaaccat aggagagaat ggagtattgc   3780
atgggtcgga gatcaggtca aagtcttcga gtggtgtaat cccaggtgtg ccccagtcac   3840
ggcttcagct cgcaagttca cctgcacatg tggatcctgc cccagcatct gcggagaatg   3900
tgaaggagat cattgaccgc ggaagatcca aactccttcc atccgaaaac acactcacca   3960
ctgtcaacac caagaaacaa ctacagccga accatgctca accaaaagac caaacaaca   4020 tctcaaatcg acagaaggct agacatgata aatttaataa aaaattaaaa gaagttaagt   4080
aaaatttaaa gaacacaata gagaaaacct aggtccgaaa gcttgccttt cagacagatc   4140
ccaaaatcat agttcaaact tcaaacacag cagcagacat gcctataata tcattaccag   4200
cagatccaac ttcacccagt caatccctta ctccgtttcc aatacaactt gataccaaag   4260
atggcaaggc agggaaactc cttaaacaga ttagaattag gtatctaaat gaacctaact   4320
ctcgtcatac accaataact ttcatcaata cgtatggatt tgtttatgct cgagacactt   4380
caggaggcat tcacagcgag atcagcagtg acctagctgc agggtccata acggcatgca   4440
tgatgacact aggtcctggt ccaaatattc agaatgcaaa tctagtgcta agatccctga   4500
atgaattcta cgtaaaagtc aagaagacat caagccagag ggaggaagca gtgtttgaat   4560
tagttaacat tccaacctta ttgagagaac atgctctttg caaacgcaaa acgttagtat   4620
gctctgcaga aaaattcctc aagaacccat caaagctaca agctggatt gaatatgtat   4680 acatcccaac ttttgtctcc attacatact caccacgaaa tctgaattac caagttgcca   4740
gacctatcct taagttcaga tcacgctttg tgtatagcat tcatttggaa ttaatcctga   4800
gattgctatg caaatctgac tccccttga tgaaatctta taatgcagat cgaacaggtc   4860
gaggatgcct cgcatcagtc tggatccacg tatgtaacat tctgaaaaac aaaagcatca   4920
agcaacaagg cagagaatca tatttcatag ctaagtgcat gagtatgcag ctgcaggtgt   4980
ccattgcaga tctttgggga ccaacaatca taattaaatc attgggtcac atccccaaga   5040
ctgcacttcc ttttttcagc aaagacggga ttgcctgtca tccactacaa gatgtttccc   5100
ctactctgac aaaatcactg tggtcagtgg gatgtgagat agaatctgcc aagttgatac   5160
ttcaagaatc tgatattaat gagctaatgg gccaccagga cttgattact gataagattg   5220
ccattagatc aggtcaacgg acatttgaga ggtccaaatt cagcccattc aaaaaatacg   5280
catcaattcc aaacttagaa gccatcaact gaatgctcca gcatctagga atagaacaac   5340
aactaagtca taccattatt gaccatacaa taatcaacaa ttttagccaa ctgattacta   5400
agatattatc ataggtccga actgatcaat ctaacaaaaa aactaaacat tcaataataa   5460
atcaaagttc aggccaaatt atccagccat gcatcacctg catccaatga tagtatgcat   5520
ttttgttatg tacactggaa ttgtaggttc agatgccatt gctggagatc aactcctcaa   5580 tgtagggtc attcaatcaa agataagatc actcatgtac tacactgatg gtggcgctag   5640
ctttattgtt gtaaaattac tacccaatct tcccccaagc aatggaacat gcaacatcac   5700
cagtctagat gcatataatg ttaccctatt taagttgcta acacccctga ttgagaacct   5760
```

```
gagcaaaatt tctgctgtta cagataccaa accccgccga gaacgatttg caggagtcgt   5820
tattgggctt gctgcactag gagtagctac agctgcacaa ataaccgcag ctgtagcaat   5880
agtaaaagcc aatgcaaatg ctgctgcgat aaacaatctt gcatcttcaa ttcaatccac   5940
caacaaggca gtatccgatg tgataactgc atcaagaaca attgcaaccg cagttcaagc   6000
gattcaggat cacatcaatg gagccattgt caacgggata acatctgcat catgccgtgc   6060
ccatgatgca ctaattgggt caatattaaa tttgtatctc actgagctta ctacaatatt   6120
tcataatcaa ataacaaacc ctgcgctgac accactttcc atccaagctt taagaatcct   6180
cctcggtagc accttgccaa ttgtcattga atccaaactc aacacaaaac tcaacacagc   6240
agagctgctc agttccggac tgttaactgg tcaaataatt tccatttccc caatgtacat   6300
gcaaatgcta attcaaatca atgttccgac atttataatg caacccggtg cgaaggtaat   6360
tgatctaatt gctatctctg caaccataa attacaagaa gtagttgtac aagttcctaa   6420
tagaattcta gaatatgcaa atgaactaca aaactaccca gccaatgatt gtgtcgtgac   6480
accaaactct gtattttgta gatacaatga gggttccccg atccctgaat cacaatatca   6540
atgcttaagg gggaatctta attcttgcac ttttacccct attatcggga actttctcaa   6600
gcgattcgca tttgccaatg gtgtgctcta tgccaactgc aaatctttgc tatgtaagtg   6660
tgccgaccct ccccatgttg tgtctcaaga tgacaaccaa ggcatcagca taattgatat   6720
taagaggtgc tctgagatga tgcttgacac ttttttcattt aggatcacat ctacattcaa   6780
tgctacatac gtgacagact tctcaatgat taatgcaaat attgtacatc taagtcctct   6840
agacttgtca aatcaaatca attcaataaa caaatctctt aaaagtgctg aggattggat   6900
tgcagatagc aacttcttcg ctaatcaagc cagaacagcc aagacacttt attcactaag   6960
tgcaatcgca ttaatactat cagtgattac tttggttgtt gtgggattgc tgattgccta   7020
catcatcaag ctggtttctc aaatccatca attcagagca ctagctgcta caacaatgtt   7080
ccacagggag aatcctgccg tcttttccaa gaacaatcat ggaaacatat atgggatatc   7140
ttaagaattc tatcataagt ccatatatgt ccatgattga cctttaagag ccaacctcca   7200
atgattatcc gttaaattca gatataacaa ttcaaaaatc aatattaagc ctccagatac   7260
caatgaatat gaatatatct cttagaaaac ttgattatta tgtgataaca tagtacaatt   7320
taagaaaaaa cctaaaataa gcacgaaccc ttaaggtgtc gtaacgtctc gtgacgccgg   7380
gttcagttca aacatcgacc cctgacccaa ttcaataccc attttcataa aggaacacag   7440
tataatttaa tcataaaaga cctcaaaatc tgatacagct taatccactc aacatataat   7500
tataagacta ataataatgg aagattacag caatctatct cttaaatcaa ttcctaaaag   7560
gacatgtaga atcattttcc gaactgccac aattcttggc atatgcacat taattgtgct   7620
atgttcaagt attcttcatg agataattca tcttgatgtt tcctctggtc ttatgaattc   7680
tgatgagtca cagcaaggca ttattcagcc tatcatagaa tcattaaaat cattgattgc   7740
tttggccaac cagattctat ataatgttgc aatagtaatt cctcttaaaa ttgacagtat   7800
cgaaactgta atactctctg ctttaaaaga tatgcacacc gggagtatgt ccaatgccaa   7860
ctgcacgcca ggaaatctgc ttctgcatga tgcagcatac atcaatggaa taaacaaatt   7920
ccttgtactt gaatcataca atgggacgcc taaatatgga cctctcctaa atatacccag   7980
ctttatcccc tcagcaacat ctccccatgg gtgtactaga ataccatcat tttcactcat   8040
caagacccat tggtgttaca ctcacaatgt aatgcttgga gattgtcttg atttcacggc   8100
atctaaccag tatttatcaa tggggataat acaacaatct gctgcagggt ttccaatttt   8160
```

```
caggactatg aaaaccattt acctaagtga tggaatcaat cgcaaaagct gttcagtcac   8220
tgctatacca ggaggttgtg tcttgtattg ctatgtagct acaaggtctg aaaaagaaga   8280
ttatgccacg actgatctag ctgaactgag acttgctttc tattattata atgatacctt   8340
tattgaaaga gtcatatctc ttccaaatac aacagggcag tgggccacaa tcaaccctgc   8400
agtcggaagc gggatctatc atctaggctt tatcttattt cctgtatatg gtggtctcat   8460
aaatgggact acttcttaca atgagcagtc ctcacgctat tttatcccaa acatcccaa    8520 cataacttgt gccggtaact ccagcaaaca ggctgcaata gcacggagtt cctatgtcat   8580
ccgttatcac tcaaacaggt taattcagag tgctgttctt atttgtccat tgtctgacat   8640
gcatacagaa gagtgtaatc tagttatgtt taacaattcc caagtcatga tgggtgcaga   8700
aggtaggctc tatgttattg gtaataattt gtattattat caacgcagtt cctcttggtg   8760
gtctgcatcg ctcttttaca ggatcaatac agattttttct aaaggaattc ctccgatcat   8820
tgaggctcaa tgggtaccgt cctatcaagt tcctcgtcct ggagtcatgc catgcaatgc   8880
aacaagtttt tgccctgcta attgcatcac aggggtgtac gcagatgtgt ggccgcttaa   8940
tgatccagaa ctcatgtcac gtaatgctct gaaccccaac tatcgatttg ctggagcctt   9000
tctcaaaaat gagtccaacc gaactaatcc cacattctac actgcatcgg ctaactccct   9060
cttaaatact accggattca acaacaccaa tcacaaagca gcatatacat cttcaacctg   9120 cttaaaaac actggaaccc aaaaaattta ttgtttaata ataattgaaa tgggctcatc     9180
tcttttaggg gagttccaaa taataccatt tttaagggaa ctaatgcttt aatcctattg   9240
aatgaagact ccagattcaa gaataattgg aaggctcttt attttatgcg atagttatac   9300
gttttggctg tattagaatg ctatagcatt ctgctgtttt tcccatatgg aaaaatcctt   9360
caacaccaac ttaggttcaa ttttctcatc atttactgtt gtaattcaat cttactaaag   9420
ttattctgat atttaagaaa aaataatctt tatataatgt aacaatacta ctaagattat   9480
aatataggcc agaatggcgg cctcttctga gatactcctt cctgaagtcc atttgaactc   9540
accaatagtc aaacacaaac tcatatacta cttattacta gggcacttcc cgcatgatct   9600
tgacatttct gaaataagcc cccttcacaa taatgattgg gatcagattg ccagagaaga   9660
atccaatctt gctgaacgac tcggagtagc taaatctgaa ttaattaaac gtgtgcccgc   9720
atttagagca accagatggc gtagtcatgc agccgtcctt tatatggcctt cttgtatacc   9780 attccttgtt aaattcctac cccattctaa gcttcaacca atagaacaat ggtacaagtt   9840
gatcaatgct tcatgcaata ctatatctga ctcaattgat agatgtatgg agaatatttc   9900
tattaagctt actgggaaaa acaatctatt ctctcgatcc agaggaactg caggcgcagg   9960
taaaaacagt aaaatcaccc tcaatgatat ccaatctatt tgggaatcaa acaaatggca   10020
gcctaatgta tctttatggc ttacaattaa ataccaaatg cgacaactta taatgcatca   10080
aagttctcgt cagccaactg atttagttca cattgttgac acacgatctg gtctaatagt   10140 tatcaccoct gaacttgtta tttgctttga tcggttgaat aatgttttaa tgtatttttac  10200 atttgagatg actttaatgg taagtgacat gtttgaggga cggatgaatg ttgccgcgct   10260
ctgcactatt agtcattact tatcaccact agggccaagg atagatagat tgttttctat   10320
tgtagatgaa ttagcacaac tattgggtga cactgtatat aaaattattg catctcttga   10380
atctttagta tatgggtgtc tacaacttaa agatccagtg gttgaattaa caggatcatt   10440
tcattccttt attacgcaag agattataga tatcctaatt gggtcaaaag cccttgataa   10500
```

```
ggatgaatca ataactgtca ctacacaatt gctagatata ttttccaacc tttctccaga    10560
tttaatcgct gagatgttgt gtctcatgag actttgggggt catcccactc ttactgctgc   10620
gcaagctgca ggtaaagtga gagaatctat gtgtgcaggt aagttacttg atttccctac   10680
aataatgaaa actcttgctt ttttccacac aattttaatc aatggttatc gtagaaagaa   10740
gaatggaatg tggcctccac ttatacttcc taaaaatgca tcaaaaagct aatagagtt    10800 tcaacatgat aatgctgaaa tatcttatga gtatacactc aagcattgga aagaaatctc   10860
tctcatagaa tttagaaagt gctttgactt tgatcctggt gaggagctaa gcatttttat   10920
gaaagacaag gcaataagtg ctccaaaaag tgattggatg agtgtattcc gtagaagtct   10980
aataaaacaa cgacatcaga gacatcatat tcctatgccc aatccattta acagacgtct   11040
attactcaat ttcttagaag atgacagttt tgatccagtt gctgagcttc aatatgttac   11100
cagtggtgaa tatctccgag atgacacatt ttgtgcatct tactcattaa aagagaaaga   11160
aataaaacca gatggaagga tatttgctaa gcttactaat agaatgcggt cttgtcaagt   11220
aattgcggaa gcaattcttg caaatcacgc aggtactcta atgaaggaaa acggagttgt   11280
cttgaatcaa ttatctctga ctaaatcatt gcttactatg agtcaaattg gcataatatc   11340
agaaaaagca aagagatata cccgagataa catctcatct caaggtttcc atacaatcaa   11400
gactgactca aaaaataaga agaaaagcaa aattgcatca tcataccctca cagatcctga   11460 tgatacattt gaacttagtg catgttttat aactactgat cttgctaaat actgtcttca   11520
atggagatat cagaccataa tccattttgc tcgaacatta aacagaatgt atggagttcc   11580
acatttattt gaatggattc atcttcgttt gattagatct acattatatg ttggtgatcc   11640
attcaatcct cctgccacaa ctgatgcctt cgatctagat aaagtattaa atggtgatat   11700
ctttatagtc tctcccaagg gaggtattga aggcctatgt cagaaaatgt ggacaatgat   11760
ctctatttct gtgatcatcc tttcttcagc cgaatccaaa acaagagtaa tgagcatggt   11820
tcaaggagat aatcaggcga ttgcagttac aacaagagtt cctagatcat tgcctagtgt   11880
tcagaaaaag gagttagcct acgcagcaag caagttattc tttgaaagac ttagggcaaa   11940
taattatggt ttgggtcatc aactaaaggc tcaagagact ataataagtt ccacgttctt   12000
catatatagt aaacgggtat tctatcaagg acgtatacta acacaggcac ttaaaaatgc   12060
tagcaagtta tgtcttactg cagatgtatt aggtgaatgt actcaggctt cctgctcaaa   12120
ttctgctact acaatcatga gattaacaga aaatggggtt gagaaagata catgttataa   12180
gcttaatatt tatcaatcta ttcgtcaact cacatatgat ctaatatttc cccaatactc   12240
cataccaggt gaaacaataa gtgaaatttt cttacagcat ccaagattaa tctcacgtat   12300
tgttctgctc ccttcacagc taggtggtct taattacctc gcatgtagca gattatttaa   12360
ccgcaatatc ggagatcccc ttggtacagc cgtggcagac ctcaagaggt taattaaatg   12420
tggtgctctt gaatcatgga tactgtacaa tttactggca agaaaaccag ggaaaggttc   12480
atgggccact ttagcagccg atccatactc attgaatcaa gaatatcttt atcctcctac   12540
tactatactt aaaagacata ctcaaaatac tttaatggag atatgtcgga tcctatgtt    12600 aaagggagtt tttacagata tgcaaaagag ggaggaaaat ctccttgcaa aatttcttct   12660
tgatcgtgat atagtattgc caagagtcgc acacattata atagatcaat ccagcattgg   12720
aaggaagaaa cagatacaag ggttttttga caccacaagg accataatga gacgatcatt   12780
tgagatcaaa ccactctcaa ctaagaagac actttcagtc atagaatata atactaatta   12840
tttatcttat aactaccctg tcatacttaa tccttttacct attcctggat atttaaatta   12900
```

-continued

```
tattactgac caaacttgca gtattgatat atctagaagt ttaagaaaat tatcatggtc    12960
ttctttattg aatggaagaa ctttagaagg attagaaact ccagatccaa ttgaagttgt    13020
caatggttcc ttgattgtag gtacaggaga ttgtgacttt tgtatgcagg gtgacgataa    13080
attcacttgg ttcttttttac ctatggggat aattattgat ggaaatcctg aaactaatcc    13140
acccatcaga gttccataca ttgggtctag aacagaggaa agaagagttg catcaatggc    13200
atatattaaa ggtgccacac acagtttgaa ggctgctctt agaggcgcag ggtatacat    13260 ttgggcattc ggagatacag tagtgaactg gaatgatgca cttgatatcg caaatactag    13320
ggttaagata tccctagagc aacttcagac tcttacacct cttcctacat ctgcaaacat    13380
tacacatcgt ttagatgatg gagccacaac acttaaattc actccagcta gttcctatgc    13440
attttctagt tatactcata tatcaaatga tcaacaatat ttagaaatag atcagagagt    13500
agtcgattcc aatattattt atcaacaatt aatgataaca gggcttggga tcattgagac    13560
ctaccataac ccacctatca ggacctctac acaggaaatc accctccatt tgcacactag    13620
ctcatcttgt tgtgttagaa gtgtagatgg ttgccttata tgtgagagca atggagaggt    13680
tcctcagatc actgttccct acactaattc atttgtatat gatcctgatc cactagcaga    13740
ttatgagatt gcacatctag attatctctc ctaccaagct aaaattggaa gtacagatta    13800
ctactcactt actgataaaa ttgatctatt ggcacattta actgcaaaac aaatgataaa    13860
ctcaataatt gggttagatg aaacagtatc aattgtcaat gatgcggtta ttctatctga    13920
ttatactaat aactggatta gtgaatgttc ttatactaag atagatttag tttttaaatt    13980
aatggcatgg aatttccttc ttgagcttgc attccagatg tactacctaa gaatatcatc    14040
ttggacaaat atatttgact atacttacat gactttacgc aggatacccg gaactgctct    14100
aaataatatt gcagctacta ttagccaccc aaaattatta agacgtgcaa tgaatcttga    14160
tattatcact cctatacatg caccgtattt ggcttcatta gattatgtca aattaagtat    14220
tgatgcaatt cagtgggggg ttaaacaagt tcttgctgat ttatcaaatg gaattgatct    14280
tgaaatcttg attctttcag aggattcaat ggaaattagt gatagggcaa tgaatctcat    14340
tgctagaaaa ctaactctcc ttgcacttgt taaaggtgag aactatacat ttccaaaaat    14400
taaagggatg ccaccagagg aaaagtgttt agtcttaact gaatacctag caatgtgtta    14460
tcagaatact caccacttag atccagatct tcaaaagtat ttatataatc taactaatcc    14520
aaaattgact gcatttccca gtaacaactt ctacttaaca aggaaaatcc ttaatcaaat    14580
tagagaatca gacgaaggac aatatattat cacctcatat tatgaatcct tcgaacaatt    14640
agaaacagat ataattcttc actctacttt aactgctcct tatgataatt cagaaactct    14700
aacaaagttt gatttatccc ttgacatctt tccacatcca gaatctctcg agaaatatcc    14760
tcttccagtt gatcatgact ctcaatctgc aatttcaaca ctaattccag gccctccctc    14820
tcatcatgta ttacgaccac taggagtgtc atctacagct tggtataaag gataagtta    14880 ttgcagatac ctggaaacgc aaaagataca gactggtgat catctttatt tagctgaagg    14940
aagcggtgct tcaatgtcac ttctagaact cctatttcca ggagatactg tctattataa    15000
tagtcttttt agtagtggag agaatcctcc acagagaaat tatgctcctc ttccaactca    15060
atttgtacag agtgttccat ataaattgtg gcaagctgat cttgctgatg atagtaactt    15120
aataaaagat tttgtcccat tatggaatgg aaacggagca gttacagact tatcgacaaa    15180
ggatgcagtt gcattcataa tacataaagt aggagcggag aaagcatccc ttgttcatat    15240
```

```
agatctcgaa tcgactgcta atataaatca gcaaactctg tccagatccc agattcattc    15300
gttaattata gcaactactg ttcttaagag gggtgggata ttagtttaca aaacatcatg    15360
gcttccgttt tctaggttta gtcaactagc aagcctactt tggtgctttt ttgaccggat    15420
ccatctaata cgtagtagtt attctgatcc tcacagtcat gaggtttatc ttgtatgtag    15480
acttgctgcg gattttagaa ctatcggttt cagtgcagct ctagtaactg ctactactct    15540
tcacaatgac ggattcacaa caatacatcc tgatgttgtt tgtagttatt ggcaacacca    15600
tcttgagaat gttgggagag tcgaaaaagt aattgatgag atacttgatg gtttagccac    15660
caacttcttc gcaggagata atgggcttat tctaagatgt ggaggaactc ccagctctag    15720
aaaatggtta gagattgatc agttagcatc atttgattca gttcaagatg ctctagtgac    15780
acttatcacc atacacctaa aggaaattat agaagtgcag tcatcacata cagaggatta    15840
tacatctctc cttttcacac cttataatat tggtgcagca gggaaagtaa gaactatcat    15900
caaattaatt ctagaacgat ctttaatgta tacagtccga aattggttag ttttacccag    15960
ttccatccgg gattccgtac gacaagatct agagttaggg tcatttagat taatgtctat    16020
tttaagtgaa cagacatttc ttaaaaagac acccaccaaa aaatacttac ttgatcagct    16080
tacaaggaca tatatcaa ccttctttaa ttctcactca gtcctcccc tccaccgtcc       16140 atatcaaaaa caaatatgga aagccttagg tagtgtaata tattgttcgg agacggttga    16200 tatcctcta attagagaca ttcagataga agatattaat gattttgaag atatcgagag     16260
gggtatcgat ggcgaagaat tatgacaaca gtgattataa gaactcatga tagtttattt    16320
taagaaaaac atattgattt tccccttggt                                     16350
```

<210> SEQ ID NO 2
<211> LENGTH: 1188
<212> TYPE: DNA
<213> ORGANISM: Artificial Sequence
<220> FEATURE:
<223> OTHER INFORMATION: Description of Artificial Sequence: Synthetic antigenomic cDNA P ORF sequence

<400> SEQUENCE: 2

```
atggccgagg aaccaacata caccactgag caagttgatg aattaatcca tgctggacta     60
ggaacagtag atttcttcct atctagaccc atagatgctc agtcttcttt aggtaaaggc    120
agcatcccac caggtgtcac ggctgttcta accaatgcag cagaggcaaa atccaaacca    180
gttgctgctg gtccagtaaa acccagacgg aagaaagtga tcagcaatac cactccatac    240
actattgcag acaacatccc ccctgagaag ctaccgatca cactccaat acccaatcca    300 ttacttccac tggcacgccc tcacggaaag atgacagaca ttgacattgt cactgggaac    360
attacagaag atcatacaa aggtgtggag cttgccaaat tagggaagca acactactc     420 acaaggttca cctcgaatga gccagtctcc tcagctggat ccgcccaaga ccccaacttt    480
aagagaggag gtgagctaat agagaaagag caagaggcaa ccataggaga gaatggagta    540
ttgcatgggt cggagatcag gtcaaagtct tcgagtggtg taatcccagg tgtgccccag    600
tcacggcttc agctcgcaag ttcacctgca catgtggatc ctgccccagc atctgcggag    660
aatgtgaagg agatcattga gctcttaaaa ggcttgatc ttcgccttca gactgtagaa      720
gggaaagtag ataaaattct tgcaacctct gcaactataa tcaatcttaa aaatgaaatg    780
actagtctta aggcgagcgt tgcaactgtg gaaggtatga acaacaat taaaatcatg     840 gatcccagta caccaaccaa tgtccctgta gaggagatca gaaagagttt acacaatgtt    900
```

```
ccagtagtaa ttgctggtcc gactagtgga ggcttcacag ccgaaggcag tgacatgatt        960
tcaatggatg aactagctag gcctacactc tcatcaacaa aaaagatcac acgaaagcct       1020
gaatccaaga aagatttaac aggcataaaa ctaaccctga tgcagcttgc aaatgactgc       1080
atctcgcgtc cagataccaa gactgagttt gtgactaaga ttcaagcagc aaccacagaa       1140
tcacagctca acgaaatcaa acggtcaata atacgctctg caatataa                    1188

<210> SEQ ID NO 3
<211> LENGTH: 678
<212> TYPE: DNA
<213> ORGANISM: Artificial Sequence
<220> FEATURE:
<223> OTHER INFORMATION: Description of Artificial Sequence: Synthetic
      antigenomic cDNA V ORF sequence

<400> SEQUENCE: 3
atggccgagg aaccaacata caccactgag caagttgatg aattaatcca tgctggacta         60
ggaacagtag atttcttcct atctagaccc atagatgctc agtcttcttt aggtaaaggc        120
agcatcccac caggtgtcac ggctgttcta accaatgcag cagaggcaaa atccaaacca        180
gttgctgctg gtccagtaaa acccagacgg aagaaagtga tcagcaatac cactccatac        240
actattgcag acaacatccc acctgagaag ctaccgatca cactccaat acccaatcca         300 ttacttccac tggcacgccc tcacggaaag atgacagaca ttgacattgt cactgggaac        360
attacagaag gatcatacaa aggtgtggag cttgccaaat tagggaagca aacactactc        420
acaaggttca cctcgaatga gccagtctcc tcagctggat ccgcccaaga ccccaacttt        480
aagagaggcg gagctaatag agaaagagca agaggcaacc ataggagaga atggagtatt        540
gcatgggtcg gagatcaggt caaagtcttc gagtggtgta atcccaggtg tgccccagtc        600
acggcttcag ctcgcaagtt cacctgcaca tgtggatcct gccccagcat ctgcggagaa        660
tgtgaaggag atcattga                                                      678

<210> SEQ ID NO 4
<211> LENGTH: 15654
<212> TYPE: DNA
<213> ORGANISM: Human parainfluenza virus

<400> SEQUENCE: 4 accaaggga gaatcagatg gcatcgttat atgacgaatt gcaaaaagat tacgtaggtc          60
cggaaccact agattccggt gccggtaacg atctcagttt tatactatct gatcattctt        120
tatctctact aaggatattt ctaatctaag gttcaaaatg tcaagtgtct taagacattt        180
tgaaagattt actatacaac aggagcttca ggagcaatct gaagacactc aatacctct        240 tgaaacaatc agacctacaa tcagagtatt tgtcatcaat aataatgatc ctattgtaag       300
atctagactt ttattcttta tctacgaat tattatgagt aacactgcaa gagagggaca        360
tagagctggt gctctcctca gtctttatc actaccttct gcagctatga gtaatcacat         420
caaactagcc atgcattcac cagaagccag catagataga gtagaaataa cagggtttga       480
gaataattca ttccgagtta ttccagatgc tcgatcaact atgtccagag agaagtgct        540 ggccttcgaa gcattagctg aggacattcc tgataccctt aatcaccaaa ctccatttgt       600
aaataatgat gtggaagatg acatatttga tgaaacagag aaattcttgg atgtttgcta       660
tagtgtactt atgcaggcat ggatagtaac atgcaagtgc atgactgctc ctgatcaacc       720
accagtatca gtagcaaagc ggatggctaa atatcaacaa caagggagaa tcaatgctag       780
```

```
atatgtacta caacctgaag cacaaagact aattcagaat gccatccgca agtcaatggt      840
agtaaggcat ttcatgacct atgagcttca actttcacaa tcaagatctt tgctagcgaa      900
ccgttattat gccatggtgg gagacattgg caagtatatt gaacacagcg gaatgggagg      960
gtttttctta acacttaaat atggacttgg aacaagatgg cctacattgg ctcttgcagc     1020
attctctggg gaactccaga aattaaaggc tctcatgcta cattatcaga gtctaggacc     1080
catggccaag tacatggctc tattagaatc accaaagctg atggattttg tcccatctga     1140
atatccatta gtttatagct atgcaatggg tattggaact gtccttgata caaacatgag     1200
aaactatgca tatggtagat catatctaaa tccacaatat tttcagctag ggtagaaaac     1260
agcaaggaaa cagcaaggag ctgttgacaa caggacagca gaggacctcg gcatgactgc     1320
tgcagataaa gcagacctca ctgcaaccat atcaaagcta tctttatccc aattacctag     1380
gggtagacaa ccaatatccg acccatttgc tggagcaaat gacagagaaa caggaggaca     1440
agcaactgat acacctgtgt ataacttcaa tccaatcaat aatcggaggt atgacaacta     1500
tgacagtgat agtgaggaca gaattgacaa cgatcaagat caggctatca gagagaacag     1560
aggagaacct ggacaaccaa acaaccagac aagcgaaaac cagcagagac tcaatctccc     1620
tgtaccgcaa agaacatcag gtatgagtag tgaagagttc caacattcaa tgaatcagta     1680
catccgtgct atgcatgagc aatacagagg ctcccaggat gatgatgcca atgatgccac     1740
agatgggaat gacatttcac ttgagctagt ggagattttt gattcctaac tctcactttc     1800
acataaccag acatacacat ccacaccacc cagagacata gctaccatcc acacactcac     1860
ccagacaaat caaactagat tcaaatcatt cggaaacaat tctcctagaa tttaagaaaa     1920
aaacataggc ccggacgggt tagagatccg gtgctcgtct gtggccagac aacctccaca     1980
ccagagccac acaatcatgg ccgaggaacc aacatacacc actgagcaag ttgatgaatt     2040
aatccatgct ggactaggaa cagtagattt cttcctatct agacccatag atgctcagtc     2100
ttctttaggt aaaggcagca tcccaccagg tgtcacggct gttctaacca atgcagcaga     2160
ggcaaaatcc aaaccagttg ctgctggtcc agtaaaaccc agacggaaga aagtgatcag     2220
caataccact ccatacacta ttgcagacaa catcccacct gagaagctac cgatcaacac     2280
tccaataccc aatccattac ttccactggc acgccctcac ggaaagatga cagacattga     2340
cattgtcact gggaacatta cagaaggatc atacaaaggt gtggagcttg ccaaattagg     2400
gaagcaaaca ctactcacaa ggttcacctc gaatgagcca gtctcctcag ctggatccgc     2460
ccaagacccc aactttaaga ggggggggagc taatagagaa agagcaagag gcaacctag     2520
gagagaatgg agtattgcat gggtcggaga tcaggtcaaa gtcttcgagt ggtgtaatcc     2580
caggtgtgcc ccagtcacgg cttcagctcg caagttcacc tgcacatgtg atcctgccc      2640
cagcatctgc ggagaatgtg aaggagatca ttgagctctt aaaagggctt gatcttcgcc     2700
ttcagactgt agaagggaaa gtagataaaa ttcttgcaac ctctgcaact ataatcaatc     2760
ttaaaaatga aatgactagt cttaaggcga gcgttgcaac tgtggaaggt atgataacaa     2820
caattaaaat catggatccc agtacaccaa ccaatgtccc tgtagaggag atcagaaaga     2880
gtttacacaa tgttccagta gtaattgctg gtccgactag tggaggcttc acagccgaag     2940
gcagtgacat gatttcaatg gatgaactag ctaggcctac actctcatca acaaaaaaga     3000
tcacacgaaa gcctgaatcc aagaaagatt taacaggcat aaaactaacc ctgatgcagc     3060
ttgcaaatga ctgcatctcg cgtccagata ccaagactga gtttgtgact aagattcaag     3120
cagcaaccac agaatcacag ctcaacgaaa tcaaacggtc aataatacgc tctgcaatat     3180
```

```
aaaatgcggt gcaatcacac aagagacatt caacatgcat ccgatcaaga tccaaactcc   3240
ttccatccga aaacacactc accactgtca acaccaagaa acaactacag ccgaaccatg   3300
ctcaaccaaa agacccaaac aacatctcaa atcgacagaa ggctagacat gataaattta   3360
ataaaaaatt aaaagaagtt aagtaaaatt taaagaacac aatagagaaa acctaggtcc   3420
gaaagcttgc ctttcagaca gatcccaaaa tcatagttca aacttcaaac acagcagcag   3480
acatgcctat aatatcatta ccagcagatc caacttcacc cagtcaatcc cttactccgt   3540
ttccaataca acttgatacc aaagatggca aggcagggaa actccttaaa cagattagaa   3600
ttaggtatct aaatgaacct aactctcgtc atacaccaat aactttcatc aatacgtatg   3660
gatttgttta tgctcgagac acttcaggag gcattcacag cgagatcagc agtgacctag   3720
ctgcagggtc cataacggca tgcatgatga cactaggtcc tggtccaaat attcagaatg   3780
caaatctagt gctaagatcc ctgaatgaat tctacgtaaa agtcaagaag acatcaagcc   3840
agagggagga agcagtgttt gaattagtta acattccaac cttattgaga gaacatgctc   3900
tttgcaaacg caaaacgtta gtatgctctg cagaaaaatt cctcaagaac ccatcaaagc   3960
tacaagctgg atttgaatat gtatacatcc caacttttgt ctccattaca tactcaccac   4020
gaaatctgaa ttaccaagtt gccagaccta tccttaagtt cagatcacgc tttgtgtata   4080
gcattcattt ggaattaatc ctgagattgc tatgcaaatc tgactcccct ttgatgaaat   4140
cttataatgc agatcgaaca ggtcgaggat gcctcgcatc agtctggatc cacgtatgta   4200
acattctgaa aaacaaaagc atcaagcaac aaggcagaga atcatatttc atagctaagt   4260
gcatgagtat gcagctgcag gtgtccattg cagatctttg gggaccaaca atcataatta   4320
aatcattggg tcacatcccc aagactgcac ttccttttt cagcaaagac gggattgcct   4380
gtcatccact acaagatgtt tcccctactc tgacaaaatc actgtggtca gtgggatgtg   4440
agatagaatc tgccaagttg atacttcaag aatctgatat taatgagcta atgggccacc   4500
aggacttgat tactgataag attgccatta gatcaggtca acggacattt gagaggtcca   4560
aattcagccc attcaaaaaa tacgcatcaa ttccaaactt agaagccatc aactgaatgc   4620
tccagcatct aggaatagaa caacaactaa gtcataccat tattgaccat acaataatca   4680
acaattttag ccaactgatt actaagatat tatcataggt ccgaactgat caatctaaca   4740
aaaaaactaa acattcaata ataaatcaaa gttcaggcca aattatccag ccatgcatca   4800
cctgcatcca atgatagtat gcattttgt tatgtacact ggaattgtag gttcagatgc   4860
cattgctgga gatcaactcc tcaatgtagg ggtcattcaa tcaaagataa gatcactcat   4920
gtactacact gatggtggcg ctagctttat tgttgtaaaa ttactaccca atcttccccc   4980
aagcaatgga acatgcaaca tcaccagtct agatgcatat aatgttaccc tatttaagtt   5040
gctaacaccc ctgattgaga acctgagcaa aatttctgct gttacagata ccaaaccccg   5100 ccgaaacga tttgcaggag tcgttattgg gcttgctgca ctaggagtag ctacagctgc   5160
acaaataacc gcagctgtag caatagtaaa agccaatgca aatgctgctg cgataaacaa   5220
tcttgcatct tcaattcaat ccaccaacaa ggcagtatcc gatgtgataa ctgcatcaag   5280
aacaattgca accgcagttc aagcgattca ggatcacatc aatggagcca ttgtcaacgg   5340
gataacatct gcatcatgcc gtgcccatga tgcactaatt gggtcaatat aaatttgta   5400 tctcactgag cttactacaa tatttcataa tcaaataaca aaccctgcgc tgacaccact   5460
ttccatccaa gctttaagaa tcctcctcgg tagcaccttg ccaattgtca ttgaatccaa   5520
```

```
actcaacaca aaactcaaca cagcagagct gctcagttcc ggactgttaa ctggtcaaat    5580
aatttccatt tccccaatgt acatgcaaat gctaattcaa atcaatgttc cgacatttat    5640
aatgcaaccc ggtgcgaagg taattgatct aattgctatc tctgcaaacc ataaattaca    5700
agaagtagtt gtacaagttc ctaatagaat tctagaatat gcaaatgaac tacaaaacta    5760
cccagccaat gattgtgtcg tgacaccaaa ctctgtattt tgtagataca atgagggttc    5820
cccgatccct gaatcacaat atcaatgctt aaggggaat cttaattctt gcacttttac      5880
ccctattatc gggaactttc tcaagcgatt cgcatttgcc aatggtgtgc tctatgccaa    5940
ctgcaaatct tgctatgta agtgtgccga ccctccccat gttgtgtctc aagatgacaa     6000
ccaaggcatc agcataattg atattaagag gtgctctgag atgatgcttg acactttttc    6060
atttaggatc acatctacat tcaatgctac atacgtgaca gacttctcaa tgattaatgc    6120
aaatattgta catctaagtc ctctagactt gtcaaatcaa atcaattcaa taaacaaatc    6180
tcttaaaagt gctgaggatt ggattgcaga tagcaacttc ttcgctaatc aagccagaac    6240
agccaagaca ctttattcac taagtgcaat cgcattaata ctatcagtga ttactttggt    6300
tgttgtggga ttgctgattg cctacatcat caagctggtt tctcaaatcc atcaattcag    6360
agcactagct gctacaacaa tgttccacag ggagaatcct gccgtctttt ccaagaacaa    6420
tcatggaaac atatatggga tatcttaaga attctatcat aagtccatat atgtccatga    6480
ttgaccttta agagccaacc tccaatgatt atccgttaaa ttcagatata acaattcaaa    6540
aatcaatatt aagcctccag ataccaatga atatgaatat atctcttaga aaacttgatt    6600
attatgtgat aacatagtac aatttaagaa aaaacctaaa ataagcacga acccttaagg    6660
tgtcgtaacg tctcgtgacg ccgggttcag ttcaaacatc gacccctgac ccaattcaat    6720
acccattttc ataaggaac acagtataat ttaatcataa aagacctcaa aatctgatac      6780
agcttaatcc actcaacata taattataag actaataata atggaagatt acagcaatct    6840
atctcttaaa tcaattccta aaaggacatg tagaatcatt ttccgaactg ccacaattct    6900
tggcatatgc acattaattg tgctatgttc aagtattctt catgagataa ttcatcttga    6960
tgtttcctct ggtcttatga attctgatga gtcacagcaa ggcattattc agcctatcat    7020
agaatcatta aaatcattga ttgctttggc caaccagatt ctatataatg ttgcaatagt    7080
aattcctctt aaaattgaca gtatcgaaac tgtaatactc tctgctttaa agatatgca    7140 caccgggagt atgtccaatg ccaactgcac gccaggaaat ctgcttctgc atgatgcagc    7200
atacatcaat ggaataaaca aattccttgt acttgaatca tacaatggga cgcctaaata    7260
tggacctctc ctaaatatac ccagctttat ccctcagca acatctcccc atgggtgtac      7320
tagaatacca tcattttcac tcatcaagac ccattggtgt tacactcaca atgtaatgct    7380
tggagattgt cttgatttca cggcatctaa ccagtattta tcaatgggga taatacaaca    7440
atctgctgca gggtttccaa ttttcaggac tatgaaaacc atttacctaa gtgatggaat    7500
caatcgcaaa agctgttcag tcactgctat accaggaggt tgtgtcttgt attgctatgt    7560
agctacaagg tctgaaaaag aagattatgc cacgactgat ctagctgaac tgagacttgc    7620
tttctattat tataatgata cctttattga aagagtcata tctcttccaa atacaacagg    7680
gcagtgggcc acaatcaacc ctgcagtcgg aagcgggatc tatcatctag gctttatctt    7740
atttcctgta tatggtggtc tcataaatgg gactacttct tacaatgagc agtcctcacg    7800 ctatttatc ccaaaacatc ccaacataac ttgtgccggt aactccagca aacaggctgc      7860
aatagcacgg agttcctatg tcatccgtta tcactcaaac aggttaattc agagtgctgt    7920
```

```
tcttatttgt ccattgtctg acatgcatac agaagagtgt aatctagtta tgtttaacaa    7980
ttcccaagtc atgatgggtg cagaaggtag gctctatgtt attggtaata atttgtatta    8040
ttatcaacgc agttcctctt ggtggtctgc atcgctcttt tacaggatca atacagattt    8100
ttctaaagga attcctccga tcattgaggc tcaatgggta ccgtcctatc aagttcctcg    8160
tcctggagtc atgccatgca atgcaacaag ttttttgccct gctaattgca tcacaggggt    8220
gtacgcagat gtgtggccgc ttaatgatcc agaactcatg tcacgtaatg ctctgaaccc    8280
caactatcga tttgctggag cctttctcaa aaatgagtcc aaccgaacta atcccacatt    8340
ctacactgca tcggctaact ccctcttaaa tactaccgga ttcaacaaca ccaatcacaa    8400
agcagcatat acatcttcaa cctgctttaa aaacactgga acccaaaaaa tttattgttt    8460
aataataatt gaaatgggct catctctttt aggggagttc caaataatac catttttaag    8520
ggaactaatg ctttaatcct attgaatgaa gactccagat tcaagaataa ttggaaggct    8580
ctttatttta tgcgatagtt atacgttttg gctgtattag aatgctatag cattctgctg    8640 ttttttcccat atggaaaaat ccttcaacac caacttaggt tcaattttct catcatttac    8700
tgttgtaatt caatcttact aaagttattc tgatatttaa gaaaaaataa tctttatata    8760
atgtaacaat actactaaga ttataatata ggccagaatg gcggcctctt ctgagatact    8820
ccttcctgaa gtccattgta actcaccaat agtcaaacac aaactcatat actacttatt    8880
actagggcac ttcccgcatg atcttgacat ttctgaaata agccccttc acaataatga    8940 ttgggatcag attgccagag aagaatccaa tcttgctgaa cgactcggag tagctaaatc    9000
tgaattaatt aaacgtgtgc ccgcatttag agcaaccaga tggcgtagtc atgcagccgt    9060
ccttatatgg ccttcttgta taccattcct tgttaaattc ctacccccatt ctaagcttca    9120 accaatagaa caatggtaca agttgatcaa tgcttcatgc aatactatat ctgactcaat    9180
tgatagatgt atggagaata tttctattaa gcttactggg aaaaacaatc tattctctcg    9240
atccagagga actgcaggcg caggtaaaaa cagtaaaatc accctcaatg atatccaatc    9300
tatttgggaa tcaaacaaat ggcagcctaa tgtatctttta tggcttacaa ttaaatacca    9360
aatgcgacaa cttataatgc atcaaagttc tcgtcagcca actgatttag ttcacattgt    9420
tgacacacga tctggtctaa tagttatcac ccctgaactt gttatttgct ttgatcggtt    9480
gaataatgtt ttaatgtatt ttacatttga gatgactttta atggtaagtg acatgtttga    9540
gggacggatg aatgttgccg cgctctgcac tattagtcat tacttatcac cactagggcc    9600
aaggatagat agattgtttt ctattgtaga tgaattagca caactattgg gtgacactgt    9660
atataaaatt attgcatctc ttgaatcttt agtatatggg tgtctacaac ttaaagatcc    9720
agtggttgaa ttaacaggat catttcattc ctttattacg caagagatta tagatatcct    9780
aattgggtca aaagcccttg ataaggatga atcaataact gtcactacac aattgctaga    9840 tatatttttcc aacctttctc cagatttaat cgctgagatt ttgtgtctca tgagactttg    9900
gggtcatccc actcttactg ctgcgcaagc tgcaggtaaa gtgagagaat ctatgtgtgc    9960
aggtaagtta cttgatttcc ctacaataat gaaaactctt gctttttcc acacaatttt    10020 aatcaatggt tatcgtagaa agaagaatgg aatgtggcct ccacttatac ttcctaaaaa    10080
tgcatcaaaa agcttaatag agtttcaaca tgataatgct gaaatatctt atgagtatac    10140
actcaagcat tggaaagaaa tctctctcat agaatttaga aagtgctttg actttgatcc    10200
tggtgaggag ctaagcattt ttatgaaaga caaggcaata agtgctccaa aaagtgattg    10260
```

```
gatgagtgta ttccgtagaa gtctaataaa acaacgacat cagagacatc atattcctat    10320
gcccaatcca tttaacagac gtctattact caatttctta gaagatgaca gttttgatcc    10380
agttgctgag cttcaatatg ttaccagtgg tgaatatctc cgagatgaca catttgtgc     10440
atcttactca ttaaaagaga aagaaataaa accagatgga aggatatttg ctaagcttac    10500
taatagaatg cggtcttgtc aagtaattgc ggaagcaatt cttgcaaatc acgcaggtac    10560
tctaatgaag gaaaacggag ttgtcttgaa tcaattatct ctgactaaat cattgcttac    10620
tatgagtcaa attggcataa tatcagaaaa agcaaagaga tatcccgag ataacatctc     10680
atctcaaggt ttccatacaa tcaagactga ctcaaaaaat aagaagaaaa gcaaaattgc    10740
atcatcatac ctcacagatc ctgatgatac atttgaactt agtgcatgtt ttataactac    10800
tgatcttgct aaatactgtc ttcaatggag atatcagacc ataatccatt ttgctcgaac    10860
attaaacaga atgtatggag ttccacattt atttgaatgg attcatcttc gtttgattag    10920
atctacatta tatgttggtg atccattcaa tcctcctgcc acaactgatg ccttcgatct    10980
agataaagta ttaaatggtg atatctttat agtctctccc aagggaggta ttgaaggcct    11040
atgtcagaaa atgtggacaa tgatctctat ttctgtgatc atcctttctt cagccgaatc    11100
caaaacaaga gtaatgagca tggttcaagg agataatcag gcgattgcag ttacaacaag    11160
agttcctaga tcattgccta gtgttcagaa aaaggagtta gcctacgcag caagcaagtt    11220
attctttgaa agacttaggg caaataatta tggtttgggt catcaactaa aggctcaaga    11280
gactataata agttccacgt tcttcatata tagtaaacgg gtattctatc aaggacgtat    11340
actaacacag gcacttaaaa atgctagcaa gttatgtctt actgcagatg tattaggtga    11400
atgtactcag gcttcctgct caaattctgc tactacaatc atgagattaa cagaaaatgg    11460
ggttgagaaa gatacatgtt ataagcttaa tatttatcaa tctattcgtc aactcacata    11520
tgatctaata tttccccaat actccatacc aggtgaaaca ataagtgaaa ttttcttaca    11580
gcatccaaga ttaatctcac gtattgttct gctcccttca cagctaggtg tcttaattaa    11640
cctcgcatgt agcagattat ttaaccgcaa tatcggagat ccccttggta cagccgtggc    11700
agacctcaag aggttaatta aatgtggtgc tcttgaatca tggatactgt acaatttact    11760
ggcaagaaaa ccagggaaag gttcatgggc cactttagca gccgatccat actcattgaa    11820
tcaagaatat ctttatcctc ctactactat acttaaaaga catactcaaa atactttaat    11880
ggagatatgt cggaatccta tgttaaaggg agttttttaca gataatgcaa agaggagga     11940
aaatctcctt gcaaaatttc ttcttgatcg tgatatagta ttgccaagag tcgcacacat    12000
tataatagat caatccagca ttggaaggaa gaaacagata caagggtttt ttgacaccac    12060
aaggaccata atgagacgat catttgagat caaaccactc tcaactaaga gacactttc    12120
agtcatagaa tataatacta attatttatc ttataactac cctgtcatac ttaatccttt    12180
acctattcct ggatatttaa attatattac tgaccaaact tgcagtattg atatatctag    12240
aagtttaaga aaattatcat ggtcttcttt attgaatgga agaactttag aaggattaga    12300
aactccagat ccaattgaag ttgtcaatgg ttccttgatt gtaggtacag agattgtga     12360
cttttgtatg cagggtgacg ataaaattca ttggttcttt ttacctatgg ggataattat    12420
tgatggaaat cctgaaacta atccacccat cagagttcca tacattgggt ctagaacaga    12480
ggaaagaaga gttgcatcaa tggcatatat taaaggtgcc acacacagtt gaaggctgc     12540
tcttagaggc gcaggggtat acattggggc attcggagat acagtagtga actgaatga    12600
tgcacttgat atcgcaaata ctagggttaa gatatcccta gagcaacttc agactcttac    12660
```

```
acctcttcct acatctgcaa acattacaca tcgtttagat gatggagcca caacacttaa   12720
attcactcca gctagttcct atgcattttc tagttatact catatatcaa atgatcaaca   12780
atatttagaa atagatcaga gagtagtcga ttccaatatt atttatcaac aattaatgat   12840
aacagggctt gggatcattg agacctacca taacccacct atcaggacct ctacacagga   12900
aatcaccctc catttgcaca ctagctcatc ttgttgtgtt agaagtgtag atggttgcct   12960
tatatgtgag agcaatggag aggttcctca gatcactgtt ccctacacta attcatttgt   13020
atatgatcct gatccactag cagattatga gattgcacat ctagattatc tctcctacca   13080
agctaaaatt ggaagtacag attactactc acttactgat aaaattgatc tattggcaca   13140
tttaactgca aaacaaatga taaactcaat aattgggtta gatgaaacag tatcaattgt   13200
caatgatgcg gttattctat ctgattatac taataactgg attagtgaat gttcttatac   13260
taagatagat ttagttttta aattaatggc atggaatttc cttcttgagc ttgcattcca   13320
gatgtactac ctaagaatat catcttggac aaatatattt gactatactt acatgacttt   13380
acgcaggata cccggaactg ctctaaataa tattgcagct actattagcc acccaaaatt   13440
attaagacgt gcaatgaatc ttgatattat cactcctata catgcaccgt atttggcttc   13500
attagattat gtcaaattaa gtattgatgc aattcagtgg ggggttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactat acatttccaa aaattaaagg gatgccacca gaggaaaagt gtttagtctt   13740
aactgaatac ctagcaatgt gttatcagaa tactcaccac ttagatccag atcttcaaaa   13800
gtatttatat aatctaacta atccaaaatt gactgcattt cccagtaaca acttctactt   13860
aacaaggaaa atccttaatc aaattagaga atcagacgaa ggacaatata ttatcacctc   13920
atattatgaa tccttcgaac aattagaaac agatataatt cttcactcta ctttaactgc   13980
tccttatgat aattcagaaa ctctaacaaa gtttgattta tcccttgaca tctttccaca   14040
tccagaatct ctcgagaaat atcctcttcc agttgatcat gactctcaat ctgcaatttc   14100
aacactaatt ccaggccctc cctctcatca tgtattacga ccactaggag tgtcatctac   14160
agcttggtat aaagggataa gttattgcag atacctggaa acgcaaaaga tacagactgg   14220
tgatcatctt tatttagctg aaggaagcgg tgcttcaatg tcacttctag aactcctatt   14280
tccaggagat actgtctatt ataatagtct ttttagtagt ggagagaatc ctccacagag   14340 aaaattatgct cctcttccaa ctcaatttgt acagagtgtt ccatataaat tgtggcaagc   14400
tgatcttgct gatgatagta acttaataaa agattttgtc ccattatgga atggaaacgg   14460
agcagttaca gacttatcga caaaggatgc agttgcattc ataatacata agtaggagc   14520 ggagaaagca tcccttgttc atatagatct cgaatcgact gctaatataa atcagcaaac   14580
tctgtccaga tcccagattc attcgttaat tatagcaact actgttctta agaggggtgg   14640
gatattagtt tacaaaacat catggcttcc gttttctagg tttagtcaac tagcaagcct   14700
actttggtgc ttttttgacc ggatccatct aatacgtagt agttattctg atcctcacag   14760
tcatgaggtt tatcttgtat gtagacttgc tgcggatttt agaactatcg gtttcagtgc   14820
agctctagta actgctacta ctcttcacaa tgacggattc acaacaatac atcctgatgt   14880
tgtttgtagt tattggcaac accatcttga gaatgtgggg agagtcgaaa aagtaattga   14940
tgagatactt gatggtttag ccaccaactt cttcgcagga gataatgggc ttattctaag   15000
```

```
atgtggagga actcccagct ctagaaaatg gttagagatt gatcagttag catcatttga    15060
ttcagttcaa gatgctctag tgacacttat caccatacac ctaaaggaaa ttatagaagt    15120
gcagtcatca catacagagg attatacatc tctccttttc acaccttata atattggtgc    15180
agcagggaaa gtaagaacta tcatcaaatt aattctagaa cgatctttaa tgtatacagt    15240
ccgaaattgg ttagttttac ccagttccat ccgggattcc gtacgacaag atctagagtt    15300
agggtcattt agattaatgt ctattttaag tgaacagaca tttcttaaaa agacacccac    15360
caaaaaatac ttacttgatc agcttacaag gacatatata tcaaccttct ttaattctca    15420
ctcagtcctc cccctccacc gtccatatca aaaacaaata tggaaagcct taggtagtgt    15480
aatatattgt tcggagacgg ttgatatacc tctaattaga gacattcaga tagaagatat    15540
taatgatttt gaagatatcg agagggtat cgatggcgaa gaattatgac aacagtgatt    15600
ataagaactc atgatagttt tatttaagaa aaacatattg attttcccct tggt          15654

<210> SEQ ID NO 5
<211> LENGTH: 15654
<212> TYPE: DNA
<213> ORGANISM: Human parainfluenza virus

<400> SEQUENCE: 5 accaaggga gaattagatg gcatcgttat atgacgaatt gcaaaaagat tacgtaggtc       60
cggaaccact agattccggt gccggtaacg attccatttt tatactatct gatcattctc      120
tatctctact aaggatattt ctagtctaaa gttcaaaatg tcaagtgtct taaagacatt      180
tgaaaggttt actatacaac aagagcttca ggagcaatct gatgacactc cagtacctct      240
tgagacaatc aaacctacaa taagggtatt tgtcatcaat aataatgatc ctgccataag      300
gtctagactt ttattcttta atctacgaat tattatgagt aacaccgcaa gagagggaca      360
tagagctggt gctctcctca gtctcttatc actaccttct gcagctatga gtaatcacat      420
caaactagcc atgcattcac cagaagccag catagataga gtagagataa cagggtttga      480
gaataattca ttccgagtta ttccagatgc tcgatcaact atgtccagag gagaggtgct      540
ggcctttgaa gcattagctg aagacattcc tgatacccct aatcaccaaa ctccatttgt      600
aaataatgat gtagaagatg acatgttga tgaaacagag aaattcttag atgtttgcta      660
cagtgtactt atgcaggcat ggatagtaac atgcaagtgt atgactgctc ctgatcagcc      720
gccagtatca gtagcaaagc ggatggctaa atatcaacaa caagggagaa tcaatgctag      780
gtatgtacta cagcctgaag cacaaagact aattcagaat gccatccgca agtcaatggt      840
agtgaggcat ttcatgactt atgagcttca acttttcacaa tcaagatctt tgctagcaaa      900
ccgctactat gctatggtgg gagacattgg caagtacatt gaacacagcg gaatgggagg      960 tttttttctta acacttaaat atggacttgg aacaagatgg cctacattgg ctcttgcagc     1020
attctctggg gaactccaga aattaaaagc tctcatgcta cattatcaga gcctaggacc     1080
catggccaag tacatggctc tattagaatc accaaagctg atggattttg tcccatctga     1140
atatccatta gtttatagtt atgcaatggg tattggaact gtccttgata caaatatgag     1200
aaactatgca tatggtagat catatttaaa tccgcaatat tttcagctag gagtagaaac     1260
agcaaggaaa cagcagggag ctgttgacaa caggacagca gaggacctcg gcatgactgc     1320
tgcagacaaa gcagacctca ctgcaaccat atcaaagcta tctttgtccc aattacctag     1380
gggtagacaa ccaatatctg acccatttgc tggagcaaat acagagaaa taggaggcca     1440 agcaaatgat acacctgtat acaacttcaa tccaatcaat actcggaggt atgacaacta     1500
```

```
tgacagtgat ggtgaggaca gaattgacaa cgatcaagat caagctatca gagagaacag    1560
aggagagcct ggacaactaa acaaccagac aagtgacaac cagcagagac tcaatctctc    1620
cataccgcaa agaacatcag gtatgagcag tgaagagttc aacattcaa tgaatcagta     1680 catccgtgcc atgcatgagc aatacagagg accccaggat gatgatacca atgatgccgc    1740
agatgggaat gacatttctc ttgagctagt tggggatttt gattcctaat tctcaatgtc    1800
atacaaccag atatacacat ccacatcact taaagataca gctgccaccc acacactcat    1860
ccagacaaat caaccagac tcacatcatt cagaaacaat tctctcataa tttaagaaaa     1920
aaacataggc ccgacgggt ttaaaatctg gtgctcgttc gtggtctgac aacctccaaa     1980
ccagaatcac acaattatgg ccgaggaacc aacatacacc actgagcaag ttgatgaact    2040
aatccatgct ggactgggaa cagtagattt cttcctatct agacccatag atgctcaatc    2100
ttccctaggc aagggcagca tcccaccagg tgtcacagct gttctaacta gtgcagcaga    2160
ggcaaaatcc aaaccagttg ccgctggtcc agtgaaaccc aggcggaaga aagtgatcag    2220
caatgctacc ccatacactg ttgcagacaa tactccacct gagaagctac caatcaacac    2280
cccaataccc aatccattac ttccactggc acgcccccaa ggaaagatga cagacattga    2340
cattgtcact gggaccatta cagaaggatc gtacaaaggt gtggagcttg ctaaattagg    2400
gaagcaaaca ctactcacaa ggttcacctc gaacgagcca gtctcctcag ctggatccgc    2460
ccaagacccc aactttaaga gggggggagc taatagagaa agagcaagag gcaaccatag    2520
gagagaatgg agtattgcat gggtcggaga tcaggtcaaa gtcttcgagt ggtgtaatcc    2580
caggtgtgcc ccagtcacgg cctcagctcg caagttcacc tgcacatgcg gatcctgccc    2640
cagcatctgc ggagaatgtg aaggagatca ttgagctctt aaaggggctt gatcttcgcc    2700
ttcagactgt agaagggaag gtagataaaa ttcttgcaac ttccgcaact ataatcaatc    2760
ttaaaaatga aatgactagt ctcaaggcga gcgttgcaac tgtggaaggt atgataacaa    2820
caattaaaat catggatccc agcacaccaa ccaatgtccc tgtagaggag atcagaaaga    2880
gcttacacaa tgctccagta gtaattgccg gtccaactag tggaggcttc acagccgaag    2940
gcagtgatat gatttcaatg gatgaactag ctagacctac actctcatca acaaaaaaga    3000
tcacacgaaa gcctgaatcc aagaaagact taacaggcac aaaactaacc ttgatgcagc    3060
ttgcaaatga ctgcatctcg cgtccagata ccaagactga gttcgtgact aagattcaag    3120
cagcaaccac agaatcacag cttaatgaaa tcaagcggtc aataatacgc tctgcaatat    3180
aaaatgaggt gcaatcacac aagagacact caacatgcat ccaatcaaga tccaaattct    3240
gtccatccga aaacacaccc acaattgtta acaccaagaa acaaccacag ccgaaccatg    3300
cttaatcaaa agatccaaac aacatctcac atcgacagaa ggctggacat gataaattta    3360 ataaaaaga aaaaaaagtc aagtaaaatt taaaggacac aatagagaaa atctaggtcc     3420
gaaagcttgc ttcccggaca gatctcaaaa tcatagtcta aacctcaaac acagcagcag    3480
acatgcccat aatatcatta ccagcagatc caacttcacc cagtcaatcc cttactccgt    3540
ttccaataca acttgacacc aaagatggca aggcagggaa actccttaaa cagattcgaa    3600
ttaggtatct aaatgagcct aattctcgcc atacaccaat aactttcatc aatacgtatg    3660
gatttgttta tgctcgagac acttcagggg gcattcacag tgagcttagt agtgacctag    3720
ctgcagggtc tataacagca tgcatgatga cgcctaggcc ctggtccaaat attcagaatg    3780 caaatctagt gctaagatct ctgaatgaat tctacgtgaa agtcaagaag acatcaagcc    3840
```

-continued

```
agagagagga agcagtgttt gaattagtta acattccaac tttattgaga gaacatgctc    3900
tttgcaaacg caaaatgtta gtttgctctg cagaaaagtt cctcaagaac ccgtcaaagc    3960
tacaagctgg atttgagtat gtatacatac caacttttgt ctccattaca tactcaccac    4020
gaaatctgaa ttaccaagtt gccagaccta tccttaagtt cagatcacgt tttgtgtata    4080
gcattcattt ggaattaatt ctgagattgc tatgcaaatc tgaatccccc ttaatgaaat    4140
cctacaatgc agacaaaaca ggtcggggat gccttgcatc agtctggatc catgtatgta    4200
acattctgaa aaacaaaagc atcaagcaac aaggcagaga atcatatttc atagccaagt    4260
gcatgagcat gcagctgcag gtgtccattg cagatctttg gggaccaaca atcataatca    4320
aatcattggg tcacatcccc aagactgcac ttccttttt cagcaaagat gggattgcct    4380
gtcatccatt acaagatgtt tcccccactc tgacaaaatc actgtggtca gttggatgtg    4440
agatagaatc tgccaagttg atacttcaag aatctgatct taatgagcta atgggccacc    4500
aggaccttat cactgataag attgccatca gatcaggtca acggacattt gagaggtcca    4560
aattcagccc atttaaaaaa tatgcatcaa ttccaaactt ggaagccatc aactgaatgc    4620
tccagcatct gagaatagaa ccacaattaa atcatactat tagtaactat acaataataa    4680
acaatttttag tcaacagatt accaagatgt tatcataggt ccgaactgat caatctaaca    4740
aaaaaactaa acgttccata ataaatcaac gttcaggtca aaatactcaa ccatgcatca    4800
cctacatcca atgatagtat gcatctttgt tatgtacact ggaattgtag gttcaggtgc    4860
cattgccgga gaccaactac ttaatatagg ggtcattcaa tcaaagataa gatcactcat    4920
gtactatact gatggtggtg ctagctttat tgttgttaaa ttgctaccta atcttccccc    4980
aagcaatgga acatgcaaca ttaccagtct agatgcatac aatgttaccc tatttaaatt    5040
actgacaccc ctgattgaga acctgagcaa aatctccgct gttacagata ccaaaacccg    5100
ccaagaacga tttgcaggag tcgttgttgg acttgctgca ttaggagtag ccacagctgc    5160
acaaataacc gcagctgtag caatagttaa agctaatgca aatgctgccg cgattaataa    5220
tcttgcatct tcaattcaat caacaaacaa ggcagtatcc gatgtgatag atgcatcaaa    5280
aacaattgca actgcagttc aagcaatcca ggatcatatc aatggagcta ttgttaatgg    5340
gataacatct gcatcatgcc gtgcccatga tgcactcatt gggtcaatat aaatctttta    5400
tctcactgag cttaccacaa tatttcacaa tcaaataaca aaccctgcgc tgacaccgct    5460
ctccatccaa gctttaagaa ttctcctcgg tagcaccttg ccaattgtca ttgagtccaa    5520
actcaacaca aacctcaaca cagcagagct gctcagctcc ggactgttaa ctggtcaaat    5580
aatttcaatt tccccaatgt acatgcaaat gctaattcaa atcaatgttc cgacatttat    5640
aatgcaaccc ggtgcgaagg taattgatct aattgctatc tctgcaaacc ataaattgca    5700
agaagtagtt gtacaagttc cgaataggat tctagagtat gcaaatgaac tacaaaatta    5760
tccagccaat gactgtgttg tgacaccgaa ctctgtattc tgtagataca atgagggttc    5820
ccctatccct gaatcacaat accaatgctt gaggggaat cttaattctt gcacttttac    5880
ccctattatc gggaactttc ttaagcgatt tgcatttgcc aatggtgtgc tctatgccaa    5940
ctgcaaatct ttgctatgta agtgtgccga ccctccccat gtggtgtccc aagatgatac    6000
ccaaggcatc agcataattg atattaagag atgctctgag atgatgcttg acactttctc    6060
atttaggatc acatctacgt tcaatgctac atacgtgaca gacttctcaa tgattaatgc    6120
aaatattgta catctcaagtc ctctagattt gtcaaaccaa atcaattcaa taaacaaatc    6180
tcttaaaagt gctgaggatt ggattgcaga tagcaacttc tttgctaatc aagccaggac    6240
```

```
agccaagaca ctttattcat taagtgcaat agcattaata ctatcagtga ttaccttggt    6300
tgttgtggga ttgctgattg cctacatcat caaactagtt tcccaaatcc atcaattcag    6360
agcgctagct gctacaacaa tgttccacag ggaaaatcct gccttctttt ccaagaacaa    6420
tcatggaaac atatatggga tatcttaaga aatctatcac aagtccatat atgtccacaa    6480
ttgattctta agaaccaact tccaatgatt atcctttaaa cttaagtata atagtttaaa    6540
aattaacatt aagcctccag ataccaatga atatgaatat atctctaaga aaacctgatt    6600
attatgtgat agtgtagtac aatttaagaa aaaacctaaa ataagcacga acccttaagg    6660
tgtcgtaacg tctcgtgaca ctgggttcag ttcaaaaatc gacttctaat ctaatttaac    6720
acccattctt atataagaac acagtataac ttaattacaa aagacctcaa aaactgacac    6780
agcttaatcc actcaacata taattgtaag attaataata atggaagatt acagcaatct    6840
atctcttaaa tcaattccta aaaggacatg tagaatcatt ttccgaactg ccacaattct    6900
tggaatatgc acattgattg ttctatgttc aagtattctt catgaaataa ttcatcttga    6960
tgcttcctct ggtctcatga attctgatga ttcacagcaa ggcattattc agcctattgt    7020
agaatcatta aaatcattga ttgctttggc taaccagatt ctgtacaatg ttgcaataat    7080
aattcctctt aaaattgaca gtattgagac cgtaatactc tctgcttyaa aggayatgca    7140
tactgggagc atgtccaaca ccaactgtac acccggaaat ctgcttctgc atgatgcagc    7200
atacatcaat ggaataaaca aattccttgt acttaaatca tacaatggta cgcctaaata    7260
tggacctctc ctaaatattc ctagctttat cccctcagca acatctcccc acgggtgcac    7320
tagaatacca tcattttcac tcagtaagac tcattggtgt tacactcaca atgtaatact    7380
tggagattgc ctcgatttca cgacatctaa tcagtattta gcaatgggga taatacaaca    7440
atctgctgca gcatttccaa tcttcaggac tatgaaaacc atttacctaa gtgatggaat    7500
caatcgcaaa agctgttcag tcactgccat accaggaggt tgtgtcttgt actgctatgt    7560
agctacaaga tctgagaaag aagattatgc cacaactgat ctagctgaac tgagacttgc    7620
tttctattat tataatgata cctttgttga aagagtcata tctcttccaa atacaacagg    7680
gcaatgggcc acaatcaatc ctgcagttgg aagcgggatc tatcatctag ctttattttt    7740
atttcctgta tatggtggtc tcataaatgg gactccttcc tacaacgagc agtcctcacg    7800
ctattttatc ccaacacatc ccaacataac ctgtgccgga aactccagtg aacgggctgc    7860
agcagcacgg ggttcctatg tcatccgtta tcattcaaac aggttgattc agagtgctat    7920
tcttatttgc ccattatctg acatgcaaac agcaaggtgt gatctagtta tgtttaacaa    7980
ttctcaagtc atgatgggtg cagaaggtag gctctatgtt attgacaaca atttgtatta    8040
ttatcaacgt agttcctctt ggtggtctgc atcgctttc tacaggatca atacagattt    8100
ctctaaagga attcctccta tcattgaggc tcaatgggta ccgtcctatc aagttccccg    8160
ccctggagtc atgccatgta atgcaacaag ttttgcct gctaattgca tcacaggagt    8220
gtatgcagat gtgtggccgc ttaacgatcc agaactcaca tcacaaaatg ctctgaatcc    8280
caactatcga tttgctggag cctttctaaa aaatgagtcc aaccgaacca atcccacatt    8340
ttacactgca tcagccaact ccctactaaa tactaccgga ttcaacaaca ccaatcacaa    8400
agcagcatat acgtcttcaa cctgctttaa gaatactgga actcagaaga tttattgttt    8460
gataataatc gaaatgggct catctctttt agggagttc caaataatac catttctaag    8520
ggaactaata ccttaatact attgaatgaa aacttaagat tcaataataa ttgaaaggct    8580
```

```
ctctatctta tgtaatagtt atacgttttg gctgtattag aatgttatag cattctgctg    8640
tgtttcccat atgaagcaag ccttcaacac cgacttaggt tcaatttct  catcatttac    8700
tgttgtaatc caatcttact aaagttattc tgatatttaa gaaaaaataa cctttatata    8760
atataacaat actattaaga ttatgatata ggccagaatg gcggcctctt ctgagatact    8820
ccttcctgaa gtccacttga actcaccaat agtcaaacac aaactcatat actacttatt    8880
actagggcac ttcccgcatg atcttgacat ttctgaaata agccctcttc acaataatga    8940
ttgggatcaa attgccagag aagaatccaa tcttgctgaa cgacttggag tagctaaatc    9000
tgaattaatt aaacgtgtgc ccgcatttag agcaactaga tggcgtagtc atgcagctgt    9060
ccttatatgg ccttcttgta taccatttct tgttaaattc ctacctcatt ctaagcttca    9120
accaatagaa caatggtaca agttgatcaa tgcttcatgt aatactatat ctgactcaat    9180
tgatagatgt atggagaata tttctattaa gcttactggg aaaaacaatc tattctctcg    9240
atccagagga actgcaggtg caggtaaaaa cagtaaaatc accctcaatg atatccaatc    9300
tatttgggaa tcaaacaagt ggcagcctaa tgtatcttta tggcttacaa ttaaatatca    9360
aatgcgacaa cttataatgc atcaaagttc tcgtcagccg actgatttag ttcacattgt    9420
tgacacacga tctggtctaa tagttatcac ccctgaactt gttatttgtt ttgatcggtt    9480
gaatagtgtt ttaatgtatt ttacatttga gatgacttta atggtaagcg acatgttcga    9540
ggggaggatg aatgtcactg ctctctgcac tattagtcat tacttatctc cactagggcc    9600
aaggatcgat agattgtttt ccattgtaga tgaattagca caactattag gtgacactgt    9660
atataaagtt attgcatctc ttgaatcttt agtatatggg tgtctacaac ttaaagatcc    9720
agtagtggaa ttagcagggt catttcattc ctttattaca caagagatta tagatatcct    9780
aattggttca aaagcccttg ataaggatga atcaataact gttactacac aattgttaga    9840
tatattttcc aacctttctc cagatttaat tgctgagatg ttgtgtctca tgagactttg    9900
gggtcatcct actcttactg ctgcgcaagc tgcaggtaaa gtgagagaat ctatgtgtgc    9960
aggtaagttg cttgatttcc ctacaataat gaaaactctt gctttttcc  acacaatttt   10020
aattaatggt taccgtagaa agaaaaatgg aatgtggcct ccactatac  ttcctaaaaa   10080
tgcatcaaaa agcttaatag aatttcaaca tgataatgct gaaatatctt acgaatatac   10140
actcaagcat tggaaagaga tctctctcat agaatttaga aagtgctttg actttgatcc   10200
tggtgaggag ctaagcattt ttatgaagga caaggcaata agtgctccaa aaagtgattg   10260
gatgagtgta tttcgtagaa gtctaataaa acaacgacat cagagacatc atattcctat   10320
gcccaatcca tttaatagac gtctattact caatttctta gaagatgaca gttttgaccc   10380
agttgctgag ctccaatatg ttaccagtgg tgaataccte caagatgaca catttgtgtgc   10440
atcttactca ttaaaagaga aagaaataaa accagatgga aggatattcg ctaagcttac   10500
taatagaatg cggtcctgtc aagtaattgc ggaagcaatt cttgcaaatc atgcaggtac   10560
tctaatgaag gaaaacggag ttgtcttgaa tcaattatca ctgaccaagt cattgcttac   10620
tatgagtcaa attggcataa tatcagaaaa ggcaaagaga tatacgcgag ataacatctc   10680
atctcaaggt ttccatacaa tcaagactga ctctaaaaat aagaggaaaa gcaaaactgc   10740
atcatcatac ctcacagatc ctgatgatac atttgaactt agtgcatgtt ttataactac   10800
tgatcttgct aaaatactgtc ttcaatggag atatcagacc ataatccatt ttgctcgaac   10860
attaaacaga atgtatggag ttccacattt atttgaatgg attcatcttc gtttaattag   10920
gtctacatta tatgttggtg atccattcaa tcccctgct  gcgactgatg ctttcgatct   10980
```

```
agataaagta ttaaatggtg atatctttat agtctctccc aaaggaggta ttgaaggcct    11040
atgtcagaaa atgtggacaa tgatctctat ttctgtgatc atcctctcct cagccgaatc    11100
caaaacaaga gtaatgagca tggttcaagg agataatcag gcaattgcag ttacaacaag    11160
agttcctaga tcattaccta gtattcagaa aaaggagtta gcctatgcag caagcaagtt    11220
atttttgaa agacttaggg caaataatta tgggttgggt catcagctaa aggctcaaga    11280
aactataata agttccacat tcttcatata tagtaaacgg gtattttatc aaggacgtat    11340
actaacacag gcactcaaaa acgctagcaa gctatgtctt actgcggatg tattaggtga    11400
atgtactcaa gcttcctgtt caaattctgc tactaccatc atgagattaa cagaaaatgg    11460
ggttgagaaa gatacatgtt ataagcttaa tatttatcag tccattcgtc aactcacata    11520
tgatctaata tttccccaat attccatacc aggtgaaacg ataagtggga ttttcctgca    11580
gcatccaaga ctaatctcac gtattgttct gctcccttca cagctaggtg gtcttaatta    11640
cctcgcatgc agcagattat ttaaccgcaa tatcggagat cctcttggta cagctgtggc    11700
ggacctcaag aggttaatta aatgtggtgc tcttgaatca tggatactgt acaatttact    11760
agcaagaaaa ccagggaaag gttcatgggc aactttagca gccgatccgt actcattgaa    11820
tcaagaatat ctttatcctc ctactactat acttaaaaga catactcaac atactttaat    11880
ggagatatgt aggaatccta tgttaaaggg agttttcaca gataatgcaa agaggagga     11940
aaatctcctt gcaaaatttc ttcttgatcg tgatatagta ttgccaagag ttgcgcacat    12000
tataatagat caatctagca tcggaaggaa gaaacagata caaggatttt ttgacaccac    12060
aaggaccatt atgagacgat catttgaaat caaaccactc tcaactaaga agactctttc    12120
agttatagaa tataatacaa attacttatc ttataactac cctgtcatac ttaatccttt    12180
acctattccc ggatatttaa attatattac tgaccaaact tgcagtattg atatatctag    12240
aagtttaaga aaattatcat ggtcttcttt attgaatgga agaactttag aaggattaga    12300
aactccagat ccaattgaag ttgtcaatgg ttccttgatt gtaggtacag agagattgtga   12360
tttttgtatg cagggtgatg acaaaattac ttggttcttt ttacctatgg ggataattat    12420
tgatggaaat cctgaaacta atccacccat cagagttcca tacattgggt ctagaacaga    12480
ggaaagaaga gttgcatcaa tggcatatat taaaggtgcc acacacagtt gaaggctgc    12540
tcttaggggt gcagggtat atatttgggc attcggggat actatagtga actggaatga    12600
tgcacttgat attgcaaata ctagagttaa gatatccccta gagcaacttc agactctcac    12660
acctcttcct acatctgcaa acattacaca ccgtttagat gatggagcca caacacttaa    12720
attcactcca gctagttcct atgcattttc tagttatact catatatcaa atgatcaaca    12780
atatttagaa atagatcaga gagtagttga ttccaatatt atttatcaac aattaatgat    12840
aacaggactt gggattattg agacctacca taacccacct ataagaactt ctacacaaga    12900
aatcactctc catttgcaca ctagctcatc ttgttgtgtt agaagtgtag atggctgcct    12960
tatatgtgaa agcaatggag aggttcccca gatcactgtt ccctatacta atacatttgt    13020
atatgatcct gacccactag cagattatga gattgcacat ctagattacc tctcctacca    13080
agctaaaatt ggaagtacag attactactc actcactgat aaaattgacc tattagcaca    13140
tttaactgca aaacaaatga taaactcaat aattgggtta gatgaaacag tatcgattgt    13200
caatgatgcg gttatcctat ctgactatac taataactgg attagtgaat gttcttatac    13260
taaaatagat ctagttttta aattaatggc atggaatttt cttcttgagc ttgcattcca    13320
```

```
gatgtactac ttaaggatat catcttggac aaatatattt gactatactt acatgacttt   13380
acgcagaata cccggaactg ctctaaataa tattgcagct actattagcc atccaaaatt   13440
actgagacgt gcaatgaatc ttgatattat cactcctata catgcaccgt atctagcttc   13500
attagattat gtcaaattaa gtattgatgc aattcagtgg ggagttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactac acttttccaa aaattaaagg gatgccacca gaagaaaagt gtttagtctt   13740
aactgaatat ctagcaatgt gttatcaaaa tactcaccac ttagatccag atcttcaaaa   13800
gtatttatat aatctaacta atccaaaatt gaccgcattt cccagtaaca acttctactt   13860
aactaggaaa atcctcaatc aaattagaga atcagacgaa ggacaatata ttatcacctc   13920
atattatgaa tccttcgaac aattgaaaac agatataatt cttcattcta ctttaactgc   13980
tccttatgat aattcagaaa ctctaacaaa gtttgattta tcccttgaca tctttccaca   14040
tccagaatct ctcgagaaat atcctcttcc agttgatcat gactctcaat ctgcaatttc   14100
aacactaatt ccaggccctc cttctcatca tgtattacga ccactgggag tgtcctctac   14160
agcttggtat aaagggataa gttattgtag gtatctagaa acacaaaaga tacagactgg   14220
tgatcatctt tatttagctg aaggaagcgg cgcttcaatg tcactcctag aactcctatt   14280
tccaggagat actgtctatt ataatagtct ttttagtagt ggagagaatc ctccacagag   14340
aaactacgcc cctcttccaa ctcaatttgt acagagtgtt ccatataaat tgtggcaagc   14400
tgatcttgct gatgatagca acttgataaa agattttgtc ccattatgga atggaaatgg   14460
tgcagttaca gacttatcaa caaaggatgc agttgcattc ataatacata agtaggagc   14520 agaaaaagca tctcttgtcc atatagatct cgaatcgact gctaatataa atcagcaaac   14580
tctgtccaga tcccagattc attcattaat tatagcaact actgttctta agaggggtgg   14640
gatattaatt tataagacat catggcttcc tttttctaga tttagtcaac tagcaagcct   14700
tctttggtgc ttttttgacc ggatccatct aatacgtagt agctattctg atcctcacag   14760
tcatgaggtt tatcttgtat gtagacttgc cgcagatttt agaactatcg gtttcagtgc   14820
agctctagta actgctacta ctcttcacaa tgacggattc acaacaatac atcctgatgt   14880
tgtttgtagt tattggcaac accatcttga aaatgttggg agagtcggaa aagtaattga   14940
tgagatactt gatggtttag ccaccaactt cttttgcagga gataatggac ttattctaag   15000
atgtggagga actcccagct ccagaaaatg gttggagatt gaccagttag catcatttga   15060
tttggttcaa gatgctctgg tgacacttat cactatacac ctaaaggaaa ttatagaagt   15120
gcaatcatca catacagaag attatacatc tctcctcttc acaccttata atattggtgc   15180
agcagggaaa gttagaacta tcatcaaatt aattctagaa cgatctttaa tgtatacagt   15240
ccgaaattgg ttagtgttac ccagttccat ccgggattct gtacgacaag atttggaatt   15300
agggtcattt agattaatgt ctattttaag tgaacagaca tttcttaaaa agacacccac   15360
aaaaaaatac ttacttgatc agcttacaag gacatatata tcaaccttct ttaactctca   15420
ctcagtcctt cctcttcacc gtccatatca aaaacaaata tggaaagcct taggtagtgt   15480
aatatattgt tcggagacag ttgatatacc tctaattaaa gacattcaga tagaagatat   15540
taatgatttt gaggatatcg agagggtat cgatggcgaa gaattatgac aacaatgatt   15600
ataagaactc atgatagttt tatttaagaa aaacatattg attttcccct tggt            15654
```

<210> SEQ ID NO 6
<211> LENGTH: 15654
<212> TYPE: DNA
<213> ORGANISM: Human parainfluenza virus

<400> SEQUENCE: 6
accaagggga gaatcagatg gcatcgttat atgacgaatt gcaaaaagat tacgtaggtc 60
cggaaccact agattccggt gccggtaacg attccagttt tatactatct gatcattctc 120
tatctctatt aaggatattt ctagtctaaa gttcaaaatg tcaagtgttt taaagacatt 180
tgaaagattt actatacaac aggagcttca ggagcaatct gatgacactc cagtacctct 240
tgagacaatc aaacctacaa tcagggtatt tgtcatcaat aataatgatc ctgtcgtaag 300
atctagactt ttattcttta atctacgaat cattatgagt aacactgcaa gagagggaca 360
tagagctggt gctctcctca gtcttttatc actaccttct gcagctatga gtaatcacat 420
caaattagcc atgcattcac cagaagccag catagataga gtagagataa cagggtttga 480
gaataattca ttccgagtca ttccagatgc tcgatcaact atgtccagag gagaggtgct 540
ggcttttgaa gcattagctg aggacattcc tgataccctt aatcaccaaa ctccatttgt 600
aaataatgat gtagaagatg acatatttga tgaaacagag aaattcttag atgtttgcta 660
cagtgtgctt atgcaggcat ggatagtaac atgcaagtgt atgactgctc ctgatcaacc 720
accagtatca gtagcaaagc ggatggctaa atatcaacaa caagggagaa tcaatgctag 780
gtatgtacta caacctgaag cacaaagact aattcagaat gccatccgca agtcaatggt 840
agtaaggcat ttcatgactt atgagcttca actttcacaa tcaagatctt tgctagcaaa 900
ccgctactat gctatggtgg gagacattgg caagtacatt gaacacagcg gaatgggagg 960
atttttctta acacttaaat atggacttgg aacaagatgg cctacattgg ctcttgcagc 1020
attttctggg gaactccaga aattaaaagc tctcatgcta cattatcaga gtctaggacc 1080
catggccaag tacatggctc tattagaatc accaaaactg atggattttg tcccatctga 1140
atatccatta gtttatagct atgcaatggg tattggaact gtccttgata caaatatgag 1200
aaattatgca tacggtagat catatttaaa tccgcaatat tttcagctag gagtagaaac 1260
agcaaggaaa cagcagggag ctgttgacaa caggacagca gaggacctcg gcatgactgc 1320
tgcagacaaa gcagacctca ctgcaaccat atcaaagcta tccttgtccc aattacctag 1380
gggtagacaa ccaatatctg acccatttgc tggagcaaat gacagagaaa tgggaggaca 1440
agcaaatgat acacctgtgt ataacttcaa tccaatcaat actcggaggt atgacaacta 1500
tgacagtgat ggtgaggaca gaattgacaa cgatcaagat caagctatca gagagaatag 1560
aggagagcct ggacaaccaa acaaccagac aagtgacaac cagcagagat tcaacccccc 1620
cataccgcaa agaacatcag gtatgagcag tgaagagttc caacattcaa tgaatcagta 1680
catccgtgct atgcatgagc aatacagagg ctcccaggat gatgatgcca atgatgccac 1740
agatgggaat gacatttctc ttgagctagt tggagatttt gattcctaac tctcaatgtc 1800
atacaaccag atatacacat ccacatcact cagagataca gctgccactc acacactcat 1860
ccagacaaat caaactagac tcacatcatt cggaaacaat tctctcataa tttaagaaaa 1920
aatcataggc ccggacgggt tagaaatccg gtgcttgttc gtgatcagat aacctccaca 1980
ccagaatcat acaatcatgg ccgaggaacc aacatacacc actgagcaag ttgatgaatt 2040
aatccatgct ggactgggaa cagtagattt cttcctatct agacccatag atgctcagtc 2100
ttctttaggc aaaggcagca tcccaccagg tgtcacagct gttctaacta gtgcagcgga 2160

```
ggcaaaatcc aaaccagttg ctgctggtcc agttaaaccc aggcggaaga aagtgatcag    2220
caatactact ccatacacta ttgcagacaa tattccacct gagaagctac cgatcaacac    2280
tccaataccc aatccattac ttccactggc acgccctcac ggaaagatga cagacattga    2340
cattgtcact gggaacatta cagaaggatc gtacaaaggt gtggagcttg ctaaattagg    2400
gaagcagaca ctactcacaa ggttcacctc gaatgagcca gtctcctcag ctggatccgc    2460
ccaagacccc aactttaaga ggggggagc taatagagaa agagcaagag gcaaccatag    2520
gagagaatgg agtattgcat gggtcggaga tcaggtcaaa gtcttcgagt ggtgtaatcc    2580
caggtgtgcc ccagtcacgg cctcagctcg caagttcacc tgcacatgcg gatcctgccc    2640
cagcatctgc ggagaatgtg aaggagatca ttgagctctt aaagggactt gatcttcgcc    2700
ttcagactgt agaagggaaa gtagataaaa ttcttgcaac ttctgcaact ataatcaatc    2760
ttaaaaatga aatgactagt ctcaaggcga gtgttgcaac tgtggaaggt atgataacaa    2820
caattaaaat catggatccc agtacaccaa ctaatgtccc tgtagaggag atcagaaaga    2880
gtttacacaa tgttccagta gtaattgccg gtccaactag tggaggcttc acagccgaag    2940
gcagtgatat gatttcaatg gatgaactag ctagacctac actctcatca acaaaaagga    3000
tcacacgaaa gcctgaatcc aagaaagatt aacaggcat aaaactaact ttgatgcagc    3060
ttgcaaatga ctgcatctcg cgtccagata ccaagactga gttcgtgact aagattcagg    3120
cagcaaccac agaatcacag cttaacgaaa ttaaacggtc aataatacgc tctgcaatat    3180
aaaatgaggt gcagtcacac aagagacact caacatgcat ccaatcaaga tccagactcc    3240
atccatccaa aaacacgccc acaattgtca acaccaagaa acaaccacag ccgaaccatg    3300
ctcaaccaaa agacccaaac aacacctcac atcaatagaa ggctggacat gataaattta    3360
ataaaaaaag aaaagaagtt aagtaaaatt taaggacac aatagagaaa atctaggtcc    3420
gaaagcttgc ctctcagaca gatcccaaaa tcatagtcca aaccccaaac acagcagcag    3480
acatgcctat aatatcatta ccagcagatc caacttcacc cagtcaatcc cttactccgt    3540
ttccaataca acttgacacc aaagatggca aggcagggaa actccttaaa cagattcgaa    3600
ttaggtatct aaatgagcct aattctcgcc atacaccaat aactttcatc aatacgtatg    3660
gatttgttta tgctcgagac acttcagggg gcattcacag tgagatcagc agtgacctag    3720
ctgcagggtc cataacagca tgcatgatga cgctaggtcc tggtccaaat attcagaatg    3780
caaatctagt gctaagatct ctgaatgaat tctacgtaaa agtcaagaag acatcaagcc    3840
agagagagga agcagtgttt gaattagtta cattccaac tttattgaga gaacatgctc    3900
tttgcaaacg caaaatgtta gtatgctctg cagaaaaatt cctcaagaac ccgtcaaagc    3960
tacaagctgg atttgagtat gtatacatac caacttttgt ctccattaca tactcaccac    4020
gaaatctgaa ttaccaagtt gccagaccta tccttaagtt cagatcacgc tttgtgtata    4080
gcattcattt ggaattaatc ctgagattgc tatgcaaatc tgactccccc ttgatgaaat    4140
cctacaatgc agacagaaca ggtcgggat gcctcgcatc agtctggatc cttgtatgta    4200
acattctgaa aaacaaaagc atcaagcaac aaggcagaga atcatatttc atagctaagt    4260
gcatgagcat gcagctgcag gtgtccattg cagatctttg ggaccaaca atcataatca    4320 aatcattggg tcacatcccc aagactgcac ttccttttt cagcaaagat gggattgcct    4380
gtcatccatt acaagatgtt tcccctaatc tgacaaaatc actgtggtca gttggatgtg    4440
agatagaatc tgccaagttg atacttcaag aatctgatct taatgagcta atgggccacc    4500
aggaccttat cactgataag attgccatta gatcaggtca acggacattt gagaggtcca    4560
```

```
aattcagccc attcaaaaaa tatgcatcaa ttccaaactt ggaagccatc aactgaatgc    4620
tccagcatct gagaatagaa ccacaatcaa gtcatactac tagtcactat acaataatca    4680
acaattttag tcaactgatt accaagatgt tatcataggt ccgaactgat caatctaaca    4740
aaaaaactaa acgttccaca ataaatcaac gttcaggcca aaatattcag ccatgcatca    4800
cctgcatcca atgatagtat gcatctttgt tatgtacact ggaattgtag gttcagatgc    4860
cattgctgga gatcaactac ttaatatagg ggtcattcaa tcaaagataa gatcactcat    4920
gtactatact gatggtggtg ctagctttat tgttgtaaaa ttgctaccta atcttccccc    4980
aagcaatgga acatgcaaca tcaccagtct agatgcatat aatgttaccc tatttaagtt    5040
actaacaccc ctgattgaga acctgagtaa aatttccact gttacagata ccaaaacccg    5100
ccaagaacga tttgcaggag tagttgttgg acttgctgca ttaggagtag ccacagccgc    5160
acaaataact gcagctgtag caatagtgaa agctaatgca aatgctgctg cgataaacaa    5220
tcttgcatct tcaattcaat ccaccaacaa ggcagtatcc gatgtgatag atgcatcaag    5280
aacaattgca accgcagttc aagcaattca ggatcacatc aatggagcta ttgttaatgg    5340
gataacatct gcatcatgcc gtgcccatga tgcactcatt gggtcaatat taaatcttta    5400
tctcactgag cttaccacaa tatttcataa tcaaataaca aaccctgcgc tgacaccact    5460
ctccatccaa gctttaagaa tcctcctcgg tagcaccttg ccaattgtca ttgagtccaa    5520
actcaacaca aacctcaaca cagcagagct gctcagttcc ggactgttaa ctggtcaaat    5580
aatttccatt tccccaatgt acatgcaaat gctaattcaa atcaatgttc cgacatttat    5640
aatgcaaccc ggtgcgaagg taattgatct aattgctatc tccgcaaacc ataaattgca    5700
agaagtggtt gtacaagttc cgaataggat tctagagtat gcaaatgaac tacaaaatta    5760
cccagccaat gactgtgtcg tgacaccgaa ctctgtattt tgtagataca atgagggttc    5820
ccctatccct gaatcacaat atcaatgctt gaggggaat cttaattctt gcacttttac    5880
ccctattatc gggaactttc ttaagcgatt cgcatttgct aatggtgtgc tctatgccaa    5940
ctgcaaatct ttgctatgta ggtgtgccga cccccccat gttgtatccc aggatgatac    6000
ccaaggcatc agcataattg atattaagag atgctctgag atgatgcttg acacttttc    6060 atttaggatc acatctactt tcaatgctac gtacgtgaca gacttctcaa tgattaatgc    6120
aaatattgta catctaagtc ctctagattt gtcaaatcaa atcaattcaa taaacaaatc    6180
tcttaaaagt gctgaggatt ggattgcaga tagcaacttc tttgctaatc aagccaggac    6240
agccaagaca ctttattcac taagtgcaat agcattaata ctatcagtga ttactttggt    6300
tgtcgtggga ttgctgattg cctacatcat caagctggtt tctcaaatcc atcaattcag    6360
atcgctagct gctacaacaa tgttccacag ggaaaatcct gccttctttt ccaagaataa    6420
ccatggaaac atatatggga tatcttaaga aatctatcac aagtctatat atgtccacaa    6480
ttgaccctta agaaccaact tccaacgatt atccgttaaa tttaagtata atagtttaaa    6540
aattaacatt aagcctccag ataccaatga atatgaatat atctcttaga aaacctgatt    6600
attatgtgat agcgtagtac aatttaagaa aaaacctaaa ataagcacga acccttaagg    6660
tgtcgtaacg tctcgtgaca ccgggttcag ttcaaatatc gacctctaac ccaatttaac    6720
acccattctt atataagaac acagtataat ttaatcacaa aagacctcaa aaactgacac    6780
agcttgatcc actcaacata taattgtaag attaataata atggaagatt acagcaatct    6840
atctcttaaa tcaattccta aaaggacatg tagaatcatt ttccgaactg ccacaattct    6900
```

```
tggaatatgc acattgattg ttctatgttc aagtattctt catgagataa ttcatcttga    6960
tgtttcctct ggtctcatgg attccgatga ttcacagcaa ggcattattc agcctattat    7020
agaatcatta aaatcattaa ttgctttggc taaccagatt ctgtacaatg ttgcaataat    7080
aattcctctt aaaattgaca gtatcgagac tgtaatatac tctgctttaa aggatatgca    7140
tactgggagc atgtccaaca ccaactgtac acccggaaat ctgcttctgc atgatgcagc    7200
gtacatcaat ggaataaaca aattccttgt acttaaatca tacaatggga cgcctaaata    7260
tggacctctc ctaaatattc ccagctttat ccctcagca acatctccca acgggtgcac     7320
tagaatacca tcattttcac tcattaagac ccattggtgt tacactcaca atgtaatact    7380
tggagattgc ctcgatttca cgacatctaa tcagtattta gcaatgggga taatacaaca    7440
atctgctgca gcatttccaa tcttcaggac tatgaaaacc atttacctaa gtgatggaat    7500
caatcgcaaa agctgttcag tcactgctat accaggaggt tgtgtcttgt attgctatgt    7560
agctacaaga tctgagaaag aagattatgc cacaactgat ctagctgaac tgagacttgc    7620
tttctattat tataatgata cctttattga aagagtcata tctcttccaa atacaacagg    7680
gcaatgggcc acaatcaatc ctgcagttgg aagcgggatc tatcatctag ctttatttt     7740
atttcctgta tatggtggtc tcataaaggg gactccttcc tacaacaagc agtcctcacg    7800
ctattttatc ccaaaacatc ccaacataac ctgtgccggt aaatccagcg aacaggctgc    7860
agcagcacgg agttcctatg taatccgtta tcactcaaac aggttgattc agagtgctgt    7920
tcttatttgc ccattgtctg acatgcacac agcaaggtgt aatctagtta tgtttaacaa    7980
ttctcaagtc atgatgggtg cagaaggtag gctctatgtt attgacaata atttgtatta    8040
ttatcaacgt agttcctctt ggtgggctgc atcgcttttt tacaggatca atacagattt    8100
ttctaaagga attcctccta tcattgaggc tcaatgggta ccgtcctatc aagttccccg    8160
tcctggagtc atgccatgca atgcaacaag ttttttgccct gctaattgca tcacaggggt    8220
gtacgcagat gtgtggccgc ttaacgatcc agaacccaca tcacaaaatg ctctgaatcc    8280
caactatcga tttgctggag cctttctcag aaatgagtcc aaccgaacca atcccacatt    8340
ctacactgca tcagccagcg ccctactaaa tactaccgga ttcaacaaca ccaatcacaa    8400
agcagcatat acgtcttcaa cctgctttaa gaatactgga actcaaaaga tttattgttt    8460
gataataatt gaaatgggct catctctttt aggggagttc caaataatac catttctaag    8520
ggaactaata ccttaatact attgaatgaa gactccagat tcaataataa ttgaaaggct    8580
ctctatctta tgcaatagtt atacgttttg gctgtattag aatgttatag cattctgctg    8640
tttttcccat atgaagcaat ccttcaacac cgacttaggt tcaattttct catcatttac    8700
tgttgtaatt caatcttact aaagttattc cgatatttaa gaaaaataa cctttatata    8760
atgtaacaat actattaaga ttatgatata ggccagaatg gcggcctctt ctgagatact    8820
ccttcctgaa gtccacttga actcaccaat agtcaaacac aaactcatat actacttatt    8880
actagggcac ttcccgcatg atcttgacat ttctgaaata agccccttc acaataatga     8940
ttgggatcaa attgccagag aagaatccaa tcttgctgaa cgacttggag tagctaaatc    9000
tgaattaatt aaacgtgtgc ccgcatttag agcaactaga tggcgtagtc atgcagccgt    9060
ccttatatgg ccttcttgta taccatttct tgttaaattc ctacctcatt ctaagcttca    9120
accagtagaa caatggtaca agttgatcaa tgcttcatgt aatactatat ctgactcaat    9180
tgatagatgt atggagaata tttctattaa gcttactggg aaaaacaatc tattctctcg    9240
atccagagga actgcaggtg caggtaaaaa cagtaaaatc accctcaatg atatccaatc    9300
```

```
tatttgggaa tcaaacaagt ggcaacctaa tgtatcttta tggcttacaa ttaaatacca   9360
aatgcgacaa cttataatgc atcaaagttc tcgtcagccg actgatttag ttcacattgt   9420
tgacacacga tctggtctaa tagttatcac ccctgaactt gttatttgtt ttgatcggtt   9480
aaatagtgtt ttaatgtatt ttacatttga gatgacttta atggtaagtg acatgtttga   9540
gggaaggatg aatgtcaccg ctctctgcac tattagtcat tacttatctc cactagggcc   9600
aaggatagat agattgtttt ccattgtaga tgaattagca caactattag gtgacactgt   9660
atataaagtt attgcatctc ttgaatcttt agtatatggg tgtctacaac ttaaagatcc   9720
agtagtggaa ttagcagggt catttcattc ctttattaca caagagatta tagatatcct   9780
aattggttca aaagcccttg ataaggatga atcaataact gttactacac aattgttaga   9840
tatattttcc aacctttctc cagatttaat tgctgagatg ttgtgtctca tgagactttg   9900
gggtcatccc actcttactg ctgcgcaagc tgcaggtaaa gtgagagaat ctatgtgtgc   9960
aggtaagtta cttgatttcc ctacaataat gaaaactctt gctttttcc acacaatttt   10020
aattaatggt taccgtagaa agaaaaatgg aatgtggcct ccacttatac ttcctaaaaa   10080
tgcatcaaaa agcttaatag aatttcaaca tgataatgct gaaatatctt acgaatatac   10140
actcaagcat tggaaagaga tctctctcat agaatttaga aagtgctttg actttgatcc   10200
tggtgaggag ctaagcattt ttatgaaaga caaggcaata agtgctccaa gaagtgattg   10260
gatgagtgta tttcgtagaa gtctaataaa acaacgacat cagagacatc atattcctat   10320
gcccaatcca tttaatagac gtctattact caatttctta aagatgaca gttttgatcc   10380
agttgccgag cttcaatatg ttaccagtgg tgaatatctc caagatgaca cattttgtgc   10440
atcttactca ttaaaagaga agaaataaa accagatgga aggatatttg ctaagcttac   10500
taatagaatg cggtcctgtc aagtaattgc ggaagcaatt ctcgcaaatc atgcaggtac   10560
tctaatgaag gaaaacggag ttgtcttgaa tcaattatca ctgactaaat cattgcttac   10620
tatgagtcaa attggcataa tatcagaaaa ggcgaagaga tatacgcgag ataacatctc   10680
atcccaaggt ttccatacaa tcaagactga ttctaaaaat aagaggaaaa gcaaaactgc   10740
atcatcatac ctcacagatc ctgatgatac atttgaactt agtgcatgtt ttataactac   10800
tgatcttgct aaatactgtc ttcaatggag atatcagacc ataatccatt ttgctcgaac   10860
attaaacaga atgtatggag ttccacattt atttgaatgg attcatcttc gtttaattag   10920
atctacatta tatgttggtg atccattcaa tcctccctgcc gcaactgatg ctttcgatct   10980
agataaagta ttaaatggtg atatctttat agtctctccc aagggaggta ttgaaggcct   11040
atgtcagaaa atgtggacaa tgatctctat ttctgtgatc atcctctctt cagccgaatc   11100
caaaacaaga gtaatgagca tggttcaagg agataatcag gcgattgcag ttacaacaag   11160
agttcctaga tcattaccta gtattcagaa aaaggagtta gcctatgcag caagcaagtt   11220
atttttttgaa agacttaggg caaataatta tgggttgggt catcagctaa aggctcaaga   11280
aactataata agttccacgt tcttcatata tagtaaacgg gtatttttatc aaggacgtat   11340
actaacacag gcactcaaaa atgctagcaa gttatgtctt actgcagatg tattaggtga   11400
atgtactcaa gcttcctgtt caaattctgc tactaccatc atgagattaa cagaaaatgg   11460
ggttgagaaa gatacatgtt ataagcttaa tatttatcag tccattcgtc aactcacata   11520
tgatctaata ttttccccaat actccatacc aggtgaaact ataagtgaga ttttcctaca   11580
gcatccaaga ctaatctcac gtattgttct gctcccttca cagctaggtg gtcttaatta   11640
```

```
cctcgcatgt agcagattat ttaaccgcaa tatcggagat cctcttggta cagctgtggc   11700
agatctcaag aggttaatta aatgtggtgc tcttgaatca tggatactgt ataatttact   11760
agcaagaaaa ccagggaaag gttcatgggc aactttagca gccgatccat actcattgaa   11820
tcaagaatat ctttatcctc ctactactat acttaaaaga catactcaaa atactttaat   11880
ggagatatgt cggaatccta tgttaaaggg agttttttaca gataatgcaa aagaggagga   11940
aaatctcctt gcaaaatttc ttcttgatcg tgatatagta ttgccaagag ttgcacacat   12000
tataatagat caatctagca tcggaaggaa gaaacagata caaggatttt ttgacaccac   12060
aaggaccata atgagacgat catttgaaat caaaccactc tcaactaaga agactctttc   12120
agtcatagaa tataatacta attacttatc ttataactac cctgtcatac ttaatccttt   12180
acctattcct ggatatttaa attatattac tgaccaaact tgcagtattg atatatctag   12240
aagtttaaga aaattatcat ggtcttcttt attgaatgga agaactttag aaggattaga   12300
aactccagat ccaattgaag ttgtcaatgg ttccttgatt gtaggtacag agattgtga   12360 tttttgtatg cagggtgacg acaaatttac ttggttcttt ttacctatgg ggataattat   12420
tgatggaaat cctgaaacta atccacccat cagagttcca tacattgggt ctagaacaga   12480
ggaaagaaga gttgcatcaa tggcatatat taaaggtgcc acacacagtt tgaaggctgc   12540
tcttagaggc gcaggggtat atatttgggc attcggggat actgtagtga actggaatga   12600
tgcacttgat atcgcaaata ctagggttaa gatatcccta gagcaacttc agacccttac   12660
acctcttcct acatctgcaa acattacaca ccgtttagat gatggagcca caacacttaa   12720
attcactcca gctagttcct atgcattttc tagttatact catatatcaa atgatcaaca   12780
atatttagaa atagatcaga gagtagtcga ttctaatatt atttatcaac aattaatgat   12840
aacaggactt gggattattg agacctacca taacccacct ataaggactt ctacacaaga   12900
aatcactctc catttgcaca ctagctcatc ttgttgtgtt agaagtgtag atggttgcct   12960
tatatgtgag agcaatggag aggttcctca gatcactgtt ccctatacta atacatttgt   13020
atatgatcct gatccactag cagattatga gattgcacac ctagattatc tctcctacca   13080
agctaaaatt ggaagtacag attactactc actcactgat aaaattgacc tattagcaca   13140
tttaactgca aaacaaatga taaactcaat aattggggtta gatgaaacag tatcaattgt   13200
caatgatgcg gttatcctat ctgactatac taataactgg attagtgaat gttcttatac   13260
taagatagat ttagtttttta aattaatggc atggaatttc cttcttgagc ttgcattcca   13320
gatgtactac ttaaggatat catccttggac aaatatattt gactatactt atatgacttt   13380
acgcaggata cccggaactg ctctaaataa tattgcagct actattagcc atccaaaatt   13440
attaagacgt gcaatgaatc ttgatattat cactcctata catgcaccgt atttagcttc   13500
attagattat gtcaaattaa gtattgatgc aattcagtgg ggagttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactat acttttccaa aaattaaagg gatgccacca aagaaaaagt gtttagtctt   13740
aactgaatat ctagcaatgt gttatcaaaa tactcatcac ttagatccag atcttcaaaa   13800
gtatttatat aatctaacta atccaaaatt gactgcattt cccagtaaca acttctactt   13860
aactagaaaa atccttaatc aaattagaga atcagacgaa ggacaatata ttatcacctc   13920
atattatgaa tccttcgaac aattagaaac agatataatt cttcactcta ctttaactgc   13980
tccttatgat aattcagaaa ctctaacaaa gttcgattta tcccttgaca tctttccaca   14040
```

```
tccagaatct ctcgagaaat atcctcttcc agttgatcat gactctcgat ctgcaatttc    14100
aacactaatt ccaggccctc cttctcatca tgtattacga ccactaggag tgtcatccac    14160
agcttggtat aaagggataa gttattgtag atacctagaa acacaaaaga tacagactgg    14220
tgatcatctt tatttagccg aaggaagcgg tgcttcaatg tcacttctag aactcttatt    14280
tccaggagat actgtctatt ataatagtct ttttagtagt ggagagaatc ctccacagag    14340
aaactatgcc cctcttccaa ctcaatttgt acagagtgtt ccatataaat tgtggcaagc    14400
tgatcttgct gatgatagca atttgataaa agattttgtc ccattatgga atggaaacgg    14460
tgcagttaca gacttatcaa caaggatgc agttgcattc ataatacata agtaggagc    14520 agagaaagca tcccttgtcc atatagatct cgaatcaact gctaatataa atcagcaaac    14580
tctgtccaga tcccagattc attcattaat tatagcaact actgttctta agaggggtgg    14640
gatattaatt tataaaacat catggcttcc gttttctagg tttagtcaac tagcaagtct    14700
actttggtgc ttcttttgacc ggatccatct aatacgtagt agctattctg atcctcacag    14760
tcatgaggtt tatcttgtat gtagacttgc cgcagatttt agaactatcg gtttcagtgc    14820
agctctagta actgctacta ctcttcacaa tgacggattc acaacaatac atcctgatgt    14880
tgtttgtagt tattggcaac accatcttga aaatgttggg agagtcggaa aagtaattga    14940
tgagatactt gatggtttag ccaccaactt cttcgcagga gataatgggc ttattctaag    15000
atgtggagga actcccagct ccagaaaatg gttagagatt gaccagttag catcatttga    15060
tttggttcaa gatgctctgg ttacacttat cactatacac ctaaaggaaa ttatagaagt    15120
gcagtcatca catacagagg attatacatc tctcctcttc acaccttata atattggtgc    15180
agcagggaaa gtcagaacta tcatcaaatt aattctagaa cgatctttaa tgtatacagt    15240
ccgaaattgg ttagttttac ccagttccat ccgggattct gtacgacaag atttagaatt    15300
agggtcattt agattaatgt ctattttaag tgaacagaca tttcttaaaa agacacccac    15360
aaaaaaatac ttacttgatc agcttacaag gacatatata tcaaccttct ttaactctca    15420
ctcagtcctt cccctccacc gtccatatca aaaacaaata tggaaagcct aggtagtgt    15480 aatatattgt tcggagacag ttgatatacc tctaattaaa gacattcaga tagaagatat    15540
taatgatttt gaagatatcg agaggggtat cgatggcgaa gaattatgac aacaatgatt    15600
ataagaactc atgatagttt tatttaagaa aaacatattg attttccct tggt          15654
```

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide spacer

<400> SEQUENCE: 7
atttaagaaa aaacatagg cccggacgg                                          29

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      Human parainfluenza virus editing site

<400> SEQUENCE: 8

```
tttaagaggg gggg                                                          14
```

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      Human parainfluenza virus editing site

<400> SEQUENCE: 9

```
tttaagagag gcgg                                                          14
```

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic Human parainfluenza virus editing site

<400> SEQUENCE: 10
tttaagagag gaggtg 16

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence: Synthetic NotI restriction site

<400> SEQUENCE: 11 gcggccgc 8

<210> SEQ ID NO 12
<211> LENGTH: 15654
<212> TYPE: DNA
<213> ORGANISM: Artificial Sequence
<220> FEATURE:
<223> OTHER INFORMATION: Description of Artificial Sequence: Synthetic antigenomic cDNA

<400> SEQUENCE: 12
accaagggga gaatcagatg gcatcgttat atgacgaatt gcaaaaagat tacgtaggtc 60
cggaaccact agattccggt gccggtaacg atctcagttt tatactatct gatcattctt 120
tatctctact aaggatattt ctaatctaag gttcaaaatg tcaagtgtct taaagacatt 180
tgaaagattt actatacaac aggagcttca ggagcaatct gaagacactc caatacctct 240
tgaaacaatc agacctacaa tcagagtatt tgtcatcaat aataatgatc ctattgtaag 300
atctagactt ttattcttta atctacgaat tattatgagt aacactgcaa gagagggaca 360
tagagctggt gctctcctca gtcttttatc actaccttct gcagctatga gtaatcacat 420
caaactagcc atgcattcac cagaagccag catagataga gtagaaataa cagggtttga 480
gaataattca ttccgagtta ttccagatgc tcgatcaact atgtccagag gagaagtgct 540
ggccttcgaa gcattagctg aggacattcc tgataccctt aatcaccaaa ctccatttgt 600
aaataatgat gtggaagatg acatatttga tgaaacagag aaattcttgg atgtttgcta 660
tagtgtactt atgcaggcat ggatagtaac atgcaagtgc atgactgctc ctgatcaacc 720
accagtatca gtagcaaagc ggatggctaa atatcaacaa caagggagaa tcaatgctag 780
atatgtacta caacctgaag cacaaagact aattcagaat gccatccgca agtcaatggt 840

```
agtaaggcat tcatgacct atgagcttca actttcacaa tcaagatctt tgctagcgaa    900
ccgttattat gccatggtgg gagacattgg caagtatatt gaacacagcg gaatgggagg    960
gtttttctta acacttaaat atggacttgg aacaagatgg cctacattgg ctcttgcagc   1020
attctctggg gaactccaga aattaaaggc tctcatgcta cattatcaga gtctaggacc   1080
catggccaag tacatggctc tattagaatc accaaagctg atggattttg tcccatctga   1140
atatccatta gttatagct atgcaatggg tattggaact gtccttgata caaacatgag   1200
aaactatgca tatggtagat catatctaaa tccacaatat tttcagctag gggtagaaac   1260
agcaaggaaa cagcaaggag ctgttgacaa caggacagca gaggacctcg gcatgactgc   1320
tgcagataaa gcagacctca ctgcaaccat atcaaagcta tctttatccc aattacctag   1380
gggtagacaa ccaatatccg acccatttgc tggagcaaat gacagagaaa caggaggaca   1440
agcaactgat acacctgtgt ataacttcaa tccaatcaat aatcggaggt atgacaacta   1500
tgacagtgat agtgaggaca gaattgacaa cgatcaagat caggctatca gagagaacag   1560
aggagaacct ggacaaccaa caaccagac aagcgaaaac cagcagagac tcaatctccc   1620
tgtaccgcaa agaacatcag gtatgagtag tgaagagttc caacattcaa tgaatcagta   1680
catccgtgct atgcatgagc aatacagagg ctcccaggat gatgatgcca atgatgccac   1740
agatgggaat gacatttcac ttgagctagt tggagatttt gattcctaac tctcactttc   1800
acataaccag acatacacat ccacaccacc cagagacata gctaccatcc acacactcac   1860
ccagacaaat caaactagat tcaaatcatt cggaaacaat tctcctagaa tttaagaaaa   1920
aaacataggc ccggacgggt tagagatccg gtgctcgtct gtggccagac aacctccaca   1980
ccagagccac acaatcatgg ccgaggaacc aacatacacc actgagcaag ttgatgaatt   2040
aatccatgct ggactaggaa cagtagattt cttcctatct agacccatag atgctcagtc   2100
ttctttaggt aaaggcagca tcccaccagg tgtcacggct gttctaacca atgcagcaga   2160
ggcaaaatcc aaaccagttg ctgctggtcc agtaaaaccc agacggaaga aagtgatcag   2220
caataccact ccatacacta ttgcagacaa catcccacct gagaagctac cgatcaacac   2280
tccaatacc aatccattac ttccactggc acgccctcac ggaaagatga cagacattga   2340
cattgtcact gggaacatta cagaaggatc atacaaggt gtggagcttg ccaaattagg   2400
gaagcaaaca ctactcacaa ggttcacctc gaatgagcca gtctcctcag ctggatccgc   2460
ccaagacccc aactttaaga gggggggagc taatagagaa agagcaagag gcaaccatag   2520
gagagaatgg agtattgcat gggtcggaga tcaggtcaaa gtcttcgagt ggtgtaatcc   2580
caggtgtgcc ccagtcacgg cttcagctcg caagttcacc tgcacatgtg gatcctgccc   2640
cagcatctgc ggagaatgtg aaggagatca ttgagctctt aaaagggctt gatcttcgcc   2700
ttcagactgt agaagggaaa gtagataaaa ttcttgcaac ctctgcaact ataatcaatc   2760
ttaaaaatga aatgactagt cttaaggcga gcgttgcaac tgtggaaggt atgataacaa   2820
caattaaaat catggatccc agtacaccaa ccaatgtccc tgtagaggag atcagaaaga   2880
gtttacacaa tgttccagta gtaattgctg gtccgactag tggaggcttc acagccgaag   2940
gcagtgacat gatttcaatg gatgaactag ctaggcctac actctcatca acaaaaaaga   3000
tcacacgaaa gcctgaatcc aagaaagatt aacaggcat aaaactaacc ctgatgcagc   3060
ttgcaaatga ctgcatctcg cgtccagata ccaagactga gtttgtgact aagattcaag   3120
cagcaaccac agaatcacag ctcaacgaaa tcaaacggtc aataatacgc tctgcaatat   3180
```

```
aaaatgcggt gcaatcacac aagagacatt caacatgcat ccgatcaaga tccaaactcc    3240
ttccatccga aaacacactc accactgtca acaccaagaa acaactacag ccgaaccatg    3300
ctcaaccaaa agacccaaac aacatctcaa atcgacagaa ggctagacat gataaattta    3360
ataaaaaatt aaaagaagtt aagtaaaatt taaagaacac aatagagaaa acctaggtcc    3420
gaaagcttgc ctttcagaca gatcccaaaa tcatagttca aacttcaaac acagcagcag    3480
acatgcctat aatatcatta ccagcagatc caacttcacc cagtcaatcc cttactccgt    3540
ttccaataca acttgatacc aaagatggca aggcagggaa actccttaaa cagattagaa    3600
ttaggtatct aaatgaacct aactctcgtc ataccaat aactttcatc aatacgtatg    3660
gatttgttta tgctcgagac acttcaggag gcattcacag cgagatcagc agtgacctag    3720
ctgcagggtc cataacggca tgcatgatga cactaggtcc tggtccaaat attcagaatg    3780
caaatctagt gctaagatcc ctgaatgaat tctacgtaaa agtcaagaag acatcaagcc    3840
agagggagga agcagtgttt gaattagtta acattccaac cttattgaga gaacatgctc    3900
tttgcaaacg caaacgtta gtatgctctg cagaaaaatt cctcaagaac ccatcaaagc    3960
tacaagctgg atttgaatat gtatacatcc caacttttgt ctccattaca tactcaccac    4020
gaaatctgaa ttaccaagtt gccagaccta tccttaagtt cagatcacgc tttgtgtata    4080
gcattcattt ggaattaatc ctgagattgc tatgcaaatc tgactcccct ttgatgaaat    4140
cttataatgc agatcgaaca ggtcgaggat gcctcgcatc agtctggatc cacgtatgta    4200
acattctgaa aaacaaaagc atcaagcaac aaggcagaga atcatatttc atagctaagt    4260
gcatgagtat gcagctgcag gtgtccattg cagatctttg ggaccaaca atcataatta    4320 aatcattggg tcacatcccc aagactgcac ttcctttttt cagcaaagac gggattgcct    4380
gtcatccact acaagatgtt tcccctactc tgacaaaatc actgtggtca gtgggatgtg    4440
agatagaatc tgccaagttg atacttcaag aatctgatat taatgagcta atgggccacc    4500
aggacttgat tactgataag attgccatta gatcaggtca acggacattt gagaggtcca    4560
aattcagccc attcaaaaaa tacgcatcaa ttccaaactt agaagccatc aactgaatgc    4620
tccagcatct aggaatagaa caacaactaa gtcataccat tattgaccat acaataatca    4680
acaattttag ccaactgatt actaagatat tatcataggt ccgaactgat caatctaaca    4740 aaaaactaa acattcaata ataaatcaaa gttcaggcca aattatccag ccatgcatca    4800
cctgcatcca atgatagtat gcatttttgt tatgtacact ggaattgtag gttcagatgc    4860
cattgctgga gatcaactcc tcaatgtagg ggtcattcaa tcaaagataa gatcactcat    4920
gtactacact gatggtggcg ctagctttat tgttgtaaaa ttactaccca atcttccccc    4980
aagcaatgga acatgcaaca tcaccagtct agatgcatat aatgttaccc tatttaagtt    5040
gctaacaccc ctgattgaga acctgagcaa aatttctgct gttacagata ccaaaccccg    5100
ccgagaacga tttgcaggag tcgttattgg gcttgctgca ctaggagtag ctacagctgc    5160
acaaataacc gcagctgtag caatagtaaa agccaatgca aatgctgctg cgataaacaa    5220
tcttgcatct tcaattcaat ccaccaacaa ggcagtatcc gatgtgataa ctgcatcaag    5280
aacaattgca accgcagttc aagcgattca ggatcacatc aatggagcca ttgtcaacgg    5340
gataacatct gcatcatgcc gtgcccatga tgcactaatt gggtcaatat taaatttgta    5400
tctcactgag cttactacaa tatttcataa tcaaataaca aaccctgcgc tgacaccact    5460
ttccatccaa gctttaagaa tcctcctcgg tagcaccttg ccaattgtca ttgaatccaa    5520
actcaacaca aaactcaaca cagcagagct gctcagttcc ggactgttaa ctggtcaaat    5580
```

```
aatttccatt tccccaatgt acatgcaaat gctaattcaa atcaatgttc cgacatttat   5640
aatgcaaccc ggtgcgaagg taattgatct aattgctatc tctgcaaacc ataaattaca   5700
agaagtagtt gtacaagttc ctaatagaat tctagaatat gcaaatgaac tacaaaacta   5760
cccagccaat gattgtgtcg tgacaccaaa ctctgtattt tgtagataca atgagggttc   5820
cccgatccct gaatcacaat atcaatgctt aaggggaat cttaattctt gcacttttac   5880
ccctattatc gggaactttc tcaagcgatt cgcatttgcc aatggtgtgc tctatgccaa   5940
ctgcaaatct ttgctatgta agtgtgccga ccctccccat gttgtgtctc aagatgacaa   6000
ccaaggcatc agcataattg atattaagag gtgctctgag atgatgcttg cacttttc     6060 atttaggatc acatctacat tcaatgctac atacgtgaca gacttctcaa tgattaatgc   6120
aaatattgta catctaagtc ctctagactt gtcaaatcaa atcaattcaa taaacaaatc   6180
tcttaaaagt gctgaggatt ggattgcaga tagcaacttc ttcgctaatc aagccagaac   6240
agccaagaca ctttattcac taagtgcaat cgcattaata ctatcagtga ttactttggt   6300
tgttgtggga ttgctgattg cctacatcat caagctggtt tctcaaatcc atcaattcag   6360
agcactagct gctacaacaa tgttccacag ggagaatcct gccgtctttt ccaagaacaa   6420
tcatggaaac atatatggga tatcttaaga attctatcat aagtccatat atgtccatga   6480 ttgacctta agagccaacc tccaatgatt atccgttaaa ttcagatata acaattcaaa   6540
aatcaatatt aagcctccag ataccaatga atatgaatat atctcttaga aaacttgatt   6600
attatgtgat aacatagtac aatttaagaa aaaacctaaa ataagcacga acccttaagg   6660
tgtcgtaacg tctcgtgacg ccgggttcag ttcaaacatc gacccctgac ccaattcaat   6720
acccattttc ataaaggaac acagtataat ttaatcataa aagacctcaa aatctgatac   6780
agcttaatcc actcaacata taattataag actaataata atggaagatt acagcaatct   6840
atctcttaaa tcaattccta aaaggacatg tagaatcatt ttccgaactg ccacaattct   6900
tggcatatgc acattaattg tgctatgttc aagtattctt catgagataa ttcatcttga   6960
tgtttcctct ggtcttatga attctgatga gtcacagcaa ggcattattc agcctatcat   7020
agaatcatta aaatcattga ttgctttggc caaccagatt ctatataatg ttgcaatagt   7080
aattcctctt aaaattgaca gtatcgaaac tgtaatactc tctgctttaa aagtatatgca  7140 caccgggagt atgtccaatg ccaactgcac gccaggaaat ctgcttctgc atgatgcagc   7200
atacatcaat ggaataaaca aattccttgt acttgaatca tacaatggga cgcctaaata   7260
tggacctctc ctaaatatac ccagctttat cccctcagca acatctcccc atgggtgtac   7320
tagaatacca tcattttcac tcatcaagac ccattggtgt tacactcaca atgtaatgct   7380
tggagattgt cttgatttca cggcatctaa ccagtattta tcaatgggga taatacaaca   7440
atctgctgca gggtttccaa tttttcaggac tatgaaaacc atttacctaa gtgatggaat   7500
caatcgcaaa agctgttcag tcactgctat accaggaggt tgtgtcttgt attgctatgt   7560
agctacaagg tctgaaaaag aagattatgc cacgactgat ctagctgaac tgagacttgc   7620
tttctattat tataatgata cctttattga aagagtcata tctcttccaa atacaacagg   7680
gcagtgggcc acaatcaacc ctgcagtcgg aagcgggatc tatcatctag ctttatctt    7740 atttcctgta tatggtggtc tcataaatgg gactacttct tacaatgagc agtcctcacg   7800
ctattttatc ccaaaacatc ccaacataac ttgtgccggt aactccagca acaggctgc    7860 aatagcacgg agttcctatg tcatccgtta tcactcaaac aggttaattc agagtgctgt   7920
```

```
tcttatttgt ccattgtctg acatgcatac agaagagtgt aatctagtta tgtttaacaa   7980
ttcccaagtc atgatgggtg cagaaggtag gctctatgtt attggtaata atttgtatta   8040
ttatcaacgc agttcctctt ggtggtctgc atcgctcttt tacaggatca atacagattt   8100
ttctaaagga attcctccga tcattgaggc tcaatgggta ccgtcctatc aagttcctcg   8160
tcctggagtc atgccatgca atgcaacaag ttttttgccct gctaattgca tcacaggggt   8220
gtacgcagat gtgtggccgc ttaatgatcc agaactcatg tcacgtaatg ctctgaaccc   8280
caactatcga tttgctggag cctttctcaa aaatgagtcc aaccgaacta atcccacatt   8340
ctacactgca tcggctaact ccctcttaaa tactaccgga ttcaacaaca ccaatcacaa   8400
agcagcatat acatcttcaa cctgctttaa aaacactgga acccaaaaaa tttattgttt   8460
aataataatt gaaatgggct catctctttt aggggagttc caaataatac cattttttaag  8520 ggaactaatg ctttaatcct attgaatgaa gactccagat tcaagaataa ttggaaggct   8580 cttatttta tgcgatagtt atacgttttg gctgtattag aatgctatag cattctgctg    8640
tttttcccat atggaaaaat ccttcaacac caacttaggt tcaattttct catcatttac    8700
tgttgtaatt caatcttact aaagttattc tgatatttaa gaaaaaataa tctttatata   8760
atgtaacaat actactaaga ttataatata ggccagaatg gcggcctctt ctgagatact   8820
ccttcctgaa gtccatttga actcaccaat agtcaaacac aaactcatat actacttatt   8880
actagggcac ttcccgcatg atcttgacat ttctgaaata agccccccttc acaataatga   8940 ttgggatcag attgccagag aagaatccaa tcttgctgaa cgactcggag tagctaaatc   9000
tgaattaatt aaacgtgtgc ccgcatttag agcaaccaga tggcgtagtc atgcagccgt   9060
ccttatatgg ccttcttgta taccattcct tgttaaattc ctaccccatt ctaagcttca    9120
accaatagaa caatggtaca agttgatcaa tgcttcatgc aatactatat ctgactcaat   9180
tgatagatgt atggagaata tttctattaa gcttactggg aaaaacaatc tattctctcg   9240
atccagagga actgcaggcg caggtaaaaa cagtaaaatc accctcaatg atatccaatc   9300
tatttgggaa tcaaacaaat ggcagcctaa tgtatcttta tggcttacaa ttaaatacca   9360
aatgcgacaa cttataatgc atcaaagttc tcgtcagcca actgatttag ttcacattgt   9420
tgacacacga tctggtctaa tagttatcac ccctgaactt gttatttgct ttgatcggtt   9480
gaataatgtt ttaatgtatt ttacatttga gatgactttta atggtaagtg acatgtttga   9540
gggacggatg aatgttgccg cgctctgcac tattagtcat tacttatcac cactagggcc   9600
aaggatagat agattgtttt ctattgtaga tgaattagca caactattgg gtgacactgt   9660
atataaaatt attgcatctc ttgaatcttt agtatatggg tgtctacaac ttaaagatcc   9720
agtggttgaa ttaacaggat catttcattc ctttattacg caagagatta tagatatcct   9780
aattgggtca aaagcccttg ataaggatga atcaataact gtcactacac aattgctaga   9840 tatatttttcc aacctttctc cagatttaat cgctgagatg ttgtgtctca tgagactttg   9900
gggtcatccc actcttactg ctgcgcaagc tgcaggtaaa gtgagagaat ctatgtgtgc   9960
aggtaagtta cttgatttcc ctacaataat gaaaactctt gcttttttcc acacaatttt   10020
aatcaatggt tatcgtagaa agaagaatgg aatgtggcct ccacttatac ttcctaaaaa   10080
tgcatcaaaa agcttaatag agtttcaaca tgataatgct gaaatatctt atgagtatac   10140
actcaagcat tggaaagaaa tctctctcat agaatttaga aagtgctttg actttgatcc   10200
tggtgaggag ctaagcattt ttatgaaaga caaggcaata agtgctccaa aaagtgattg   10260
gatgagtgta ttccgtagaa gtctaataaa acaacgacat cagagacatc atattcctat   10320
```

```
gcccaatcca tttaacagac gtctattact caatttctta gaagatgaca gttttgatcc   10380
agttgctgag cttcaatatg ttaccagtgg tgaatatctc cgagatgaca cattttgtgc   10440
atcttactca ttaaaagaga aagaaataaa accagatgga aggatatttg ctaagcttac   10500
taatagaatg cggtcttgtc aagtaattgc ggaagcaatt cttgcaaatc acgcaggtac   10560
tctaatgaag gaaaacggag ttgtcttgaa tcaattatct ctgactaaat cattgcttac   10620
tatgagtcaa attggcataa tatcagaaaa agcaaagaga tatacccgag ataacatctc   10680
atctcaaggt ttccatacaa tcaagactga ctcaaaaaat aagaagaaaa gcaaaattgc   10740
atcatcatac ctcacagatc ctgatgatac atttgaactt agtgcatgtt ttataactac   10800
tgatcttgct aaatactgtc ttcaatggag atatcagacc ataatccatt ttgctcgaac   10860
attaaacaga atgtatggag ttccacattt atttgaatgg attcatcttc gtttgattag   10920
atctacatta tatgttggtg atccattcaa tcctcctgcc acaactgatg ccttcgatct   10980
agataaagta ttaaatggtg atatctttat agtctctccc aagggaggta ttgaaggcct   11040
atgtcagaaa atgtggacaa tgatctctat ttctgtgatc atcctttctt cagccgaatc   11100
caaaacaaga gtaatgagca tggttcaagg agataatcag gcgattgcag ttacaacaag   11160
agttcctaga tcattgccta gtgttcagaa aaaggagtta gcctacgcag caagcaagtt   11220
attctttgaa agacttaggg caaataatta tggtttgggt catcaactaa aggctcaaga   11280
gactataata agttccacgt tcttcatata tagtaaacgg gtattctatc aaggacgtat   11340
actaacacag gcacttaaaa atgctagcaa gttatgtctt actgcagatg tattaggtga   11400
atgtactcag gcttcctgct caaattctgc tactacaatc atgagattaa cagaaaatgg   11460
ggttgagaaa gatacatgtt ataagcttaa tatttatcaa tctattcgtc aactcacata   11520
tgatctaata tttccccaat actccatacc aggtgaaaca ataagtgaaa ttttcttaca   11580
gcatccaaga ttaatctcac gtattgttct gctcccttca cagctaggtg gtcttaatta   11640
cctcgcatgt agcagattat ttaaccgcaa tatcggagat ccccttggta cagccgtggc   11700
agacctcaag aggttaatta aatgtggtgc tcttgaatca tggatactgt acaatttact   11760
ggcaagaaaa ccagggaaag gttcatgggc cactttagca gccgatccat actcattgaa   11820
tcaagaatat ctttatcctc ctactactat acttaaaaga catactcaaa atactttaat   11880
ggagatatgt cggaatccta tgttaaaggg agttttttaca gataatgcaa aagaggagga   11940
aaatctcctt gcaaaatttc ttcttgatcg tgatatagta ttgccaagag tcgcacacat   12000
tataatagat caatccagca ttggaaggaa gaaacagata caagggtttt ttgacaccac   12060
aaggaccata atgagacgat catttgagat caaaccactc tcaactaaga agacactttc   12120
agtcatagaa tataatacta attatttatc ttataactac cctgtcatac ttaatccttt   12180
acctattcct ggatatttaa attatattac tgaccaaact tgcagtattg atatatctag   12240
aagtttaaga aaattatcat ggtcttcttt attgaatgga agaactttag aaggattaga   12300
aactccagat ccaattgaag ttgtcaatgg ttccttgatt gtaggtacag agattgtga   12360 cttttgtatg cagggtgacg ataaattcac ttggttcttt ttacctatgg ggataattat   12420
tgatggaaat cctgaaacta atccaccca cagagttcca tacattgggt ctagaacaga   12480
ggaaagaaga gttgcatcaa tggcatatat taaaggtgcc acacacagtt tgaaggctgc   12540
tcttagaggc gcaggggtat acatttgggc attcggagat acagtagtga actggaatga   12600
tgcacttgat atcgcaaata ctagggttaa gatatcccta gagcaacttc agactcttac   12660
```

```
acctcttcct acatctgcaa acattacaca tcgtttagat gatggagcca caacacttaa   12720
attcactcca gctagttcct atgcattttc tagttatact catatatcaa atgatcaaca   12780
atatttagaa atagatcaga gagtagtcga ttccaatatt atttatcaac aattaatgat   12840
aacagggctt gggatcattg agacctacca taacccacct atcaggacct ctacacagga   12900
aatcaccctc catttgcaca ctagctcatc ttgttgtgtt agaagtgtag atggttgcct   12960
tatatgtgag agcaatggag aggttcctca gatcactgtt ccctacacta attcatttgt   13020
atatgatcct gatccactag cagattatga gattgcacat ctagattatc tctcctacca   13080
agctaaaatt ggaagtacag attactactc acttactgat aaaattgatc tattggcaca   13140
tttaactgca aaacaaatga taaactcaat aattgggtta gatgaaacag tatcaattgt   13200
caatgatgcg gttattctat ctgattatac taataactgg attagtgaat gttcttatac   13260
taagatagat ttagttttta aattaatggc atggaatttc cttcttgagc ttgcattcca   13320
gatgtactac ctaagaatat catcttggac aaatatattt gactatactt acatgacttt   13380
acgcaggata cccggaactg ctctaaataa tattgcagct actattagcc acccaaaatt   13440
attaagacgt gcaatgaatc ttgatattat cactcctata catgcaccgt atttggcttc   13500
attagattat gtcaaattaa gtattgatgc aattcagtgg ggggttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactat acatttccaa aaattaaagg gatgccacca gaggaaaagt gtttagtctt   13740
aactgaatac ctagcaatgt gttatcagaa tactcaccac ttagatccag atcttcaaaa   13800
gtatttatat aatctaacta atccaaaatt gactgcattt cccagtaaca acttctactt   13860
aacaaggaaa atccttaatc aaattagaga atcagacgaa ggacaatata ttatcaccct   13920
atattatgaa tccttcgaac aattagaaac agatataatt cttcactcta ctttaactgc   13980
tccttatgat aattcagaaa ctctaacaaa gtttgattta tcccttgaca tctttccaca   14040
tccagaatct ctcgagaaat atcctcttcc agttgatcat gactctcaat ctgcaatttc   14100
aacactaatt ccaggccctc cctctcatca tgtattacga ccactaggag tgtcatctac   14160
agcttggtat aaagggataa gttattgcag atacctggaa acgcaaaaga tacagactgg   14220
tgatcatctt tatttagctg aaggaagcgg tgcttcaatg tcacttctag aactcctatt   14280
tccaggagat actgtctatt ataatagtct ttttagtagt ggagagaatc ctccacagag   14340
aaattatgct cctcttccaa ctcaatttgt acagagtgtt ccatataaat tgtggcaagc   14400
tgatcttgct gatgatagta acttaataaa agattttgtc ccattatgga atggaaacgg   14460
agcagttaca gacttatcga caaaggatgc agttgcattc ataatacata agtaggagc   14520
ggagaaagca tcccttgttc atatagatct cgaatcgact gctaatataa atcagcaaac   14580
tctgtccaga tcccagattc attcgttaat tatagcaact actgttctta agaggggtgg   14640
gatattagtt tacaaaacat catggcttcc gttttctagg tttagtcaac tagcaagcct   14700
actttggtgc ttttttgacc ggatccatct aatacgtagt agttattctg atcctcacag   14760
tcatgaggtt tatcttgtat gtagacttgc tgcggatttt agaactatcg gtttcagtgc   14820
agctctagta actgctacta ctcttcacaa tgacggattc acaacaatac atcctgatgt   14880
tgtttgtagt tattggcaac accatcttga gaatgtgggg agagtcgaaa agtaattga   14940
tgagatactt gatggtttag ccaccaactt cttcgcagga gataatgggc ttattctaag   15000
atgtggagga actcccagct ctagaaaatg gttagagatt gatcagttag catcatttga   15060
```

```
ttcagttcaa gatgctctag tgacacttat caccatacac ctaaaggaaa ttatagaagt    15120
gcagtcatca catacagagg attatacatc tctcctttt c acaccttata atattggtgc   15180
agcagggaaa gtaagaacta tcatcaaatt aattctagaa cgatctttaa tgtatacagt    15240
ccgaaattgg ttagttttac ccagttccat ccgggattcc gtacgacaag atctagagtt    15300
agggtcattt agattaatgt ctattttaag tgaacagaca tttcttaaaa agacacccac    15360
caaaaaatac ttacttgatc agcttacaag gacatatata tcaaccttct ttaattctca    15420
ctcagtcctc ccctccacc gtccatatca aaacaaata tggaaagcct taggtagtgt     15480
aatatattgt tcggagacgg ttgatatacc tctaattaga gacattcaga tagaagatat    15540
taatgatttt gaagatatcg agagggtat cgatggcgaa gaattatgac aacagtgatt    15600
ataagaactc atgatagttt tatttaagaa aaacatattg attttccc ct tggt        15654
```

<210> SEQ ID NO 13
<211> LENGTH: 15654
<212> TYPE: DNA
<213> ORGANISM: Human parainfluenza virus

<400> SEQUENCE: 13

```
accaagggga gaatcagatg gcatcgttat atgacgaatt gcaaaagat tacgtaggtc      60 cggaaccact agattccggt gccggtaacg atctcagttt tatactatct gatcattctt    120
tatctctact aaggatattt ctaatctagc ggccgcaatg tcaagtgtct taaagacatt    180
tgaaagattt actatacaac aggagcttca ggagcaatct gaagacactc caatacctct    240
tgaaacaatc agacctacaa tcagagtatt tgtcatcaat aataatgatc ctattgtaag    300
atctagactt ttattcttta atctacgaat tattatgagt aacactgcaa gagagggaca    360
tagagctggt gctctcctca gtcttttatc actaccttct gcagctatga gtaatcacat    420
caaactagcc atgcattcac cagaagccag catagataga gtagaaataa cagggtttga    480
gaataattca ttccgagtta ttccagatgc tcgatcaact atgtccagag agaagtgct    540 ggccttcgaa gcattagctg aggacattcc tgatacccct aatcaccaaa ctccatttgt    600
aaataatgat gtggaagatg acatatttga tgaaacagag aaattcttgg atgtttgcta    660
tagtgtactt atgcaggcat ggatagtaac atgcaagtgc atgactgctc ctgatcaacc    720
accagtatca gtagcaaagc ggatggctaa atatcaacaa caaggagaa tcaatgctag    780 atatgtacta caacctgaag cacaaagact aattcagaat gccatccgca agtcaatggt    840
agtaaggcat tcatgacct atgagcttca acttcacaa tcaagatctt tgctagcgaa    900
ccgttattat gccatggtgg gagacattgg caagtatatt gaacacagcg gaatgggagg    960
gtttttctta acacttaaat atggacttgg aacaagatgg cctacattgg ctcttgcagc    1020
attctctggg gaactccaga aattaaaggc tctcatgcta cattatcaga gtctaggacc    1080
catggccaag tacatggctc tattagaatc accaaagctg atggattttg tcccatctga    1140
atatccatta gtttatagct atgcaatggg tattggaact gtccttgata caaacatgag    1200
aaactatgca tatggtagat catatctaaa tccacaatat tttcagctag gggtagaaac    1260
agcaaggaaa cagcaaggag ctgttgacaa caggacagca gaggacctcg gcatgactgc    1320
tgcagataaa gcagacctca ctgcaaccat atcaaagcta tctttatccc aattacctag    1380
gggtagacaa ccaatatccg acccatttgc tggagcaaat gacagagaaa caggaggaca    1440
agcaactgat acacctgtgt ataacttcaa tccaatcaat aatcggaggt atgacaacta    1500
```

```
tgacagtgat agtgaggaca gaattgacaa cgatcaagat caggctatca gagagaacag    1560
aggagaacct ggacaaccaa acaaccagac aagcgaaaac cagcagagac tcaatctccc    1620
tgtaccgcaa agaacatcag gtatgagtag tgaagagttc caacattcaa tgaatcagta    1680
catccgtgct atgcatgagc aatacagagg ctcccaggat gatgatgcca atgatgccac    1740
agatgggaat gacatttcac ttgagctagt tggagatttt gattcctaac tctcactttc    1800
acataaccag acatacacat ccacaccacc cagagacata gctaccatcc acacactcac    1860
ccagacaaat caaactagat tcaaatcatt cggaaacaat tctcctagaa tttaagaaaa    1920
aaacataggc ccggacgggt tagagatccg gtgctcgtct gtggccagac aacctccaca    1980
ccagagccac acaatcatgg ccgaggaacc aacatacacc actgagcaag ttgatgaatt    2040
aatccatgct ggactaggaa cagtagattt cttcctatct agacccatag atgctcagtc    2100
ttctttaggt aaaggcagca tcccaccagg tgtcacggct gttctaacca atgcagcaga    2160
ggcaaaatcc aaaccagttg ctgctggtcc agtaaaaccc agacggaaga aagtgatcag    2220
caataccact ccatacacta ttgcagacaa catcccacct gagaagctac cgatcaacac    2280
tccaataccc aatccattac ttccactggc acgccctcac ggaaagatga cagacattga    2340
cattgtcact gggaacatta cagaaggatc atacaaaggt gtggagcttg ccaaattagg    2400
gaagcaaaca ctactcacaa ggttcacctc gaatgagcca gtctcctcag ctggatccgc    2460
ccaagacccc aactttaaga ggggggagc taatagagaa agagcaagag gcaaccatag    2520
gagagaatgg agtattgcat gggtcggaga tcaggtcaaa gtcttcgagt ggtgtaatcc    2580
caggtgtgcc ccagtcacgg cttcagctcg caagttcacc tgcacatgtg atcctgccc    2640 cagcatctgc ggagaatgtg aaggagatca ttgagctctt aaaagggctt gatcttcgcc    2700
ttcagactgt agaagggaaa gtagataaaa ttcttgcaac ctctgcaact ataatcaatc    2760
ttaaaaatga aatgactagt cttaaggcga gcgttgcaac tgtggaaggt atgataacaa    2820
caattaaaat catggatccc agtacaccaa ccaatgtccc tgtagaggag atcagaaaga    2880
gtttacacaa tgttccagta gtaattgctg gtccgactag tggaggcttc acagccgaag    2940
gcagtgacat gatttcaatg gatgaactag ctaggcctac actctcatca acaaaaaaga    3000
tcacacgaaa gcctgaatcc aagaaagatt taacaggcat aaaactaacc ctgatgcagc    3060
ttgcaaatga ctgcatctcg cgtccagata ccaagactga gtttgtgact aagattcaag    3120
cagcaaccac agaatcacag ctcaacgaaa tcaaacggtc aataatacgc tctgcaatat    3180
aaaatgcggt gcaatcacac aagagacatt caacatgcat ccgatcaaga tccaaactcc    3240
ttccatccga aaacacactc accactgtca acaccaagaa acaactacag ccgaaccatg    3300
ctcaaccaaa agacccaaac aacatctcaa atcgacagaa ggctagacat gataaattta    3360
ataaaaaatt aaaagaagtt aagtaaaatt taaagaacac aatagagaaa acctaggtcc    3420
gaaagcttgc ctttcagaca gatcccaaaa tcatagttca aacttcaaac acagcagcag    3480
acatgcctat aatatcatta ccagcagatc caacttcacc cagtcaatcc cttactccgt    3540
ttccaataca acttgatacc aaagatggca aggcagggaa actccttaaa cagattagaa    3600
ttaggtatct aaatgaacct aactctcgtc atacaccaat aactttcatc aatacgtatg    3660
gatttgttta tgctcgagac acttcaggag gcattcacag cgagatcagc agtgacctag    3720
ctgcagggtc cataacggca tgcatgatga cactaggtcc tggtccaaat attcagaatg    3780 caaatcagt gctaagatcc ctgaatgaat tctcacgtaa agtcaagaag acatcaagcc    3840 agaggggagga agcagtgttt gaattagtta acattccaac cttattgaga gaacatgctc    3900
```

```
tttgcaaacg caaaacgtta gtatgctctg cagaaaaatt cctcaagaac ccatcaaagc   3960
tacaagctgg atttgaatat gtatacatcc aacttttgt ctccattaca tactcaccac   4020
gaaatctgaa ttaccaagtt gccagaccta tccttaagtt cagatcacgc tttgtgtata   4080
gcattcattt ggaattaatc ctgagattgc tatgcaaatc tgactcccct ttgatgaaat   4140
cttataatgc agatcgaaca ggtcgaggat gcctcgcatc agtctggatc cacgtatgta   4200
acattctgaa aaacaaaagc atcaagcaac aaggcagaga atcatatttc atagctaagt   4260
gcatgagtat gcagctgcag gtgtccattg cagatctttg ggaccaaca atcataatta   4320 aatcattggg tcacatcccc aagactgcac ttcctttttt cagcaaagac gggattgcct   4380
gtcatccact acaagatgtt tccctactc tgacaaaatc actgtggtca gtgggatgtg   4440
agatagaatc tgccaagttg atacttcaag aatctgatat taatgagcta atgggccacc   4500
aggacttgat tactgataag attgccatta gatcaggtca acggacattt gagaggtcca   4560
aattcagccc attcaaaaaa tacgcatcaa ttccaaactt agaagccatc aactgaatgc   4620
tccagcatct aggaatagaa caacaactaa gtcataccat tattgaccat acaataatca   4680
acaattttag ccaactgatt actaagatat tatcataggt ccgaactgat caatctaaca   4740
aaaaaactaa acattcaata ataaatcaaa gttcaggcca aattatccag ccatgcatca   4800
cctgcatcca atgatagtat gcatttttgt tatgtacact ggaattgtag gttcagatgc   4860
cattgctgga gatcaactcc tcaatgtagg ggtcattcaa tcaaagataa gatcactcat   4920
gtactacact gatggtggcg ctagctttat tgttgtaaaa ttactaccca atcttccccc   4980
aagcaatgga acatgcaaca tcaccagtct agatgcatat aatgttaccc tatttaagtt   5040
gctaacaccc ctgattgaga acctgagcaa aatttctgct gttacagata ccaaacccg   5100 ccgagaacga tttgcaggag tcgttattgg gcttgctgca ctaggagtag ctacagctgc   5160
acaaataacc gcagctgtag caatagtaaa agccaatgca aatgctgctg cgataaacaa   5220
tcttgcatct tcaattcaat ccaccaacaa ggcagtatcc gatgtgataa ctgcatcaag   5280
aacaattgca accgcagttc aagcgattca ggatcacatc aatggagcca ttgtcaacgg   5340
gataacatct gcatcatgcc gtgcccatga tgcactaatt gggtcaatat taaatttgta   5400
tctcactgag cttactacaa tatttcataa tcaaataaca aaccctgcgc tgacaccact   5460
ttccatccaa gctttaagaa tcctcctcgg tagcaccttg ccaattgtca ttgaatccaa   5520
actcaacaca aaactcaaca cagcagagct gctcagttcc ggactgttaa ctggtcaaat   5580
aatttccatt tccccaatgt acatgcaaat gctaattcaa atcaatgttc cgacatttat   5640
aatgcaaccc ggtgcgaagg taattgatct aattgctatc tctgcaaacc ataaattaca   5700
agaagtagtt gtacaagttc ctaatagaat tctagaatat gcaaatgaac tacaaaacta   5760
cccagccaat gattgtgtcg tgacaccaaa ctctgtattt tgtagataca atgagggttc   5820
cccgatccct gaatcacaat atcaatgctt aagggggaat cttaattctt gcacttttac   5880
ccctattatc gggaactttc tcaagcgatt cgcatttgcc aatggtgtgc tctatgccaa   5940
ctgcaaatct tgctatgta agtgtgccga ccctccccat gttgtgtctc aagatgacaa   6000
ccaaggcatc agcataattg atattaagag gtgctctgag atgatgcttg acactttttc   6060
atttaggatc acatctacat tcaatgctac atacgtgaca gacttctcaa tgattaatgc   6120
aaatattgta catctcaagtc ctctagactt gtcaaatcaa atcaattcaa taaacaaatc   6180
tcttaaaagt gctgaggatt ggattgcaga tagcaacttc ttcgctaatc aagccagaac   6240
```

```
agccaagaca ctttattcac taagtgcaat cgcattaata ctatcagtga ttactttggt    6300
tgttgtggga ttgctgattg cctacatcat caagctggtt tctcaaatcc atcaattcag    6360
agcactagct gctacaacaa tgttccacag ggagaatcct gccgtctttt ccaagaacaa    6420
tcatggaaac atatatggga tatcttaaga attctatcat aagtccatat atgtccatga    6480 ttgacccttta agagccaacc tccaatgatt atccgttaaa ttcagatata acaattcaaa    6540
aatcaatatt aagcctccag ataccaatga atatgaatat atctcttaga aaacttgatt    6600
attatgtgat aacatagtac aatttaagaa aaaacctaaa ataagcacga acccttaagg    6660
tgtcgtaacg tctcgtgacg ccgggttcag ttcaaacatc gaccccctgac ccaattcaat    6720 acccatttte ataaaggaac acagtataat ttaatcataa aagacctcaa aatctgatac    6780
agcttaatcc actcaacata taattataag actaataata atggaagatt acagcaatct    6840
atctcttaaa tcaattccta aaaggacatg tagaatcatt ttccgaactg ccacaattct    6900
tggcatatgc acattaattg tgctatgttc aagtattctt catgagataa ttcatcttga    6960
tgtttcctct ggtcttatga attctgatga gtcacagcaa ggcattattc agcctatcat    7020
agaatcatta aaatcattga ttgctttggc caaccagatt ctatataatg ttgcaatagt    7080
aattcctctt aaaattgaca gtatcgaaac tgtaatactc tctgctttaa aagatatgca    7140
caccgggagt atgtccaatg ccaactgcac gccaggaaat ctgcttctgc atgatgcagc    7200
atacatcaat ggaataaaca aattccttgt acttgaatca tacaatggga cgcctaaata    7260
tggacctctc ctaaatatac ccagctttat cccctcagca acatctcccc atgggtgtac    7320
tagaatacca tcattttcac tcatcaagac ccattggtgt tacactcaca atgtaatgct    7380
tggagattgt cttgatttca cggcatctaa ccagtattta tcaatgggga taatacaaca    7440
atctgctgca gggtttccaa ttttcaggac tatgaaaacc atttacctaa gtgatggaat    7500
caatcgcaaa agctgttcag tcactgctat accaggaggt tgtgtcttgt attgctatgt    7560
agctacaagg tctgaaaaag aagattatgc cacgactgat ctagctgaac tgagacttgc    7620
tttctattat tataatgata cctttattga agagtcata tctcttccaa atacaacagg    7680
gcagtgggcc acaatcaacc ctgcagtcgg aagcgggatc tatcatctag ctttatctt    7740 atttcctgta tatggtggtc tcataaatgg gactacttct tacaatgagc agtcctcacg    7800
ctattttatc ccaaaacatc ccaacataac ttgtgccggt aactccagca acaggctgc    7860 aatagcacgg agttcctatg tcatccgtta tcactcaaac aggttaattc agagtgctgt    7920
tcttatttgt ccattgtctg acatgcatac agaagagtgt aatctagtta tgtttaacaa    7980
ttcccaagtc atgatgggtg cagaaggtag gctctatgtt attggtaata atttgtatta    8040
ttatcaacgc agttcctctt ggtggtctgc atcgctcttt tacaggatca atacagatt    8100 ttctaaagga attcctccga tcattgaggc tcaatgggta ccgtcctatc aagttcctcg    8160
tcctggagtc atgccatgca atgcaacaag tttttgccct gctaattgca tcacaggggt    8220
gtacgcagat gtgtggccgc ttaatgatcc agaactcatg tcacgtaatg ctctgaaccc    8280
caactatcga tttgctggag cctttctcaa aaatgagtcc aaccgaacta atcccacatt    8340
ctacactgca tcggctaact ccctcttaaa tactaccgga ttcaacaaca ccaatcacaa    8400
agcagcatat acatcttcaa cctgctttaa aaacactgga acccaaaaaa tttattgttt    8460
aataataatt gaaatgggct catctctttt aggggagttc caaataatac cattttaag    8520 ggaactaatg ctttaatcct attgaatgaa gactccagat tcaagaataa ttggaaggct    8580
ctttatttta tgcgatagtt atacgttttg gctgtattag aatgctatag cattctgctg    8640
```

```
tttttcccat atggaaaaat ccttcaacac caacttaggt tcaatttcct catcatttac    8700
tgttgtaatt caatcttact aaagttattc tgatatttaa gaaaaaataa tctttatata    8760
atgtaacaat actactaaga ttataatata ggccagaatg gcggcctctt ctgagatact    8820
ccttcctgaa gtccatttga actcaccaat agtcaaacac aaactcatat actacttatt    8880
actagggcac ttcccgcatg atcttgacat ttctgaaata agccccttc acaataatga     8940
ttgggatcag attgccagag aagaatccaa tcttgctgaa cgactcggag tagctaaatc    9000
tgaattaatt aaacgtgtgc ccgcatttag agcaaccaga tggcgtagtc atgcagccgt    9060
ccttatatgg ccttcttgta taccattcct tgttaaattc ctaccccatt ctaagcttca    9120
accaatagaa caatggtaca agttgatcaa tgcttcatgc aatactatat ctgactcaat    9180
tgatagatgt atggagaata tttctattaa gcttactggg aaaaacaatc tattctctcg    9240
atccagagga actgcaggcg caggtaaaaa cagtaaaatc accctcaatg atatccaatc    9300
tatttgggaa tcaaacaaat ggcagcctaa tgtatcttta tggcttacaa ttaaatacca    9360
aatgcgacaa cttataatgc atcaaagttc tcgtcagcca actgatttag ttcacattgt    9420
tgacacacga tctggtctaa tagttatcac ccctgaactt gttatttgct ttgatcggtt    9480
gaataatgtt ttaatgtatt ttacatttga gatgacttta atggtaagtg acatgtttga    9540
gggacggatg aatgttgccg cgctctgcac tattagtcat tacttatcac cactagggcc    9600
aaggatagat agattgtttt ctattgtaga tgaattagca caactattgg gtgacactgt    9660
atataaaatt attgcatctc ttgaatcttt agtatatggg tgtctacaac ttaaagatcc    9720
agtggttgaa ttaacaggat catttcattc ctttattacg caagagatta tagatatcct    9780
aattgggtca aaagcccttg ataaggatga atcaataact gtcactacac aattgctaga    9840
tatattttcc aacctttctc cagatttaat cgctgagatg ttgtgtctca tgagactttg    9900
gggtcatccc actcttactg ctgcgcaagc tgcaggtaaa gtgagagaat ctatgtgtgc    9960
aggtaagtta cttgatttcc ctacaataat gaaaactctt gctttttcc acacaatttt    10020
aatcaatggt tatcgtagaa agaagaatgg aatgtggcct ccactatac ttcctaaaaa     10080
tgcatcaaaa agcttaatag agtttcaaca tgataatgct gaaatatctt atgagtatac    10140
actcaagcat tggaaagaaa tctctctcat agaatttaga aagtgctttg actttgatcc    10200
tggtgaggag ctaagcattt ttatgaaaga caaggcaata agtgctccaa aaagtgattg    10260
gatgagtgta ttccgtagaa gtctaataaa acaacgacat cagagacatc atattcctat    10320
gcccaatcca tttaacagac gtctattact caatttctta gaagatgaca gttttgatcc    10380
agttgctgag cttcaatatg ttaccagtgg tgaatatctc cgagatgaca cattttgtgc    10440
atcttactca ttaaaagaga agaaaataaa accagatgga aggatatttg ctaagcttac    10500
taatagaatg cggtcttgtc aagtaattgc ggaagcaatt cttgcaaatc acgcaggtac    10560
tctaatgaag gaaaacggag ttgtcttgaa tcaattatct ctgactaaat cattgcttac    10620
tatgagtcaa attggcataa tatcagaaaa agcaaagaga tatacccgag ataacatctc    10680
atctcaaggt ttccatacaa tcaagactga ctcaaaaaat aagaagaaaa gcaaaattgc    10740
atcatcatac ctcacagatc ctgatgatac atttgaactt agtgcatgtt ttataactac    10800
tgatcttgct aaaatactgtc ttcaatggag atatcagacc ataatccatt ttgctcgaac   10860
attaaacaga atgtatggag ttccacattt atttgaatgg attcatcttc gtttgattag    10920
atctacatta tatgttggtg atccattcaa tcctccctgcc acaactgatg ccttcgatct   10980
```

```
agataaagta ttaaatggtg atatctttat agtctctccc aagggaggta ttgaaggcct    11040
atgtcagaaa atgtggacaa tgatctctat ttctgtgatc atcctttctt cagccgaatc    11100
caaaacaaga gtaatgagca tggttcaagg agataatcag gcgattgcag ttacaacaag    11160
agttcctaga tcattgccta gtgttcagaa aaaggagtta gcctacgcag caagcaagtt    11220
attctttgaa agacttaggg caaataatta tggtttgggt catcaactaa aggctcaaga    11280
gactataata agttccacgt tcttcatata tagtaaacgg gtattctatc aaggacgtat    11340
actaacacag gcacttaaaa atgctagcaa gttatgtctt actgcagatg tattaggtga    11400
atgtactcag gcttcctgct caaattctgc tactacaatc atgagattaa cagaaaatgg    11460
ggttgagaaa gatacatgtt ataagcttaa tatttatcaa tctattcgtc aactcacata    11520
tgatctaata tttccccaat actccatacc aggtgaaaca ataagtgaaa ttttcttaca    11580
gcatccaaga ttaatctcac gtattgttct gctcccttca cagctaggtg gtcttaatta    11640
cctcgcatgt agcagattat ttaaccgcaa tatcggagat ccccttggta cagccgtggc    11700
agacctcaag aggttaatta aatgtggtgc tcttgaatca tggatactgt acaatttact    11760
ggcaagaaaa ccagggaaag gttcatgggc cactttagca gccgatccat actcattgaa    11820
tcaagaatat ctttatcctc ctactactat acttaaaaga catactcaaa atactttaat    11880
ggagatatgt cggaatccta tgttaaaggg agttttaca gataatgcaa aagaggagga    11940
aaatctcctt gcaaaatttc ttcttgatcg tgatatagta ttgccaagag tcgcacacat    12000
tataatagat caatccagca ttggaaggaa gaaacagata caagggtttt ttgacaccac    12060
aaggaccata atgagacgat catttgagat caaaccactc tcaactaaga agacactttc    12120
agtcatagaa tataatacta attatttatc ttataactac cctgtcatac ttaatccttt    12180
acctattcct ggatatttaa attatattac tgaccaaact tgcagtattg atatatctag    12240
aagtttaaga aaattatcat ggtcttcttt attgaatgga agaactttag aaggattaga    12300
aactccagat ccaattgaag ttgtcaatgg ttccttgatt gtaggtacag agattgtga    12360 cttttgtatg cagggtgacg ataaattcac ttggttcttt ttacctatgg ggataattat    12420
tgatggaaat cctgaaacta atccacccat cagagttcca tacattgggt ctagaacaga    12480
ggaaagaaga gttgcatcaa tggcatatat taaaggtgcc acacacagtt tgaaggctgc    12540
tcttagaggc gcagggtat acatttgggc attcggagat acagtagtga actggaatga    12600
tgcacttgat atcgcaaata ctagggttaa gatatcccta gagcaacttc agactcttac    12660
acctcttcct acatctgcaa acattacaca tcgtttagat gatggagcca caacacttaa    12720
attcactcca gctagttcct atgcattttc tagttatact catatatcaa atgatcaaca    12780
atatttagaa atagatcaga gagtagtcga ttccaatatt attttatcaac aattaatgat    12840 aacagggctt gggatcattg agacctacca taacccacct atcaggacct ctacacagga    12900
aatcaccctc catttgcaca ctagctcatc ttgttgtgtt agaagtgtag atggttgcct    12960
tatatgtgag agcaatggag aggttcctca gatcactgtt ccctacacta attcatttgt    13020
atatgatcct gatccactag cagattatga gattgcacat ctagattatc tctcctacca    13080
agctaaaatt ggaagtacag attactactc acttactgat aaaattgatc tattggcaca    13140
tttaactgca aaacaaatga taaactcaat aattggggtta gatgaaacag tatcaattgt    13200
caatgatgcg gttattctat ctgattatac taataactgg attagtgaat gttcttatac    13260
taagatagat ttagttttta aattaatggc atggaatttc cttcttgagc ttgcattcca    13320
gatgtactac ctaagaatat catcttggac aaatatattt gactatactt acatgacttt    13380
```

```
acgcaggata cccggaactg ctctaaataa tattgcagct actattagcc acccaaaatt      13440
attaagacgt gcaatgaatc ttgatattat cactcctata catgcaccgt atttggcttc      13500
attagattat gtcaaattaa gtattgatgc aattcagtgg ggggttaaac aagttcttgc      13560
tgatttatca aatggaattg atcttgaaat cttgattctt tcagaggatt caatggaaat      13620
tagtgatagg gcaatgaatc tcattgctag aaaactaact ctccttgcac ttgttaaagg      13680
tgagaactat acatttccaa aaattaaagg gatgccacca gaggaaaagt gtttagtctt      13740
aactgaatac ctagcaatgt gttatcagaa tactcaccac ttagatccag atcttcaaaa      13800
gtatttatat aatctaacta atccaaaatt gactgcattt cccagtaaca acttctactt      13860
aacaaggaaa atccttaatc aaattagaga atcagacgaa ggacaatata ttatcaccte      13920 atattatgaa tccttcgaac aattagaaac agatataatt cttcactcta ctttaactgc      13980
tccttatgat aattcagaaa ctctaacaaa gtttgattta tcccttgaca tctttccaca      14040
tccagaatct ctcgagaaat atcctcttcc agttgatcat gactctcaat ctgcaatttc      14100
aacactaatt ccaggccctc cctctcatca tgtattacga ccactaggag tgtcatctac      14160
agcttggtat aaagggataa gttattgcag atacctggaa acgcaaaaga tacagactgg      14220
tgatcatctt tatttagctg aaggaagcgg tgcttcaatg tcacttctag aactcctatt      14280
tccaggagat actgtctatt ataatagtct ttttagtagt ggagagaatc ctccacagag      14340
aaattatgct cctcttccaa ctcaatttgt acagagtgtt ccatataaat tgtggcaagc      14400
tgatcttgct gatgatagta acttaataaa agattttgtc ccattatgga atggaaacgg      14460
agcagttaca gacttatcga caaaggatgc agttgcattc ataatacata aagtaggagc      14520
ggagaaagca tcccttgttc atatagatct cgaatcgact gctaatataa atcagcaaac      14580
tctgtccaga tcccagattc attcgttaat tatagcaact actgttctta agaggggtgg      14640
gatattagtt tacaaaacat catggcttcc gttttctagg tttagtcaac tagcaagcct      14700
actttggtgc ttttttgacc ggatccatct aatacgtagt agttattctg atcctcacag      14760
tcatgaggtt tatcttgtat gtagacttgc tgcggatttt agaactatcg gtttcagtgc      14820
agctctagta actgctacta ctcttcacaa tgacggattc acaacaatac atcctgatgt      14880
tgtttgtagt tattggcaac accatcttga gaatgttggg agagtcgaaa agtaattga      14940 tgagatactt gatggtttag ccaccaactt cttcgcagga gataatgggc ttattctaag      15000
atgtggagga actcccagct ctagaaaatg gttagagatt gatcagttag catcatttga      15060
ttcagttcaa gatgctctag tgacacttat caccatacac ctaaaggaaa ttatagaagt      15120
gcagtcatca catacagagg attatacatc tctccttttc acaccttata atattggtgc      15180
agcagggaaa gtaagaacta tcatcaaatt aattctagaa cgatctttaa tgtatacagt      15240
ccgaaattgg ttagttttac ccagttccat ccgggattcc gtacgacaag atctagagtt      15300
agggtcattt agattaatgt ctatttttaag tgaacagaca tttcttaaaa agacacccac      15360
caaaaaatac ttacttgatc agcttacaag gacatatata tcaaccttct ttaattctca      15420
ctcagtcctc cccctccacc gtccatatca aaaacaaata tggaaagcct taggtagtgt      15480
aatatattgt tcggagacgg ttgatatacc tctaattaga gacattcaga tagaagatat      15540
taatgatttt gaagatatcg agaggggtat cgatggcgaa gaattatgac aacagtgatt      15600
ataagaactc atgatagttt tatttaagaa aaacatattg attttcccct tggt           15654
```

<210> SEQ ID NO 14

-continued

```
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 tgac                                                                   4

<210> SEQ ID NO 15
<211> LENGTH: 395
<212> TYPE: PRT
<213> ORGANISM: Parainfluenza virus

<400> SEQUENCE: 15
```

Met Ala Glu Glu Pro Thr Tyr Thr Thr Glu Gln Val Asp Glu Leu Ile
1               5                   10                  15

His Ala Gly Leu Gly Thr Val Asp Phe Phe Leu Ser Arg Pro Ile Asp
            20                  25                  30

Ala Gln Ser Ser Leu Gly Lys Gly Ser Ile Pro Pro Gly Val Thr Ala
        35                  40                  45

Val Leu Thr Asn Ala Ala Glu Ala Lys Ser Lys Pro Val Ala Ala Gly
50                  55                  60

Pro Val Lys Pro Arg Arg Lys Lys Val Ile Ser Asn Thr Thr Pro Tyr
65                  70                  75                  80

Thr Ile Ala Asp Asn Ile Pro Pro Glu Lys Leu Pro Ile Asn Thr Pro
                85                  90                  95

Ile Pro Asn Pro Leu Leu Pro Leu Ala Arg Pro His Gly Lys Met Thr
            100                 105                 110

Asp Ile Asp Ile Val Thr Gly Asn Ile Thr Glu Gly Ser Tyr Lys Gly
        115                 120                 125

Val Glu Leu Ala Lys Leu Gly Lys Gln Thr Leu Leu Thr Arg Phe Thr
130                 135                 140

Ser Asn Glu Pro Val Ser Ser Ala Gly Ser Ala Gln Asp Pro Asn Phe
145                 150                 155                 160

Lys Arg Gly Gly Glu Leu Ile Glu Lys Glu Gln Glu Ala Thr Ile Gly
                165                 170                 175

Glu Asn Gly Val Leu His Gly Ser Glu Ile Arg Ser Lys Ser Ser Ser
            180                 185                 190

Gly Val Ile Pro Gly Val Pro Gln Ser Arg Leu Gln Leu Ala Ser Ser
        195                 200                 205

Pro Ala His Val Asp Pro Ala Pro Ser Ala Glu Asn Val Lys Glu
210                 215                 220

Ile Ile Glu Leu Leu Lys Gly Leu Asp Leu Arg Leu Gln Thr Val Glu
225                 230                 235                 240

Gly Lys Val Asp Lys Ile Leu Ala Thr Ser Ala Thr Ile Ile Asn Leu
                245                 250                 255

Lys Asn Glu Met Thr Ser Leu Lys Ala Ser Val Ala Thr Val Glu Gly
            260                 265                 270

Met Ile Thr Thr Ile Lys Ile Met Asp Pro Ser Thr Pro Thr Asn Val
        275                 280                 285

Pro Val Glu Glu Ile Arg Lys Ser Leu His Asn Val Pro Val Val Ile
    290                 295                 300

Ala Gly Pro Thr Ser Gly Gly Phe Thr Ala Glu Gly Ser Asp Met Ile
305                 310                 315                 320

```
Ser Met Asp Glu Leu Ala Arg Pro Thr Leu Ser Ser Thr Lys Lys Ile
            325                 330                 335

Thr Arg Lys Pro Glu Ser Lys Lys Asp Leu Thr Gly Ile Lys Leu Thr
            340                 345                 350

Leu Met Gln Leu Ala Asn Asp Cys Ile Ser Arg Pro Asp Thr Lys Thr
            355                 360                 365

Glu Phe Val Thr Lys Ile Gln Ala Ala Thr Thr Glu Ser Gln Leu Asn
        370                 375                 380

Glu Ile Lys Arg Ser Ile Ile Arg Ser Ala Ile
385                 390                 395

<210> SEQ ID NO 16
<211> LENGTH: 543
<212> TYPE: PRT
<213> ORGANISM: Parainfluenza virus

<400> SEQUENCE: 16

Met Ser Ser Val Leu Lys Thr Phe Glu Arg Phe Thr Ile Gln Gln Glu
1               5                   10                  15

Leu Gln Glu Gln Ser Glu Asp Thr Pro Ile Pro Leu Glu Thr Ile Arg
            20                  25                  30

Pro Thr Ile Arg Val Phe Val Ile Asn Asn Asn Asp Pro Ile Val Arg
        35                  40                  45

Ser Arg Leu Leu Phe Phe Asn Leu Arg Ile Ile Met Ser Asn Thr Ala
    50                  55                  60

Arg Glu Gly His Arg Ala Gly Ala Leu Leu Ser Leu Leu Ser Leu Pro
65                  70                  75                  80

Ser Ala Ala Met Ser Asn His Ile Lys Leu Ala Met His Ser Pro Glu
                85                  90                  95

Ala Ser Ile Asp Arg Val Glu Ile Thr Gly Phe Glu Asn Asn Ser Phe
            100                 105                 110

Arg Val Ile Pro Asp Ala Arg Ser Thr Met Ser Arg Gly Glu Val Leu
        115                 120                 125

Ala Phe Glu Ala Leu Ala Glu Asp Ile Pro Asp Thr Leu Asn His Gln
    130                 135                 140

Thr Pro Phe Val Asn Asn Asp Val Glu Asp Ile Phe Asp Glu Thr
145                 150                 155                 160

Glu Lys Phe Leu Asp Val Cys Tyr Ser Val Leu Met Gln Ala Trp Ile
                165                 170                 175

Val Thr Cys Lys Cys Met Thr Ala Pro Asp Gln Pro Pro Val Ser Val
            180                 185                 190

Ala Lys Arg Met Ala Lys Tyr Gln Gln Gln Gly Arg Ile Asn Ala Arg
        195                 200                 205

Tyr Val Leu Gln Pro Glu Ala Gln Arg Leu Ile Gln Asn Ala Ile Arg
    210                 215                 220

Lys Ser Met Val Val Arg His Phe Met Thr Tyr Glu Leu Gln Leu Ser
225                 230                 235                 240

Gln Ser Arg Ser Leu Leu Ala Asn Arg Tyr Tyr Ala Met Val Gly Asp
                245                 250                 255

Ile Gly Lys Tyr Ile Glu His Ser Gly Met Gly Gly Phe Phe Leu Thr
            260                 265                 270

Leu Lys Tyr Gly Leu Gly Thr Arg Trp Pro Thr Leu Ala Leu Ala Ala
        275                 280                 285

Phe Ser Gly Glu Leu Gln Lys Leu Lys Ala Leu Met Leu His Tyr Gln
    290                 295                 300
```

Ser Leu Gly Pro Met Ala Lys Tyr Met Ala Leu Leu Glu Ser Pro Lys
305 310 315 320

Leu Met Asp Phe Val Pro Ser Glu Tyr Pro Leu Val Tyr Ser Tyr Ala
325 330 335

Met Gly Ile Gly Thr Val Leu Asp Thr Asn Met Arg Asn Tyr Ala Tyr
340 345 350

Gly Arg Ser Tyr Leu Asn Pro Gln Tyr Phe Gln Leu Gly Val Glu Thr
355 360 365

Ala Arg Lys Gln Gln Gly Ala Val Asp Asn Arg Thr Ala Glu Asp Leu
370 375 380

Gly Met Thr Ala Ala Asp Lys Ala Asp Leu Thr Ala Thr Ile Ser Lys
385 390 395 400

Leu Ser Leu Ser Gln Leu Pro Arg Gly Arg Gln Pro Ile Ser Asp Pro
405 410 415

Phe Ala Gly Ala Asn Asp Arg Glu Thr Gly Gly Gln Ala Thr Asp Thr
420 425 430

Pro Val Tyr Asn Phe Asn Pro Ile Asn Asn Arg Arg Tyr Asp Asn Tyr
435 440 445

Asp Ser Asp Ser Glu Asp Arg Ile Asp Asn Asp Gln Asp Gln Ala Ile
450 455 460

Arg Glu Asn Arg Gly Glu Pro Gly Gln Pro Asn Asn Gln Thr Ser Glu
465 470 475 480

Asn Gln Gln Arg Leu Asn Leu Pro Val Pro Gln Arg Thr Ser Gly Met
485 490 495

Ser Ser Glu Glu Phe Gln His Ser Met Asn Gln Tyr Ile Arg Ala Met
500 505 510

His Glu Gln Tyr Arg Gly Ser Gln Asp Asp Asp Ala Asn Asp Ala Thr
515 520 525

Asp Gly Asn Asp Ile Ser Leu Glu Leu Val Gly Asp Phe Asp Ser
530 535 540

<210> SEQ ID NO 17
<211> LENGTH: 2263
<212> TYPE: PRT
<213> ORGANISM: Parainfluenza virus

<400> SEQUENCE: 17

Met Ala Ala Ser Ser Glu Ile Leu Leu Pro Glu Val His Leu Asn Ser
1 5 10 15

Pro Ile Val Lys His Lys Leu Ile Tyr Tyr Leu Leu Leu Gly His Phe
20 25 30

Pro His Asp Leu Asp Ile Ser Glu Ile Ser Pro Leu His Asn Asn Asp
35 40 45

Trp Asp Gln Ile Ala Arg Glu Glu Ser Asn Leu Ala Glu Arg Leu Gly
50 55 60

Val Ala Lys Ser Glu Leu Ile Lys Arg Val Pro Ala Phe Arg Ala Thr
65 70 75 80

Arg Trp Arg Ser His Ala Ala Val Leu Ile Trp Pro Ser Cys Ile Pro
85 90 95

Phe Leu Val Lys Phe Leu Pro His Ser Lys Leu Gln Pro Ile Glu Gln
100 105 110

Trp Tyr Lys Leu Ile Asn Ala Ser Cys Asn Thr Ile Ser Asp Ser Ile
115 120 125

Asp Arg Cys Met Glu Asn Ile Ser Ile Lys Leu Thr Gly Lys Asn Asn

```
                130             135             140
Leu Phe Ser Arg Ser Arg Gly Thr Ala Gly Ala Gly Lys Asn Ser Lys
145                 150                 155                 160

Ile Thr Leu Asn Asp Ile Gln Ser Ile Trp Glu Ser Asn Lys Trp Gln
                165                 170                 175

Pro Asn Val Ser Leu Trp Leu Thr Ile Lys Tyr Gln Met Arg Gln Leu
            180                 185                 190

Ile Met His Gln Ser Ser Arg Gln Pro Thr Asp Leu Val His Ile Val
            195                 200                 205

Asp Thr Arg Ser Gly Leu Ile Val Ile Thr Pro Glu Leu Val Ile Cys
        210                 215                 220

Phe Asp Arg Leu Asn Asn Val Leu Met Tyr Phe Thr Phe Glu Met Thr
225                 230                 235                 240

Leu Met Val Ser Asp Met Phe Glu Gly Arg Met Asn Val Ala Ala Leu
                245                 250                 255

Cys Thr Ile Ser His Tyr Leu Ser Pro Leu Gly Pro Arg Ile Asp Arg
                260                 265                 270

Leu Phe Ser Ile Val Asp Glu Leu Ala Gln Leu Leu Gly Asp Thr Val
            275                 280                 285

Tyr Lys Ile Ile Ala Ser Leu Glu Ser Leu Val Tyr Gly Cys Leu Gln
            290                 295                 300

Leu Lys Asp Pro Val Val Glu Leu Thr Gly Ser Phe His Ser Phe Ile
305                 310                 315                 320

Thr Gln Glu Ile Ile Asp Ile Leu Ile Gly Ser Lys Ala Leu Asp Lys
                325                 330                 335

Asp Glu Ser Ile Thr Val Thr Thr Gln Leu Leu Asp Ile Phe Ser Asn
            340                 345                 350

Leu Ser Pro Asp Leu Ile Ala Glu Met Leu Cys Leu Met Arg Leu Trp
            355                 360                 365

Gly His Pro Thr Leu Thr Ala Ala Gln Ala Ala Gly Lys Val Arg Glu
        370                 375                 380

Ser Met Cys Ala Gly Lys Leu Leu Asp Phe Pro Thr Ile Met Lys Thr
385                 390                 395                 400

Leu Ala Phe Phe His Thr Ile Leu Ile Asn Gly Tyr Arg Arg Lys Lys
                405                 410                 415

Asn Gly Met Trp Pro Pro Leu Ile Leu Pro Lys Asn Ala Ser Lys Ser
                420                 425                 430

Leu Ile Glu Phe Gln His Asp Asn Ala Glu Ile Ser Tyr Glu Tyr Thr
            435                 440                 445

Leu Lys His Trp Lys Glu Ile Ser Leu Ile Glu Phe Arg Lys Cys Phe
        450                 455                 460

Asp Phe Asp Pro Gly Glu Glu Leu Ser Ile Phe Met Lys Asp Lys Ala
465                 470                 475                 480

Ile Ser Ala Pro Lys Ser Asp Trp Met Ser Val Phe Arg Arg Ser Leu
                485                 490                 495

Ile Lys Gln Arg His Gln Arg His His Ile Pro Met Pro Asn Pro Phe
            500                 505                 510

Asn Arg Arg Leu Leu Leu Asn Phe Leu Glu Asp Asp Ser Phe Asp Pro
            515                 520                 525

Val Ala Glu Leu Gln Tyr Val Thr Ser Gly Glu Tyr Leu Arg Asp Asp
        530                 535                 540

Thr Phe Cys Ala Ser Tyr Ser Leu Lys Glu Lys Glu Ile Lys Pro Asp
545                 550                 555                 560
```

-continued

```
Gly Arg Ile Phe Ala Lys Leu Thr Asn Arg Met Arg Ser Cys Gln Val
            565                 570                 575
Ile Ala Glu Ala Ile Leu Ala Asn His Ala Gly Thr Leu Met Lys Glu
        580                 585                 590
Asn Gly Val Val Leu Asn Gln Leu Ser Leu Thr Lys Ser Leu Leu Thr
        595                 600                 605
Met Ser Gln Ile Gly Ile Ile Ser Glu Lys Ala Lys Arg Tyr Thr Arg
    610                 615                 620
Asp Asn Ile Ser Ser Gln Gly Phe His Thr Ile Lys Thr Asp Ser Lys
625                 630                 635                 640
Asn Lys Lys Ser Lys Ile Ala Ser Ser Tyr Leu Thr Asp Pro Asp
                645                 650                 655
Asp Thr Phe Glu Leu Ser Ala Cys Phe Ile Thr Thr Asp Leu Ala Lys
            660                 665                 670
Tyr Cys Leu Gln Trp Arg Tyr Gln Thr Ile Ile His Phe Ala Arg Thr
        675                 680                 685
Leu Asn Arg Met Tyr Gly Val Pro His Leu Phe Glu Trp Ile His Leu
    690                 695                 700
Arg Leu Ile Arg Ser Thr Leu Tyr Val Gly Asp Pro Phe Asn Pro Pro
705                 710                 715                 720
Ala Thr Thr Asp Ala Phe Asp Leu Asp Lys Val Leu Asn Gly Asp Ile
                725                 730                 735
Phe Ile Val Ser Pro Lys Gly Gly Ile Glu Gly Leu Cys Gln Lys Met
            740                 745                 750
Trp Thr Met Ile Ser Ile Ser Val Ile Leu Ser Ser Ala Glu Ser
        755                 760                 765
Lys Thr Arg Val Met Ser Met Val Gln Gly Asp Asn Gln Ala Ile Ala
    770                 775                 780
Val Thr Thr Arg Val Pro Arg Ser Leu Pro Ser Val Gln Lys Lys Glu
785                 790                 795                 800
Leu Ala Tyr Ala Ala Ser Lys Leu Phe Phe Glu Arg Leu Arg Ala Asn
                805                 810                 815
Asn Tyr Gly Leu Gly His Gln Leu Lys Ala Gln Glu Thr Ile Ile Ser
            820                 825                 830
Ser Thr Phe Phe Ile Tyr Ser Lys Arg Val Phe Tyr Gln Gly Arg Ile
        835                 840                 845
Leu Thr Gln Ala Leu Lys Asn Ala Ser Lys Leu Cys Leu Thr Ala Asp
    850                 855                 860
Val Leu Gly Glu Cys Thr Gln Ala Ser Cys Ser Asn Ser Ala Thr Thr
865                 870                 875                 880
Ile Met Arg Leu Thr Glu Asn Gly Val Glu Lys Asp Thr Cys Tyr Lys
                885                 890                 895
Leu Asn Ile Tyr Gln Ser Ile Arg Gln Leu Thr Tyr Asp Leu Ile Phe
            900                 905                 910
Pro Gln Tyr Ser Ile Pro Gly Glu Thr Ile Ser Glu Ile Phe Leu Gln
        915                 920                 925
His Pro Arg Leu Ile Ser Arg Ile Val Leu Pro Ser Gln Leu Gly
    930                 935                 940
Gly Leu Asn Tyr Leu Ala Cys Ser Arg Leu Phe Asn Arg Asn Ile Gly
945                 950                 955                 960
Asp Pro Leu Gly Thr Ala Val Ala Asp Leu Lys Arg Leu Ile Lys Cys
                965                 970                 975
```

-continued

Gly Ala Leu Glu Ser Trp Ile Leu Tyr Asn Leu Leu Ala Arg Lys Pro
         980                 985                 990

Gly Lys Gly Ser Trp Ala Thr Leu Ala Ala Asp Pro Tyr Ser Leu Asn
         995                 1000                1005

Gln Glu Tyr Leu Tyr Pro Pro Thr Thr Ile Leu Lys Arg His Thr
        1010                1015                1020

Gln Asn Thr Leu Met Glu Ile Cys Arg Asn Pro Met Leu Lys Gly
        1025                1030                1035

Val Phe Thr Asp Asn Ala Lys Glu Glu Asn Leu Leu Ala Lys
        1040                1045                1050

Phe Leu Leu Asp Arg Asp Ile Val Leu Pro Arg Val Ala His Ile
        1055                1060                1065

Ile Ile Asp Gln Ser Ser Ile Gly Arg Lys Lys Gln Ile Gln Gly
        1070                1075                1080

Phe Phe Asp Thr Thr Arg Thr Ile Met Arg Arg Ser Phe Glu Ile
        1085                1090                1095

Lys Pro Leu Ser Thr Lys Lys Thr Leu Ser Val Ile Glu Tyr Asn
        1100                1105                1110

Thr Asn Tyr Leu Ser Tyr Asn Tyr Pro Val Ile Leu Asn Pro Leu
        1115                1120                1125

Pro Ile Pro Gly Tyr Leu Asn Tyr Ile Thr Asp Gln Thr Cys Ser
        1130                1135                1140

Ile Asp Ile Ser Arg Ser Leu Arg Lys Leu Ser Trp Ser Ser Leu
        1145                1150                1155

Leu Asn Gly Arg Thr Leu Glu Gly Leu Glu Thr Pro Asp Pro Ile
        1160                1165                1170

Glu Val Val Asn Gly Ser Leu Ile Val Gly Thr Gly Asp Cys Asp
        1175                1180                1185

Phe Cys Met Gln Gly Asp Asp Lys Phe Thr Trp Phe Phe Leu Pro
        1190                1195                1200

Met Gly Ile Ile Ile Asp Gly Asn Pro Glu Thr Asn Pro Pro Ile
        1205                1210                1215

Arg Val Pro Tyr Ile Gly Ser Arg Thr Glu Glu Arg Arg Val Ala
        1220                1225                1230

Ser Met Ala Tyr Ile Lys Gly Ala Thr His Ser Leu Lys Ala Ala
        1235                1240                1245

Leu Arg Gly Ala Gly Val Tyr Ile Trp Ala Phe Gly Asp Thr Val
        1250                1255                1260

Val Asn Trp Asn Asp Ala Leu Asp Ile Ala Asn Thr Arg Val Lys
        1265                1270                1275

Ile Ser Leu Glu Gln Leu Gln Thr Leu Thr Pro Leu Pro Thr Ser
        1280                1285                1290

Ala Asn Ile Thr His Arg Leu Asp Asp Gly Ala Thr Thr Leu Lys
        1295                1300                1305

Phe Thr Pro Ala Ser Ser Tyr Ala Phe Ser Ser Tyr Thr His Ile
        1310                1315                1320

Ser Asn Asp Gln Gln Tyr Leu Glu Ile Asp Gln Arg Val Val Asp
        1325                1330                1335

Ser Asn Ile Ile Tyr Gln Gln Leu Met Ile Thr Gly Leu Gly Ile
        1340                1345                1350

Ile Glu Thr Tyr His Asn Pro Pro Ile Arg Thr Ser Thr Gln Glu
        1355                1360                1365

Ile Thr Leu His Leu His Thr Ser Ser Ser Cys Cys Val Arg Ser

-continued

```
        1370              1375              1380
Val Asp Gly Cys Leu Ile Cys Glu Ser Asn Gly Glu Val Pro Gln
    1385              1390              1395
Ile Thr Val Pro Tyr Thr Asn Ser Phe Val Tyr Asp Pro Asp Pro
    1400              1405              1410
Leu Ala Asp Tyr Glu Ile Ala His Leu Asp Tyr Leu Ser Tyr Gln
    1415              1420              1425
Ala Lys Ile Gly Ser Thr Asp Tyr Tyr Ser Leu Thr Asp Lys Ile
    1430              1435              1440
Asp Leu Leu Ala His Leu Thr Ala Lys Gln Met Ile Asn Ser Ile
    1445              1450              1455
Ile Gly Leu Asp Glu Thr Val Ser Ile Val Asn Asp Ala Val Ile
    1460              1465              1470
Leu Ser Asp Tyr Thr Asn Asn Trp Ile Ser Glu Cys Ser Tyr Thr
    1475              1480              1485
Lys Ile Asp Leu Val Phe Lys Leu Met Ala Trp Asn Phe Leu Leu
    1490              1495              1500
Glu Leu Ala Phe Gln Met Tyr Tyr Leu Arg Ile Ser Ser Trp Thr
    1505              1510              1515
Asn Ile Phe Asp Tyr Thr Tyr Met Thr Leu Arg Arg Ile Pro Gly
    1520              1525              1530
Thr Ala Leu Asn Asn Ile Ala Ala Thr Ile Ser His Pro Lys Leu
    1535              1540              1545
Leu Arg Arg Ala Met Asn Leu Asp Ile Ile Thr Pro Ile His Ala
    1550              1555              1560
Pro Tyr Leu Ala Ser Leu Asp Tyr Val Lys Leu Ser Ile Asp Ala
    1565              1570              1575
Ile Gln Trp Gly Val Lys Gln Val Leu Ala Asp Leu Ser Asn Gly
    1580              1585              1590
Ile Asp Leu Glu Ile Leu Ile Leu Ser Glu Asp Ser Met Glu Ile
    1595              1600              1605
Ser Asp Arg Ala Met Asn Leu Ile Ala Arg Lys Leu Thr Leu Leu
    1610              1615              1620
Ala Leu Val Lys Gly Glu Asn Tyr Thr Phe Pro Lys Ile Lys Gly
    1625              1630              1635
Met Pro Pro Glu Glu Lys Cys Leu Val Leu Thr Glu Tyr Leu Ala
    1640              1645              1650
Met Cys Tyr Gln Asn Thr His His Leu Asp Pro Asp Leu Gln Lys
    1655              1660              1665
Tyr Leu Tyr Asn Leu Thr Asn Pro Lys Leu Thr Ala Phe Pro Ser
    1670              1675              1680
Asn Asn Phe Tyr Leu Thr Arg Lys Ile Leu Asn Gln Ile Arg Glu
    1685              1690              1695
Ser Asp Glu Gly Gln Tyr Ile Ile Thr Ser Tyr Tyr Glu Ser Phe
    1700              1705              1710
Glu Gln Leu Glu Thr Asp Ile Ile Leu His Ser Thr Leu Thr Ala
    1715              1720              1725
Pro Tyr Asp Asn Ser Glu Thr Leu Thr Lys Phe Asp Leu Ser Leu
    1730              1735              1740
Asp Ile Phe Pro His Pro Glu Ser Leu Glu Lys Tyr Pro Leu Pro
    1745              1750              1755
Val Asp His Asp Ser Gln Ser Ala Ile Ser Thr Leu Ile Pro Gly
    1760              1765              1770
```

-continued

Pro Pro Ser His His Val Leu Arg Pro Leu Gly Val Ser Ser Thr
1775             1780                 1785

Ala Trp Tyr Lys Gly Ile Ser Tyr Cys Arg Tyr Leu Glu Thr Gln
1790             1795                 1800

Lys Ile Gln Thr Gly Asp His Leu Tyr Leu Ala Glu Gly Ser Gly
1805             1810                 1815

Ala Ser Met Ser Leu Leu Glu Leu Leu Phe Pro Gly Asp Thr Val
1820             1825                 1830

Tyr Tyr Asn Ser Leu Phe Ser Ser Gly Glu Asn Pro Pro Gln Arg
1835             1840                 1845

Asn Tyr Ala Pro Leu Pro Thr Gln Phe Val Gln Ser Val Pro Tyr
1850             1855                 1860

Lys Leu Trp Gln Ala Asp Leu Ala Asp Asp Ser Asn Leu Ile Lys
1865             1870                 1875

Asp Phe Val Pro Leu Trp Asn Gly Asn Gly Ala Val Thr Asp Leu
1880             1885                 1890

Ser Thr Lys Asp Ala Val Ala Phe Ile Ile His Lys Val Gly Ala
1895             1900                 1905

Glu Lys Ala Ser Leu Val His Ile Asp Leu Glu Ser Thr Ala Asn
1910             1915                 1920

Ile Asn Gln Gln Thr Leu Ser Arg Ser Gln Ile His Ser Leu Ile
1925             1930                 1935

Ile Ala Thr Thr Val Leu Lys Arg Gly Gly Ile Leu Val Tyr Lys
1940             1945                 1950

Thr Ser Trp Leu Pro Phe Ser Arg Phe Ser Gln Leu Ala Ser Leu
1955             1960                 1965

Leu Trp Cys Phe Phe Asp Arg Ile His Leu Ile Arg Ser Ser Tyr
1970             1975                 1980

Ser Asp Pro His Ser His Glu Val Tyr Leu Val Cys Arg Leu Ala
1985             1990                 1995

Ala Asp Phe Arg Thr Ile Gly Phe Ser Ala Ala Leu Val Thr Ala
2000             2005                 2010

Thr Thr Leu His Asn Asp Gly Phe Thr Thr Ile His Pro Asp Val
2015             2020                 2025

Val Cys Ser Tyr Trp Gln His His Leu Glu Asn Val Gly Arg Val
2030             2035                 2040

Glu Lys Val Ile Asp Glu Ile Leu Asp Gly Leu Ala Thr Asn Phe
2045             2050                 2055

Phe Ala Gly Asp Asn Gly Leu Ile Leu Arg Cys Gly Gly Thr Pro
2060             2065                 2070

Ser Ser Arg Lys Trp Leu Glu Ile Asp Gln Leu Ala Ser Phe Asp
2075             2080                 2085

Ser Val Gln Asp Ala Leu Val Thr Leu Ile Thr Ile His Leu Lys
2090             2095                 2100

Glu Ile Ile Glu Val Gln Ser Ser His Thr Glu Asp Tyr Thr Ser
2105             2110                 2115

Leu Leu Phe Thr Pro Tyr Asn Ile Gly Ala Ala Gly Lys Val Arg
2120             2125                 2130

Thr Ile Ile Lys Leu Ile Leu Glu Arg Ser Leu Met Tyr Thr Val
2135             2140                 2145

Arg Asn Trp Leu Val Leu Pro Ser Ser Ile Arg Asp Ser Val Arg
2150             2155                 2160

```
Gln Asp Leu Glu Leu Gly Ser Phe Arg Leu Met Ser Ile Leu Ser
    2165                2170                2175

Glu Gln Thr Phe Leu Lys Lys Thr Pro Thr Lys Lys Tyr Leu Leu
    2180                2185                2190

Asp Gln Leu Thr Arg Thr Tyr Ile Ser Thr Phe Phe Asn Ser His
    2195                2200                2205

Ser Val Leu Pro Leu His Arg Pro Tyr Gln Lys Gln Ile Trp Lys
    2210                2215                2220

Ala Leu Gly Ser Val Ile Tyr Cys Ser Glu Thr Val Asp Ile Pro
    2225                2230                2235

Leu Ile Arg Asp Ile Gln Ile Glu Asp Ile Asn Asp Phe Glu Asp
    2240                2245                2250

Ile Glu Arg Gly Ile Asp Gly Glu Glu Leu
    2255                2260

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      3' signal sequence

<400> SEQUENCE: 18
accaagggga gaattagatg gcatcgttat                                         30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      3' signal sequence

<400> SEQUENCE: 19
accaagggga gaatyagatg gcatcgttat                                         30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      3' signal sequence

<400> SEQUENCE: 20
accaagggga gaatcagatg gcatcgttat                                         30

<210> SEQ ID NO 21
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 aatcaga                                                                   7

<210> SEQ ID NO 22
<211> LENGTH: 7
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 22 aattaga                                                                  7

<210> SEQ ID NO 23
<211> LENGTH: 51
<212> TYPE: PRT
<213> ORGANISM: Human parainfluenza virus

<400> SEQUENCE: 23

His Arg Arg Glu Trp Ser Ile Ala Trp Val Gly Asp Gln Val Lys Val
1               5                   10                  15

Phe Glu Trp Cys Asn Pro Arg Cys Ala Pro Val Thr Ala Ser Ala Arg
            20                  25                  30

Lys Phe Thr Cys Thr Cys Gly Ser Cys Pro Ser Ile Cys Gly Glu Cys
        35                  40                  45

Glu Gly Asp
    50

<210> SEQ ID NO 24
<211> LENGTH: 51
<212> TYPE: PRT
<213> ORGANISM: Simian virus

<400> SEQUENCE: 24

His Arg Arg Glu Trp Ser Ile Ala Trp Val Gly Asp Glu Val Lys Val
1               5                   10                  15

Tyr Glu Trp Cys Asn Pro Thr Cys Ala Pro Val Thr Ala Thr Asp Arg
            20                  25                  30

Lys Phe Ser Cys Thr Cys Gly Thr Cys Pro Asp Arg Cys Gly Glu Cys
        35                  40                  45

Glu Gly Asp
    50

<210> SEQ ID NO 25
<211> LENGTH: 51
<212> TYPE: PRT
<213> ORGANISM: Simian virus

<400> SEQUENCE: 25

His Arg Arg Glu Tyr Ser Ile Gly Trp Val Gly Asp Glu Val Lys Val
1               5                   10                  15

Thr Glu Trp Cys Asn Pro Ser Cys Ser Pro Ile Thr Ala Ala Ala Arg
            20                  25                  30

Arg Phe Glu Cys Thr Cys His Gln Cys Pro Val Thr Cys Ser Glu Cys
        35                  40                  45

Glu Arg Asp
    50

<210> SEQ ID NO 26
<211> LENGTH: 51
<212> TYPE: PRT
<213> ORGANISM: Mumps virus

<400> SEQUENCE: 26

His Arg Arg Glu Trp Ser Leu Ser Trp Val Gln Gly Glu Val Arg Val
1               5                   10                  15

Phe Glu Trp Cys Asn Pro Ile Cys Ser Pro Ile Thr Ala Ala Ala Arg

```
                    20                  25                  30

Phe His Ser Cys Lys Cys Gly Asn Cys Pro Ala Lys Cys Asp Gln Cys
        35                  40                  45

Glu Arg Asp
    50

<210> SEQ ID NO 27
<211> LENGTH: 51
<212> TYPE: PRT
<213> ORGANISM: Human parainfluenza virus

<400> SEQUENCE: 27

His Arg Arg Glu Tyr Ser Ile Ser Trp Val Asn Gly Arg Thr Thr Ile
1               5                   10                  15

Ser Glu Trp Cys Asn Pro Cys Cys Ala Pro Val Lys Ser Thr Ala Ser
                20                  25                  30

Val Glu Lys Cys Thr Cys Gly Arg Cys Pro Lys Ile Cys Glu Leu Cys
            35                  40                  45

Ile Arg Asp
    50

<210> SEQ ID NO 28
<211> LENGTH: 51
<212> TYPE: PRT
<213> ORGANISM: Human parainfluenza virus

<400> SEQUENCE: 28

His Arg Arg Glu His Ser Ile Ser Trp Val Asn Gly Arg Thr Thr Ile
1               5                   10                  15

Ser Glu Trp Cys Asn Pro Cys Cys Ala Pro Val Lys Ser Ile Ala Ser
                20                  25                  30

Val Glu Lys Cys Thr Cys Gly Arg Cys Pro Lys Ile Cys Glu Leu Cys
            35                  40                  45

Ile Arg Asp
    50

<210> SEQ ID NO 29
<211> LENGTH: 51
<212> TYPE: PRT
<213> ORGANISM: Newcastle disease virus

<400> SEQUENCE: 29

His Arg Arg Glu His Ser Ile Ser Trp Thr Met Gly Val Thr Thr
1               5                   10                  15

Ile Ser Trp Cys Asn Pro Ser Cys Ser Pro Ile Arg Ala Glu Pro Arg
                20                  25                  30

Gln Tyr Ser Cys Thr Cys Gly Ser Cys Pro Ala Thr Cys Arg Leu Cys
            35                  40                  45

Ala Ser Asp
    50

<210> SEQ ID NO 30
<211> LENGTH: 51
<212> TYPE: PRT
<213> ORGANISM: Tioman virus

<400> SEQUENCE: 30

His Arg Arg Glu Ile Ala Ile Ser Trp Ala Thr Gly Pro Arg Val
1               5                   10                  15
```

```
Thr Glu Trp Cys Asn Pro Ile Cys His Pro Ile Ser Gln Phe Thr Tyr
            20                  25                  30

Arg Gly Thr Cys Arg Cys Gly Cys Pro Asp Val Cys Ser Leu Cys
        35                  40                  45

Glu Arg Asp
    50

<210> SEQ ID NO 31
<211> LENGTH: 51
<212> TYPE: PRT
<213> ORGANISM: Menangle virus

<400> SEQUENCE: 31

His Arg Arg Glu Ile Ala Ile Asp Trp Ile Gly Gly Arg Pro Arg Val
1               5                   10                  15

Thr Glu Trp Cys Asn Pro Ile Cys His Pro Ile Ser Gln Ser Thr Phe
            20                  25                  30

Arg Gly Ser Cys Arg Cys Gly Asn Cys Pro Gly Ile Cys Ser Leu Cys
        35                  40                  45

Glu Arg Asp
    50

<210> SEQ ID NO 32
<211> LENGTH: 51
<212> TYPE: PRT
<213> ORGANISM: Porcine rubulavirus

<400> SEQUENCE: 32

His Arg Arg Glu Tyr Ser Ile Gly Trp Val Cys Gly Thr Val Arg Val
1               5                   10                  15

Leu Glu Trp Cys Asn Pro Ala Cys Ser Pro Ile Ser Met Glu Pro Arg
            20                  25                  30

Tyr Tyr Gln Cys Thr Cys Gly Thr Cys Pro Ala Lys Cys Pro Gln Cys
        35                  40                  45

Ala Gly Asp
    50

<210> SEQ ID NO 33
<211> LENGTH: 51
<212> TYPE: PRT
<213> ORGANISM: Canine distemper virus

<400> SEQUENCE: 33

His Arg Arg Glu Val Ser Leu Thr Trp Asn Gly Asp Ser Cys Trp Ile
1               5                   10                  15

Asp Lys Trp Cys Asn Pro Ile Cys Thr Gln Val Asn Trp Gly Ile Ile
            20                  25                  30

Arg Ala Lys Cys Val Cys Gly Glu Cys Pro Pro Thr Cys Ser Glu Cys
        35                  40                  45

Lys Asp Asp
    50

<210> SEQ ID NO 34
<211> LENGTH: 51
<212> TYPE: PRT
<213> ORGANISM: Phocine distemper virus

<400> SEQUENCE: 34

His Arg Arg Glu Val Ser Leu Thr Trp Asn Asp Asp Arg Cys Trp Ile
1               5                   10                  15
```

```
Asp Lys Trp Cys Asn Pro Ile Cys Thr Gln Val Asn Trp Gly Val Ile
             20                  25                  30

Arg Ala Lys Cys Ile Cys Gly Glu Cys Pro Pro Val Cys Asp Asp Cys
         35                  40                  45

Lys Asp Asp
    50

<210> SEQ ID NO 35
<211> LENGTH: 51
<212> TYPE: PRT
<213> ORGANISM: Rinderpest virus

<400> SEQUENCE: 35

His Arg Arg Glu Ile Asp Leu Ile Trp Asn Asp Gly Arg Val Phe Ile
1               5                  10                  15

Asp Arg Trp Cys Asn Pro Thr Cys Ser Lys Val Thr Val Gly Thr Val
             20                  25                  30

Arg Ala Lys Cys Ile Cys Gly Glu Cys Pro Arg Val Cys Glu Gln Cys
         35                  40                  45

Ile Thr Asp
    50

<210> SEQ ID NO 36
<211> LENGTH: 51
<212> TYPE: PRT
<213> ORGANISM: Measles virus

<400> SEQUENCE: 36

His Arg Arg Glu Ile Ser Leu Ile Trp Asn Gly Asp Arg Val Phe Ile
1               5                  10                  15

Asp Arg Trp Cys Asn Pro Met Cys Ser Lys Val Thr Leu Gly Thr Ile
             20                  25                  30

Arg Ala Arg Cys Thr Cys Gly Glu Cys Pro Arg Val Cys Glu Gln Cys
         35                  40                  45

Arg Thr Asp
    50

<210> SEQ ID NO 37
<211> LENGTH: 51
<212> TYPE: PRT
<213> ORGANISM: Salem virus

<400> SEQUENCE: 37

His Arg Arg Glu Tyr Ser Ile Ile Trp Asp Ser Glu Gly Ile Gln Ile
1               5                  10                  15

Glu Ser Trp Cys Asn Pro Val Cys Ser Lys Val Arg Ser Thr Pro Arg
             20                  25                  30

Arg Glu Lys Cys Arg Cys Gly Lys Cys Pro Ala Arg Cys Ser Glu Cys
         35                  40                  45

Gly Asp Asp
    50

<210> SEQ ID NO 38
<211> LENGTH: 51
<212> TYPE: PRT
<213> ORGANISM: Fer-de-lance virus

<400> SEQUENCE: 38

His Arg Arg Glu Ile Ser Thr Ser Thr Ile Asp Gly Ile Phe Glu Val
```

```
                1               5                      10                      15
        Trp Glu Phe Cys Asn Pro Met Cys Ser Arg Ile Thr Pro Asp Phe Lys
                        20                      25                      30

Pro Lys Ile Cys Val Cys Gly Glu Cys Pro Arg Tyr Cys Pro Arg Cys
                    35                      40                      45

Lys Glu Gln
            50

<210> SEQ ID NO 39
<211> LENGTH: 51
<212> TYPE: PRT
<213> ORGANISM: Bovine parainfluenza virus

<400> SEQUENCE: 39

His Arg Arg Glu His Ser Ile Tyr Arg Lys Gly Asp Tyr Ile Ile Thr
        1               5                   10                      15

Glu Ser Trp Cys Asn Pro Ile Cys Ser Lys Ile Arg Pro Ile Pro Arg
                        20                      25                      30

Gln Glu Ser Cys Val Cys Gly Glu Cys Pro Lys Gln Cys Arg Tyr Cys
                    35                      40                      45

Ile Lys Asp
            50

<210> SEQ ID NO 40
<211> LENGTH: 51
<212> TYPE: PRT
<213> ORGANISM: Sendai virus

<400> SEQUENCE: 40

His Arg Arg Glu His Ile Ile Tyr Glu Arg Asp Gly Tyr Ile Val Asn
        1               5                   10                      15

Glu Ser Trp Cys Asn Pro Val Cys Ser Arg Ile Arg Val Ile Ser Arg
                        20                      25                      30

Arg Glu Leu Cys Val Cys Lys Ala Cys Pro Lys Ile Cys Lys Leu Cys
                    35                      40                      45

Arg Asp Asp
            50

<210> SEQ ID NO 41
<211> LENGTH: 51
<212> TYPE: PRT
<213> ORGANISM: Mossman virus

<400> SEQUENCE: 41

His Arg Arg Glu Tyr Asn Phe Val Trp Thr Asp Ser Gly Phe Arg Val
        1               5                   10                      15

Glu Ala Trp Cys Asn Pro Ile Cys Ser Arg Ile Arg Asn Leu Pro Arg
                        20                      25                      30

Arg Glu Lys Cys Arg Cys Gly Trp Cys Pro Lys Glu Cys Pro Glu Cys
                    35                      40                      45

Ala Leu Gly
            50

<210> SEQ ID NO 42
<211> LENGTH: 51
<212> TYPE: PRT
<213> ORGANISM: Tupaia paramyxovirus

<400> SEQUENCE: 42
```

-continued

His Arg Arg Glu Tyr Ser Met Val Trp Ser Asn Asp Gly Val Phe Ile
1               5                   10                  15

Glu Ser Trp Cys Asn Pro Met Cys Ala Arg Ile Arg Pro Leu Pro Ile
            20                  25                  30

Arg Glu Ile Cys Val Cys Gly Arg Cys Pro Leu Lys Cys Ser Lys Cys
        35                  40                  45

Leu Leu Asp
    50

<210> SEQ ID NO 43
<211> LENGTH: 51
<212> TYPE: PRT
<213> ORGANISM: Hendra virus

<400> SEQUENCE: 43

His Arg Arg Glu Val Ser Ile Cys Trp Asp Gly Arg Arg Ala Trp Val
1               5                   10                  15

Glu Glu Trp Cys Asn Pro Val Cys Ser Arg Ile Thr Pro Gln Pro Arg
            20                  25                  30

Lys Gln Glu Cys Tyr Cys Gly Glu Cys Pro Thr Glu Cys Ser Gln Cys
        35                  40                  45

Cys His Glu
    50

<210> SEQ ID NO 44
<211> LENGTH: 49
<212> TYPE: PRT
<213> ORGANISM: Nipah virus

<400> SEQUENCE: 44

His Arg Arg Glu Ile Ser Ile Cys Trp Asp Gly Lys Arg Ala Trp Val
1               5                   10                  15

Glu Glu Trp Cys Asn Pro Ala Cys Ser Arg Ile Thr Pro Leu Pro Arg
            20                  25                  30

Arg Gln Glu Cys Gln Cys Gly Glu Cys Pro Thr Glu Cys Phe His Cys
        35                  40                  45

Gly

<210> SEQ ID NO 45
<211> LENGTH: 225
<212> TYPE: PRT
<213> ORGANISM: Human parainfluenza virus

<400> SEQUENCE: 45

Met Ala Glu Glu Pro Thr Tyr Thr Thr Glu Gln Val Asp Glu Leu Ile
1               5                   10                  15

His Ala Gly Leu Gly Thr Val Asp Phe Phe Leu Ser Arg Pro Ile Asp
            20                  25                  30

Ala Gln Ser Ser Leu Gly Lys Gly Ser Ile Pro Pro Gly Val Thr Ala
        35                  40                  45

Val Leu Thr Asn Ala Ala Glu Ala Lys Ser Lys Pro Val Ala Ala Gly
    50                  55                  60

Pro Val Lys Pro Arg Arg Lys Lys Val Ile Ser Asn Thr Thr Pro Tyr
65                  70                  75                  80

Thr Ile Ala Asp Asn Ile Pro Pro Glu Lys Leu Pro Ile Asn Thr Pro
                85                  90                  95

Ile Pro Asn Pro Leu Leu Pro Leu Ala Arg Pro His Gly Lys Met Thr
            100                 105                 110

-continued

```
Asp Ile Asp Ile Val Thr Gly Asn Ile Thr Glu Gly Ser Tyr Lys Gly
            115                 120                 125

Val Glu Leu Ala Lys Leu Gly Lys Gln Thr Leu Leu Thr Arg Phe Thr
    130                 135                 140

Ser Asn Glu Pro Val Ser Ser Ala Gly Ser Ala Gln Asp Pro Asn Phe
145                 150                 155                 160

Lys Arg Gly Gly Ala Asn Arg Glu Arg Ala Arg Gly Asn His Arg Arg
                165                 170                 175

Glu Trp Ser Ile Ala Trp Val Gly Asp Gln Val Lys Val Phe Glu Trp
            180                 185                 190

Cys Asn Pro Arg Cys Ala Pro Val Thr Ala Ser Ala Arg Lys Phe Thr
            195                 200                 205

Cys Thr Cys Gly Ser Cys Pro Ser Ile Cys Gly Glu Cys Glu Gly Asp
    210                 215                 220

His
225

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tttaagaggg ggggagctaa taga                                          24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tttaagaggg gggggagct aata                                           24

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tagcggccgc aatg                                                     14

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agaggcgcgc catca                                                    15

<210> SEQ ID NO 50
```

-continued

```
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgcggttacc ggtcacaaga gacattcaac atgcatccgc ggaa                  44

<210> SEQ ID NO 51
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aactttaaga gaggaggtga gctaattgag aaagagcaag aggcaaccat aggtgagaat     60
ggagtattgc atgggtctga gattaggtca                                  90
```